(12) United States Patent
Benarous et al.

(10) Patent No.: US 9,260,395 B2
(45) Date of Patent: Feb. 16, 2016

(54) INHIBITORS OF VIRAL REPLICATION, THEIR PROCESS OF PREPARATION AND THEIR THERAPEUTICAL USES

(71) Applicant: LABORATOIRE BIODIM, Paris (FR)

(72) Inventors: Richard Benarous, Paris (FR); Francis Chevreuil, Chantilly (FR); Benoit Ledoussal, Pommerit Jaudy (FR); Sophie Chasset, Nandy (FR); Frédéric Le Strat, Combs-la-Ville (FR)

(73) Assignee: LABORATOIRE BIODIM, Paris (FR)

( * ) Notice: Subject to any disclaimer, the term of this patent is extended or adjusted under 35 U.S.C. 154(b) by 0 days.

(21) Appl. No.: 14/432,671

(22) PCT Filed: Oct. 7, 2013

(86) PCT No.: PCT/EP2013/070861
§ 371 (c)(1),
(2) Date: Mar. 31, 2015

(87) PCT Pub. No.: WO2014/053665
PCT Pub. Date: Apr. 10, 2014

(65) Prior Publication Data
US 2015/0274673 A1      Oct. 1, 2015

Related U.S. Application Data

(60) Provisional application No. 61/710,498, filed on Oct. 5, 2012.

(30) Foreign Application Priority Data

Oct. 5, 2012   (EP) .................................... 12306222

(51) Int. Cl.
*A61K 31/427* (2006.01)
*A61K 31/415* (2006.01)
*A61K 31/4741* (2006.01)
*A61K 31/4439* (2006.01)
*C07D 417/14* (2006.01)
*C07D 401/04* (2006.01)
*C07D 405/14* (2006.01)
*C07D 409/14* (2006.01)
*C07D 409/04* (2006.01)
*C07D 405/04* (2006.01)
*C07D 231/12* (2006.01)
*A61K 31/4155* (2006.01)
*A61K 45/06* (2006.01)

(52) U.S. Cl.
CPC ............ *C07D 231/12* (2013.01); *A61K 31/415* (2013.01); *A61K 31/4155* (2013.01); *A61K 31/427* (2013.01); *A61K 31/4439* (2013.01); *A61K 31/4741* (2013.01); *A61K 45/06* (2013.01); *C07D 401/04* (2013.01); *C07D 405/04* (2013.01); *C07D 405/14* (2013.01); *C07D 409/04* (2013.01); *C07D 409/14* (2013.01); *C07D 417/14* (2013.01)

(58) Field of Classification Search
CPC .............. A61K 31/427; A61K 31/415; A61K 31/4741; A61K 31/4439; A61K 31/4155; C07D 417/14; C07D 401/04; C07D 405/14; C07D 409/14; C07D 409/04; C07D 405/04; C07D 231/12
See application file for complete search history.

(56) References Cited

U.S. PATENT DOCUMENTS

| | | |
|---|---|---|
| 5,910,506 A | 6/1999 | Sugimoto et al. |
| 2003/0100554 A1 | 5/2003 | Jones et al. |
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2012/0059028 A1 | 3/2012 | Bardiot et al. |
| 2012/0129840 A1 | 5/2012 | Chaltin et al. |
| 2013/0190491 A1 | 7/2013 | Tsantrizos et al. |
| 2013/0197231 A1 | 8/2013 | Tsantrizos et al. |
| 2013/0203747 A1 | 8/2013 | Yoakim et al. |
| 2014/0128383 A1 | 5/2014 | Chasset et al. |
| 2014/0296272 A1 | 10/2014 | Bardiot et al. |

OTHER PUBLICATIONS

International Search Report for PCT/EP2013/070861 dated Oct. 28, 2013.

Genin M J et al: "Novel 1,5-Diphenylpyrazole Nonnucleoside HIV-1 Reverse Transcriptase Inhibitors With Enhanced Activity Versus the Delavirdine-Resistant P236L Mutant: Lead Identification and SAR of 3- and 4-Substituted Derivatives", Journal of Medicinal Chemistry, American Chemical Society, US, vol. 43, (Jan. 1, 2000), pp. 1034-1040.

(Continued)

*Primary Examiner* — Samantha Sherengarts
(74) *Attorney, Agent, or Firm* — B. Aaron Schulman, Esq.; Stites & Harbison, PLLC.

(57) ABSTRACT

The present invention relates to compounds of formula (I), their the treatment or the prevention of viral disorders, including HIV.

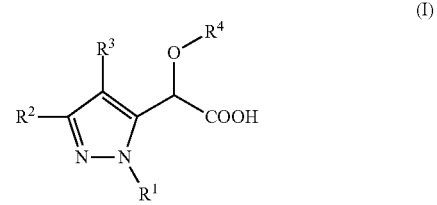

(I)

13 Claims, No Drawings

(56) References Cited

OTHER PUBLICATIONS

Inder Pal Singh et al: "Small molecule HIV entry inhibitors: Part I. Chemokine receptor antagonists: 2004—2010", Expert Opinion on Therapeutic Patents, vol. 21, No. 2, (Feb. 1, 2011), pp. 227-269.

David Tejedor et al: "Tertiary Skipped Diynes: A Pluripotent Building Block for the Modular and Diversity-Oriented Synthesis of Nitrogen Heterocycles", Chemistry—A European Journal, vol. 16, No. 11, (Mar. 15, 2010), pp. 3276-3280.

Cervia et al: "Enfuvirtide (T-20): A Novel Human Immunodeficiency Virus Type 1 Fusion Inhibitor", Clinical Infectious Diseases (Oct. 15, 2003), vol. 37, No. 8, pp. 1102-1106.

Hughes et al: New Treatment Options for HIV Salvage Patients: An Overview of Second Generation PIs, NNRTIs, integrase inhibitors and CCR5 antagonists, Journal Of Infection, The British Infection Society, 2008, vol. 57, pp. 1-10.

Daar Es: "Emerging resistance Profiles of Newly Approved Antiretroviral Drugs" Topics in HIV Medicine, (Oct. 11, 2008), vol. 16, No. 4, pp. 110-116.

De Clercq E: "Emerging antiviral drugs" Expert Opinion Emerging Drugs, Informa UK Ltd., (2008), vol. 13, No. 3, pp. 393-416.

Christ et al: "Rational design of small-molecule inhibitors of the LEDGF/p75-integrase interaction and HIV replication"; Nature Chemical Biology, (May 16, 2010), pp. 1-7.

Gregg S. Jones et al: "Preclinical Evaluation of GS-9160, a Novel Inhibitor of Human Immunodificiency Virus Type 1 Integrase" Antimicrobial Agents and Chemotherapy, (Mar. 2009), vol. 53, No. 3, pp. 1194-1203.

Adachi et al: "Production of acquired immunodeficiency syndrome-associated retrovirus in human and nonhuman cells transfected with an infectious molecular clone", Journal of Virology, American Society for Microbiology, (Aug. 1986), vol. 59, No. 2, pp. 284-291.

Lopez-Verges et al: "Tail-interacting protein TIP47 is a connector between Gag and Env and is required for Env incorporation into HIV-1 virions", PNAS, U S A., (Oct. 3, 2006), vol. 103, No. 40, pp. 14947-14952.

INHIBITORS OF VIRAL REPLICATION, THEIR PROCESS OF PREPARATION AND THEIR THERAPEUTICAL USES

The present invention relates to compounds, their use in the treatment or the prevention of viral disorders, including HIV. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases.

Currently HIV infected patients are treated with Highly Active Anti Retroviral Therapies (HAART) that rely on a combination of several drugs belonging to different classes. Up to 2003, all approved anti-HIV drugs were inhibitor S of the catalytic activity of two viral enzymes, Reverse Transcriptase (RT) inhibitor S and Protease (PR) inhibitor S. Reverse Transcriptase inhibitor S include two different classes, Nucleoside/Nucleotide RT Inhibitor S (NRTI) and Non Nucleoside RT Inhibitor S (NNRTI). In 2003, a new class of Anti-retroviral drug (ARV), Fusion inhibitor (Enfuvirtide) was introduced (Cervia et al., Clin Infect Dis., 2003, 37(8):1102-6). And lately, in 2007, two other classes of ARV were approved, Entry inhibitor S (Maraviroc (Pfizer)) targeting the CCR5 co-receptor, and Integrase inhibitor S (Raltegravir (Merck)) (Hughes et al., J Infect., 2008, 57(1):1-10.). Although these three novel drugs were very useful to treat patients in therapeutic failure due to multiresistance to RT and PR inhibitor S, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or agents to overcome the problems of resistance to the existing drugs and to improve treatment efficiency (Daar E S, Top HIV Med, 2008, 16(4):110-6; De Clercq E, Expert Opin Emerg Drugs. 2008, 13(3):393-416.).

Document of Christ et al. (Christ et al., Nat. Chem. Biol., 2010, 6: 442.) and documents WO 2007/131350, WO 2009/062285, WO 2009/062288, WO 2009/062289, WO 2009/062308, WO 2010/130034, WO 2010/130842 or WO 2011/015641 describe partially or totally unsaturated 6-membered heterocyclic derivatives as anti-HIV agents.

Document U.S. Pat. No. 5,910,506 describes imidazole derivatives as anti-HIV agents.

It is also known 5-membered carbo- or heterocyclic derivatives as anti-HIV agents.

Surprisingly, the inventors have identified and prepared compounds having an improved antiviral activity, especially against HIV in comparison with prior art compounds.

SUMMARY OF THE INVENTION

The present invention relates to compounds that are able to totally or partially solve the above-mentioned problems and drawbacks.

The present invention provides new antiviral agents, especially anti-retroviral agents, and more particularly anti-HIV compounds.

The compounds according the invention are inhibitor S of HIV replication as assessed by HIV-1 replication assay as herein-detailed. These compounds are thus useful agents for treating and/or preventing virus infection, in particular retroviral infection such as HIV infection, or other viral pathogenic diseases or disorders, by inhibiting replication of the virus into the host infected cells.

Therefore, the compounds according to the invention constitute a useful class of new potent antiviral compounds that can be used in the treatment and/or prevention of viral infections in animals, mammals and humans, more specifically for the treatment and/or prevention of HIV in humans.

The present invention further relates to such compounds for their use as a medicament, to the use of such compounds as medicaments, more specifically as antiviral agents, and to their use for the manufacture of medicaments for treating and/or preventing viral infections, in particular retroviral infections such as, but not limited to, HIV in humans.

The invention also relates to pharmaceutical compositions comprising such compounds in an antiviral effective amount, optionally in combination with at least one further antiviral agent.

The present invention further relates to such pharmaceutical composition for its use for the treatment of an HIV infection in a mammal being infected or having a risk to be infected by the HIV.

The present invention also relates to a method of treatment and/or prevention of viral infections, in particular retroviral infections such as, but not limited to HIV in humans by the administration of one or more such compounds, optionally in combination with one or more other antiviral agents, to a patient in need thereof.

The invention also relates to pharmaceutical composition comprising such compound as an active ingredient and at least a pharmaceutically acceptable carrier. This pharmaceutical composition further comprises at least a further antiviral agent.

The present invention further relates to such pharmaceutical composition for use for the prevention and/or the treatment of viral infection, preferably for the prevention and/or the treatment of retroviral infection, more preferably for the prevention and/or the treatment of an HIV infection.

The present invention further relates to such pharmaceutical composition for its use for the treatment of an HIV infection in a mammal being infected or having a risk to be infected by the HIV.

The present invention also relates to a method of inhibiting the replication of HIV comprising exposing the virus to an effective amount of one or more such compounds under conditions where replication of HIV is inhibited.

The invention provides compounds comprising a five membered heterocycle, said compounds having a structure according to formula (I):

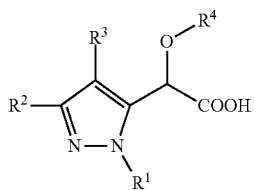

(I)

wherein
R¹ represents -CF₃; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl, —CH₂OH; or —CH₂—O—CH₃;

R², non-substituted or substituted by at least one T¹, represents a linear or branched $C_2$-$C_8$ alkyl; a linear or branched $C_2$-$C_8$ alkenyl; a linear or branched $C_2$-$C_8$ alkynyl; a linear or branched $C_1$-$C_8$ heteroalkyl; a linear or branched $C_2$-$C_8$ heteroalkenyl; a linear or branched $C_2$-$C_8$ heteroalkynyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated or aromatic 4-, 5-, 6- or 7-membered heterocycle; a $C_1$-$C_8$ alkyl-(saturated, partially or totally unsaturated or aromatic $C_3$-$C_7$ carbocycle); a $C_1$-$C_8$ alkenyl-(saturated, partially or totally unsaturated or aromatic $C_3$-$C_7$ carbocycle); a $C_1$-$C_8$ heteroalkyl-(saturated, partially or totally unsaturated or aromatic $C_3$-$C_7$ carbocycle); a $C_1$-$C_8$ alkyl-(saturated, partially or totally unsaturated or aromatic $C_4$-$C_7$ heterocycle); a $C_1$-$C_8$ heteroalkyl-(saturated, partially or totally unsaturated or aromatic $C_4$-$C_7$ heterocycle); a bicyclo[2.2.1]heptane; a bicyclo[2.2.1]heptene; a bicyclo[2.2.2]octane; or a bicyclo[2.2.2]octene;

R³, non-substituted or substituted by at least one T², represents an aryl; an aryl fused with a saturated, partially or totally unsaturated or aromatic 3-, 4-, 5-, 6- or 7-membered carbocycle; an aryl fused with a saturated, partially or totally unsaturated or aromatic 4-, 5-, 6- or 7-membered heterocycle; a heteroaryl; a heteroaryl fused with a saturated, partially or totally unsaturated or aromatic 3-, 4-, 5-, 6- or 7-membered carbocycle; a heteroaryl fused with a saturated, partially or totally unsaturated or aromatic 4-, 5-, 6- or 7-membered heterocycle; or an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 4-, 5-, 6- or 7-membered heterocycle;

R⁴, substituted or non-substituted by at least one T⁵, represents a linear or branched $C_2$-$C_6$ alkyl; a linear or branched $C_1$-$C_6$ fluoroalkyl; or a $C_3$-$C_6$ cycloalkyl;

T¹ independently represents a hydrogen atom, a halogen atom; an alkyl; —OH; —(X)ₓ—$C_1$-$C_6$ alkyl; a linear or branched fluoroalkyl; a linear or branched —O—$C_1$-$C_3$ fluoroalkyl; —(X)ₓ—$C_3$-$C_6$ cycloalkyl; —(X)ₓ—(CT⁵T⁶)ᵧ-$C_3$-$C_6$ cycloalkyl; —(X)ₓ—(CT⁵T⁶)ᵧ-aryl; —(X)ₓ—(CT⁵T⁶)ᵧCN; —(X)ₓ—(CT⁵T⁶)ᵧOT³; —(X)ₓ—(CT⁵T⁶)ᵧST³; —(X)ₓ—(CT⁵T⁶)ᵧS(O)T³; —(X)ₓ—(CT⁵T⁶)ᵧS(O)₂T³; —(X)ₓ—(CT⁵T⁶)ᵧNT³T⁴; —(X)ₓ—(CT⁵T⁶)ᵧC(O)T³; —(X)ₓ—(CT⁵T % C(O)OT³; —(X)ₓ—(CT⁵T⁶)ᵧC(O)NT³T⁴; —(X)ₓ—(CT⁵T⁶)ᵧNT³C(O)NT³T⁴; —(X)ₓ—(CT⁵T⁶)ᵧNT³C(O)T⁴; —(X)ₓ—(CT⁵T⁶)ᵧNT³C(O)OT⁴; —(X)ₓ—(CT⁵T⁶)ᵧOC(O)NT³T⁴; —(X)ₓ—(CT⁵T⁶)ᵧS(O)₂NT³T⁴ or —(X)ₓ—(CT⁵T⁶)ᵧNT³S(O)₂T⁴;

T² independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal T² form with the carbon atom to which they are bonded, a $C_3$-$C_7$ cycloalkyl;

X independently represents an oxygen atom; a sulphur atom; NT³; S=O or S(O)₂;

T³ and T⁴, identical or different, independently represent a hydrogen atom; a branched or linear $C_1$-$C_6$ alkyl; or a $C_3$-$C_6$ cycloalkyl; optionally T³, T⁴ and the nitrogen atom to which they are bonded form a $C_4$-$C_6$ heterocycloalkyl;

T⁵ and T⁶, identical or different, independently represent a hydrogen atom; a fluorine atom; a linear or branched $C_1$-$C_3$ alkyl; or a $C_3$-$C_6$ cycloalkyl; optionally T⁵, T⁶ and the carbon atom to which they are bonded form a cyclopropyl;

x independently represents 0 or 1;

y independently represents 0, 1, 2 or 3;

and a racemate, enantiomer, tautomer, atropisomer, diastereoisomer or a pharmaceutically acceptable salt thereof.

The invention provides compounds of formula (I) wherein
R¹ represents a linear or branched $C_1$-$C_6$ alkyl; a linear or branched fluoroalkyl; a $C_3$-$C_6$ cycloalkyl; or —CH₂OH;

R², non-substituted or substituted by at least one T¹, represents a linear or branched $C_2$-$C_8$ alkyl; a linear or branched $C_2$-$C_8$ alkenyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated or aromatic 4-, 5-, 6- or 7-membered heterocycle; a $C_1$-$C_8$ alkyl-(saturated, partially or totally unsaturated or aromatic $C_3$-$C_7$ carbocycle); a $C_1$-$C_8$ alkenyl-(saturated, partially or totally unsaturated or aromatic $C_3$-$C_7$ carbocycle); or a bicyclo[2.2.1]heptene;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle;

$R^4$, substituted or non-substituted by at least one $T^5$, represents a linear or branched $C_1$-$C_6$-alkyl; a linear or branched $C_1$-$C_6$ fluoroalkyl; or a $C_3$-$C_6$ cycloalkyl;

$T^1$ independently represents a hydrogen atom, a halogen atom; an alkyl; —OH; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$S(O)$_2$NT$^3$T$^4$ or —$(X)_x$—$(CT^5T^6)_y$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S=O or S(O)$_2$; $T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; a linear or branched $C_1$-$C_3$ alkyl; or a $C_3$-$C_6$ cycloalkyl; optionally $T^5$, $T^6$ and the carbon atom to which they are bonded form a cyclopropyl;

x independently represents 0 or 1;

y independently represents 0, 1, 2 or 3;

and a racemate, enantiomer, tautomer, atropisomer, diastereoisomer or a pharmaceutically acceptable salt thereof.

The invention also provides compounds comprising a five membered heterocycle, said compounds having a structure according to formula (I) wherein:

$R^1$ represents a linear or branched $C_1$-$C_6$ alkyl; a linear or branched fluoroalkyl; a $C_3$-$C_6$ cycloalkyl or CH$_2$OH;

$R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated 5-, 6- or 7-membered carbocycle; a partially or totally unsaturated or aromatic 5-, 6- or 7-membered carbocycle fused with a saturated, partially or totally unsaturated 5-, 6- or 7-membered heterocycle; a partially or totally unsaturated or aromatic 5-, 6- or 7-membered heterocycle fused with a saturated, partially or totally unsaturated 5-, 6- or 7-membered carbocycle; a partially or totally unsaturated or aromatic 5-, 6- or 7-membered heterocycle fused with a saturated, partially or totally unsaturated 5-, 6- or 7-membered heterocycle;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle or a $C_3$-$C_7$ cycloalkenyl;

$R^4$ represents a linear or branched $C_1$-$C_6$-alkyl; a linear or branched $C_1$-$C_6$ fluoroalkyl or a $C_3$-$C_6$ cycloalkyl;

$T^1$ represents a hydrogen atom, a halogen atom; an alkyl; —$(X)_x$—$C_1$-$C_6$ alkyl; a linear or branched fluorooalkyl; a linear or branched —O—$C_1$-$C_3$ fluorooalkyl; —$(X)_x$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$S(O)$_2$NT$^3$T$^4$ or —$(X)_x$—$(CT^5T^6)_y$NT$^3$S(O)$_2$T$^4$;

$T^2$ represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; cyclopropyl or —CN;

X represents an oxygen atom; a sulphur atom; NT$^3$; S=O or S(O)$_2$;

$T^3$ and $T^4$, identical or different, independently represent H; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ cycloalkyl;

$T^5$ and $T^6$, identical or different, independently represent a hydrogen atom, a fluorine atom, a linear or branched $C_1$-$C_3$ alkyl or a $C_3$-$C_6$ cycloalkyl; optionally $T^5$, $T^6$ and the carbon atom to which they are bonded form a cyclopropyl;

x represents 0 or 1;

y represents 0, 1, 2 or 3;

and a racemate, enantiomer, isomer, tautomer, atropoisomer, diastereoisomer or a pharmaceutically acceptable salt thereof.

DETAILED DESCRIPTION OF THE INVENTION

Even if described in particular or preferred embodiments, the present invention is not to be understood as being limited to such particular or preferred embodiments.

The term "alkyl" as used herein, either alone or in combination with another radical, refers to acyclic, linear or branched chain alkyl radicals.

The term "cycloalkyl", as used herein, either alone or in combination with another radical, refers to a monocyclic or polycyclic saturated hydrocarbon radical.

The term "aryl", as used herein, either alone or in combination with another radical, refers to a carbocyclic aromatic monocyclic group containing 6 carbon atoms which can be fused with at least another saturated, unsaturated or aromatic carbocycle.

The term "carbocycle", as used herein and unless specified otherwise, either alone or in combination with another radical, refers in particular to a 3- to 8 membered saturated, unsaturated or aromatic cyclic radical in which all of the ring members are carbon atoms and which can be fused with at least another carbocycle.

The term "heterocycle" as used herein means a saturated, unsaturated or aromatic ring system, in particular of 3 to 18 atoms including at least one N, O or S and which can be fused with at least another carbocycle or heterocycle.

The terms "alkyl—(saturated, partially or totally unsaturated or aromatic carbocycle)" or "alkyl—(saturated, partially or totally unsaturated or aromatic heterocycle)" as used herein, alone or in combination with another radical, refer to an alkyl radical in which one of the hydrogen atoms bonded to a carbon atom of the alkyl moiety, is replaced respectively by a saturated, partially or totally unsaturated or aromatic carbocycle radical or a saturated, partially or totally unsaturated or aromatic heterocycle radical.

The term "alkyl—(saturated, partially or totally unsaturated or aromatic carbocycle)" as used herein, means an alkyl—(saturated carbocycle), an alkyl—(partially unsaturated carbocycle), an alkyl—(totally unsaturated carbocycle) or an alkyl—(aromatic carbocycle).

The term "alkyl—(saturated, partially or totally unsaturated or aromatic heterocycle)" as used herein, means an alkyl—(saturated heterocycle), an alkyl—(partially unsaturated heterocycle), an alkyl—(totally unsaturated heterocycle) or an alkyl—(aromatic heterocycle).

The terms "heteroalkyl—(saturated, partially or totally unsaturated or aromatic carbocycle)" or "heteroalkyl—(saturated, partially or totally unsaturated or aromatic heterocycle)" as used herein, alone or in combination with another radical, refer to a heteroalkyl radical in which one of the hydrogen atoms bonded to a carbon atom or a heteroatom of the heteroalkyl moiety, is replaced respectively by a saturated, partially or totally unsaturated or aromatic carbocycle radical or a saturated, partially or totally unsaturated or aromatic heterocycle radical.

The term "heteroalkyl—(saturated, partially or totally unsaturated or aromatic carbocycle)" as used herein, means a heteroalkyl—(saturated carbocycle), a heteroalkyl—(partially unsaturated carbocycle), a heteroalkyl—(totally unsaturated carbocycle) or a heteroalkyl—(aromatic carbocycle).

The term "heteroalkyl—(saturated, partially or totally unsaturated or aromatic heterocycle)" as used herein, means a heteroalkyl—(saturated heterocycle), a heteroalkyl—(partially unsaturated heterocycle), a heteroalkyl—(totally unsaturated heterocycle) or a heteroalkyl—(aromatic heterocycle).

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods.

The term "enantiomer" is employed herein to refer to one of the two specific stereoisomers which is a non-superimposable mirror image with one other but is related to one other by reflection.

The term "diastereoisomer" is employed herein to refer to one of the stereoisomers which is a non-superimposable mirror image with one other but is not related to one other by reflection.

The term "racemate" is employed herein to refer to an equal amount of two specific enantiomers.

The term "atropisomer" is employed herein to refer to stereoisomer obtained by a sterically hindered single bond whereby the free rotation of functional groups on either side of this bond is not allowed.

The term "tautomer" is employed herein to refer to constitutional isomer obtained by a formal migration of a hydrogen atom or a proton accompanied by a switch of a single bond and adjacent double bond.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factor S as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient Such a therapeutically effective amount can be determined routinely by one of ordinary skill in the art having regard to their own knowledge, the state of the art, and this disclosure.

The term "mammal" as used herein is intended to encompass humans, as well as non-human mammals which are susceptible to infection by HIV or non human equivalents of HIV. Non-human mammals include but are not limited to domestic animals, such as cows, pigs, dogs, cats, rabbits, rats and mice, and non domestic animals.

The compounds according to the invention are compounds of formula (I) as previously defined and including the embodiments described in the summary of the invention.

Particularly, according to a feature (a), the compounds according to the invention are compounds of formula (I) wherein $R^4$ represents tBu.

More particularly, according to a feature (b), the compounds according to the invention are compounds of formula (I) wherein $R^2$ represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered heterocycle fused with a saturated, partially or totally unsaturated 5-, 6- or 7-membered carbocycle or a partially or totally unsaturated or aromatic 5-, 6- or 7-membered heterocycle fused with a saturated, partially or totally unsaturated 5-, 6- or 7-membered heterocycle;

$T^1$ represents a hydrogen atom; a halogen atom; —$CH_3$; —$CH_2F$; —$CHF_2$; —$CF_3$; —OMe; —$OCH_2F$; —$OCHF_2$; —$OCF_3$, —$(X)_x$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or $(X)_x$—$(CT^5T^6)_y$NT$^3$S(O)$_2$T$^4$;

X represents an oxygen atom; a sulphur atom; NT$^3$; S=O or S(O)$_2$;

$T^3$ and $T^4$, identical or different, independently represent H; a branched or linear $C_1$-$C_6$ alkyl or a $C_3$-$C_6$ cycloalkyl; optionally
$T^3$, $T^4$ and the nitrogen atom to which they are bonded form a $C_4$-$C_6$ heterocycloalkyl;

$T^5$ and $T^6$, identical or different, independently represent a hydrogen atom, a fluorine atom or methyl;

x represents 0 or 1;

y independently represents 0, 1, 2 or 3.

Particularly, according to a feature (c), the compounds according to the invention are compounds of formula (I) wherein $R^2$, non-substituted or substituted by at least one $T^1$, represents a linear or branched $C_2$-$C_8$ alkyl; a linear or branched $C_2$-$C_8$ alkenyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated 4-, 5-, 6- or 7-membered heterocycle; a bicyclo[2.2.1]heptene; or a $C_1$-$C_8$ alkyl-(saturated, partially or totally unsaturated or aromatic $C_3$-$C_7$ carbocycle); or a $C_1$-$C_8$ alkenyl-(saturated, partially or totally unsaturated or aromatic $C_3$-$C_7$ carbocycle);

$T^1$ independently represents a hydrogen atom; a halogen atom; —$CH_3$; —$CH_2F$; —$CHF_2$; —$CF_3$; —$OCH_3$; —$OCH_2F$; —$OCHF_2$; —$OCF_3$; —OH; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or $(X)_x$—$(CT^5T^6)_y$NT$^3$S(O)$_2$T$^4$;

X independently represents an oxygen atom; a sulphur atom; NT$^3$; S=O or S(O)$_2$;

$T^3$ and $T^4$, identical or different, independently represent H; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; or methyl;

x independently represents 0 or 1;

y independently represents 0, 1, 2 or 3.

Preferably, according to a feature (d), the invention provides compounds of formula (I) wherein $R^1$ represents:
a linear or branched $C_1$-$C_3$ alkyl;
a linear or branched fluoroalkyl;
a $C_3$-$C_6$ cycloalkyl; or
—$CH_2OH$.

Preferably, according to a feature (e), the invention provides compounds of formula (I) wherein $R^1$ represents:
a linear or branched $C_1$-$C_3$ alkyl;
a linear or branched $C_1$-$C_3$ fluoroalkyl;
a $C_3$-$C_6$ cycloalkyl; or
—$CH_2OH$.

Advantageously, according to a feature (f), the invention provides compounds of formula (I) wherein $R^1$ represents:
—$CH_3$;
—$CH_2CH_3$;
—$CH_2F$;
—$CHF_2$;
—$CH_2CH_2F$;
—$CH_2CHF_2$;
—$CH_2CF_3$; or
—$CH_2OH$.

More advantageously, according to a feature (g), the invention provides compounds of formula (I) wherein $R^1$ represents $CH_3$ or —$CH_2CF_3$.

Preferably, according to a feature (h), the invention provides compounds of formula (I), wherein $R^2$, non-substituted or substituted by at least one $T^1$, represents a linear or branched $C_2$-$C_8$ alkyl; a linear or branched $C_2$-$C_8$ alkenyl; a saturated, partially or totally unsaturated or aromatic 3-, 4-, 5-, 6- or 7-membered carbocycle; a saturated, partially or totally unsaturated or aromatic 5- or 6-membered heterocycle; a saturated, partially or totally unsaturated or aromatic 5- or 6-membered heterocycle fused with a saturated, partially or totally unsaturated or aromatic 5-, 6-membered carbocycle; a $C_1$-$C_8$ alkyl-(saturated, partially or totally unsaturated or aromatic $C_3$-$C_7$ carbocycle); a $C_2$-$C_8$ alkenyl-(saturated, partially or totally unsaturated or aromatic $C_3$-$C_7$ carbocycle); or a bicyclo[2.2.1]heptene.

Advantageously, according to a feature (i), the invention provides compounds of formula (I), wherein $R^2$, non-substituted or substituted by at least one $T^1$, represents a propyl; an isopropyl; an isoprenyl; a propylenyl; a cyclopropyl, a cyclopentyl; a cyclohexyl; a methylcyclopentyl; an ethylcyclopropyl; an ethylenylcyclopropyl; a phenyl, a cyclohexenyl, a cycloheptenyl; a bicyclo[2.2.1]heptene; a pyridinyl, a cyclopentenyl, a thiophenyl, a thiazolyl; a cyclopenta[b]thiophenyl; or a thianaphthenyl.

Preferably, according to a feature (j), the invention provides compounds of formula (I), wherein $R^3$, non-substituted or substituted by at least one $T^2$, represents an aryl; an aryl fused with a saturated, partially or totally unsaturated or aromatic 4-, 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; or a $C_5$-$C_7$ cycloalkenyl.

Advantageously, according to a feature (k), the invention provides compounds of formula (I), wherein $R^3$, non-substituted or substituted by at least one $T^2$, represents a cyclohexenyl or a dihydrobenzopyranyl.

Preferably, according to a feature (I), the invention provides compounds of formula (I), wherein $T^1$ independently represents a hydrogen atom; a halogen atom; an alkyl; a linear or branched fluoroalkyl; —OH; —(X)$_x$—$C_1$-$C_6$ alkyl; —(X)$_x$—$C_1$-$C_6$ cycloalkyl; —(X)$_x$—(CT$^5$T$^6$)$_y$-($C_1$-$C_6$cycloalkyl); or (X)$_x$—(CT$^5$T$^6$)$_y$-aryl;

$T^2$ independently represents a hydrogen atom; a halogen atom; a linear or branched —O—$C_1$-$C_3$ alkyl; a linear or branched $C_1$-$C_3$ fluoroalkyl; or a linear or branched $C_1$-$C_3$ alkyl; optionally two geminal $T^2$ form with the carbon atom to which they are bonded, a cyclopropyl; and/or;

X represents an oxygen atom;

$T^3$ and $T^4$, identical or different, independently represent a hydrogen atom; or a branched or linear $C_1$-$C_6$ alkyl;

$T^5$ and $T^6$, identical or different, independently represent a hydrogen atom; a fluorine atom; or a linear or branched $C_1$-$C_3$ alkyl;

x independently represents 0 or 1;

y independently represents 0, 1, 2 or 3.

Advantageously, according to a feature (m), the invention provides compounds of formula (I), wherein $T^1$ independently represents a hydrogen atom, a chlorine atom, a methyl, a propyl, a cyclopropryl; a cyclopentyl; —OH; or (X)$_x$—(CT$^5$T$^6$)$_y$-($C_3$-$C_5$cycloalkyl);

$T^2$ independently represents a hydrogen atom; a fluorine atom; a chlorine atom; a methyl; or an isopropyl;

X represents an oxygen atom;

$T^5$ and $T^6$ represent a hydrogen atom;

x independently represents 0 or 1;

y independently represents 0, 1, 2 or 3.

Preferably, the invention provides compounds of formula (I) comprising the two features: (a) and (b); (a) and (c); (a) and (d); (a) and (e); (a) and (f); (a) and (g); (a) and (h); (a) and (i); (a) and (j); (a) and (k); (a) and (l); (a) and (m); (b) and (d); (b) and (e); (b) and (f); (b) and (g); (b) and (j); (b) and (k); (c) and (d); (c) and (e); (c) and (f); (c) and (g); (c) and (j); (c) and (k); (d) and (h); (d) and (i); (d) and (j); (d) and (k); (d) and (l); (d) and (m); (e) and (h); (e) and (i); (e) and (j); (e) and (k); (e) and (l); (e) and (m); (f) and (h); (f) and (i); (f) and (j); (f) and (k); (f) and (l); (f) and (m); (g) and (h); (g) and (i); (g) and (j); (g) and (k); (g) and (l); (g) and (m); (h) and (j); (h) and (k); (h) and (l); (h) and (m); (i) and (j); (i) and (k); (i) and (l); (i) and (m); (j) and (l); (j) and (m); (k) and (l); or (k) and (m).

Preferably, the invention provides compounds of formula (I) comprising the three features: (a), (b) and (d); (a), (b) and (e); (a), (b) and (f); (a), (b) and (g); (a), (b) and (j); (a), (b) and (k); (a), (c) and (d); (a), (c) and (e); (a), (c) and (f); (a), (c) and (g); (a), (c) and (j); (a), (c) and (k); (a), (d) and (h); (a), (d) and (i); (a), (d) and (j); (a), (d) and (k); (a), (d) and (l); (a), (d) and (m); (a), (e) and (h); (a), (e) and (i); (a), (e) and (j); (a), (e) and (k); (a), (e) and (l); (a), (e) and (m); (a), (f) and (h); (a), (f) and (i); (a), (f) and a); (a), (f) and (k); (a), (f) and (l); (a), (f) and (m); (a), (g) and (h); (a), (g) and (i); (a), (g) and (j); (a), (g) and (k); (a), (g) and (l); (a), (g) and (m); (a), (h) and (j); (a), (h) and (k); (a), (h) and (l); (a), (h) and (m); (a), (i) and (j); (a), (i) and (k); (a), (i) and (l); (a), (i) and (m); (a), (j) and (l); (a), (j) and (m); (a), (k) and (l); or (a), (k) and (m).

Preferably, the invention provides compounds of formula (I) comprising the four features: (a), (b), (d) and (j); (a), (b), (d) and (k); (a), (c), (d) and (j); (a), (c), (d) and (k); (a), (d), (h) and a); (a), (d), (h) and (k); (a), (d), (h) and (l); (a), (d), (h) and (m); (a), (e), (h) and a); (a), (e), (h) and (k); (a), (e), (h) and (l); (a), (e), (h) and (m); (a), (f), (h) and a); (a), (f), (h) and (k); (a), (f), (h) and (l); (a), (f), (h) and (m); (a), (g), (h) and a); (a), (g), (h) and (k); (a), (g), (h) and (l); (a), (g), (h) and (m); (a), (h), (j) and (l); or (a), (h), (j) and (m).

Preferably, the invention provides compounds of formula (I) comprising the five features: (a), (d), (h), (j) and (l); (a), (d), (h), (j) and (m); (a), (e), (h), (j) and (l); (a), (f), (h), (j) and (l); (a), (g), (h), (j) and (l); (a), (e), (h), (j) and (m); (a), (f), (h), (j) and (m); (a), (g), (h), (j) and (m); (a), (d), (i), (j) and (l); (a), (d), (i), (j) and (m); (a), (e), (i), (j) and (l); (a), (f), (i), (j) and (l); (a), (g), (i), (j) and (l); (a), (e), (i), (j) and (m); (a), (f), (i), (j) and (m); (a), (g), (i), (j) and (m); (a), (d), (h), (k) and (l); (a), (d), (h), (k) and (m); (a), (e), (h), (k) and (l); (a), (f), (h), (k) and (l); (a), (g), (h), (k) and (l); (a), (e), (h), (k) and (m); (a), (f), (h), (k) and (m); (a), (g), (h), (k) and (m); (a), (d), (i), (k) and (l); (a), (d), (i), (k) and (m); (a), (e), (i), (k) and (l); (a), (f), (i), (k) and (l); (a), (g), (i), (k) and (l); (a), (e), (i), (k) and (m); (a), (f), (i), (k) and (m); or (a), (g), (i), (k) and (m).

Advantageously, the invention provides a compound of formula (A), (B), (C) or (D):

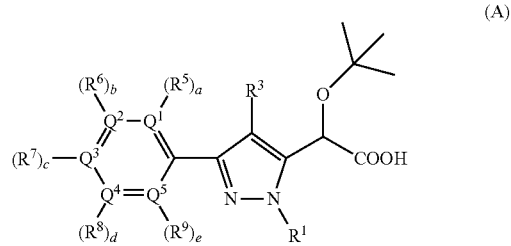

(A)

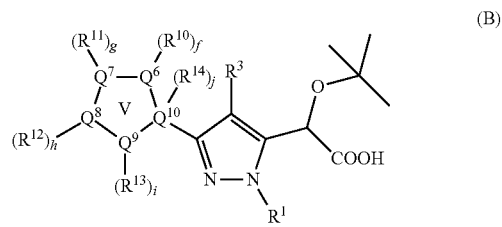

(B)

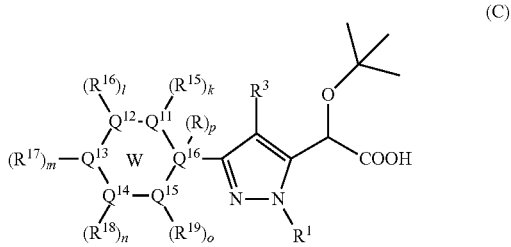

(C)

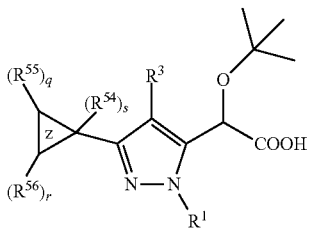

(D)

wherein
f, g, h, i, k, l, m, no, q or r independently represent 0, 1 or 2;
a, b, c, d, e, j, p or s independently represent 0 or 1;
V represents a substituted or non substituted, saturated, partially or totally unsaturated carbocycle or aromatic carbocyle; or a substituted or non substituted, saturated, partially or totally unsaturated or aromatic heterocycle;
W represents a substituted or non-substituted, saturated or partially unsaturated carbocycle; or a substituted or non substituted, saturated, partially unsaturated heterocycle;
Z represents a substituted or non-substituted, cyclopropyl;
$Q^1$ represents $CR^5$ or N;
$Q^2$ represents $CR^6$ or N;
$Q^3$ represents $CR^7$ or N;
$Q^4$ represents $CR^8$ or N;
$Q^5$ represents $CR^9$ or N;
$Q^6$ represents $CR^{10}$, C=O, N, $NR^{16}$, O, S, S=O or $S(O)_2$;
$Q^7$ represents $CR^{11}$, C=O, N, $NR^{11}$, O, S, S=O or $S(O)_2$;
$Q^8$ represents $CR^{12}$, C=O, N, $NR^{12}$, O, S, S=O or $S(O)_2$;
$Q^9$ represents $CR^{13}$, C=O, N, $NR^{13}$, O, S, S=O or $S(O)_2$;
$Q^{10}$ represents C, $CR^{14}$, or N;
$Q^{11}$ represents C, $CR^{15}$, C=O, N, $NR^{15}$, O, S, S=O or $S(O)_2$;
$Q^{12}$ represents C, $CR^{16}$, C=O, N, $NR^{16}$, O, S, S=O or $S(O)_2$;
$Q^{13}$ represents C, $CR^{17}$, C=O, N, $NR^{17}$, O, S, S=O or $S(O)_2$;
$Q^{14}$ represents C, $CR^{18}$, C=O, N, $NR^{18}$, O, S, S=O or $S(O)_2$;
$Q^{15}$ represents C, $CR^{19}$, C=O, N, $NR^{19}$, O, S, S=O or $S(O)_2$;
$Q^{16}$ represents C, CR, N;
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, R, $R^{54}$, $R^{55}$ or $R^{56}$ identical or different, independently represent a hydrogen atom; a halogen atom; —OH; —$CH_3$; —$CH_2CH_3$; —CH—$(CH_3)_2$; —$(CH_2)_2$ $CH_3$—$CH_2F$; —$CHF_2$; —$CF_3$; —$OCH_3$; —$OCH_2F$; —$OCHF_2$; —$OCF_3$; —$(X)_x$—$C_1$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$$OT^3$; —$(X)_x$—$(CT^5T^6)_y$$ST^3$; —$(X)_x$—$(CT^5T^6)_y$$S(O)T^3$; —$(X)_x$—$(CT^5T^6)_y$$S(O)_2T^3$; —$(X)_x$—$(CT^5T^6)_y$$NT^3T^4$; —$(X)_x$—$(CT^5T^6)_y$$C(O)T^3$; —$(X)_x$—$(CT^5T^6)_y$$C(O)OT^3$; —$(X)_x$—$(CT^5T^6)_y$$C(O)NT^3T^4$; —$(X)_x$—$(CT^5T^6)_y$$NT^3C(O)NT^3T^4$; —$(X)_x$—$(CT^5T^6)_y$$NT^3C(O)T^4$; —$(X)_x$—$(CT^5T^6)_y$$NT^3C(O)OT^4$; —$(X)_x$—$(CT^5T^6)_y$$OC(O)NT^3T^4$; —$(X)_x$—$(CT^5T^6)_y$ $S(O)_2$$NT^3T^4$ or —$(X)_x$—$(CT^5T^6)_y$$NT^3S(O)_2T^4$;
$T^2$ independently represents a hydrogen atom; a halogen atom; methyl; —$CH_2F$; —$CHF_2$; —$CF_3$; —OMe; —$OCH_2F$; —$OCHF_2$; —$OCF_3$; or —CN; optionally two geminal $T^2$ form with the carbon atom to which they are bonded, a $C_3$-$C_7$ cycloalkyl;
$R^1$, $R^3$, X, x, y and $T^3$ to $T^6$ are independently defined as for the compounds of formula (I).

Advantageously, the invention provides a compound of formula (A), (B), (C) or (D) wherein:

$R^5$, $Q^1$, $Q^2$ and $R^6$ form a saturated, partially or totally unsaturated or aromatic 5-, 6-membered carbo- or heterocycle;

$R^6$, $Q^2$, $Q^3$ and $R^7$ form a saturated, partially or totally unsaturated or aromatic 5-, 6-membered carbo- or heterocycle;

$R^7$, $Q^3$, $Q^4$ and $R^8$ form a saturated, partially or totally unsaturated or aromatic 5-, 6-membered carbo- or heterocycle;

$R^8$, $Q^4$, $Q^5$ and $R^9$ form a saturated, partially or totally unsaturated or aromatic 5-, 6-membered carbo- or heterocycle;

$R^{10}$, $Q^6$, $Q^7$ and $R^{11}$ form a saturated, partially or totally unsaturated or aromatic 5-, 6-membered carbo- or heterocycle;

$R^{11}$, $Q^7$, $Q^8$ and $R^{12}$ form a saturated, partially or totally unsaturated or aromatic 5-, 6-membered carbo- or heterocycle;

$R^{12}$, $Q^8$, $Q^9$ and $R^{13}$ form a saturated, partially or totally unsaturated or aromatic 5-, 6-membered carbo- or heterocycle.

More advantageously, in compounds of formula (A), (B), (C) or (D), $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, R, $R^{55}$ or $R^{56}$, identical or different, independently represent a hydrogen atom; a halogen atom; a linear or branched $C_1$-$C_6$ alkyl; a linear or branched —O—$C_1$-$C_6$ alkyl; a linear or branched —O—$C_1$-$C_{10}$ alkylaryl; —OH; —$C(O)NH_2$ or —$CH_2NHC(O)Me$.

Preferably, the invention provides compounds of formulae (A1) to (A10), (B1) to (B7), (C1) to (C10) or (D1):

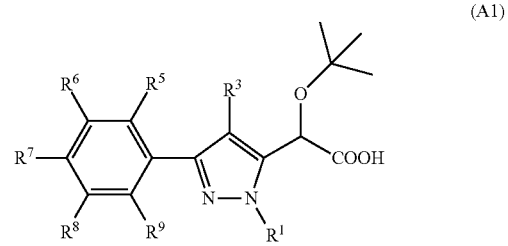

(A1)

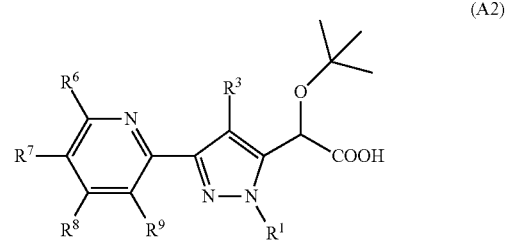

(A2)

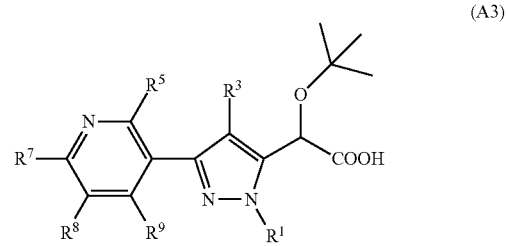

(A3)

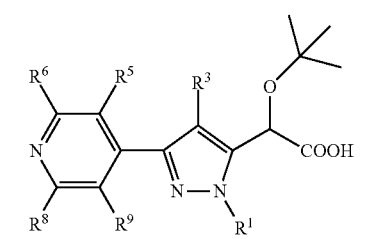
(A4)
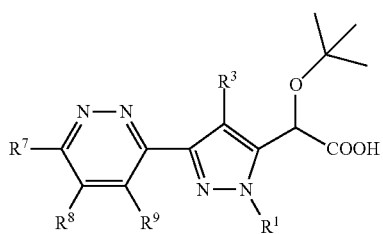
(A5)
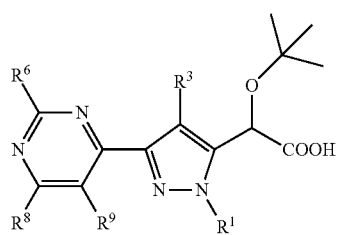
(A6)
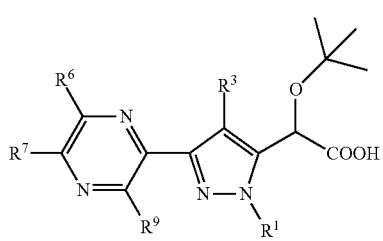
(A7)
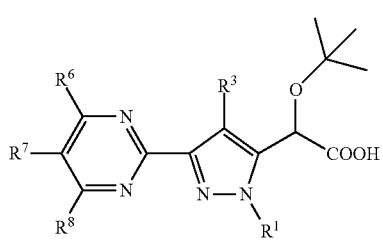
(A8)
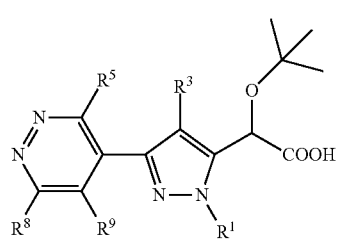
(A9)
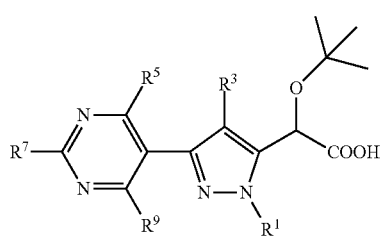
(A10)
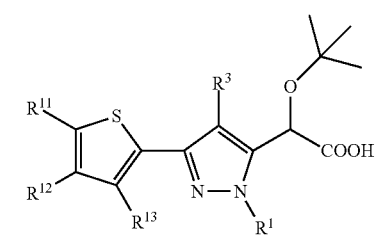
(B1)
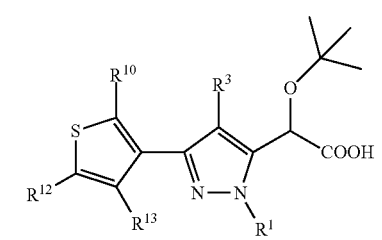
(B2)
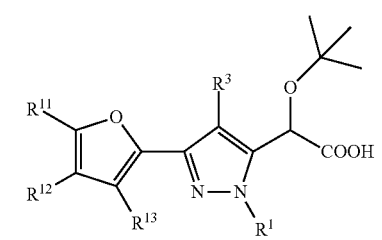
(B3)
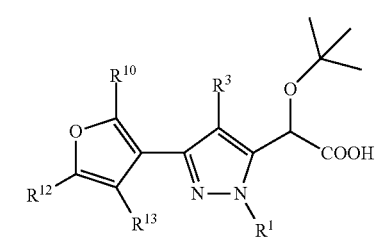
(B4)
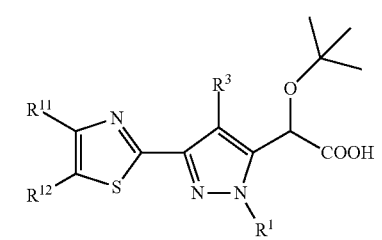
(B5)

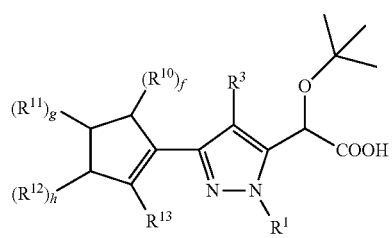
(B6)
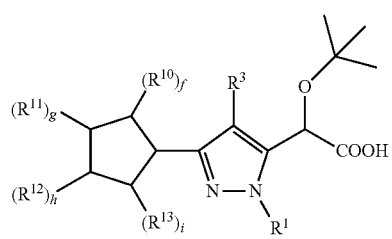
(B7)
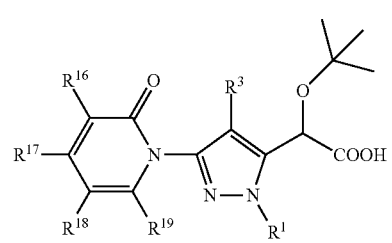
(C1)
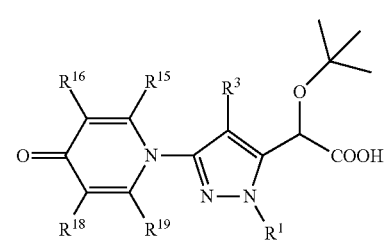
(C2)
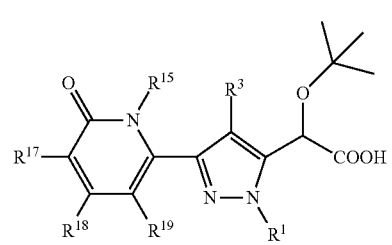
(C3)
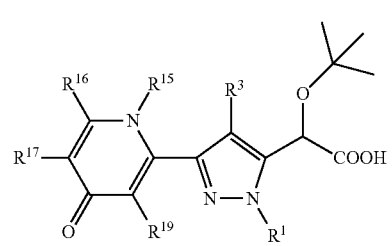
(C4)
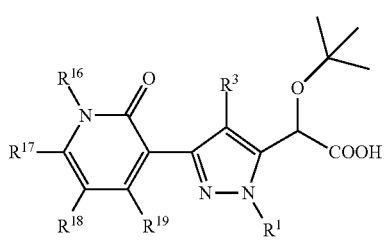
(C5)
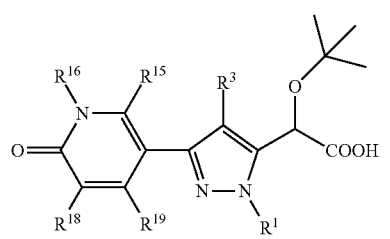
(C6)
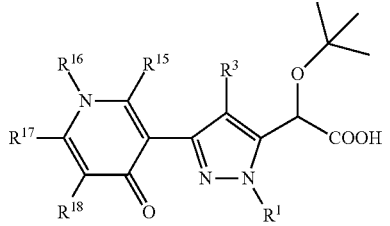
(C7)
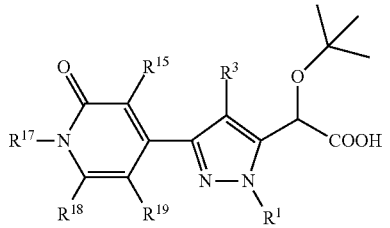
(C8)
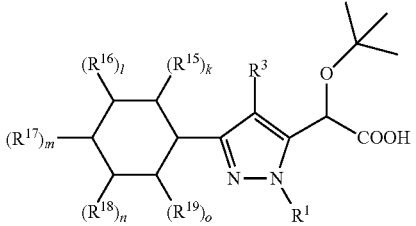
(C9)
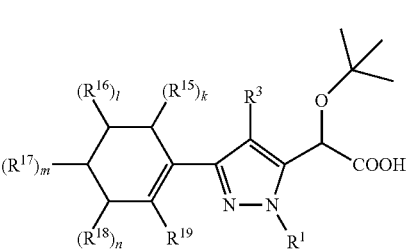
(C10)

-continued

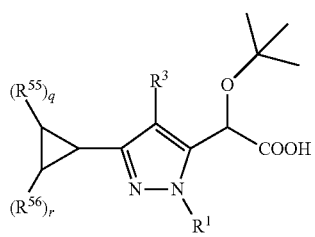

(D1)

wherein:
R$^5$, R$^6$, R$^7$, R$^8$, R$^9$, R$^{10}$, R$^{11}$, R$^{12}$, R$^{13}$, R$^{15}$, R$^{16}$, R$^{17}$, R$^{18}$, R$^{19}$, R$^{55}$ or R$^{56}$, identical or different, independently represent a hydrogen atom; a halogen atom; —CH$_3$; —CH$_2$—CH$_3$; —CH—(CH$_3$)$_2$; —(CH$_2$)$_2$CH$_3$; —CH$_2$F; —CHF$_2$; —CF$_3$; —OMe; —OH; —OCH$_2$F; —OCHF$_2$; —OCF$_3$; —(X)$_x$—C$_1$-C$_6$ cycloalkyl; —(X)$_x$—(CT$^5$T$^6$)$_y$-aryl; —(X)$_x$—(CT$^5$T$^6$)$_y$CN; —(X)$_x$—(CT$^5$T$^6$)$_y$OT$^3$; —(X)$_x$—(CT$^5$T$^6$)$_y$ST$^3$; —(X)$_x$—(CT$^5$T$^6$)$_y$S(O)T$^3$; —(X)$_x$—(CT$^5$T$^6$)$_y$S(O)$_2$T$^3$; —(X)$_x$—(CT$^5$T$^6$)$_y$NT$^3$T$^4$; —(X)$_x$—(CT$^5$T$^6$)$_y$C(O)T$^3$; —(X)$_x$—(CT$^5$T$^6$)$_y$C(O)OT$^3$; —(X)$_x$—(CT$^5$T$^6$)$_y$C(O)NT$^3$T$^4$; —(X)$_x$—(CT$^5$T$^6$)$_y$NT$^3$C(O)NT$^3$T$^4$; —(X)$_x$—(CT$^5$T$^6$)$_y$NT$^3$C(O)T$^4$; —(X)$_x$—(CT$^5$T$^6$)$_y$NT$^3$C(O)OT$^4$; —(X)$_x$—(CT$^5$T$^6$)$_y$OC(O)NT$^3$T$^4$; —(X)$_x$—(CT$^5$T$^6$)$_y$S(O)$_2$NT$^3$T$^4$ or (X)$_x$—(CT$^5$T$^6$)$_y$NT$^3$S(O)$_2$T$^4$;

T$^2$ independently represents a hydrogen atom; a halogen atom; —CH$_3$; —CH$_2$F; —CHF$_2$; —CF$_3$; —OCH$_3$; —OCH$_2$F; —OCHF$_2$; —OCF$_3$; or —CN; optionally two geminal T$^2$ form with the carbon atom to which they are bonded, a C$_3$-C$_7$ cycloalkyl;

R$^1$, R$^3$, X, f, g, h, i, k, l, m, n, o, x, y and T$^3$ to T$^6$ are independently defined as for the compounds of formula (I).

Advantageously, the invention provides a compound of formula (A1) to (A10), (B1) to (B4) or (C1) to (C10) or (D1), wherein:
R$^5$, R$^6$ and the carbon atoms to which they are bonded form a saturated, partially or totally unsaturated or aromatic 6-membered carbo- or heterocycle;
R$^6$, R$^7$ and the carbon atoms to which they are bonded form a saturated, partially or totally unsaturated or aromatic 6-membered carbo- or heterocycle;
R$^7$, R$^8$ and the carbon atoms to which they are bonded form a saturated, partially or totally unsaturated or aromatic 6-membered carbo- or heterocycle;
R$^8$, R$^9$ and the carbon atoms to which they are bonded form a saturated, partially or totally unsaturated or aromatic 6-membered carbo- or heterocycle;
R$^{11}$, R$^{12}$ and the carbon atoms to which they are bonded form a saturated, partially or totally unsaturated or aromatic 5-, 6-membered carbo- or heterocycle;
R$^{12}$, R$^{13}$ and the carbon atoms to which they are bonded form a saturated, partially or totally unsaturated or aromatic 5-, 6-membered carbo- or heterocycle.

More advantageously, in compounds of formulae (A1) to (A10), (B1) to (B4) or (C1) to (C10) or (D1), R$^5$, R$^6$, R$^7$, R$^8$, R$^9$, R$^{19}$, R$^{11}$, R$^{12}$, R$^{13}$, R$^{15}$, R$^{16}$, R$^{17}$, R$^{18}$, R$^{19}$, R$^{55}$ or R$^{56}$, identical or different, independently represent a hydrogen atom; a halogen atom; a linear or branched C$_1$-C$_6$ alkyl; a linear or branched —O—C$_1$-C$_6$ alkyl; a linear or branched —O—C$_1$-C$_{10}$ alkylaryl; —OH; —C(O)NH$_2$ or —CH$_2$NHC(O)Me.

Advantageously, the invention provides compounds of formulae (A1a) to (A10a), (A1b) to (A10b), (A1c) to (A10c), (A1d) to (A10d), (B1a) to (B4a), (B1b) to (B4b), (B1c) to (B7c), (B1d) to (B4d), (C1a) to (C8a), (C1b) to (C8b), (C1c) to (C10c) or (C1d) to (C8d), (D1a), (D1b), (D1c), or (D1d):

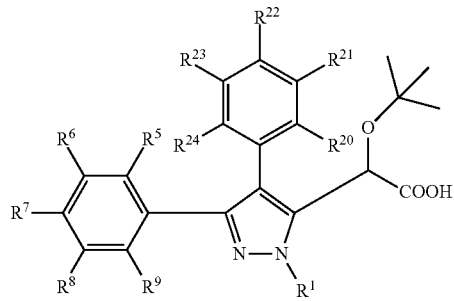

(A1a)

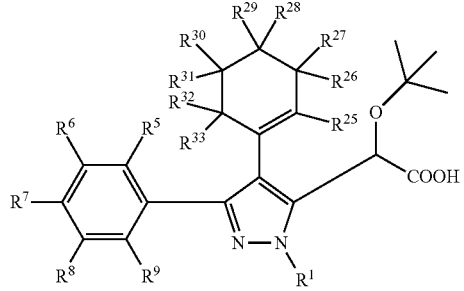

(A1b)

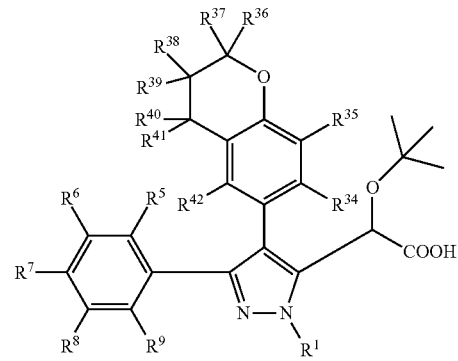

(A1c)

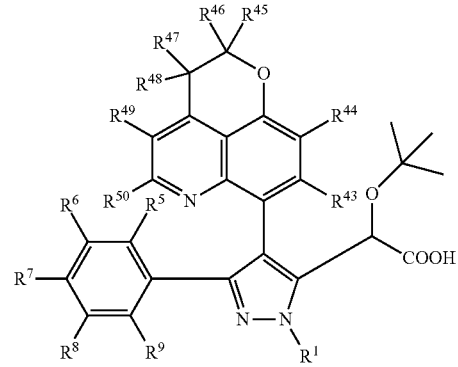

(A1d)

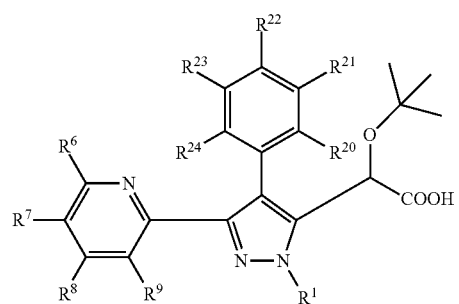 (A2a)
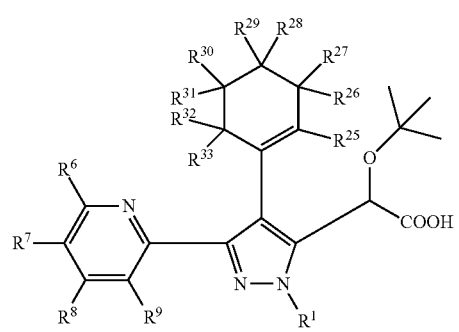 (A2b)
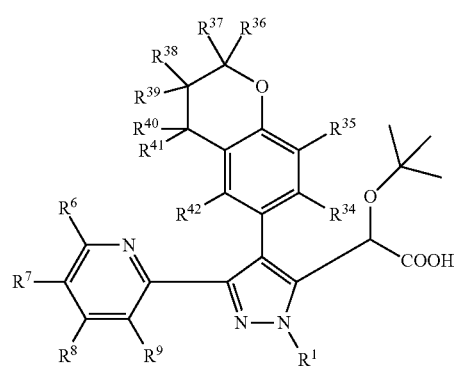 (A2c)
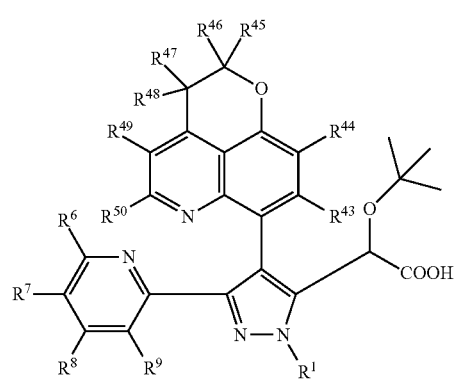 (A2d)
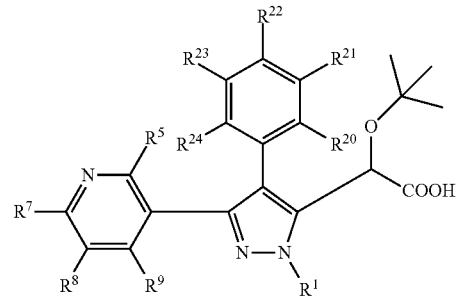 (A3a)
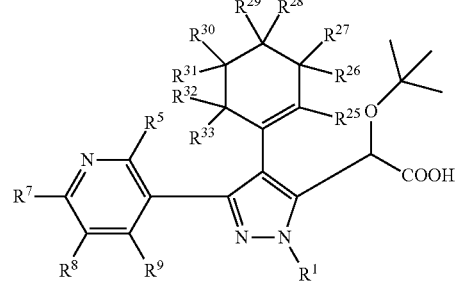 (A3b)
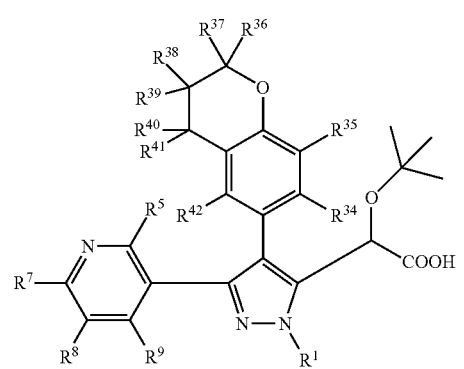 (A3c)
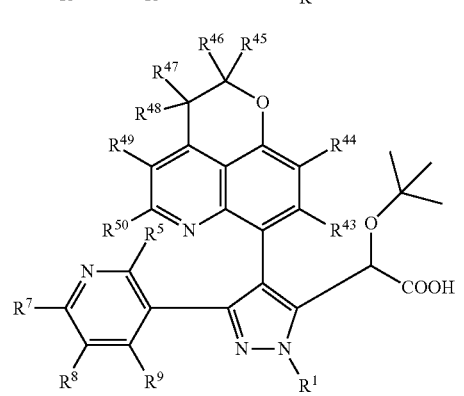 (A3d)
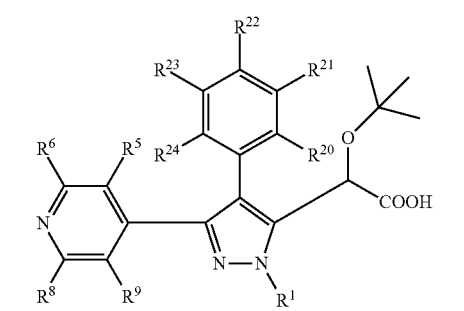 (A4a)

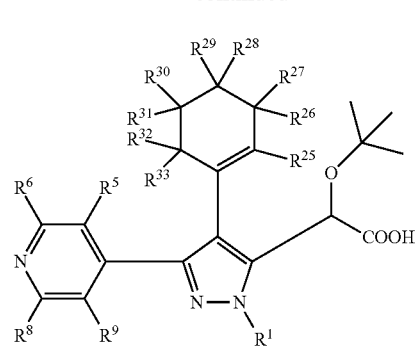
(A4b)
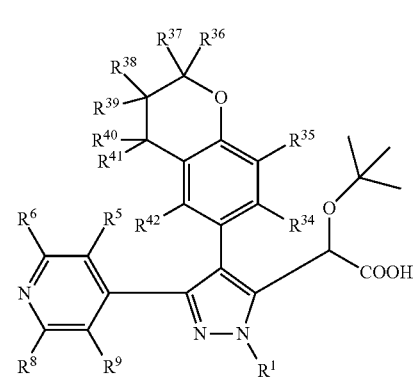
(A4c)
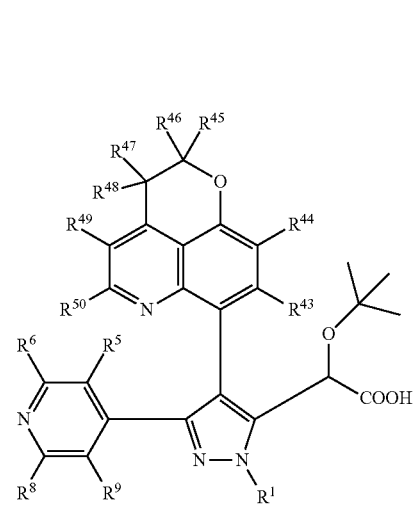
(A4d)
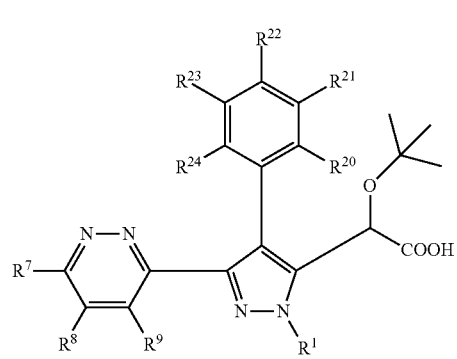
(A5a)
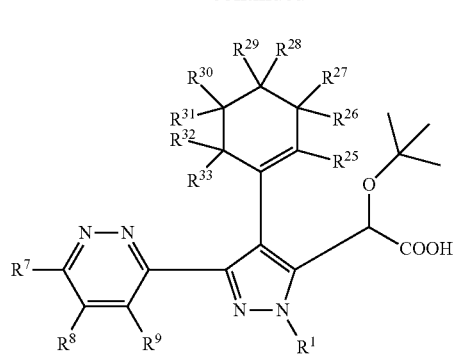
(A5b)
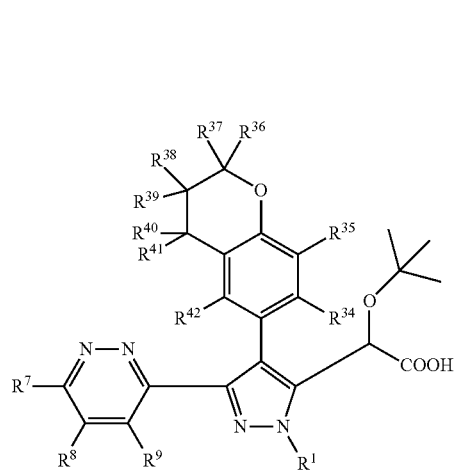
(A5c)
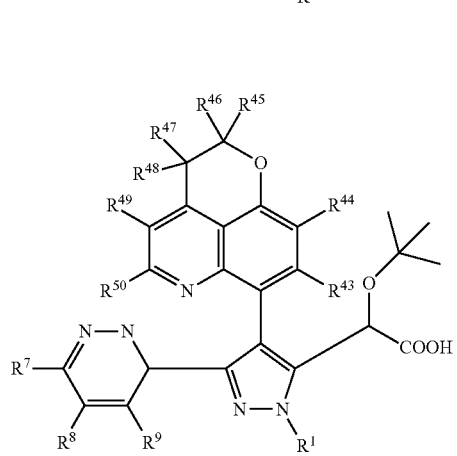
(A5d)
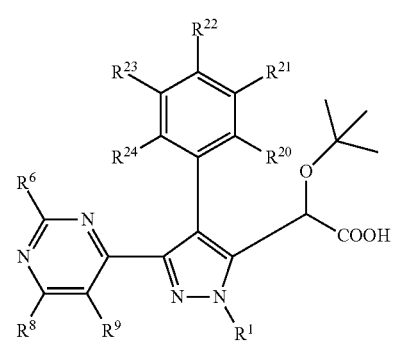
(A6a)

-continued
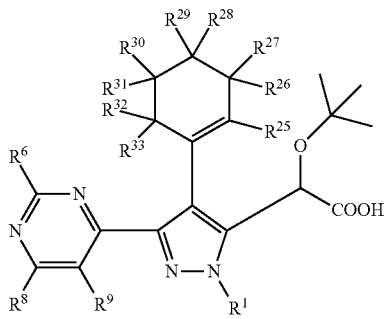
(A6b)
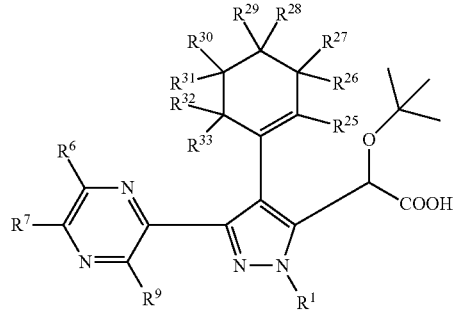
(A7b)
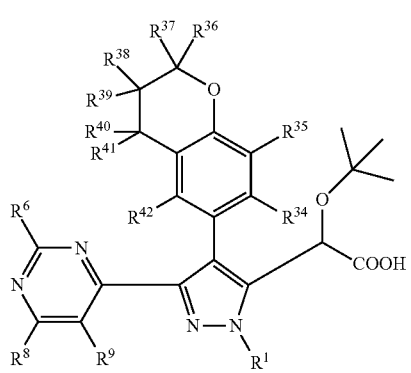
(A6c)
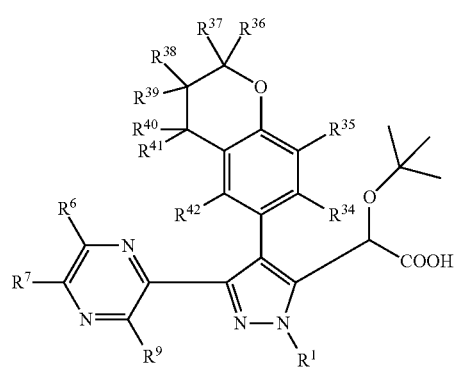
(A7c)
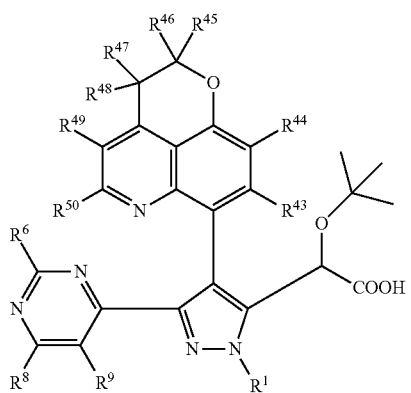
(A6d)
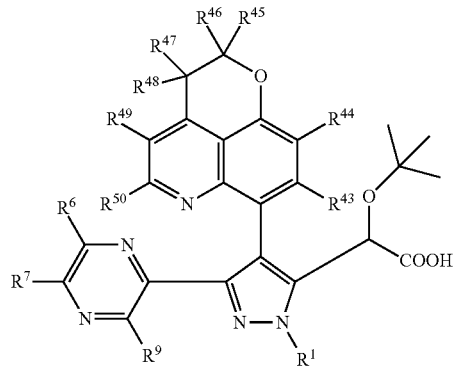
(A7d)
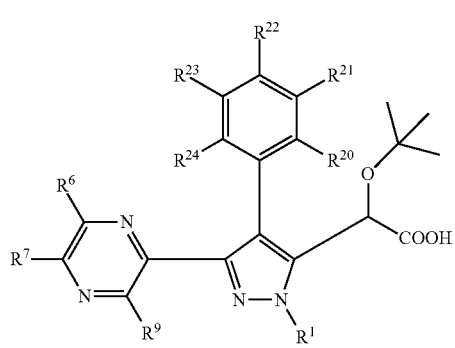
(A7a)
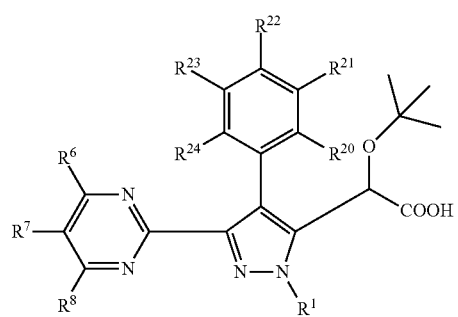
(A8a)

-continued
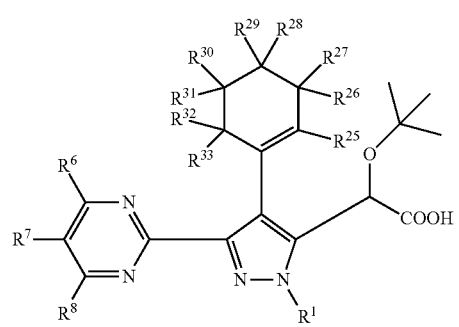
(A8b)
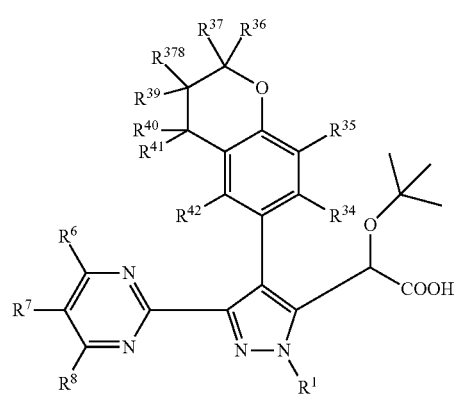
(A8c)
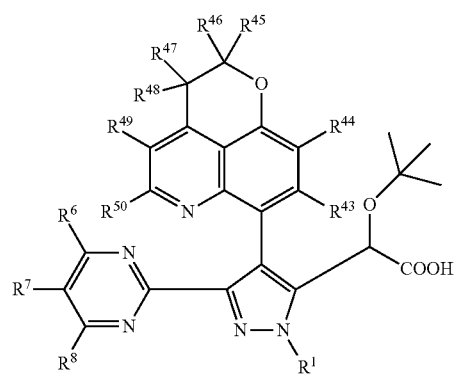
(A8d)
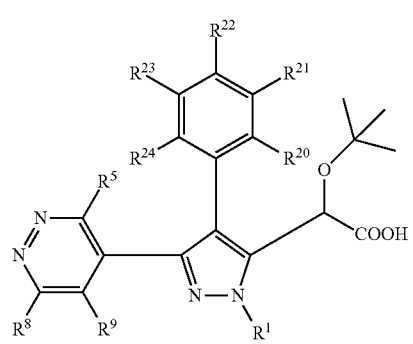
(A9a)
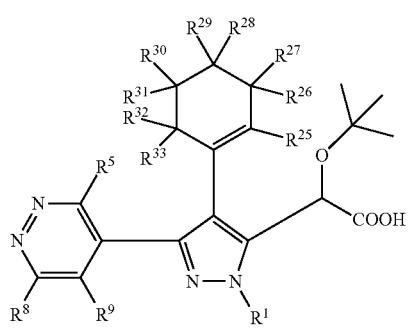
(A9b)
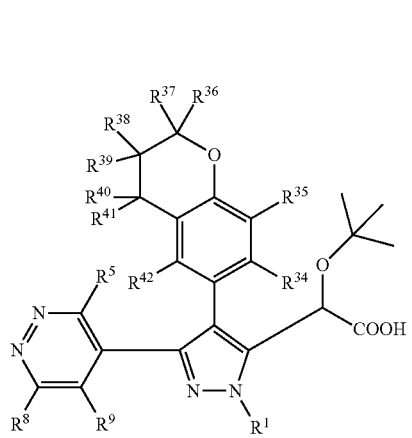
(A9c)
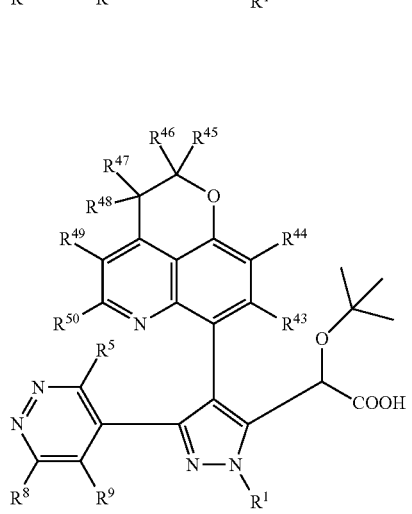
(A9d)
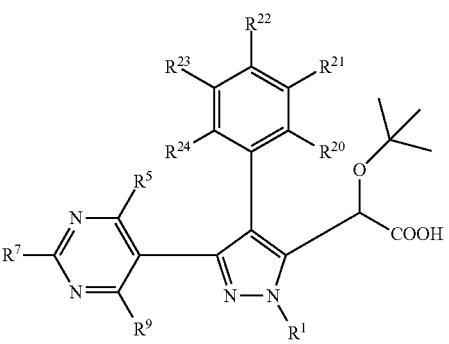
(A10a)

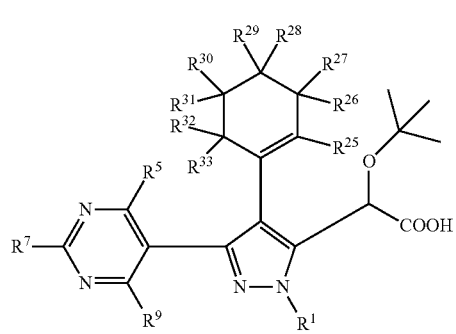
(A10b)
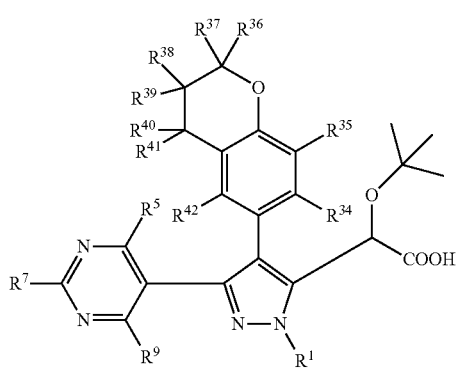
(A10c)
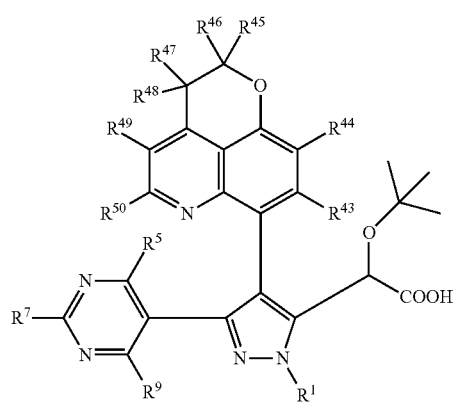
(A10d)
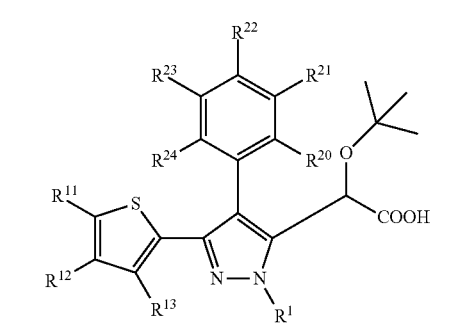
(B1a)
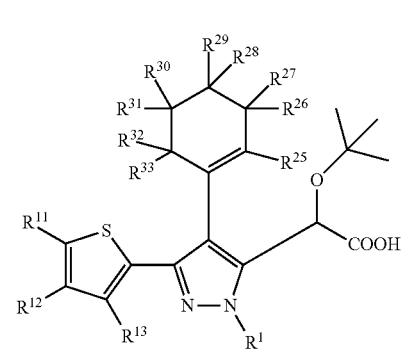
(B1b)
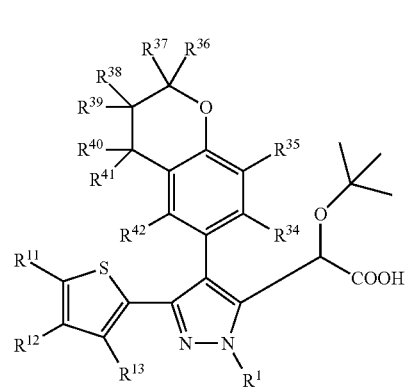
(B1c)
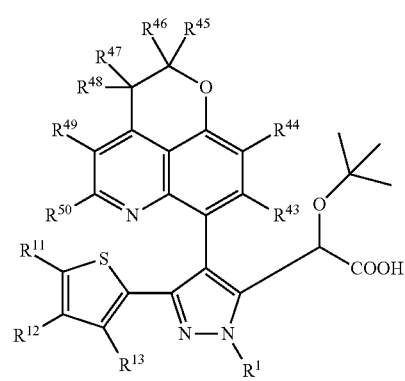
(B1d)
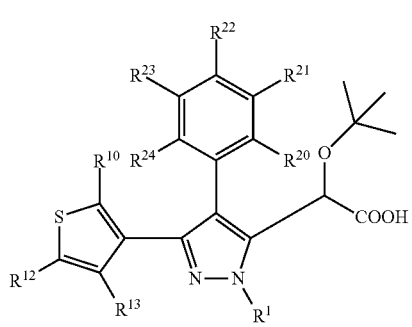
(B2a)

(B2b) 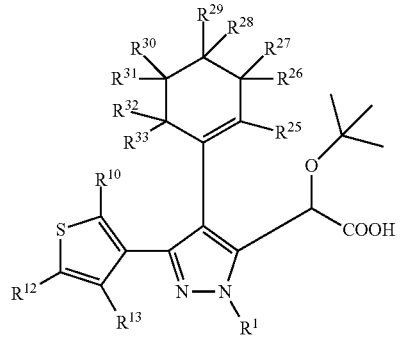
(B2c) 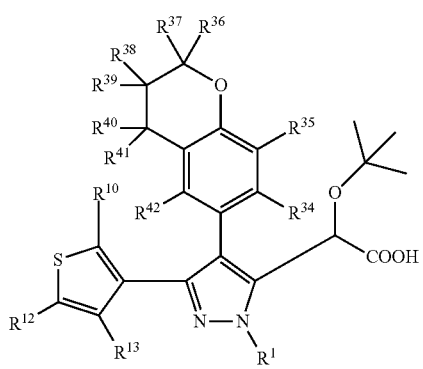
(B2d) 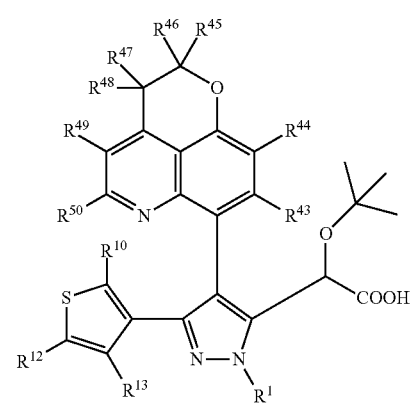
(B3a) 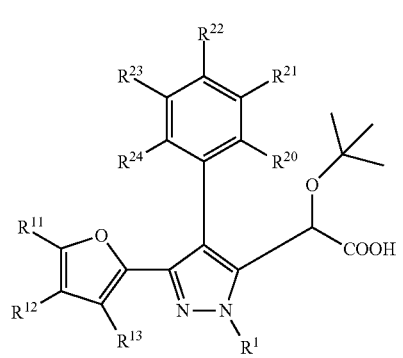
(B3b) 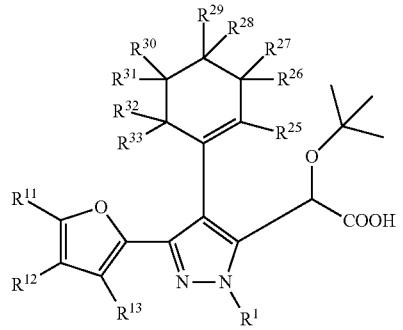
(B3c) 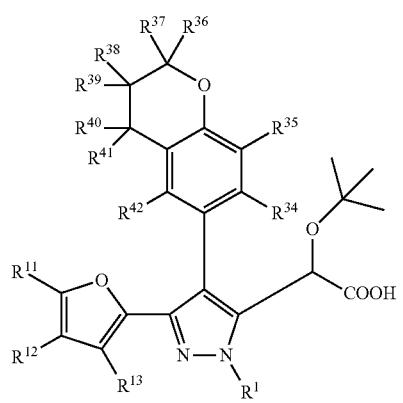
(B3d) 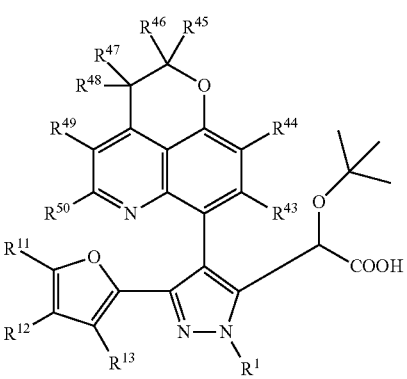
(B4a) 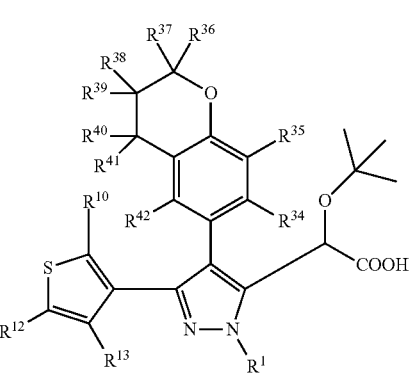

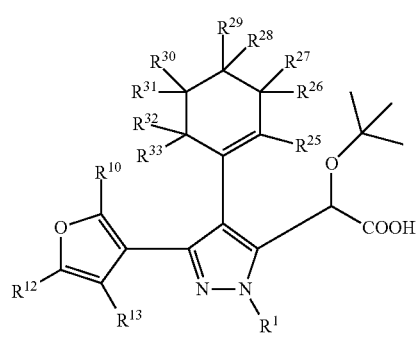
(B4b)
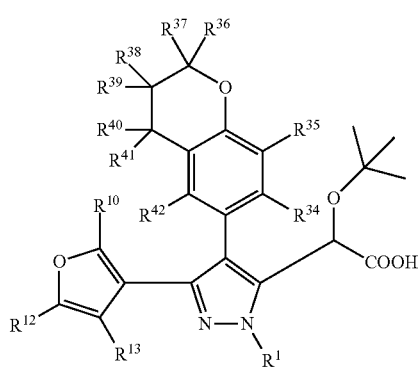
(B4c)
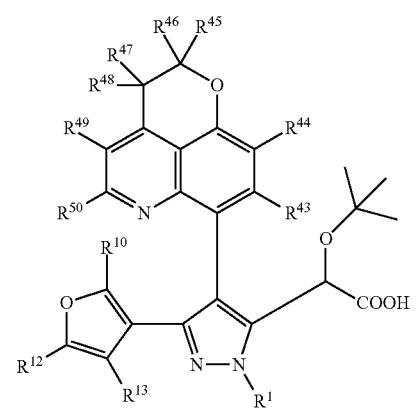
(B4d)
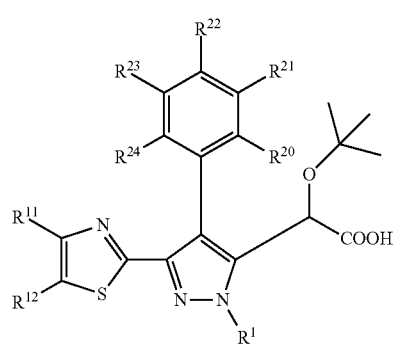
(B5a)
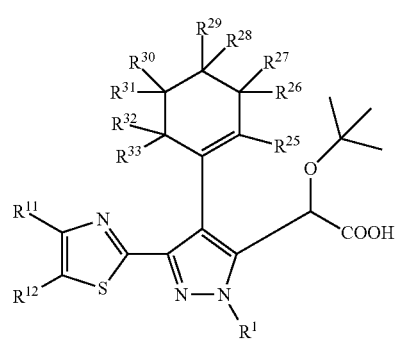
(B5b)
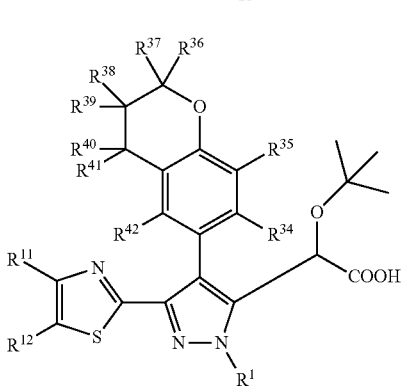
(B5c)
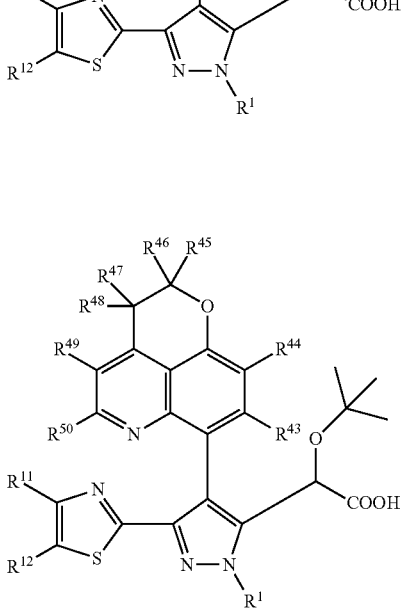
(B5d)
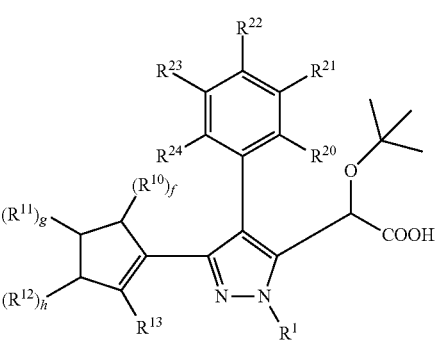
(B6a)

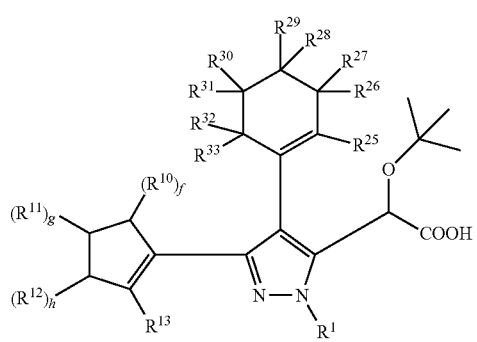 (B6b)
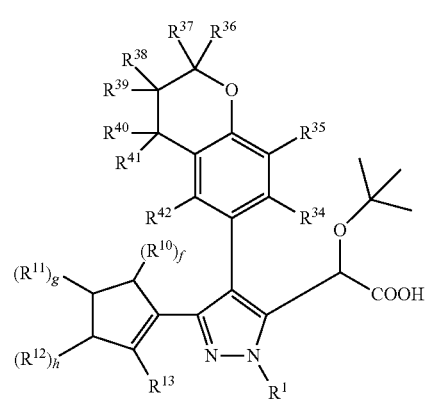 (B6c)
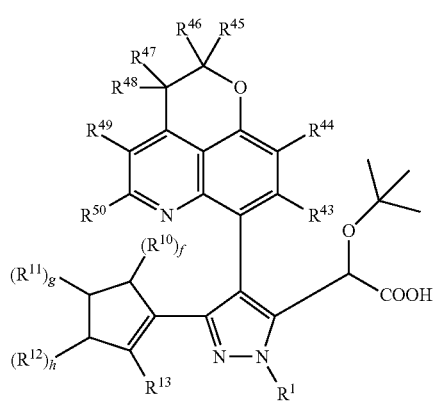 (B6d)
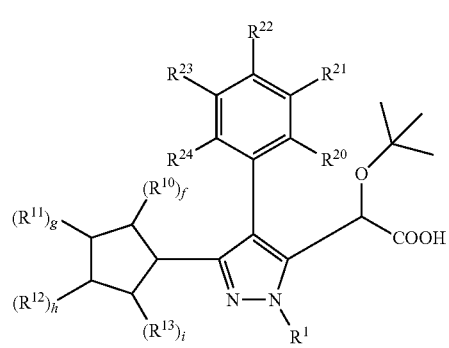 (B7a)
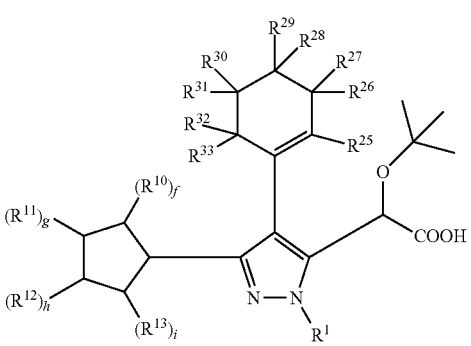 (B7b)
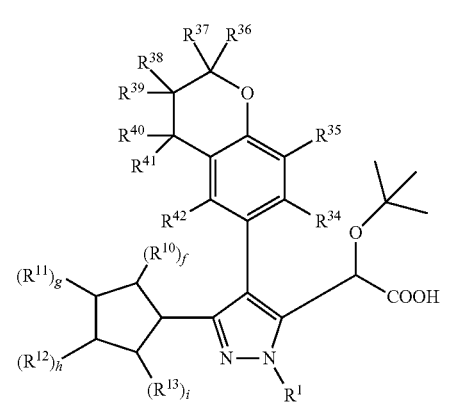 (B7c)
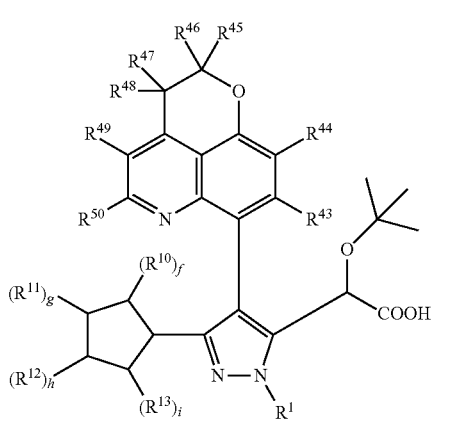 (B7d)
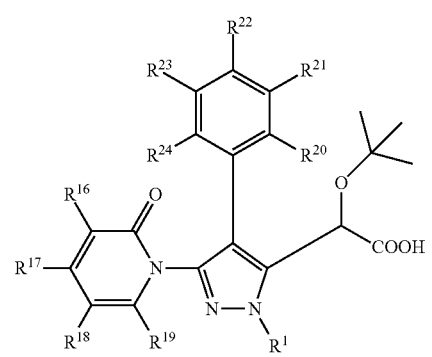 (C1a)

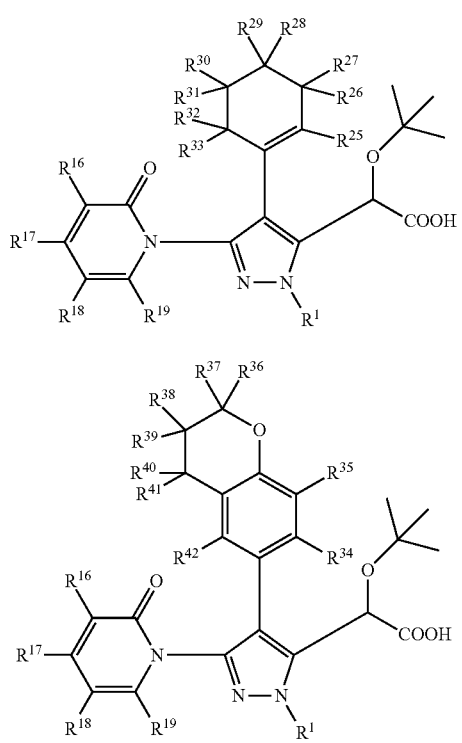
(C1b)
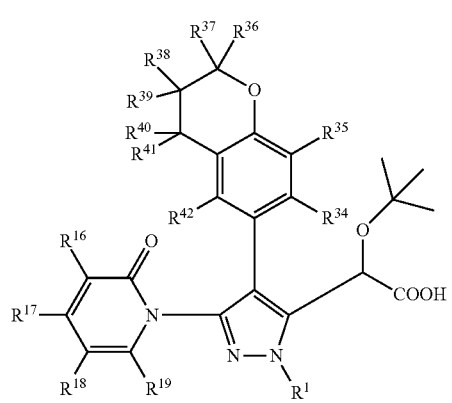
(C1c)
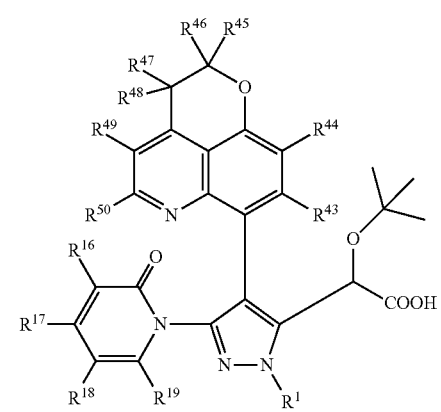
(C1d)
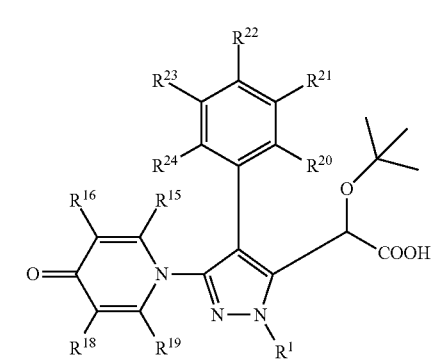
(C2a)
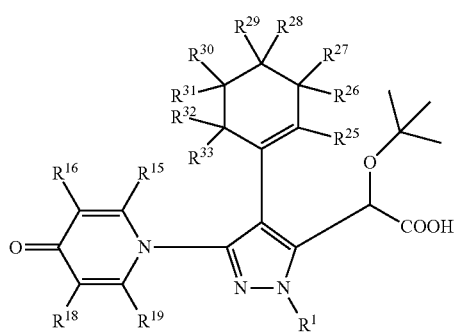
(C2b)
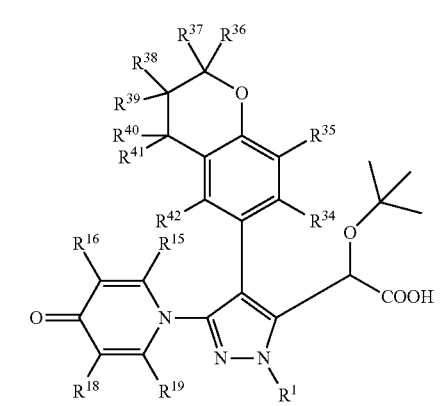
(C2c)
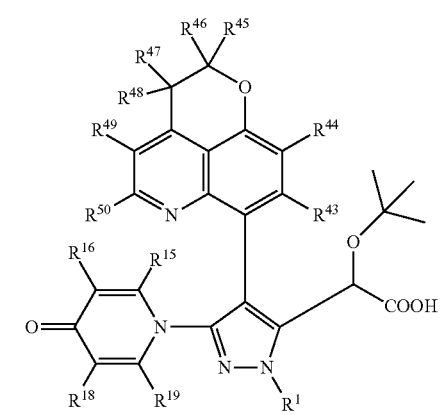
(C2d)
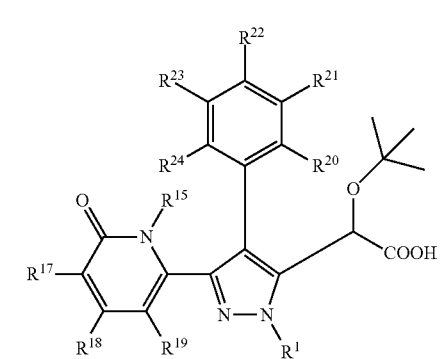
(C3a)

(C3b) 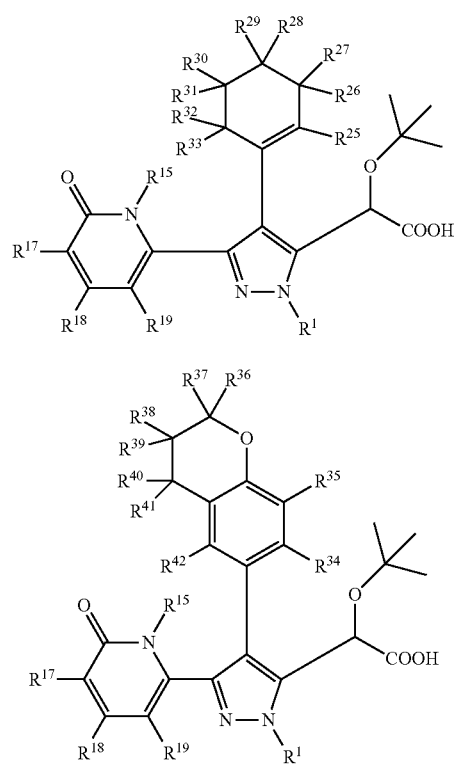
(C3c) 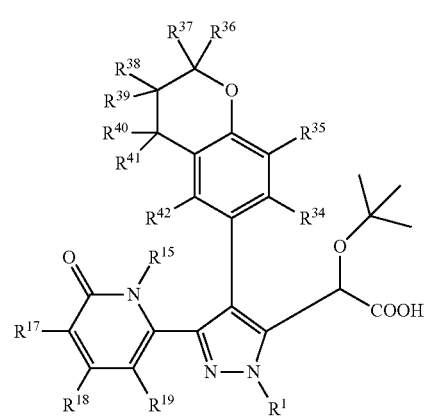
(C3d) 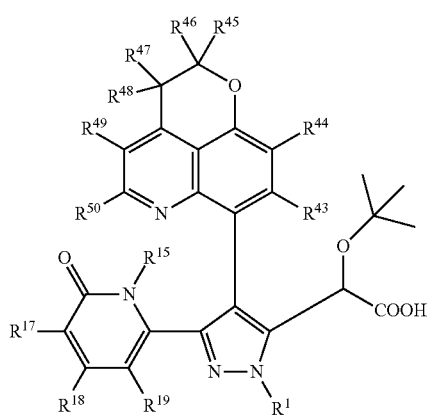
(C4a) 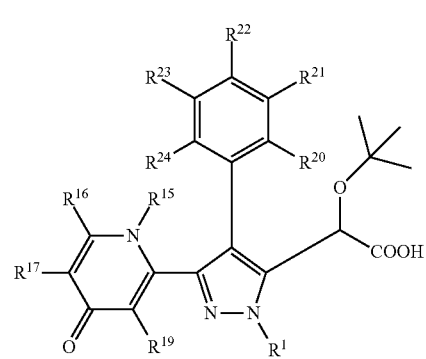
(C4b) 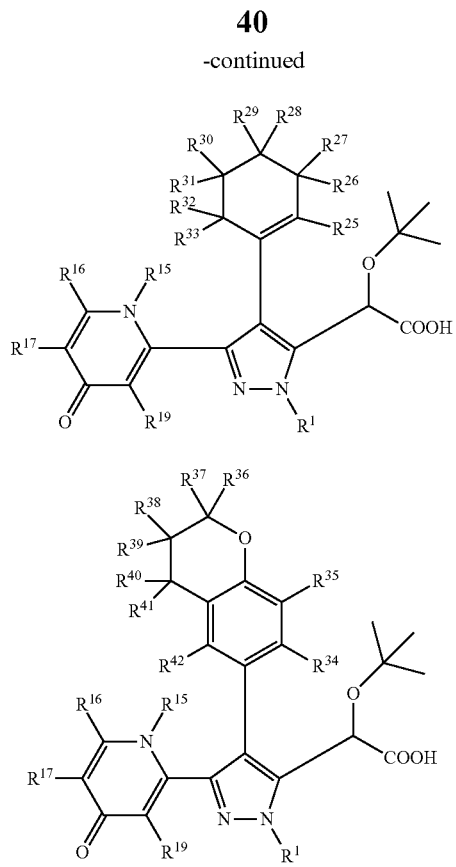
(C4c) 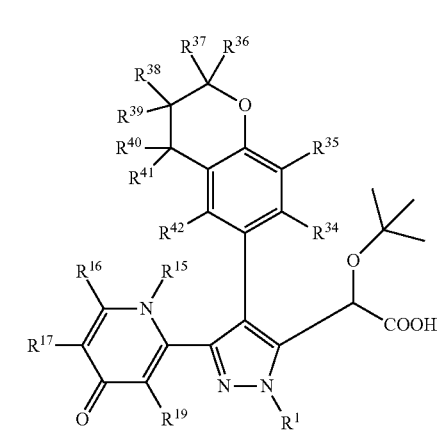
(C4d) 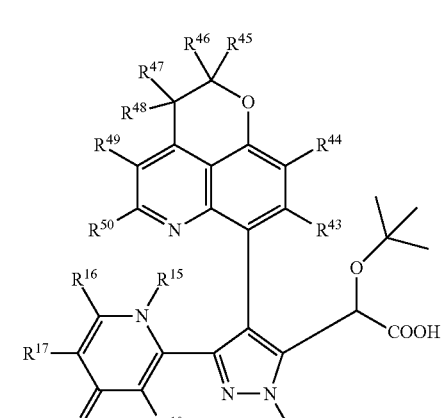
(C5a) 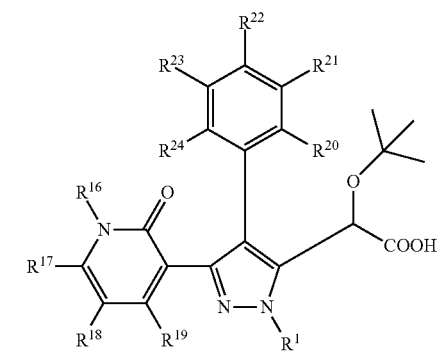

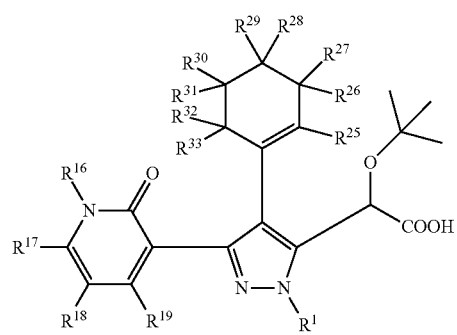
(C5b)
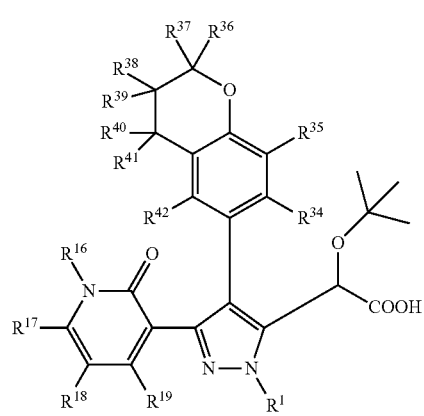
(C5c)
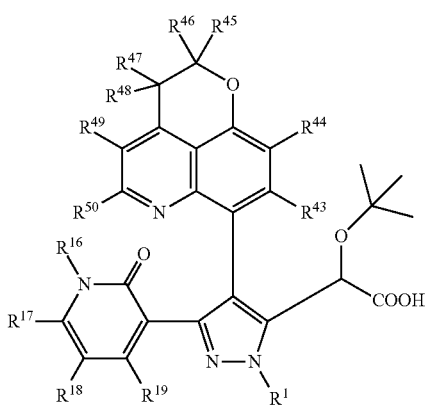
(C5d)
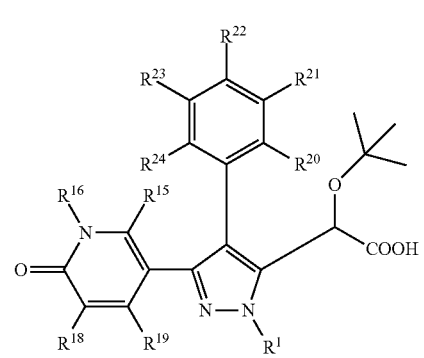
(C6a)
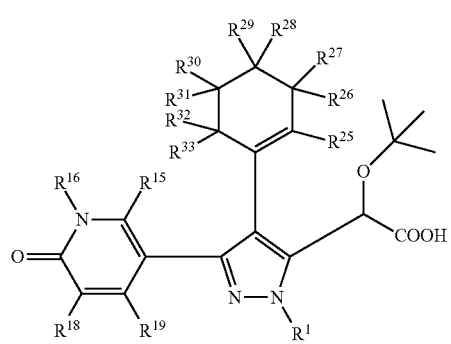
(C6b)
(C6c)
(C6d)
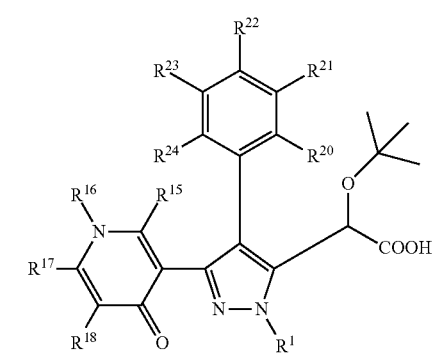
(C7a)

(C7b), (C7c), (C7d), (C8a), (C8b), (C8c), (C8d), (C9a)

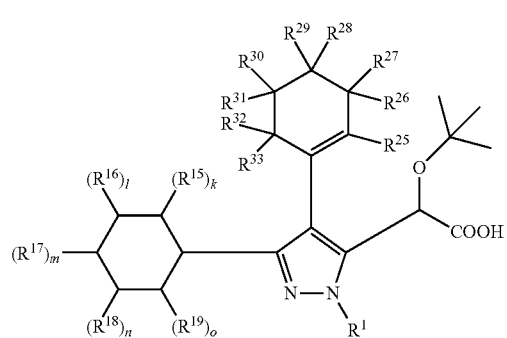
(C9b)
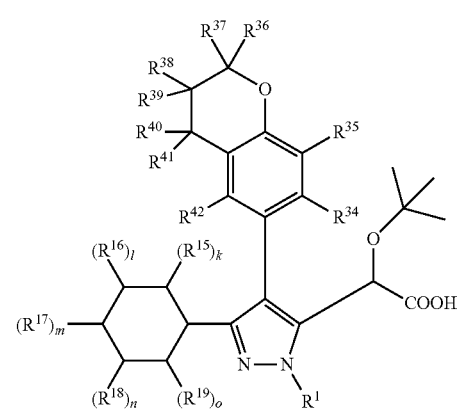
(C9c)
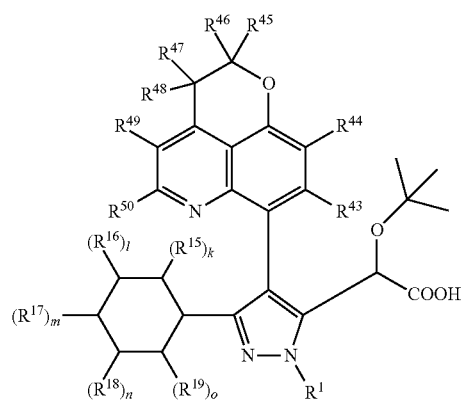
(C9d)
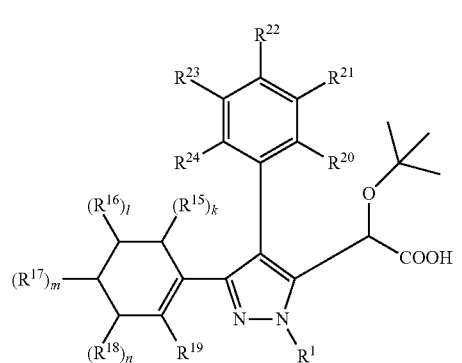
(C10a)
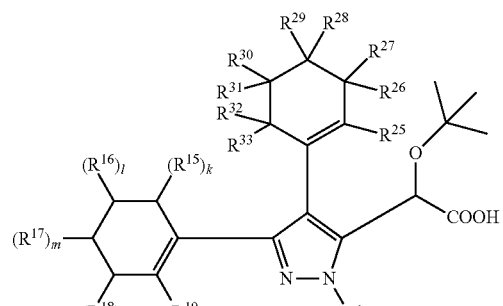
(C10b)
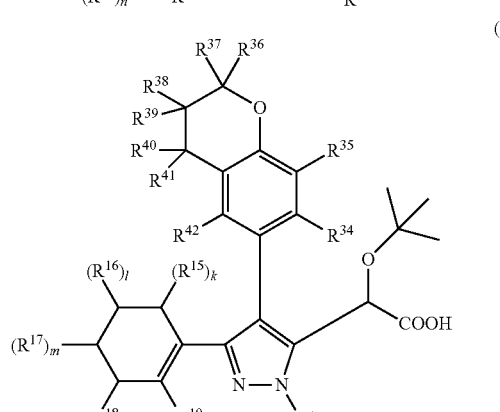
(C10c)
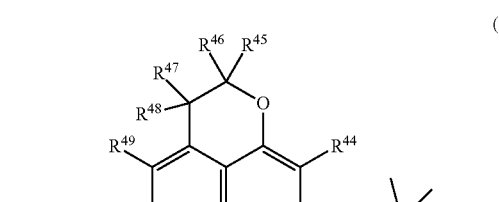
(C10d)
(D1a)

-continued

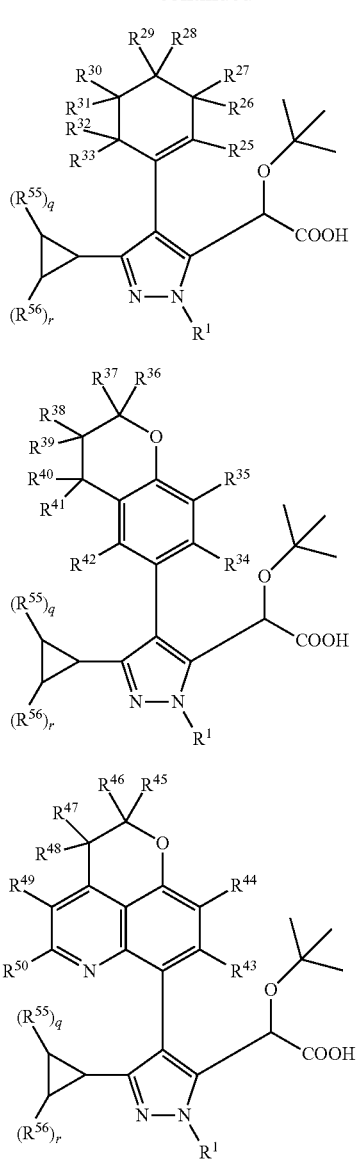

wherein
$R^5$, $R^6$, $R^7$, $R^8$, $R^9$, $R^{19}$, $R^{11}$, $R^{12}$, $R^{13}$, $R^{15}$, $R^{16}$, $R^{17}$, $R^{18}$, $R^{19}$, $R^{55}$ or $R^{56}$, identical or different, independently represent a hydrogen atom; a halogen atom; —$CH_3$; —$CH_2$—$CH_3$; —CH—$(CH_3)_2$—$(CH_2)_2CH_3$; —$CH_2F$; —$CHF_2$; —$CF_3$; —OMe; —OH; —$OCH_2F$; —$OCHF_2$; —$OCF_3$; —$(X)_x$—$C_1$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$ OC(O)NT$^3$T$^4$; —$(X)_x$—$(CT^5T^6)_y$ S(O)$_2$NT$^3$T$^4$; or —$(X)_x$—$(CT^5T^6)_y$NT$^3$S(O)$_2$T$^4$;
$R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$ and $R^{50}$, identical or different, independently represent a hydrogen atom; a halogen atom or a linear or branched $C_1$-$C_6$ alkyl; optionally $R^{28}$, $R^{29}$ and the carbon atom to which they are bounded form a saturated 3, 4, 5 or 6 membered carbocycle;
$R^1$, X, x, y and $T^3$ to $T^6$ are independently defined as for the compounds of formula (I), (A), (B), (C), (A1) to (A10), (B1) to (B7), (C1) to (C10) or (D1).

Advantageously, the invention provides compounds of formulae (A1a) to (A10a), (A1b) to (A10b), (A1c) to (A10c), (A1d) to (A10d), (B1a) to (B4a), (B1b) to (B4b), (B1c) to (B7c), (B1d) to (B4d), (C1a) to (C8a), (C1b) to (C8b), (C1c) to (C10c) or (C1d) to (C8d), (D1a), (D1b), (D1c), or (D1d), wherein:
$R^5$, $R^6$ and the carbon atoms to which they are bonded form a saturated, partially or totally unsaturated or aromatic 6-membered carbo- or heterocycle;
$R^6$, $R^7$ and the carbon atoms to which they are bonded form a saturated, partially or totally unsaturated or aromatic 6-membered carbo- or heterocycle;
$R^7$, $R^8$ and the carbon atoms to which they are bonded form a saturated, partially or totally unsaturated or aromatic 6-membered carbo- or heterocycle;
$R^8$, $R^9$ and the carbon atoms to which they are bonded form a saturated, partially or totally unsaturated or aromatic 6-membered carbo- or heterocycle;
$R^{11}$, $R^{12}$ and the carbon atoms to which they are bonded form a saturated, partially or totally unsaturated or aromatic 5-, 6-membered carbo- or heterocycle;
$R^{12}$, $R^{13}$ and the carbon atoms to which they are bonded form a saturated, partially or totally unsaturated or aromatic 5-, 6-membered carbo- or heterocycle.

More advantageously, in compounds of formulae (A1a) to (A10a), (A1b) to (A10b), (A1c) to (A10c), (A1d) to (A10d), (B1a) to (B4a), (B1b) to (B4b), (B1c) to (B7c), (B1d) to (B4d), (C1a) to (C8a), (C1 b) to (C8b), (C1c) to (C10c), (C1d) to (C8d), (D1a), (D1b), (D1c), or (D1d), $R^5$, $R^6$, $R^7$, $R^8$, $R^9$, $R^{19}$, $R^{11}$, $R^{12}$, $R^{13}$, $R^{15}$, $R^{16}$, $R^{17}$, $R^{18}$, $R^{19}$, $R^{55}$ and $R^{56}$, identical or different, independently represent a hydrogen atom; a halogen atom; a linear or branched $C_1$-$C_6$ alkyl; a linear or branched —O—$C_1$-$C_6$ alkyl; a linear or branched —O—$C_1$-$C_{10}$ alkylaryl; —OH; —C(O)NH$_2$ or —CH$_2$NHC(O)Me.

As examples of compounds of formula (A1b), the invention provides:
2-(tert-butoxy)-2-[4-(4,4-dimethylcyclohex-1-en-1-yl)-1-methyl-3-phenyl-1H-pyrazol-5-yl]acetic acid;
2-(tert-butoxy)-2-{1-methyl-3-phenyl-4-[4-(propan-2-yl)cyclohex-1-en-1-yl]-1H-pyrazol-5-yl}acetic acid.

As examples of compounds of formula (A1c), the invention provides:
2-(tert-butoxy)-2-[4-(3,4-dihydro-2H-1-benzopyran-6-yl)-1-methyl-3-phenyl-1H-pyrazol-5-yl]acetic acid. As example of compounds of formula (A2c), the invention provides:
2-(tert-butoxy)-2-[4-(3,4-dihydro-2H-1-benzopyran-6-yl)-1-methyl-3-(pyridin-2-yl)-1H-pyrazol-5-yl]acetic acid.

As an example of compound of formula (A4b), the invention provides 2-(tert-butoxy)-2-[4-(4,4-dimethylcyclohex-1-en-1-yl)-1-methyl-3-(pyridin-4-yl)-1H-pyrazol-5-yl]acetic acid.

As an example of compound of formula (A4c), the invention provides 2-(tert-butoxy)-2-[4-(3,4-dihydro-2H-1-benzopyran-6-yl)-1-methyl-3-(pyridin-4-yl)-1H-pyrazol-5-yl]acetic acid.

As an example of compounds of formula (B1b), the invention provides 2-(tert-butoxy)-2-[4-(4,4-dimethylcyclohex-1-en-1-yl)-1-methyl-3-(thiophen-2-yl)-1H-pyrazol-5-yl]acetic acid.

As examples of compounds of formula (B1c), the invention provides:

-2-(tert-butoxy)-2-[4-(3,4-dihydro-2H-1-benzopyran-6-yl)-1-methyl-3-(thiophen-2-yl)-1H-pyrazol-5-yl]acetic acid;

2-(tert-butoxy)-2-[1-methyl-4-(5-methyl-3,4-dihydro-2H-1-benzopyran-6-yl)-3-(thiophen-2-yl)-1H-pyrazol-5-yl]acetic acid;

2-(tert-butoxy)-2-[3-(5-chlorothiophen-2-yl)-4-(3,4-dihydro-2H-1-benzopyran-6-yl)-1-methyl-1H-pyrazol-5-yl]acetic acid;

2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetic acid;

2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetic acid;

2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetic acid;

2-(tert-butoxy)-2-[4-(8-fluoro-3,4-dihydro-2H-1-benzopyran-6-yl)-1-methyl-3-(thiophen-2-yl)-1H-pyrazol-5-yl]acetic acid;

2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetic acid.

As an example of compound of formula (B2b), the invention provides 2-(tert-butoxy)-2-[4-(4,4-dimethylcyclohex-1-en-1-yl)-1-methyl-3-(thiophen-3-yl)-1H-pyrazol-5-yl]acetic acid.

As examples of compounds of formula (B2c), the invention provides:

2-(tert-butoxy)-2-[4-(3,4-dihydro-2H-1-benzopyran-6-yl)-1-methyl-3-(thiophen-3-yl)-1H-pyrazol-5-yl]acetic acid;

2-(tert-butoxy)-2-[4-(3,4-dihydro-2H-1-benzopyran-6-yl)-1-methyl-3-(5-propylthiophen-3-yl)-1H-pyrazol-5-yl]acetic acid;

2-[3-benzo[b]thiophen-3-yl-4-(3,4-dihydro-2H-1-benzopyran-6-yl)-1-methyl-1H-pyrazol-5-yl]-2-(tert-butoxy)acetic acid.

As an example of compound of formula (B5c), the invention provides 2-(tert-butoxy)-2-[4-(3,4-dihydro-2H-1-benzopyran-6-yl)-1-methyl-3-(1,3-thiazol-2-yl)-1H-pyrazol-5-yl]acetic acid.

As examples of compounds of formula (B6c), the invention provides:

2-(tert-butoxy)-2-[3-(cyclopent-1-en-1-yl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-3-(5,5-dimethylcyclopent-1-en-1-yl)-1-methyl-1H-pyrazol-5-yl]acetic acid;

2-(tert-butoxy)-2-[4-(3,4-dihydro-2H-1-benzopyran-6-yl)-1-methyl-3-(5-methylcyclopent-1-en-1-yl)-1H-pyrazol-5-yl]acetic acid.

As an example of compound of formula (B7c), the invention provides 2-(tert-butoxy)-2-[3-cyclopentyl-4-(3,4-dihydro-2H-1-benzopyran-6-yl)-1-methyl-1H-pyrazol-5-yl]acetic acid.

As an example of compound of formula (C9c), the invention provides 2-(tert-butoxy)-2-[3-cyclohexyl-4-(3,4-dihydro-2H-1-benzopyran-6-yl)-1-methyl-1H-pyrazol-5-yl]acetic acid.

As examples of compounds of formula (C10c), the invention provides:

2-(tert-butoxy)-2-[3-(cyclohex-1-en-1-yl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid;

2-(tert-butoxy)-2-[4-(3,4-dihydro-2H-1-benzopyran-6-yl)-1-methyl-3-(3-methylcyclohex-1-en-1-yl)-1H-pyrazol-5-yl]acetic acid 2-(tert-butoxy)-2-[4-(3,4-dihydro-2H-1-benzopyran-6-yl)-1-methyl-3-(6-methylcyclohex-1-en-1-yl)-1H-pyrazol-5-yl]acetic acid;

2-(tert-butoxy)-2-[4-(3,4-dihydro-2H-1-benzopyran-6-yl)-1-methyl-3-(4-methylcyclohex-1-en-1-yl)-1H-pyrazol-5-yl]acetic acid;

2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetic acid.

As an example of compound of formula (D1c), the invention provides 2-(tert-butoxy)-2-[3-cyclopropyl-4-(3,4-dihydro-2H-1-benzopyran-6-yl)-1-methyl-1H-pyrazol-5-yl]acetic acid.

As examples of compounds of formula (I), the invention provides:

2-(3-{bicyclo[2.2.1]hept-2-en-2-yl}-4-(3,4-dihydro-2H-1-benzopyran-6-yl)-1-methyl-1H-pyrazol-5-yl)-2-(tert-butoxy)acetic acid 2-(tert-butoxy)-2-[3-(cyclohept-1-en-1-yl)-4-(3,4-dihydro-2H-1-benzopyran-6-yl)-1-methyl-1H-pyrazol-5-yl]acetic acid;

2-(tert-butoxy)-2-[3-(cyclopentylmethyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-(prop-1-en-2-yl)-1H-pyrazol-5-yl]acetic acid;

2-(tert-butoxy)-2-[3-(1-cyclopentylethenyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-(propan-2-yl)-1H-pyrazol-5-yl]acetic acid;

2-(tert-butoxy)-2-[3-(1-cyclopentylethyl)-4-(3,4-dihydro-2H-1-benzopyran-6-yl)-1-methyl-1H-pyrazol-5-yl]acetic acid;

2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid;

2-(tert-butoxy)-2-[3-(2-cyclopropylethyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid;

2-(tert-butoxy)-2-[4-(3,4-dihydro-2H-1-benzopyran-6-yl)-1-methyl-3-propyl-1H-pyrazol-5-yl]acetic acid.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antiviral activity of compounds according to the invention.

Preparation of the Compounds

Abbreviations or symbols used herein include:

DMSO: dimethylsulfoxide
MS: Mass Spectrometry
NMR: Nuclear Magnetic Resonance Spectroscopy s: singlet
bs: broad singlet
d: doublet
t: triplet
q: quadruplet
quin: quintet
dd: doubled doublet
ddd: doubled doubled doublet
dt: doubled triplet
sex: sextet
m: massif
TLC: Thin Layer Chromatography Example 1 synthesis of 2-(tert-butoxy)-2-[4-(4,4-dimethylcyclohex-1-en-1-yl)-1-methyl-3-phenyl-1H-pyrazol-5-yl]acetic acid

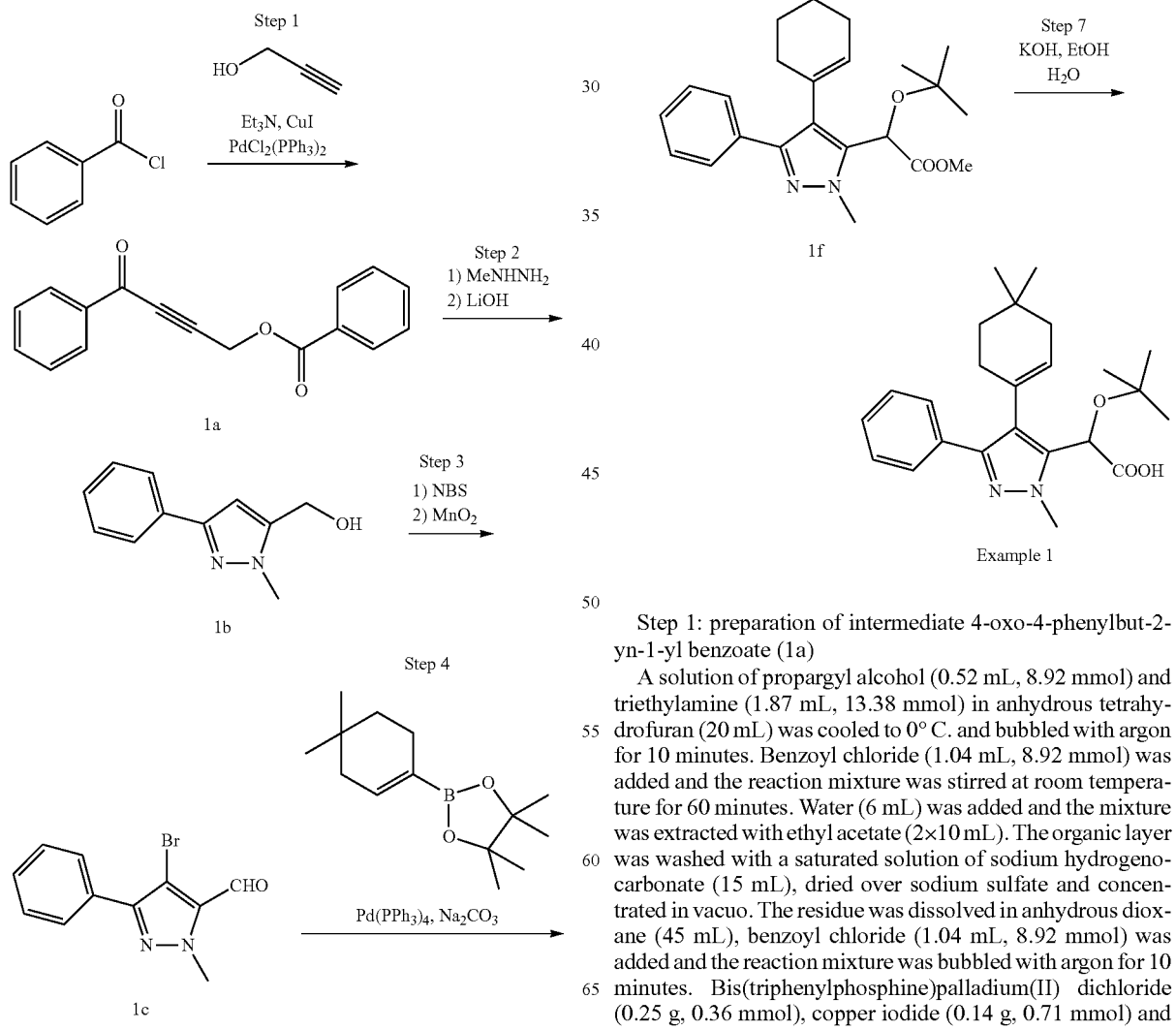

Step 1: preparation of intermediate 4-oxo-4-phenylbut-2-yn-1-yl benzoate (1a)

A solution of propargyl alcohol (0.52 mL, 8.92 mmol) and triethylamine (1.87 mL, 13.38 mmol) in anhydrous tetrahydrofuran (20 mL) was cooled to 0° C. and bubbled with argon for 10 minutes. Benzoyl chloride (1.04 mL, 8.92 mmol) was added and the reaction mixture was stirred at room temperature for 60 minutes. Water (6 mL) was added and the mixture was extracted with ethyl acetate (2×10 mL). The organic layer was washed with a saturated solution of sodium hydrogenocarbonate (15 mL), dried over sodium sulfate and concentrated in vacuo. The residue was dissolved in anhydrous dioxane (45 mL), benzoyl chloride (1.04 mL, 8.92 mmol) was added and the reaction mixture was bubbled with argon for 10 minutes. Bis(triphenylphosphine)palladium(II) dichloride (0.25 g, 0.36 mmol), copper iodide (0.14 g, 0.71 mmol) and triethylamine (3.73 mL, 26.76 mmol) were added, and the reaction mixture was stirred for 3 hours at room temperature, under argon atmosphere. The solution was filtered and water (20 mL) was added to the filtrate. Layers were separated and the aqueous layer was extracted with dichloromethane (2×20 mL). The combined organic layers were dried over sodium sulfate and concentrated in vacuo. The residue was purified by flash chromatography on silica gel (cyclohexane/ethyl acetate 100/0 to 95/5) to provide 4-oxo-4-phenylbut-2-yn-1-yl benzoate (1a) (751 mg, 2.84 mmol, 32%).

$^1$H NMR (300 MHz, CDCl$_3$) δ 5.21 (s, 2H), 7.44-7.53 (m, 4H), 7.57-7.67 (m, 2H), 8.07-8.17 (m, 4H).

MS m/z ([M+H]$^+$) 265.

Step 2: preparation of intermediate (1-methyl-3-phenyl-1H-pyrazol-5-yl)methanol (1b)

A solution of 4-oxo-4-phenylbut-2-yn-1-yl benzoate (1a) (750 mg, 2.84 mmol) and methylhydrazine (0.30 mL, 5.68 mmol) in ethanol (25 mL) was stirred overnight at room temperature. The reaction mixture was concentrated in vacuo and the residue was taken in a mixture of ethanol (3 mL) and tetrahydrofuran (9 mL). Lithium hydroxide (204 mg, 8.51 mmol), previously dissolved in water (3 mL) was added and the mixture was stirred at room temperature for 2 hours. Ethanol and tetrahydrofuran were removed under reduced pressure and the resulting aqueous layer was extracted with ethyl acetate (2×5 mL). The organic layer was successively washed with a saturated solution of sodium hydrogenocarbonate (5 mL) and brine (5 mL) before being dried over sodium sulfate and concentrated in vacuo. The residue was purified by flash chromatography on silica gel (cyclohexane/ethyl acetate 100/0 to 50/50) to provide (1-methyl-3-phenyl-1H-pyrazol-5-yl)methanol (1b) (341 mg, 1.81 mmol, 64%).

$^1$H NMR (400 MHz, CDCl$_3$) δ 3.97 (s, 3H), 4.68 (s, 2H), 6.47 (s, 1H), 7.26-7.32 (m, 1H), 7.35-7.42 (m, 2H), 7.72-7.78 (m, 2H).

MS m/z ([M+H]$^+$) 189.

Step 3: preparation of intermediate 4-bromo-1-methyl-3-phenyl-1H-pyrazole-5-carbaldehyde (1c)

A solution of (1-methyl-3-phenyl-1H-pyrazol-5-yl)methanol (1b) (340 mg, 1.81 mmol) and N-bromosuccinimide (338 mg, 1.90 mmol) in acetonitrile (30 mL) was stirred at room temperature for 1 hour. The reaction mixture was concentrated in vacuo. Water (10 mL) was added and the aqueous layer was extracted with ethyl acetate (2×12 mL). The organic layer was dried over sodium sulfate and concentrated in vacuo. The residue was taken in dichloromethane (5 mL) and manganese dioxide (1.57 g, 18.06 mmol) was added. The reaction mixture was stirred at room temperature for 40 hours, filtered over Celite®, and the filtrate was concentrated in vacuo. The residue was dissolved in a minimum of dichloromethane and purified thought a pad of silice, (cyclohexane/ethyl acetate 80/20), to provide 4-bromo-1-methyl-3-phenyl-1H-pyrazole-5-carbaldehyde (1c) (304 mg, 1.15 mmol, 63%).

$^1$H NMR (400 MHz, CDCl$_3$) δ 4.21 (s, 3H), 7.38-7.49 (m, 3H), 7.84-7.90 (m, 2H), 9.96 (s, 1H). Ms m/z ([M+H]$^+$) 265/267.

Step 4: preparation of intermediate 4-(4,4-dimethylcyclohex-1-en-1-yl)-1-methyl-3-phenyl-1H-pyrazole-5-carbaldehyde (1d)

A solution of 4-bromo-1-methyl-3-phenyl-1H-pyrazole-5-carbaldehyde (1c) (150 mg, 0.57 mmol), sodium carbonate (240 mg, 2.26 mmol), and 4,4-(dimethylcyclohexene-1-yl) boronic acid pinacol ester (174 mg, 0.74 mmol) in a mixture of toluene (0.8 mL), ethanol (0.3 mL) and water (0.3 mL) was bubbled with nitrogen for 5 minutes. Palladium tetrakis(triphenylphosphine) (32.7 mg, 0.028 mmol) was added and the reaction mixture was heated at 95° C. overnight. The solution was concentrated in vacuo. Water (3 mL) was added to the residue. The aqueous layer was extracted with ethyl acetate (2×5 mL) and the organic layer was dried over sodium sulfate and concentrated in vacuo. The crude was purified by preparative TLC (cyclohexane/ethyl acetate 80/20) to provide 4-(4,4-dimethylcyclohex-1-en-1-yl)-1-methyl-3-phenyl-1H-pyrazole-5-carbaldehyde (1d) (135 mg, 0.46 mmol, 81%).

$^1$H NMR (400 MHz, CDCl$_3$) δ 0.99 (s, 6H), 1.43 (t, J=6.2 Hz, 2H), 2.02-2.11 (m, 4H), 4.20 (s, 3H), 5.81-5.85 (m, 1H), 7.30-7.36 (m, 1H), 7.36-7.42 (m, 2H), 7.67-7.72 (m, 2H), 9.73 (s, 1H). Ms m/z ([M+H]$^+$) 295.

Step 5: preparation of intermediate methyl 2-[4-(4,4-dimethylcyclohex-1-en-1-yl)-1-methyl-3-phenyl-1H-pyrazol-5-yl]-2-hydroxyacetate (1e)

Under nitrogen atmosphere, to a solution of 4-(4,4-dimethylcyclohex-1-en-1-yl)-1-methyl-3-phenyl-1H-pyrazole-5-carbaldehyde (1d) (135 mg, 0.46 mmol) in anhydrous dichloromethane (2 mL) at 0° C. were successively added zinc iodide (15 mg, 0.05 mmol) and trimethylsilyl cyanide (69 μL, 0.55 mmol). The mixture was stirred at room temperature for 24 hours. An aqueous saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (3 mL) was added to a solution of acetyl chloride (0.39 mL, 5.50 mmol) in anhydrous methanol (2 mL), previously stirred for 20 minutes at 0° C. under nitrogen atmosphere. The mixture was heated at 65° C. for 5 hours and stirred at room temperature overnight. The solution was concentrated in vacuo and a saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (cyclohexane/ethyl acetate 70/30) to provide methyl 2-[4-(4,4-dimethylcyclohex-1-en-1-yl)-1-methyl-3-phenyl-1H-pyrazol-5-yl]-2-hydroxyacetate (1e) (135 mg, 0.38 mmol, 83%).

$^1$H NMR (300 MHz, CDCl$_3$) δ 0.97 (s, 6H), 1.33-1.42 (m, 2H), 1.93-2.04 (m, 4H), 3.82 (s, 3H), 3.87 (s, 3H), 5.34 (s, 1H), 5.71-5.77 (m, 1H), 7.27-7.40 (m, 3H), 7.66-7.73 (m, 2H).

Ms m/z ([M+H]$^+$) 355.

Step 6: preparation of intermediate methyl 2-(tert-butoxy)-2-[4-(4,4-dimethylcyclohex-1-en-1-yl)-1-methyl-3-phenyl-1H-pyrazol-5-yl]acetate (1f)

To a solution of methyl 2-[4-(4,4-dimethylcyclohex-1-en-1-yl)-1-methyl-3-phenyl-1H-pyrazol-5-yl]-2-hydroxyacetate (1e) (135 mg, 0.38 mmol) in tert-butyl acetate (7 mL) at 0° C. was added perchloric acid (0.87 mL). The mixture was stirred for 80 minutes at room temperature before being slowly quenched with a saturated solution of potassium carbonate (20 mL). The layers were separated and the aqueous layer was extracted with ethyl acetate (2×30 mL). The organic layers were dried over sodium sulfate and concentrated in vacuo. The residue was purified by preparative TLC (cyclohexane/ethyl acetate 80/20) to provide methyl 2-(tert-butoxy)-2-[4-(4,4-dimethylcyclohex-1-en-1-yl)-1-methyl-3-phenyl-1H-pyrazol-5-yl]acetate (1f) (121 mg, 0.29 mmol, 77%) as a clear yellow oil.

$^1$H NMR (400 MHz, CDCl$_3$) δ 0.99 (s, 3H), 1.10 (s, 3H), 1.19 (s, 9H), 1.32-1.45 (m, 2H), 1.82-1.95 (m, 1H), 2.01-2.16 (m, 3H), 3.73 (s, 3H), 3.99 (s, 3H), 5.28 (s, 1H), 5.75-5.82 (m, 1H), 7.24-7.31 (m, 1H), 7.31-7.39 (m, 2H), 7.67-7.74 (m, 2H).

MS m/z ([M+H]$^+$) 411.

Step 7: preparation of 2-(tert-butoxy)-2-[4-(4,4-dimethyl-cyclohex-1-en-1-yl)-1-methyl-3-phenyl-1H-pyrazol-5-yl] acetic acid (example 1)

A mixture of methyl 2-(tert-butoxy)-2-[4-(4,4-dimethyl-cyclohex-1-en-1-yl)-1-methyl-3-phenyl-1H-pyrazol-5-yl] acetate (1f) (121 mg, 0.29 mmol) and potassium hydroxide (144 mg, 1.18 mmol) in a mixture of ethanol (1.5 mL) and water (1.5 mL) was refluxed for 6 hours. The reaction mixture was concentrated in vacuo. Water (2 mL) was added to the residue and the aqueous layer was washed with diethyl ether (2×2 mL), acidified with concentrated hydrochloric acid until pH 2 and extracted with diethyl ether (2×3 mL). The organic layer was dried over sodium sulfate and concentrated in vacuo to provide 2-(tert-butoxy)-2-[4-(4,4-dimethylcyclohex-1-en-1-yl)-1-methyl-3-phenyl-1H-pyrazol-5-yl]acetic acid (example 1) (101 mg, 0.25 mmol, 86%).

$^1$H NMR (300 MHz, CDCl$_3$) δ 0.97 (s, 3H), 1.00 (s, 3H), 1.22 (s, 9H), 1.30-1.45 (m, 2H), 1.77-1.94 (m, 1H), 1.99-2.20 (m, 3H), 3.94 (s, 3H), 5.33 (s, 1H), 5.86-5.91 (m, 1H), 7.26-7.39 (m, 3H), 7.63-7.71 (m, 2H).

MS m/z ([M−H]$^-$) 395.
MS m/z ([M+H]$^+$) 397.

Example 2 synthesis of 2-(tert-butoxy)-2-[4-(3,4-dihydro-2H-1-benzopyran-6-yl)-1-methyl-3-phenyl-1H-pyrazol-5-yl]acetic acid

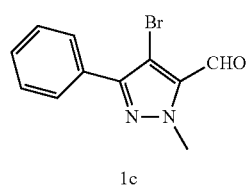

Step 1

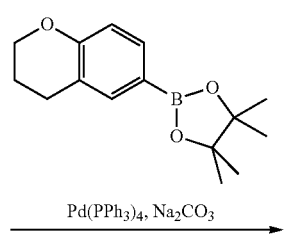

Pd(PPh$_3$)$_4$, Na$_2$CO$_3$

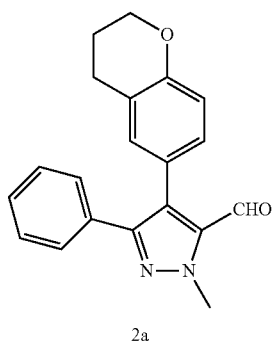

2a

Step 2
1) TMSCN, ZnI$_2$
2) AcCl, MeOH

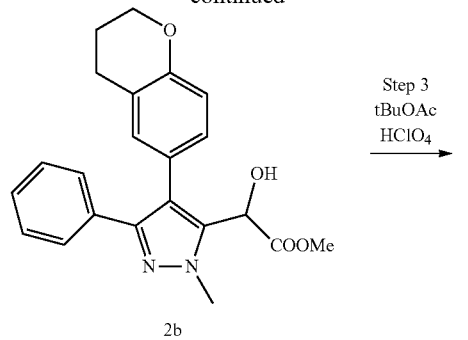

Step 3
tBuOAc
HClO$_4$

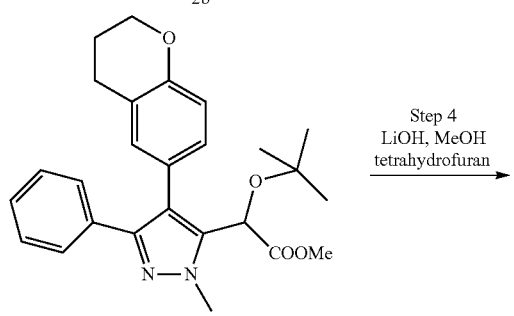

Step 4
LiOH, MeOH
tetrahydrofuran

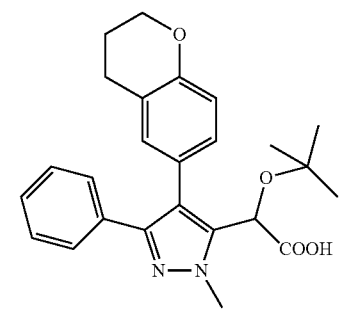

Example 2

Step 1: preparation of intermediate 4-(3,4-dihydro-2H-1-benzopyran-6-yl)-1-methyl-3-phenyl-1H-pyrazole-5-carbaldehyde (2a)

Using the procedure described in example 1, step 4, 4-bromo-1-methyl-3-phenyl-1H-pyrazole-5-carbaldehyde (1c) (415 mg, 1.57 mmol) is converted by reaction with 6-(4,4,5,5-tetramethyl-1,3,2-dioxaborolan-2-yl)chroman (488 mg, 1.88 mmol), into 4-(3,4-dihydro-2H-1-benzopyran-6-yl)-1-methyl-3-phenyl-1H-pyrazole-5-carbaldehyde (2a) (317 mg, 1.00 mmol, 64%), after purification by flash chromatography (cyclohexane/ethyl acetate 100/0 to 90/10).

$^1$H NMR (300 MHz, CDCl$_3$) δ 1.99 (m, 2H), 2.71 (t, J=6.5 Hz, 2H), 4.19 (m, 2H), 4.21 (s, 3H), 6.75 (d, J=8.1 Hz, 1H), 6.96 (m, 2H), 7.23 (m, 3H), 7.42 (m, 2H), 9.60 (s, 1H).

Ms m/z ([M+H]$^+$) 319.

Step 2: preparation of intermediate methyl 2-[4-(3,4-dihydro-2H-1-benzopyran-6-yl)-1-methyl-3-phenyl-1H-pyrazol-5-yl]-2-hydroxyacetate (2b)

Using the procedure described in example 1, step 5, 4-(3,4-dihydro-2H-1-benzopyran-6-yl)-1-methyl-3-phenyl-1H-pyrazole-5-carbaldehyde (2a) (57 mg, 0.179 mmol) is converted into methyl 2-[4-(3,4-dihydro-2H-1-benzopyran-6-yl)-1-methyl-3-phenyl-1H-pyrazol-5-yl]-2-hydroxyacetate (2b) (50 mg, 0.132 mmol, 74%).

$^1$H NMR (300 MHz, CDCl$_3$) δ 2.01 (m, 2H), 2.73 (t, J=6.5 Hz, 2H), 3.40 (d, J=2.5 Hz, 1H), 3.75 (s, 3H), 3.91 (s, 3H), 4.21 (t, J=5.2 Hz, 2H), 5.25 (d, J=2.5 Hz, 1H), 6.75 (d, J=8.1 Hz, 1H), 6.96-6.91 (m, 2H), 7.22 (m, 2H), 7.43 (m, 2H).

MS m/z ([M+H]$^+$) 379.

Step 3: preparation of intermediate methyl 2-(tert-butoxy)-2-[4-(3,4-dihydro-2H-1-benzopyran-6-yl)-1-methyl-3-phenyl-1H-pyrazol-5-yl]acetate (2c)

Using the procedure described in example 1, step 6, methyl 2-[4-(3,4-dihydro-2H-1-benzopyran-6-yl)-1-methyl-3-phenyl-1H-pyrazol-5-yl]-2-hydroxyacetate (2b) (32 mg, 0.084 mmol) is converted, after purification by preparative TLC (cyclohexane/ethyl acetate 60/40) into methyl 2-(tert-butoxy)-2-[4-(3,4-dihydro-2H-1-benzopyran-6-yl)-1-methyl-3-phenyl-1H-pyrazol-5-yl]acetate (2c) (22 mg, 0.051 mmol, 60%).

$^1$H NMR (300 MHz, CDCl$_3$) δ 1.04 (s, 9H), 2.03 (m, 2H), 2.74 (t, J=6.3 Hz, 2H), 7.46 (m, 2H), 3.78 (s, 3H), 4.02 (s, 3H), 4.23 (t, J=5.1 Hz, 2H), 5.08 (s, 1H), 6.78 (d, J=8.1 Hz, 1H), 6.99-6.94 (m, 2H), 7.24 (m, 2H).

MS m/z ([M+H]$^+$) 435.

Step 4: preparation of 2-(tert-butoxy)-2-[4-(3,4-dihydro-2H-1-benzopyran-6-yl)-1-methyl-3-phenyl-1H-pyrazol-5-yl]acetic acid (example 2)

To a solution of methyl 2-(tert-butoxy)-2-[4-(3,4-dihydro-2H-1-benzopyran-6-yl)-1-methyl-3-phenyl-1H-pyrazol-5-yl]acetate (2c) (48 mg, 0.11 mmol) in a 1/1 mixture of tetrahydrofurane/methanol (2 mL) was added a solution of lithium hydroxide (11 mg, 0.44 mmol) in water (0.25 mL). The mixture was stirred at 65° C. for 2 hours. TLC analysis showed no more starting material. The mixture was concentrated under reduced pressure. Water (0.5 mL) and ethyl acetate (2 mL) were added to the residue. The aqueous layer was acidified with 1M hydrochloric acid until pH 5 and extracted with ethyl acetate (3×2 mL). The organic layer was dried over sodium sulfate and concentrated under reduced pressure to provide 2-(tert-butoxy)-2-[4-(3,4-dihydro-2H-1-benzopyran-6-yl)-1-methyl-3-phenyl-1H-pyrazol-5-yl]acetic acid (example 2) (40 mg, 0.095 mmol, 85%) as a white solid.

$^1$H NMR (300 MHz, CDCl$_3$) δ 1.05 (s, 9H), 2.02 (m, 2H), 2.74 (t, J=6.5 Hz, 2H), 3.98 (s, 3H), 4.22 (t, J=5.1 Hz, 2H), 5.15 (s, 1H), 6.77 (d, J=8.7 Hz, 1H), 7.00-6.97 (m, 2H), 7.23 (m, 2H), 7.45 (m, 2H).

MS m/z ([M+H]$^+$) 421.

Example 3 synthesis of 2-(tert-butoxy)-2-[4-(3,4-dihydro-2H-1-benzopyran-6-yl)-1-methyl-3-(thiophen-2-yl)-1H-pyrazol-5-yl]acetic acid

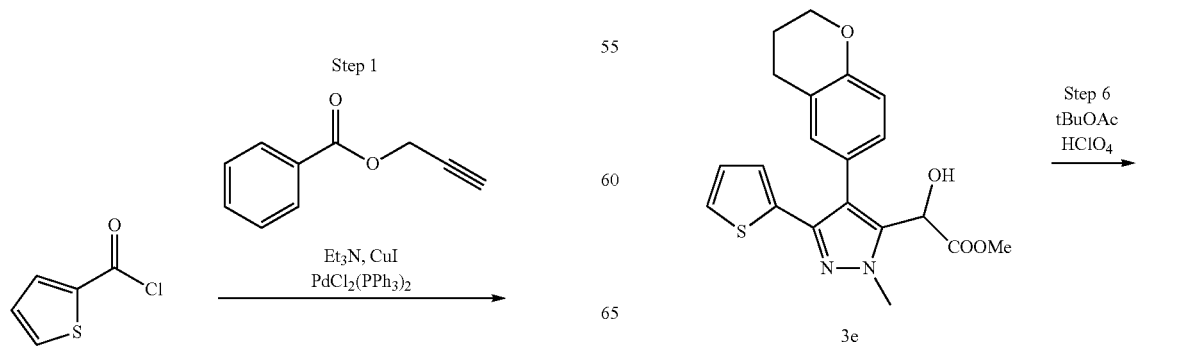

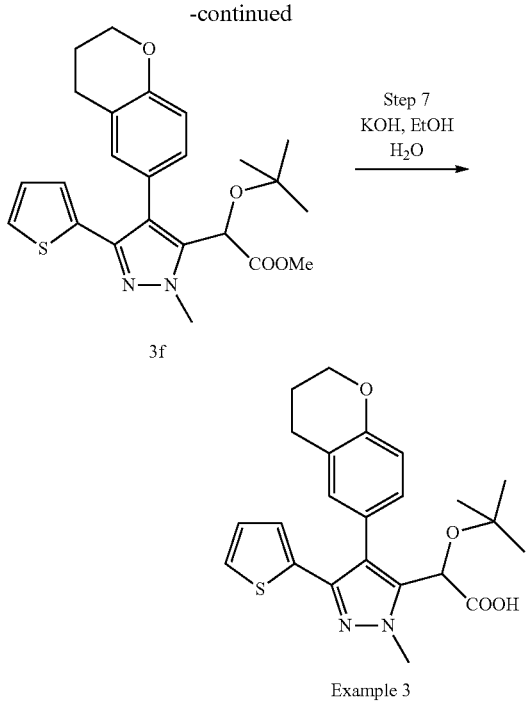

Step 7
KOH, EtOH
H₂O

3f

Example 3

Step 1: preparation of intermediate 4-oxo-4-(thiophen-2-yl)„ut-2-yn-1-yl benzoate (3a)

A solution of 2-thiophenecarbonyl chloride (549 mg, 3.75 mmol) in anhydrous dioxane (15 mL) was bubbled with argon for 10 minutes. Triethylamine (1.31 mL, 9.36 mmol) was added and the bubbling was maintained for 5 minutes. Bis(triphenylphosphine)palladium(II) dichloride (88 mg, 0.12 mmol), copper iodide (48 mg, 0.25 mmol) and propargyl benzoate (0.45 mL, 3.12 mmol) were added, and the reaction mixture was stirred for 1 hour at room temperature, under argon atmosphere. The solution was filtered and water (20 mL) was added to the filtrate. Layers were separated, and the aqueous layer was extracted with dichloromethane (2×20 mL). The combined organic layers were washed with a saturated solution of sodium hydrogenocarbonate (20 mL), dried over sodium sulfate and concentrated in vacuo. The residue was purified by flash chromatography on silica gel (cyclohexane/ethyl acetate 100/0 to 95/5) to provide 4-oxo-4-(thiophen-2-yl)but-2-yn-1-yl benzoate (3a) (333 mg, 1.23 mmol, 39%).

¹H NMR (300 MHz, CDCl₃) δ 5.17 (s, 2H), 7.16 (dd, J=3.9 Hz, J=4.9 Hz, 1H), 7.43-7.53 (m, 2H), 7.57-7.67 (m, 1H), 7.72 (dd, J=1.2 Hz, J=4.9 Hz, 1H), 7.94 (dd, J=1.2 Hz, J=3.9 Hz, 1H), 8.06-8.13 (m, 2H).

MS m/z ([M+H]⁺) 271.

Step 2: preparation of intermediate [1-methyl-3-(thiophen-2-yl)-1H-pyrazol-5-yl]methanol (3b)

Using the procedure described in example 1, step 2, 4-oxo-4-(thiophen-2-yl)„ut-2-yn-1-yl benzoate (3a) (330 mg, 1.22 mmol) is converted, after purification by preparative TLC (cyclohexane/ethyl acetate 30/70) into [1-methyl-3-(thiophen-2-yl)-1H-pyrazol-5-yl]nethanol (3b) (185 mg, 0.95 mmol, 78%).

¹H NMR (300 MHz, CDCl₃) δ 3.88 (s, 3H), 4.65 (s, 2H), 6.37 (s, 1H), 7.03 (dd, J=3.6 Hz, J=5.1 Hz, 1H), 7.22 (dd, J=1.1 Hz, J=5.1 Hz, 1H), 7.26 (dd, J=1.1 Hz, J=3.6 Hz, 1H).

Ms m/z ([M+H]⁺) 195.

Step 3: preparation of intermediate 4-bromo-1-methyl-3-(thiophen-2-yl)-1H-pyrazole-5-carbaldehyde (3c)

Using the procedure described in example 1, step 3, [1-methyl-3-(thiophen-2-yl)-1H-pyrazol-5-yl]methanol (3b) (185 mg, 0.95 mmol) is converted, after purification by preparative TLC (cyclohexane/ethyl acetate 80/20) into 4-bromo-1-methyl-3-(thiophen-2-yl)-1H-pyrazole-5-carbaldehyde (3c) (197 mg, 0.73 mmol, 76%).

¹H NMR (300 MHz, CDCl₃) δ 4.18 (s, 3H), 7.12 (dd, J=3.6 Hz, J=5.1 Hz, 1H), 7.37 (dd, J=1.1 Hz, J=5.1 Hz, 1H), 7.75 (dd, J=1.1 Hz, J=3.6 Hz, 1H), 9.93 (s, 1H).

Step 4: preparation of intermediate 4-(3,4-dihydro-2H-1-benzopyran-6-yl)-1-methyl-3-(thiophen-2-yl)-1H-pyrazole-5-carbaldehyde (3d)

Using the procedure described in example 1, step 4,4-bromo-1-methyl-3-(thiophen-2-yl)-1H-pyrazole-5-carbaldehyde (3c) (195 mg, 0.72 mmol) is converted, after purification by preparative TLC (cyclohexane/ethyl acetate 80/20), into 4-(3,4-dihydro-2H-1-benzopyran-6-yl)-1-methyl-3-(thiophen-2-yl)-1H-pyrazole-5-carbaldehyde (3d) (172 mg, 0.53 mmol, 74%).

¹H NMR (400 MHz, CDCl₃) δ 2.00-2.10 (m, 2H), 2.75-2.84 (m, 2H), 4.22 (s, 3H), 4.22-4.29 (m, 2H), 6.86 (d, J=8.3 Hz, 1H), 6.89-6.94 (m, 1H), 6.95-7.00 (m, 1H), 7.02-7.06 (s, 1H), 7.09 (d, J=8.3 Hz, 1H), 7.20 (d, J=5.0 Hz, 1H), 9.58 (s, 1H).

MS m/z ([M+H]⁺) 325.

Step 5: preparation of intermediate methyl 2-[4-(3,4-dihydro-2H-1-benzopyran-6-yl)-1-methyl-3-(thiophen-2-yl)-1H-pyrazol-5-yl]-2-hydroxyacetate (3e)

Using the procedure described in example 1, step 5, 4-(3,4-dihydro-2H-1-benzopyran-6-yl)-1-methyl-3-(thiophen-2-yl)-1H-pyrazole-5-carbaldehyde (3d) (170 mg, 0.52 mmol) is converted, after purification by preparative TLC (cyclohexane/ethyl acetate 50/50), into methyl 2-[4-(3,4-dihydro-2H-1-benzopyran-6-yl)-1-methyl-3-(thiophen-2-yl)-1H-pyrazol-5-yl]-2-hydroxyacetate (3e) (141 mg, 0.37 mmol, 70%).

¹H NMR (400 MHz, CDCl₃) δ 1.96-2.08 (m, 2H), 2.71-2.81 (m, 2H), 3.73 (s, 3H), 3.89 (s, 3H), 4.17-4.26 (m, 2H), 5.19 (s, 1H), 6.81 (d, J=8, 2 Hz, 1H), 6.84-6.89 (m, 2H), 6.94-7.05 (m, 2H), 7.09-7.10 (m, 1H).

MS m/z ([M+H]⁺) 385.

Step 6: preparation of intermediate methyl 2-(tert-butoxy)-2-[4-(3,4-dihydro-2H-1-benzopyran-6-yl)-1-methyl-3-(thiophen-2-yl)-1H-pyrazol-5-yl]acetate (3f)

Using the procedure described in example 1, step 6, methyl 2-[4-(3,4-dihydro-2H-1-benzopyran-6-yl)-1-methyl-3-(thiophen-2-yl)-1H-pyrazol-5-yl]-2-hydroxyacetate (3e) (140 mg, 0.36 mmol) is converted, after purification by preparative TLC (cyclohexane/ethyl acetate 70/30), into methyl 2-(tert-butoxy)-2-[4-(3,4-dihydro-2H-1-benzopyran-6-yl)-1-methyl-3-(thiophen-2-yl)-1H-pyrazol-5-yl]acetate (3f) (113 mg, 0.26 mmol, 70%).

¹H NMR (400 MHz, CDCl₃) δ 1.05 (s, 9H), 2.00-2.09 (m, 2H), 2.73-2.85 (m, 2H), 3.75 (s, 3H), 3.99 (s, 3H), 4.21-4.28 (m, 2H), 5.00 (s, 1H), 6.81-6.88 (m, 3H), 6.98-7.07 (m, 2H), 7.09-7.14 (m, 1H).

MS m/z ([M+H]⁺) 441.

Step 7: preparation of 2-(tert-butoxy)-2-[4-(3,4-dihydro-2H-1-benzopyran-6-yl)-1-methyl-3-(thiophen-2-yl)-1H-pyrazol-5-yl]acetic acid (example 3)

Using the procedure described in example 1, step 7, methyl 2-(tert-butoxy)-2-[4-(3,4-dihydro-2H-1-benzopyran-6-yl)-1-methyl-3-(thiophen-2-yl)-1H-pyrazol-5-yl]acetate (3f) (110 mg, 0.25 mmol) is converted into methyl 2-(tert-butoxy)-2-[4-(3,4-dihydro-2H-1-benzopyran-6-yl)-1-methyl-3-(thiophen-2-yl)-1H-pyrazol-5-yl]acetic acid (example 3) (97 mg, 0.23 mmol, 91%).

$^1$H NMR (400 MHz, CDCl$_3$) δ 1.08 (s, 9H), 2.00-2.09 (m, 2H), 2.75-2.83 (m, 2H), 3.95 (s, 3H), 4.21-4.28 (m, 2H), 5.07 (s, 1H), 6.80-6.90 (m, 3H), 7.05-7.11 (m, 2H), 7.11-7.16 (m, 1H).

MS m/z ([M−H]$^-$) 425.

MS m/z ([M+H]$^+$) 427.

Example 4 synthesis of 2-(tert-butoxy)-2-[4-(3,4-dihydro-2H-1-benzopyran-6-yl)-1-methyl-3-(thiophen-3-yl)-1H-pyrazol-5-yl]acetic acid

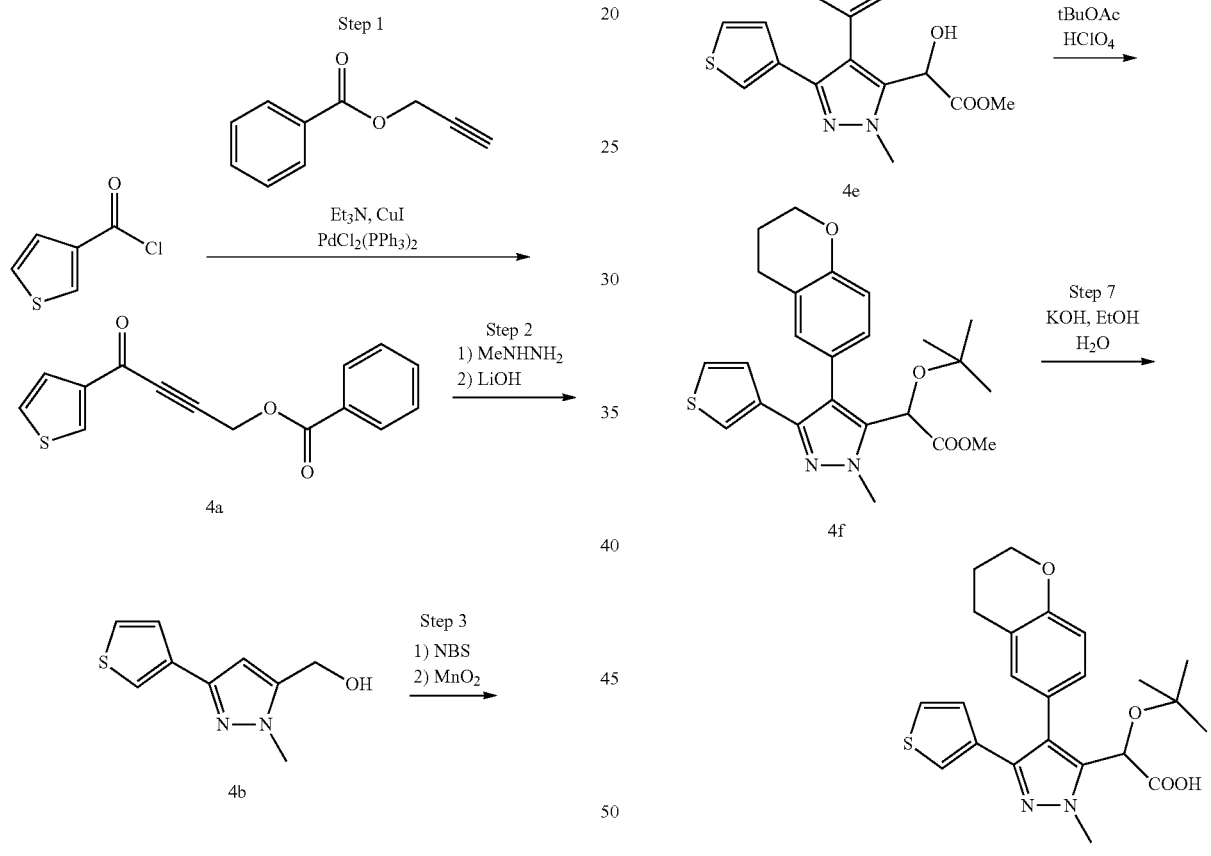

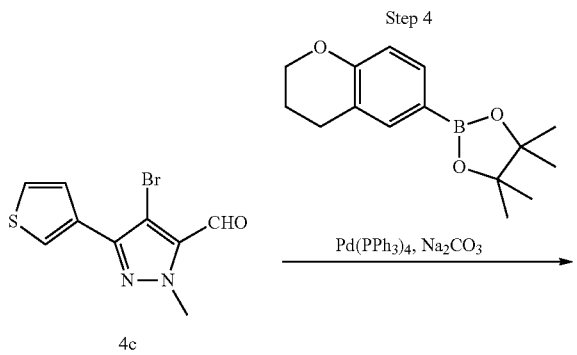

Step 1: preparation of intermediate 4-oxo-4-(thiophen-3-yl)but-2-yn-1-yl benzoate (4a)

Using the procedure described in example 1, step 1, thiophene-3-carbonyl chloride (824 mg, 5.62 mmol) is converted, after purification by flash chromatography on silica gel (cyclohexane/ethyl acetate 100/0 to 95/05), into 4-oxo-4-(thiophen-3-yl)but-2-yn-1-yl benzoate (4a) (552 mg, 2.04 mmol, 44%).

$^1$H NMR (400 MHz, CDCl$_3$) δ 5.17 (s, 2H), 7.33 (dd, J=2.9 Hz, J=5.1 Hz, 1H), 7.45-7.52 (m, 2H), 7.58-7.65 (m, 2H), 8.07-8.12 (m, 2H), 8.30 (dd, J=1.2 Hz, J=2.9 Hz, 1H).

MS m/z ([M+H]$^+$) 271.

Step 2: preparation of intermediate [1-methyl-3-(thiophen-3-yl)-1H-pyrazol-5-yl]methanol (4b)

Using the procedure described in example 1, step 2, 4-oxo-4-(thiophen-3-yl)but-2-yn-1-yl benzoate (4a) (552 mg, 2.04 mmol) is converted, after purification by trituration in diethyl ether, into [1-methyl-3-(thiophen-3-yl)-1H-pyrazol-5-yl]methanol (4b) (271 mg, 1.39 mmol, 68%).

$^1$H NMR (400 MHz, CDCl$_3$) δ 3.90 (s, 3H), 4.67 (s, 2H), 6.36 (s, 1H), 7.30-7.37 (m, 1H), 7.40-7.46 (m, 1H), 7.48-7.54 (m, 1H).

MS m/z ([M+H]$^+$) 195.

Step 3: preparation of intermediate 4-bromo-1-methyl-3-(thiophen-3-yl)-1H-pyrazole-5-carbaldehyde (4c)

A solution of [1-methyl-3-(thiophen-3-yl)-1H-pyrazol-5-yl]methanol (4b) (271 mg, 1.39 mmol) and N-bromosuccinimide (236 mg, 1.32 mmol) in acetonitrile (23 mL) was stirred at room temperature for 1 hour. The reaction mixture was concentrated in vacuo. Water (10 mL) was added and the aqueous layer was extracted with ethyl acetate (2×12 mL). The organic layer was dried over sodium sulfate and concentrated in vacuo. The residue was taken in dichloromethane (5 mL) and manganese dioxide (1.21 g, 13.95 mmol) was added. The reaction mixture was stirred at room temperature for 24 hours, filtered over Celite®, and the filtrate was concentrated in vacuo. to provide 4-bromo-1-methyl-3-(thiophen-3-yl)-1H-pyrazole-5-carbaldehyde (4c) (297 mg, 1.10 mmol, 78%), which was used without further purification.

$^1$H NMR (300 MHz, CDCl$_3$) δ 4.19 (s, 3H), 7.40 (dd, J=2.9 Hz, J=5.1 Hz, 1H), 7.66 (dd, J=1.2 Hz, J=5.1 Hz, 1H), 7.96 (dd, J=1.2 Hz, J=2.9 Hz, 1H), 9.94 (s, 1H).

Step 4: preparation of intermediate 4-(3,4-dihydro-2H-1-benzopyran-6-yl)-1-methyl-3-(thiophen-3-yl)-1H-pyrazole-5-carbaldehyde (4d)

Using the procedure described in example 1, step 4, 4-bromo-1-methyl-3-(thiophen-3-yl)-1H-pyrazole-5-carbaldehyde (4c) (150 mg, 0.55 mmol) is converted, after purification by preparative TLC (cyclohexane/ethyl acetate 80/20), into 4-(3,4-dihydro-2H-1-benzopyran-6-yl)-1-methyl-3-(thiophen-3-yl)-1H-pyrazole-5-carbaldehyde (4d) (150 mg, 0.46 mmol, 83%).

$^1$H NMR (400 MHz, CDCl$_3$) δ 2.01-2.10 (m, 2H), 2.80 (t, J=6.5 Hz, 2H), 4.24 (s, 3H), 4.25 (t, J=5.2 Hz, 2H), 6.85 (d, J=8.3 Hz, 1H), 7.02 (d, J=2.1 Hz, 1H), 7.06 (dd, J=2.1 Hz, J=8.3 Hz, 1H), 7.23-7.29 (m, 3H), 9.60 (s, 1H).

Step 5: preparation of intermediate methyl 2-[4-(3,4-dihydro-2H-1-benzopyran-6-yl)-1-methyl-3-(thiophen-3-yl)-1H-pyrazol-5-yl]-2-hydroxyacetate (4e)

Under nitrogen atmosphere, to a solution of 4-(3,4-dihydro-2H-1-benzopyran-6-yl)-1-methyl-3-(thiophen-3-yl)-1H-pyrazole-5-carbaldehyde (4d) (150 mg, 0.46 mmol) in anhydrous dichloromethane (2 mL) at 0° C. were successively added zinc iodide (15 mg, 0.05 mmol) and trimethylsilyl cyanide (69 μL, 0.55 mmol). The reaction mixture was stirred at room temperature for 2 hours. A saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (3 mL) was added to a solution of acetyl chloride (0.39 mL, 5.55 mmol) in anhydrous methanol (2 mL), previously stirred for 20 minutes at 0° C. under nitrogen atmosphere. The mixture was stirred at room temperature for 24 hours. The solution was concentrated in vacuo and saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (cyclohexane/ethyl acetate 45/55) to provide methyl 2-[4-(3,4-dihydro-2H-1-benzopyran-6-yl)-1-methyl-3-(thiophen-3-yl)-1H-pyrazol-5-yl]-2-hydroxyacetate (4e) (117 mg, 0.30 mmol, 66%).

$^1$H NMR (400 MHz, CDCl$_3$) δ 1.98-2.07 (m, 2H), 2.76 (t, J=6.5 Hz, 2H), 3.42 (bs, 1H), 3.73 (s, 3H), 3.89 (s, 3H), 4.22 (t, J=5.2 Hz, 2H), 5.21 (s, 1H), 6.79 (d, J=8.3 Hz, 1H), 6.95 (d, J=2.1 Hz, 1H), 6.99 (dd, J=2.1 Hz, J=8.3 Hz, 1H), 7.13 (dd, J=1.2 Hz, J=2.9 Hz, 1H), 7.19 (dd, J=2.9 Hz, J=5.0 Hz, 1H), 7.23 (dd, J=1.2 Hz, J=5.0 Hz, 1H).

Step 6: preparation of intermediate methyl 2-(tert-butoxy)-2-[4-(3,4-dihydro-2H-1-benzopyran-6-yl)-1-methyl-3-(thiophen-3-yl)-1H-pyrazol-5-yl]acetate (4f)

Using the procedure described in example 1, step 6, methyl 2-[4-(3,4-dihydro-2H-1-benzopyran-6-yl)-1-methyl-3-(thiophen-3-yl)-1H-pyrazol-5-yl]-2-hydroxyacetate (4e) (117 mg, 0.30 mmol) is converted, after purification by preparative TLC (dichloromethane/ethyl acetate 85/15), into methyl 2-(tert-butoxy)-2-[4-(3,4-dihydro-2H-1-benzopyran-6-yl)-1-methyl-3-(thiophen-3-yl)-1H-pyrazol-5-yl]acetate (4f) (74 mg, 0.22 mmol, 74%).

$^1$H NMR (400 MHz, CDCl$_3$) δ 1.05 (s, 9H), 2.00-2.10 (m, 2H), 2.74-2.81 (m, 2H), 3.75 (s, 3H), 4.00 (s, 3H), 4.21-4.28 (m, 2H), 5.03 (s, 1H), 6.79-6.85 (m, 1H), 6.95-7.05 (m, 2H), 7.11-7.16 (m, 1H), 7.16-7.21 (m, 1H), 7.23-7.28 (m, 1H).

MS m/z ([M+H]$^+$) 441.

Step 7: preparation of 2-(tert-butoxy)-2-[4-(3,4-dihydro-2H-1-benzopyran-6-yl)-1-methyl-3-(thiophen-3-yl)-1H-pyrazol-5-yl]acetic acid (example 4)

Using the procedure described in example 1, step 7, methyl 2-(tert-butoxy)-2-[4-(3,4-dihydro-2H-1-benzopyran-6-yl)-1-methyl-3-(thiophen-3-yl)-1H-pyrazol-5-yl]acetate (4f) (99 mg, 0.22 mmol) is converted into 2-(tert-butoxy)-2-[4-(3,4-dihydro-2H-1-benzopyran-6-yl)-1-methyl-3-(thiophen-3-yl)-1H-pyrazol-5-yl]acetic acid (example 4) (80 mg, 0.19 mmol, 83%).

$^1$H NMR (400 MHz, CDCl$_3$) δ 1.09 (s, 9H), 1.99-2.08 (m, 2H), 2.74-2.81 (m, 2H), 3.96 (s, 3H), 4.21-4.27 (m, 2H), 5.10 (s, 1H), 6.79-6.84 (m, 1H), 7.02-7.08 (m, 2H), 7.15-7.20 (m, 2H), 7.21-7.25 (m, 1H).

MS m/z ([M−H]$^-$) 425.
MS m/z ([M+H]$^+$) 427.

Example 5 synthesis of 2-(tert-butoxy)-2-[4-(4,4-dimethylcyclohex-1-en-1-yl)-1-methyl-3-(thiophen-3-yl)-1H-pyrazol-5-yl]acetic acid

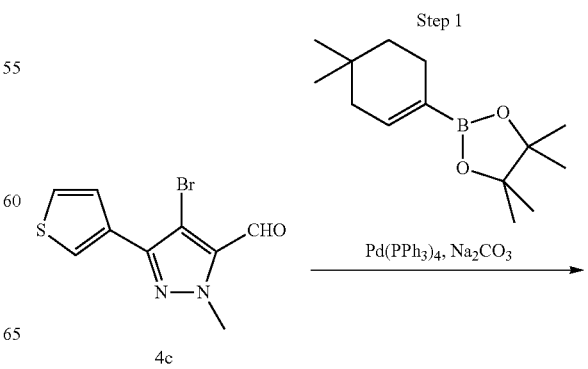

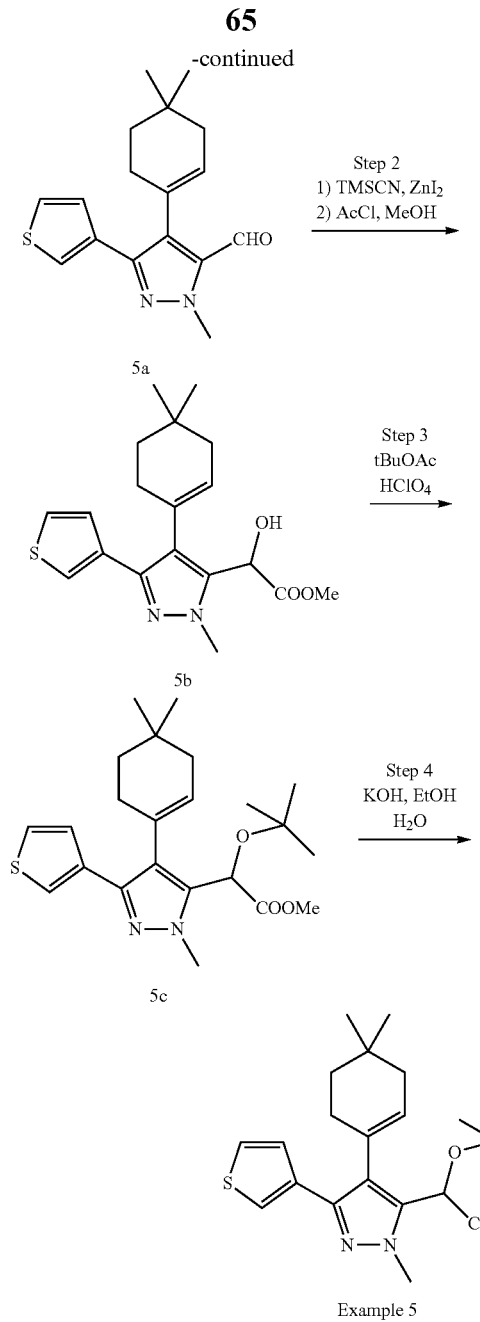

Example 5

Step 1: preparation of intermediate 4-(4,4-dimethylcyclohex-1-en-1-yl)-1-methyl-3-(thiophen-3-yl)-1H-pyrazole-5-carbaldehyde (5a)

Using the procedure described in example 1, step 4,4-bromo-1-methyl-3-(thiophen-3-yl)-1H-pyrazole-5-carbaldehyde (4c) (147 mg, 0.54 mmol) is converted, after purification by preparative TLC (cyclohexane/ethyl acetate 80/20), into 4-(4,4-dimethylcyclohex-1-en-1-yl)-1-methyl-3-(thiophen-3-yl)-1H-pyrazole-5-carbaldehyde (5a) (119 mg, 0.40 mmol, 73%).

$^1$H NMR (400 MHz, CDCl$_3$) δ 1.01 (s, 6H), 1.45-1.52 (m, 2H), 2.01-2.07 (m, 2H), 2.12-2.19 (m, 2H), 4.18 (s, 3H), 5.79-5.84 (m, 1H), 7.32-7.37 (m, 1H), 7.43-7.48 (m, 1H), 7.51-7.56 (m, 1H), 9.70 (s, 1H).

MS m/z ([M+H]$^+$) 301.

Step 2: preparation of intermediate methyl 2-[4-(4,4-dimethylcyclohex-1-en-1-yl)-1-methyl-3-(thiophen-3-yl)-1H-pyrazol-5-yl]-2-hydroxyacetate (5b)

Under nitrogen atmosphere, to a solution of 4-(4,4-dimethylcyclohex-1-en-1-yl)-1-methyl-3-(thiophen-3-yl)-1H-pyrazole-5-carbaldehyde (5a) (119 mg, 0.40 mmol) in anhydrous dichloromethane (2 mL) at 0° C. were successively added zinc iodide (13 mg, 0.04 mmol) and trimethylsilyl cyanide (59 μL, 0.48 mmol). The mixture was stirred at room temperature for 2 days. A saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (3 mL) was added to a solution of acetyl chloride (0.34 mL, 4.75 mmol) in anhydrous methanol (2 mL), previously stirred for 20 minutes at 0° C. under nitrogen atmosphere. The mixture was stirred at room temperature for 24 hours. The solution was concentrated in vacuo and saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (dichloromethane/ethyl acetate 70/30) to provide methyl 2-[4-(4,4-dimethylcyclohex-1-en-1-yl)-1-methyl-3-(thiophen-3-yl)-1H-pyrazol-5-yl]-2-hydroxyacetate (5b) (88 mg, 0.24 mmol, 61%).

$^1$H NMR (300 MHz, CDCl$_3$) δ 0.99 (s, 6H), 1.39-1.48 (m, 2H), 1.95-2.15 (m, 4H), 3.36 (d, J=3.0 Hz, 1H), 3.81 (s, 3H), 3.84 (s, 3H), 5.29 (d, J=3.0 Hz, 1H), 5.69-5.75 (m, 1H), 7.30 (dd, J=2.9 Hz, J=5.0 Hz, 1H), 7.44 (dd, J=1.2 Hz, J=5.0 Hz, 1H), 7.49 (dd, J=1.2 Hz, J=2.9 Hz, 1H).

Step 3: preparation of intermediate methyl 2-(tert-butoxy)-2-[4-(4,4-dimethylcyclohex-1-en-1-yl)-1-methyl-3-(thiophen-3-yl)-1H-pyrazol-5-yl]acetate (5c)

Using the procedure described in example 1, step 6, methyl 2-[4-(4,4-dimethylcyclohex-1-en-1-yl)-1-methyl-3-(thiophen-3-yl)-1H-pyrazol-5-yl]-2-hydroxyacetate (5b) (88 mg, 0.24 mmol) is converted, after purification by preparative TLC (dichloromethane/7M ammonia in methanol 99/1), into methyl 2-(tert-butoxy)-2-[4-(4,4-dimethylcyclohex-1-en-1-yl)-1-methyl-3-(thiophen-3-yl)-1H-pyrazol-5-yl]acetate (5c) (79 mg, 0.19 mmol, 78%).

$^1$H NMR (300 MHz, CDCl$_3$) δ 1.01 (s, 3H), 1.03 (s, 3H), 1.19 (s, 9H), 1.38-1.50 (m, 2H), 1.90-2.07 (m, 3H), 2.10-2.20 (m, 1H), 3.71 (s, 3H), 3.97 (s, 3H), 5.23 (s, 1H), 5.72-5.79 (m, 1H), 7.29 (dd, J=2.9 Hz, J=5.0 Hz, 1H), 7.45 (dd, J=1.2 Hz, J=5.0 Hz, 1H), 7.48 (dd, J=1.2 Hz, J=2.9 Hz, 1H).

MS m/z ([M+H]$^+$) 417.

Step 4: preparation of 2-(tert-butoxy)-2-[4-(4,4-dimethylcyclohex-1-en-1-yl)-1-methyl-3-(thiophen-3-yl)-1H-pyrazol-5-yl]acetic acid (example 5)

Using the procedure described in example 1, step 7, methyl 2-(tert-butoxy)-2-[4-(4,4-dimethylcyclohex-1-en-1-yl)-1-methyl-3-(thiophen-3-yl)-1H-pyrazol-5-yl]acetate (5c) (79 mg, 0.19 mmol) is converted into 2-(tert-butoxy)-2-[4-(4,4-dimethylcyclohex-1-en-1-yl)-1-methyl-3-(thiophen-3-yl)-1H-pyrazol-5-yl]acetic acid (example 5) (58 mg, 0.14 mmol, 76%).

$^1$H NMR (300 MHz, CDCl$_3$) δ 0.99 (s, 3H), 1.01 (s, 3H), 1.22 (s, 9H), 1.34-1.52 (m, 2H), 1.87-2.06 (m, 3H), 2.14-2.29 (m, 1H), 3.92 (s, 3H), 5.27 (s, 1H), 5.81-5.89 (m, 1H), 7.29 (dd, J=2.9 Hz, J=5.0 Hz, 1H), 7.41 (dd, J=1.2 Hz, J=5.0 Hz, 1H), 7.47 (dd, J=1.2 Hz, J=2.9 Hz, 1H).

MS m/z ([M−H]$^−$) 401

MS m/z ([M+H]$^+$) 403. .

Example 6 synthesis of 2-(tert-butoxy)-2-[4-(4,4-dimethylcyclo-hex-1-en-1-yl)-1-methyl-3-(thiophen-2-yl)-1H-pyrazol-5-yl]acetic acid

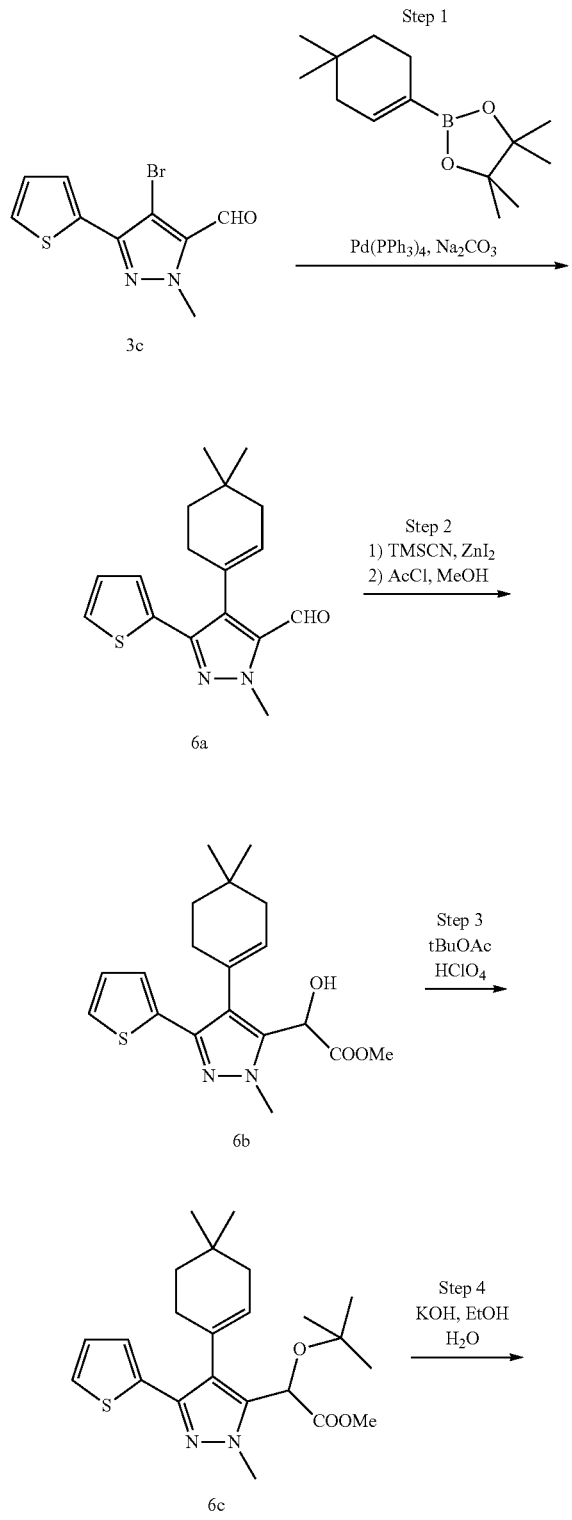

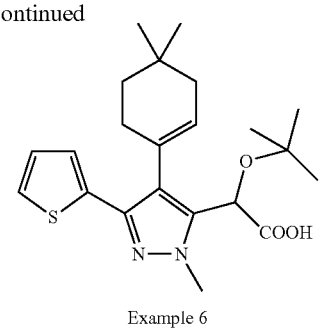

Example 6

Step 1: preparation of intermediate 4-(4,4-dimethylcyclohex-1-en-1-yl)-1-methyl-3-(thiophen-2-yl)-1H-pyrazole-5-carbaldehyde (6a)

Using the procedure described in example 1, step 4,4-bromo-1-methyl-3-(thiophen-2-yl)-1H-pyrazole-5-carbaldehyde (3c) (200 mg, 0.74 mmol) is converted, after purification by preparative TLC (cyclohexane/ethyl acetate 80/20), into 4-(4,4-dimethylcyclohex-1-en-1-yl)-1-methyl-3-(thiophen-2-yl)-1H-pyrazole-5-carbaldehyde (6a) (138 mg, 0.46 mmol, 62%).

$^1$H NMR (400 MHz, CDCl$_3$) δ 1.02 (s, 6H), 1.51 (t, J=6.3 Hz, 2H), 2.02-2.07 (m, 2H), 2.17-2.24 (m, 2H), 4.17 (s, 3H), 5.80-5.85 (m, 1H), 7.05 (dd, J=3.6 Hz, J=5.1 Hz, 1H), 7.28 (dd, J=1.1 Hz, J=5.1 Hz, 1H), 7.31 (dd, J=1.1 Hz, J=3.6 Hz, 1H), 9.70 (s, 1H).

Ms m/z ([M+H]$^+$) 301.

Step 2: preparation of intermediate methyl 2-[4-(4,4-dimethylcyclohex-1-en-1-yl)-1-methyl-3-(thiophen-2-yl)-1H-pyrazol-5-yl]-2-hydroxyacetate (6b)

Using the procedure described in example 1, step 5, 4-(4,4-dimethylcyclohex-1-en-1-yl)-1-methyl-3-(thiophen-2-yl)-1H-pyrazole-5-carbaldehyde (6a) (138 mg, 0.46 mmol) is converted, after purification by preparative TLC (dichloromethane/ethyl acetate 80/20), to methyl 2-[4-(4,4-dimethylcyclohex-1-en-1-yl)-1-methyl-3-(thiophen-2-yl)-1H-pyrazol-5-yl]-2-hydroxyacetate (6b) (120 mg, 0.33 mmol, 72%).

$^1$H NMR (300 MHz, CDCl$_3$) δ 0.99 (s, 3H), 1.00 (s, 3H), 1.46 (t, J=6.3 Hz, 2H), 1.95-2.03 (m, 2H), 2.06-2.18 (m, 2H), 3.36 (bs, 1H), 3.81 (s, 3H), 3.84 (s, 3H), 5.27 (s, 1H), 5.68-5.75 (m, 1H), 7.02 (dd, J=3.6 Hz, J=5.1 Hz, 1H), 7.23 (dd, J=1.1 Hz, J=5.1 Hz, 1H), 7.26 (dd, J=1.1 Hz, J=3.6 Hz, 1H).

MS m/z ([M+H]$^+$) 361.

Step 3: preparation of intermediate methyl 2-(tert-butoxy)-2-[4-(4,4-dimethylcyclohex-1-en-1-yl)-1-methyl-3-(thiophen-2-yl)-1H-pyrazol-5-yl]acetate (6c)

Using the procedure described in example 1, step 6, methyl 2-[4-(4,4-dimethylcyclohex-1-en-1-yl)-1-methyl-3-(thiophen-2-yl)-1H-pyrazol-5-yl]-2-hydroxyacetate (6b) (120 mg, 0.33 mmol) is converted, after purification by preparative TLC (dichloromethane/ethyl acetate 97/03), into methyl 2-(tert-butoxy)-2-[4-(4,4-dimethylcyclohex-1-en-1-yl)-1-methyl-3-(thiophen-2-yl)-1H-pyrazol-5-yl]acetate (6c) (92 mg, 0.22 mmol, 66%).

$^1$H NMR (300 MHz, CDCl$_3$) δ 1.03 (s, 3H), 1.04 (s, 3H), 1.19 (s, 9H), 1.38-1.55 (m, 2H), 1.94-2.31 (m, 4H), 3.71 (s, 3H), 3.97 (s, 3H), 5.20 (s, 1H), 5.71-5.79 (m, 1H), 7.01 (dd, J=3.6 Hz, J=5.1 Hz, 1H), 7.21 (dd, J=1.1 Hz, J=5.1 Hz, 1H), 7.24 (dd, J=1.1 Hz, J=3.6 Hz, 1H).

Step 4: preparation of 2-(tert-butoxy)-2-[4-(4,4-dimethylcyclohex-1-en-1-yl)-1-methyl-3-(thiophen-2-yl)-1H-pyrazol-5-yl]acetic acid (example 6)

Using the procedure described in example 1, step 7, methyl 2-(tert-butoxy)-2-[4-(4,4-dimethylcyclohex-1-en-1-yl)-1-methyl-3-(thiophen-2-yl)-1H-pyrazol-5-yl]acetate (6c) (92 mg, 0.22 mmol) is converted into 2-(tert-butoxy)-2-[4-(4,4-dimethylcyclohex-1-en-1-yl)-1-methyl-3-(thiophen-2-yl)-1H-pyrazol-5-yl]acetic acid (example 6) (88 mg, 0.22 mmol, 99%).

$^1$H NMR (300 MHz, CDCl$_3$) δ 1.01 (s, 3H), 1.02 (s, 3H), 1.23 (s, 9H), 1.39-1.54 (m, 2H), 1.92-2.37 (m, 4H), 3.92 (s, 3H), 5.25 (s, 1H), 5.80-5.87 (m, 1H), 7.01 (dd, J=3.6 Hz, J=5.1 Hz, 1H), 7.22 (dd, J=1.1 Hz, J=5.1 Hz, 1H), 7.24 (dd, J=1.1 Hz, J=3.6 Hz, 1H).

Ms m/z ([M−H]$^-$) 401.

MS m/z ([M+H]$^+$) 403.

Example 7 synthesis of 2-(tert-butoxy)-2-[1-methyl-4-(5-methyl-3,4-dihydro-2H-1-benzopyran-6-yl)-3-(thiophen-2-yl)-1H-pyrazol-5-yl]acetic acid

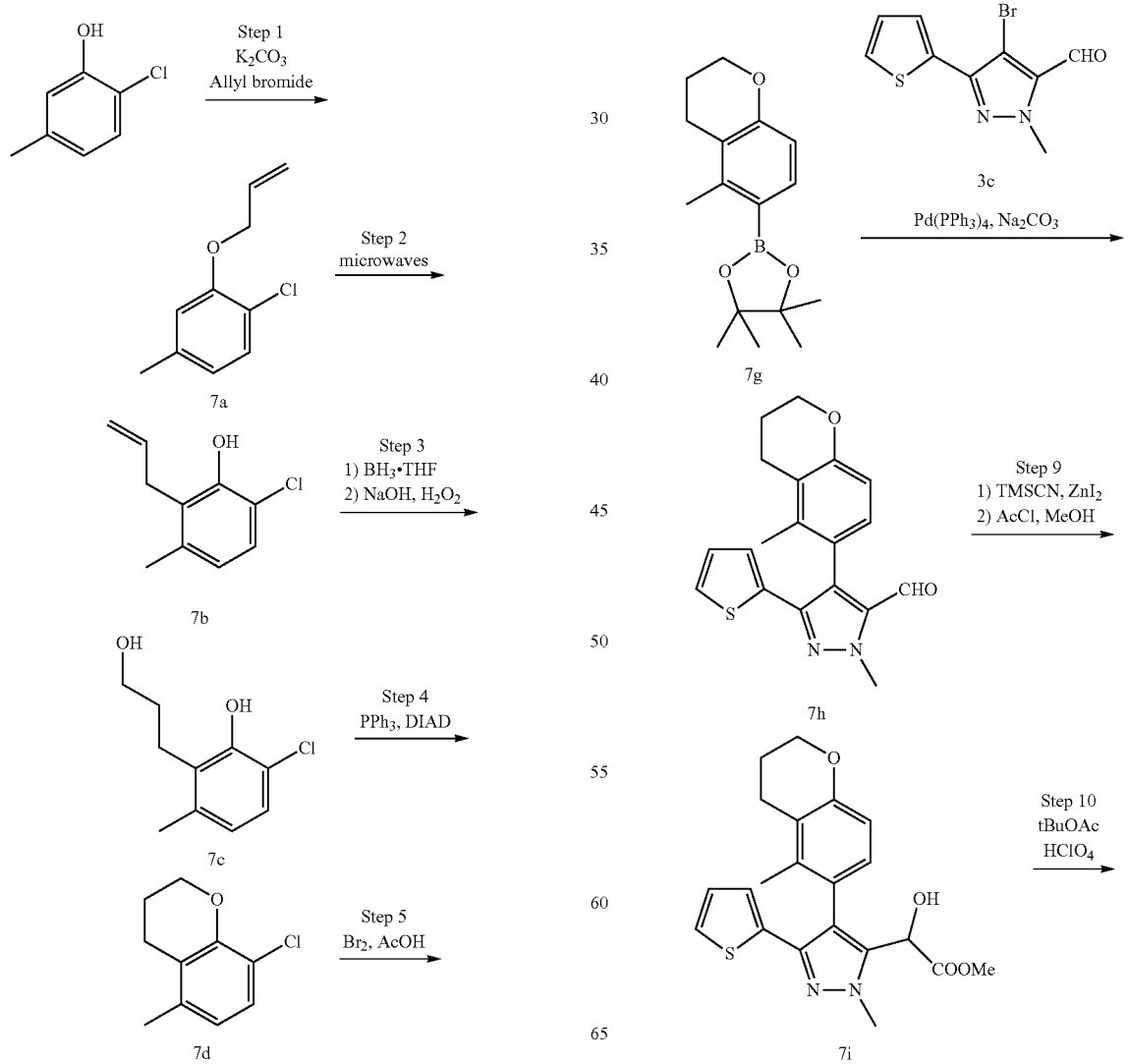

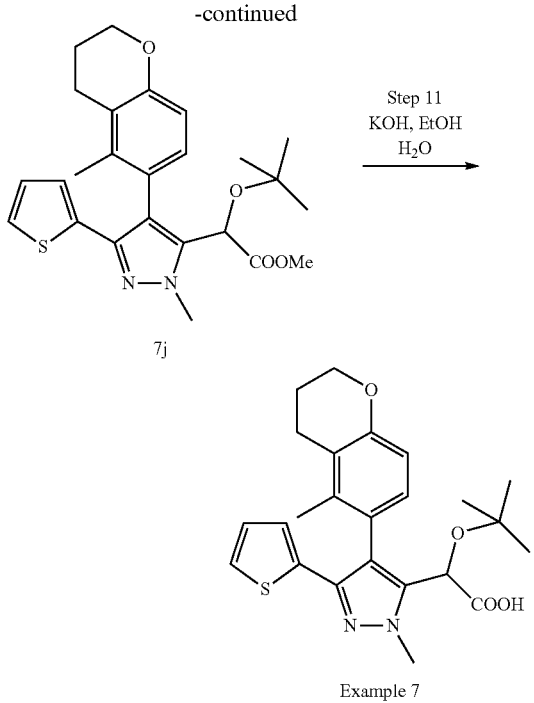

Example 7

Step 1: preparation of intermediate 1-chloro-4-methyl-2-(prop-2-en-1-yloxy)benzene (7a)

To a suspension of 2-chloro-5-methylphenol (10.0 g, 0.07 mol) and potassium carbonate (11.7 g, 0.08 mol) in acetonitrile (200 mL) at 82° C., was dropwise added a solution of allyl bromide (9.6 mL, 0.11 mol) in acetonitrile (50 mL). The mixture was reflux overnight. Once at room temperature, the mixture was filtered and the precipitate rinsed with diethyl ether. The filtrate was then concentrated in vacuo. The residue was dissolved in diethyl ether (250 mL) and washed with a 2N sodium hydroxide solution (150 mL). The organic layer was dried over sodium sulfate and concentrated in vacuo to provide 1-chloro-4-methyl-2-(prop-2-en-1-yloxy)benzene (7a) (12.72 g, 0.07 mol, 99%) which was used without further purification.

$^1$H NMR (300 MHz, CDCl$_3$) δ 2.31 (s, 3H), 4.58-4.61 (m, 2H), 5.28-5.32 (m, 1H), 5.43-5.50 (m, 1H), 6.01-6.14 (m, 1H), 6.69-6.73 (m, 2H), 7.22 (d, J=8.0 Hz, 1H).

MS m/z ([M+H]$^+$) 183.

Step 2: preparation of intermediate 6-chloro-3-methyl-2-(prop-2-en-1-yl)phenol (7b)

1-chloro-4-methyl-2-(prop-2-en-1-yloxy)benzene (7a) (12.6 g, 0.07 mol) was irradiated in a microwaves for 20 minutes at 240° C. to provide 6-chloro-3-methyl-2-(prop-2-en-1-yl)phenol (7b) (12.6 g, 0.07 mol, 100%) which was used without further purification.

$^1$H NMR (300 MHz, CDCl$_3$) δ 2.26 (s, 3H), 3.45 (dt, J=5.9 Hz, J=1.6 Hz, 2H), 4.90-5.07 (m, 2H), 5.56 (s, 1H), 5.85-6.01 (m, 1H), 6.69 (d, J=8.2 Hz, 1H), 7.08 (d, J=8.2 Hz, 1H).

Step 3: preparation of intermediate 6-chloro-2-(3-hydroxypropyl)-3-methylphenol (7c)

Under nitrogen atmosphere, a solution of 6-chloro-3-methyl-2-(prop-2-en-1-yl)phenol (7b) (8.70 g, 47.6 mmol) in anhydrous tetrahydrofuran (300 mL) was cooled to 0° C. Borane-tetrahydrofuran complex, 1.0M solution in tetrahydrofuran (100 mL, 0.10 mol) was dropwise added. The reaction mixture was stirred at room temperature for 2 hours then cooled again to 0° C. A 10N sodium hydroxide solution (32.7 mL) was added dropwise, followed by a 30% hydrogen peroxide solution. The resulting mixture was warm to room temperature and stirred for 90 minutes. The reaction mixture was quenched with a 10% hydrochloric acid solution (163 mL). Layers were separated and the aqueous layer was extract with ethyl acetate (2×70 mL). The combined organics layers were washed with brine (3×100 mL) then cooled with an ice bath. A saturated solution of sodium sulfite (150 mL) was carefully added and the mixture was stirred for few minutes. The organic layer was separated, dried over sodium sulfate and concentrated in vacuo. The residue was purified by flash chromatography on silica gel (cyclohexane/ethyl acetate 100/0 to 75/25), to provide 6-chloro-2-(3-hydroxypropyl)-3-methylphenol (7c) (6.74 g, 33.6 mmol, 70%).

$^1$H NMR (300 MHz, CDCl$_3$) δ 1.76-1.88 (m, 2H), 2.28 (s, 3H), 2.81 (t, J=7.2 Hz, 2H), 3.63 (t, J=6.0 Hz, 2H), 6.69 (d, J=8.2 Hz, 1H), 7.08 (d, J=8.2 Hz, 1H).

Step 4: preparation of intermediate 8-chloro-5-methyl-3,4-dihydro-2H-1-benzopyran (7d)

Under nitrogen atmosphere, a solution of 6-chloro-2-(3-hydroxypropyl)-3-methylphenol (7c) (6.74 g, 33.6 mmol) in anhydrous tetrahydrofuran (500 mL) was cooled to 0° C. Triphenylphosphine (11.45 g, 43.7 mmol) was added, followed by diisopropyl azodicarboxylate (8.60 mL, 43.7 mmol). The reaction mixture was stirred for 16 hours at room temperature. After concentration in vacuo, the residue was dissolved in diethyl ether and the precipitate was filtered off. The filtrate was concentrated in vacuo and the residue was purified by flash chromatography on silica gel (cyclohexane/ethyl acetate 100/0 to 90/10), to provide 8-chloro-5-methyl-3,4-dihydro-2H-1-benzopyran (7d) (5.74 g, 31.4 mmol, 94%), as a light yellow oil.

$^1$H NMR (300 MHz, CDCl$_3$) δ 2.00-2.11 (m, 2H), 2.18 (s, 3H), 2.65 (t, J=6.6 Hz, 2H), 4.21-4.28 (m, 2H), 6.65 (d, J=8.1 Hz, 1H), 7.08 (d, J=8.1 Hz, 1H).

Step 5: preparation of intermediate 6-bromo-8-chloro-5-methyl-3,4-dihydro-2H-1-benzopyran (7e)

A mixture of the 8-chloro-5-methyl-3,4-dihydro-2H-1-benzopyran (7d) (5.74 g, 31.4 mmol) and acetic acid (75 mL) is treated with bromine (1.93 mL, 37.7 mmol) in AcOH (35 mL). The mixture was stirred at room temperature for 15 minutes, then diluted with toluene (100 mL). The mixture was concentrated in vacuo. The residue was dissolved in ethyl acetate (70 mL) and successively washed with a 15% sodium thiosulfate solution (50 mL) and a saturated solution of sodium hydrogenocarbonate (50 mL). The organic layer was dried over sodium sulfate and concentrated in vacuo. The product was recrystallized in ethanol, to provide 6-bromo-8-chloro-5-methyl-3,4-dihydro-2H-1-benzopyran (7e) (4.44 g, 17.0 mmol, 54%) as a white solid.

$^1$H NMR (300 MHz, CDCl$_3$) δ 1.99-2.11 (m, 2H), 2.27 (s, 3H), 2.71 (t, J=6.6 Hz, 2H), 4.18-4.26 (m, 2H), 7.41 (s, 1H).

Step 6: preparation of intermediate 2-(8-chloro-5-methyl-3,4-dihydro-2H-1-benzopyran-6-yl)-4,4,5,5-tetramethyl-1,3,2-dioxaborolane (7f)

[1,1'-Bis(diphenylphosphino)ferrocene]dichloropalladium(11) (761 mg, 0.93 mmol) was added to a previously degassed solution of 6-bromo-8-chloro-5-methyl-3,4-dihydro-2H-1-benzopyran (7e) (2.44 g, 9.33 mmol), bis(pinacolato)diboron (3.55 g, 14.0 mmol) and potassium acetate (3.20 g, 32.6 mmol) in anhydrous N,N-dimethylformamide (100 mL). The reaction mixture was heated at 95° C. for 16 hours. Water (50 mL) was added and the reaction mixture was concentrated in vacuo. The residue was taken in water (50 mL) and extracted with ethyl acetate (2×50 mL). The organic layer was washed with brine (30 mL) then dried over sodium sulfate, concentrated in vacuo, and co-elutated with toluene. The crude was purified by flash chromatography on silica gel (cyclohexane/ethyl acetate 100/0 to 98/2). The product was triturated in cyclohexane and filtered to provide 2-(8-chloro-5-methyl-3,4-dihydro-2H-1-benzopyran-6-yl)-4,4,5,5-tetramethyl-1,3,2-dioxaborolane (7f) (1.62 g, 5.24 mmol, 58%) as a white solid.

$^{1}$H NMR (300 MHz, CDCl$_3$) δ 1.33 (s, 12H), 1.99-2.11 (m, 2H), 2.40 (s, 3H), 2.65 (t, J=6.6 Hz, 2H), 4.19-4.30 (m, 2H), 7.63 (s, 1H).

Step 7: preparation of intermediate 4,4,5,5-tetramethyl-2-(5-methyl-3,4-dihydro-2H-1-benzopyran-6-yl)-1,3,2-dioxaborolane (7g)

Palladium on activated charcoal (10% Pd by weight, 120 mg) was added to a solution of 2-(8-chloro-5-methyl-3,4-dihydro-2H-1-benzopyran-6-yl)-4,4,5,5-tetramethyl-1,3,2-dioxaborolane (7f) (1.20 g, 3.89 mmol) and ammonium formate (2.45 g, 38.89 mmol) in methanol (20 mL). The mixture was refluxed for 60 minutes. The mixture was then cooled to room temperature, filtered through a pad of Celite® and rinsed with methanol. The filtrate was concentrated in vacuo. The residue was dissolved in ethyl acetate (20 mL) and washed with water (20 mL). The organic layer was dried over sodium sulfate, concentrated in vacuo to provide 4,4,5,5-tetramethyl-2-(5-methyl-3,4-dihydro-2H-1-benzopyran-6-yl)-1,3,2-dioxaborolane (7g) (1.00 g, 3.66 mmol, 94%) as a white solid, which was used without further purification.

$^{1}$H NMR (300 MHz, CDCl$_3$) δ 1.32 (s, 12H), 1.96-2.10 (m, 2H), 2.43 (s, 3H), 2.65 (t, J=6.6 Hz, 2H), 4.09-4.17 (m, 2H), 6.66 (d, J=8.3 Hz, 1H), 7.55 (d, J=8.3 Hz, 1H).

Step 8: preparation of intermediate 1-methyl-4-(5-methyl-3,4-dihydro-2H-1-benzopyran-6-yl)-3-(thiophen-2-yl)-1H-pyrazole-5-carbaldehyde (7h)

Using the procedure described in example 1, step 4,4-bromo-1-methyl-3-(thiophen-2-yl)-1H-pyrazole-5-carbaldehyde (3c) (84 mg, 0.31 mmol) is converted by reaction with 4,4,5,5-tetramethyl-2-(5-methyl-3,4-dihydro-2H-1-benzopyran-6-yl)-1,3,2-dioxaborolane (7g) (102 mg, 0.372 mmol) into 1-methyl-4-(5-methyl-3,4-dihydro-2H-1-benzopyran-6-yl)-3-(thiophen-2-yl)-1H-pyrazole-5-carbaldehyde (7h) (103 mg, 0.30 mmol, 98%), after purification by preparative TLC (cyclohexane/ethyl acetate 70/30).

$^{1}$H NMR (300 MHz, CDCl$_3$) δ 1.95 (s, 3H), 2.04-2.16 (m, 2H), 2.69 (t, J=6.5 Hz, 2H), 4.18-4.24 (m, 2H), 4.25 (s, 3H), 6.76 (d, J=8.4 Hz, 1H), 6.80 (dd, J=1.1 Hz, J=3.6 Hz, 1H), 6.88 (dd, J=3.6 Hz, J=5.0 Hz, 1H), 7.01 (d, J=8.4 Hz, 1H), 7.17 (dd, J=1.1 Hz, J=5.0 Hz, 1H), 9.43 (s, 1H).

MS m/z ([M+H]$^+$) 339.

Step 9: preparation of intermediate methyl 2-hydroxy-2-[1-methyl-4-(5-methyl-3,4-dihydro-2H-1-benzopyran-6-yl)-3-(thiophen-2-yl)-1H-pyrazol-5-yl]acetate (7i)

Under nitrogen atmosphere, to a solution of 1-methyl-4-(5-methyl-3,4-dihydro-2H-1-benzopyran-6-yl)-3-(thiophen-2-yl)-1H-pyrazole-5-carbaldehyde (7h) (103 mg, 0.30 mmol) in anhydrous dichloromethane (2 mL) at 0° C. were successively added zinc iodide (10 mg, 0.03 mmol) and trimethylsilyl cyanide (46 µL, 0.37 mmol). The mixture was stirred at room temperature for 88 hours then heated at 40° C. for 4 hours. A saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (1 mL), was added to a solution of acetyl chloride (0.26 mL, 3.65 mmol) in anhydrous methanol (2 mL), previously stirred for 20 minutes at 0° C. under nitrogen atmosphere. The mixture was stirred at room temperature overnight. The solution was concentrated in vacuo and a saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (dichloromethane/ethyl acetate 80/20) to provide methyl 2-hydroxy-2-[1-methyl-4-(5-methyl-3,4-dihydro-2H-1-benzopyran-6-yl)-3-(thiophen-2-yl)-1H-pyrazol-5-yl]acetate (7i) (79 mg, 0.20 mmol, 65%).

$^{1}$H NMR (300 MHz, CDCl$_3$) δ 1.93 (s, 3H), 2.05-2.15 (m, 2H), 2.67 (t, J=6.5 Hz, 2H), 3.69 and 3.71 (s, 3H), 3.91 and 3.92 (s, 3H), 4.14-4.23 (m, 2H), 5.05 and 5.06 (s, 1H), 6.68 and 6.71 (dd, J=1.1 Hz, J=3.6 Hz, 1H), 6.72 (d, J=8.3 Hz, 1H), 6.81-6.87 (m, 1H), 6.92 and 6.97 (d, J=8.3 Hz, 1H), 7.10 and 7.11 (m, 1H).

Step 10: preparation of intermediate methyl 2-(tert-butoxy)-2-[1-methyl-4-(5-methyl-3,4-dihydro-2H-1-benzopyran-6-yl)-3-(thiophen-2-yl)-1H-pyrazol-5-yl]acetate (7j)

Using the procedure described in example 1, step 6, methyl 2-hydroxy-2-[1-methyl-4-(5-methyl-3,4-dihydro-2H-1-benzopyran-6-yl)-3-(thiophen-2-yl)-1H-pyrazol-5-yl]acetate (7i) (79 mg, 0.20 mmol) is converted, after purification by preparative TLC (dichloromethane/ethyl acetate 95/5), into methyl 2-(tert-butoxy)-2-[1-methyl-4-(5-methyl-3,4-dihydro-2H-1-benzopyran-6-yl)-3-(thiophen-2-yl)-1H-pyrazol-5-yl]acetate (7j) (55 mg, 0.12 mmol, 61%).

$^{1}$H NMR (300 MHz, CDCl$_3$) δ 1.04 and 1.15 (s, 9H), 1.87 and 1.89 (s, 3H), 2.03-2.17 (m, 2H), 2.64 and 2.70 (t, J=6.6 Hz, 2H), 3.65 and 3.75 (s, 3H), 4.00 and 4.03 (s, 3H), 4.17-4.25 (m, 2H), 4.86 and 4.88 (s, 1H), 6.64 and 6.67 (dd, J=1.1 Hz, J=3.6 Hz, 1H), 6.72 and 6.76 (d, J=8.4 Hz, 1H), 6.79-6.86 (m, 1H), 6.92 and 7.02 (d, J=8.4 Hz, 1H), 7.08 and 7.10 (dd, J=1.1 Hz, J=5.2 Hz, 1H).

MS m/z ([M+H]$^+$) 455.

Step 11: preparation of 2-(tert-butoxy)-2-[1-methyl-4-(5-methyl-3,4-dihydro-2H-1-benzopyran-6-yl)-3-(thiophen-2-yl)-1H-pyrazol-5-yl]acetic acid (example 7)

Using the procedure described in example 1, step 7, methyl 2-(tert-butoxy)-2-[1-methyl-4-(5-methyl-3,4-dihydro-2H-1-benzopyran-6-yl)-3-(thiophen-2-yl)-1H-pyrazol-5-yl]acetate (7j) (55 mg, 0.12 mmol) is converted into 2-(tert-butoxy)-2-[1-methyl-4-(5-methyl-3,4-dihydro-2H-1-benzopyran-6-yl)-3-(thiophen-2-yl)-1H-pyrazol-5-yl]acetic acid (example 7) (53 mg, 0.12 mmol, 99%).

$^{1}$H NMR (300 MHz, CDCl$_3$) δ 1.08 and 1.18 (s, 9H), 1.86 and 1.97 (s, 3H), 2.02-2.14 (m, 2H), 2.63 and 2.69 (t, J=6.5 Hz, 2H), 3.97 and 3.99 (s, 3H), 4.16-4.23 (m, 2H), 4.91 and 4.99 (s, 1H), 6.67 and 6.70 (dd, J=1.1 Hz, J=3.6 Hz, 1H), 6.71 and 6.77 (d, J=8.4 Hz, 1H), 6.80-6.86 (m, 1H), 6.92 and 7.17 (d, J=8.4 Hz, 1H), 7.09 and 7.11 (dd, J=1.1 Hz, J=5.0 Hz, 1H).

MS m/z ([M−H]$^−$) 439.

MS m/z ([M+H]$^+$) 441.

Example 8 synthesis of 2-(tert-butoxy)-2-[4-(3,4-dihydro-2H-1-benzopyran-6-yl)-1-methyl-3-(1,3-thiazol-2-yl)-1H-pyrazol-5-yl]acetic acid

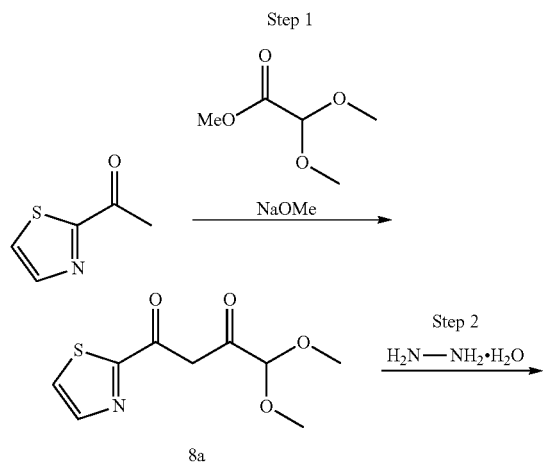

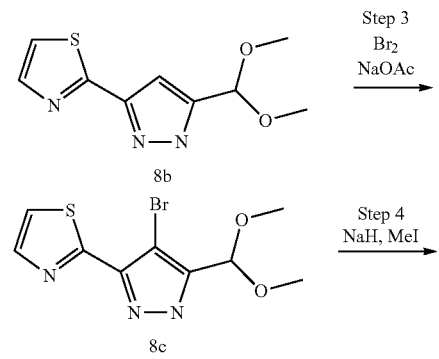

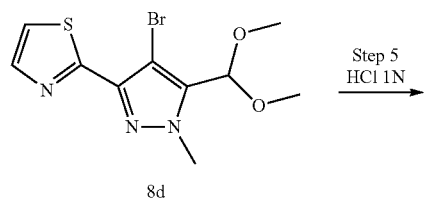

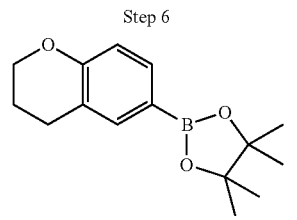

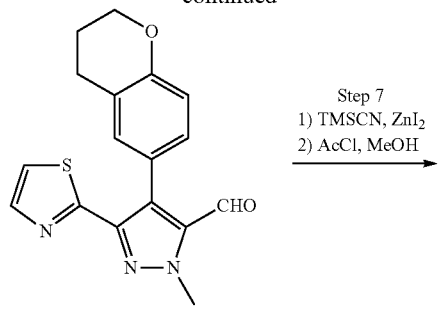

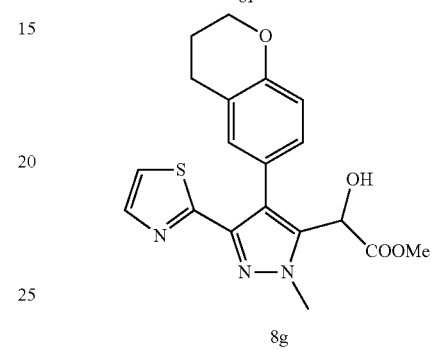

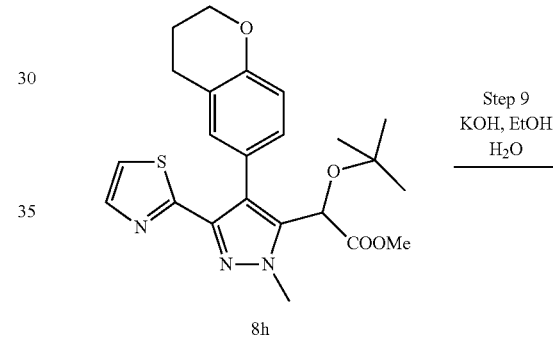

Step 1: preparation of intermediate 4,4-dimethoxy-1-(1,3-thiazol-2-yl)butane-1,3-dione (8a)

A mixture of 4-acetylthiazole (1.0 g, 7.86 mmol) and methyl dimethoxyacetate (1.05 g, 7.86 mmol) in anhydrous diethyl ether (15 mL) was treated with sodium methoxide 4.37M in methanol (1.80 mL, 7.86 mmol) at 0° C. The resulting mixture was stirred at room temperature for 3 hours, and then diluted with ethyl acetate (10 mL). After cooling to 0° C., the reaction mixture was neutralized with 1N hydrochloric acid until pH 3 was reached. Water was added (6 mL) and layers were separated. The organic layer was washed with brine (10 mL), dried over sodium sulfate and concentrated in vacuo to provide 4,4-dimethoxy-1-(1,3-thiazol-2-yl)butane-1,3-dione (8a) (1.58 g, 6.89 mmol, 88%) which was used without further purification.

MS m/z ([M−H]$^-$) 228.

Step 2: preparation of intermediate 2-[5-(dimethoxymethyl)-1H-pyrazol-3-yl]-1,3-thiazole (8b)

To a stirred slurry of 4,4-dimethoxy-1-(1,3-thiazol-2-yl)butane-1,3-dione (8a) (1.55 g, 6.76 mmol) in ethanol (63 mL) was added dropwise hydrazine monohydrate (0.38 mL, 7.77 mmol). The mixture was stirred at room temperature overnight, then concentrated in vacuo. A saturated solution of sodium hydrogenocarbonate (8 mL) was added to the residue and the aqueous layer was extracted with ethyl acetate (2×10 mL). The organic layer was dried over sodium sulfate and concentrated in vacuo. The resulting solid was triturated in diethyl ether and the precipitate was filtrated. The filtrate was concentrated and the treatment was repeated as much as necessary. The combined precipitates were dried in vacuo to provide 2-[5-(dimethoxymethyl)-1H-pyrazol-3-yl]-1,3-thiazole (8b) (714 mg, 3.17 mmol, 47%) which was used without further purification.

MS m/z ([M+H]$^+$) 226.

Step 3: preparation of intermediate 2-[4-bromo-5-(dimethoxymethyl)-1H-pyrazol-3-yl]-1,3-thiazole (8c)

Sodium acetate (0.26 g, 3.17 mmol) was added to a solution of 2-[5-(dimethoxymethyl)-1H-pyrazol-3-yl]-1,3-thiazole (8b) (714 mg, 3.17 mmol) in chloroform (7.7 mL) and acetic acid (7.7 mL). The mixture was stirred at room temperature for 1 hour. After cooling to 0° C., a solution of bromine (0.155 mL, 3.01 mmol) in acetic acid (1.8 mL) was added dropwise. The reaction mixture was stirred at the same temperature for 40 minutes before being diluted with dichloromethane (10 mL). The mixture was neutralized with 2N sodium hydroxyde to pH 6. The layers were separated and the aqueous layer was extracted with dichloromethane (10 mL). The combined organic layers were dried over sodium sulfate, concentrated in vacuo, and co-evaporated with toluene to provide 2-[4-bromo-5-(dimethoxymethyl)-1H-pyrazol-3-yl]-1,3-thiazole (8c) (900 mg, 2.96 mmol, 93%) which was used without further purification.

$^1$H NMR (400 MHz, CDCl$_3$) δ 3.43 (s, 6H), 5.60 (s, 1H), 7.46 (d, J=3.2 Hz, 1H), 8.00 (d, J=3.2 Hz, 1H).

MS m/z ([M+H]$^+$) 304/306.

Step 4: preparation of intermediate 2-[4-bromo-5-(dimethoxymethyl)-1-methyl-1H-pyrazol-3-yl]-1,3-thiazole (8d)

Under a nitrogen atmosphere, sodium hydride 60% in oil (0.236 g, 5.92 mmol) was added portionwise to a solution of 2-[4-bromo-5-(dimethoxymethyl)-1H-pyrazol-3-yl]-1,3-thiazole (8c) (900 mg, 2.96 mmol) in dry dimethylformamide (5 mL). After 10 minutes stirring, iodomethane (0.28 mL, 4.44 mmol) was added and the reaction mixture was stirred at room temperature for 40 minutes. Water (15 mL) was added and the mixture was extracted with ethyl acetate (2×15 mL). The organic layer was washed with brine (2×10 mL), dried over sodium sulfate and concentrated in vacuo. The residue was purified by flash chromatography on silica gel (dichloromethane/ethyl acetate 100/0 to 95/5) to provide 2-[4-bromo-5-(dimethoxymethyl)-1-methyl-1H-pyrazol-3-yl]-1,3-thiazole (8d) (586 mg, 1.84 mmol, 62%) and the regioisomer 2-[4-bromo-3-(dimethoxymethyl)-1-methyl-1H-pyrazol-5-yl]-1,3-thiazole (199 mg, 0.62 mmol, 21%).

$^1$H NMR (300 MHz, CDCl$_3$) δ 3.46 (s, 6H), 4.03 (s, 3H), 5.42 (s, 1H), 7.35 (d, J=3.2 Hz, 1H), 7.94 (d, J=3.2 Hz, 1H).

MS m/z ([M+H]$^+$) 318/320.

Step 5: preparation of intermediate 4-bromo-1-methyl-3-(1,3-thiazol-2-yl)-1H-pyrazole-5-carbaldehyde (8e)

A solution of 2-[4-bromo-5-(dimethoxymethyl)-1-methyl-1H-pyrazol-3-yl]-1,3-thiazole (8d) (586 mg, 1.84 mmol) in tetrahydrofuran (15 mL) was treated with 1N hydrochloric acid (2.26 mL) and the mixture was stirred at 50° C. for 5 hours. The reaction was cooled to room temperature and then neutralized with 1N sodium hydroxide (2.26 mL). The resulting mixture was extracted with ethyl acetate (2×15 mL) and the organic layer was dried over sodium sulfate and concentrated in vacuo to provide 4-bromo-1-methyl-3-(1,3-thiazol-2-yl)-1H-pyrazole-5-carbaldehyde (8e) (480 mg, 1.76 mmol, 96%) which was used without further purification.

$^1$H NMR (300 MHz, CDCl$_3$) δ 4.24 (s, 3H), 7.42 (d, J=3.2 Hz, 1H), 7.99 (d, J=3.2 Hz, 1H), 9.98 (s, 1H).

Step 6: preparation of intermediate 4-(3,4-dihydro-2H-1-benzopyran-6-yl)-1-methyl-3-(1,3-thiazol-2-yl)-1H-pyrazole-5-carbaldehyde (8f)

Using the procedure described in example 1, step 4,4-bromo-1-methyl-3-(1,3-thiazol-2-yl)-1H-pyrazole-5-carbaldehyde (8e) (200 mg, 0.73 mmol) is converted by reaction with 6-(4,4,5,5-tetramethyl-1,3,2-dioxaborolan-2-yl)chroman (226 mg, 0.87 mmol) into 4-(3,4-dihydro-2H-1-benzopyran-6-yl)-1-methyl-3-(1,3-thiazol-2-yl)-1H-pyrazole-5-carbaldehyde (8f) (171 mg, 0.53 mmol, 71%), after purification by preparative TLC (dichloromethane/ethyl acetate 95/5).

$^1$H NMR (300 MHz, CDCl$_3$) δ 1.99-2.10 (m, 2H), 2.81 (t, J=6.5 Hz, 2H), 4.24 (t, J=5.2 Hz, 2H), 4.28 (s, 3H), 6.86 (d, J=8.3 Hz, 1H), 7.13 (d, J=2.2 Hz, 1H), 7.17 (dd, J=8.3 Hz, J=2.2 Hz, 1H), 7.25 (d, J=3.2 Hz, 1H), 7.80 (d, J=3.2 Hz, 1H), 9.64 (s, 1H).

MS m/z ([M+H]$^+$) 326.

Step 7: preparation of intermediate methyl 2-[4-(3,4-dihydro-2H-1-benzopyran-6-yl)-1-methyl-3-(1,3-thiazol-2-yl)-1H-pyrazol-5-yl]-2-hydroxyacetate (8g)

Under nitrogen atmosphere, to a solution of 4-(3,4-dihydro-2H-1-benzopyran-6-yl)-1-methyl-3-(1,3-thiazol-2-yl)-1H-pyrazole-5-carbaldehyde (8f) (171 mg, 0.53 mmol) in anhydrous dichloromethane (2 mL) at 0° C. were successively added zinc iodide (17 mg, 0.05 mmol) and trimethylsilyl cyanide (79 µL, 0.63 mmol). The mixture was stirred at room temperature overnight and then heated at 40° C. for 4 days. After cooling to room temperature, a saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (3 mL) was added to a solution of acetyl chloride (0.45 mL, 6.30 mmol) in anhydrous methanol (2 mL), previously stirred for 20 minutes at 0° C. under nitrogen atmosphere. The mixture was stirred at room temperature overnight. The solution was concentrated in vacuo and saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (dichloromethane/7M ammonia in methanol 95/5) to provide methyl 2-[4-(3,4-dihydro-2H-1-benzopyran-6-yl)-1-methyl-3-(1,3-thiazol-2-yl)-1H-pyrazol-5-yl]-2-hydroxyacetate (8g) (86 mg, 0.22 mmol, 42%).

$^1$H NMR (400 MHz, CDCl$_3$) δ 1.97-2.08 (m, 2H), 2.78 (t, J=6.5 Hz, 2H), 3.74 (s, 3H), 3.94 (s, 3H), 4.22 (t, J=5.2 Hz, 2H), 5.24 (s, 1H), 6.81 (d, J=8.3 Hz, 1H), 7.03 (d, J=1.6 Hz, 1H), 7.06 (dd, J=8.3 Hz, J=1.6 Hz, 1H), 7.18 (d, J=3.2 Hz, 1H), 7.75 (d, J=3.2 Hz, 1H).

Step 8: preparation of intermediate methyl 2-(tert-butoxy)-2-[4-(3,4-dihydro-2H-1-benzopyran-6-yl)-1-methyl-3-(1,3-thiazol-2-yl)-1H-pyrazol-5-yl]acetate (8h)

Using the procedure described in example 1, step 6, methyl 2-[4-(3,4-dihydro-2H-1-benzopyran-6-yl)-1-methyl-3-(1,3-thiazol-2-yl)-1H-pyrazol-5-yl]-2-hydroxyacetate (8g) (86 mg, 0.22 mmol) is converted into methyl 2-(tert-butoxy)-2-[4-(3,4-dihydro-2H-1-benzopyran-6-yl)-1-methyl-3-(1,3-thiazol-2-yl)-1H-pyrazol-5-yl]acetate (8h) (50 mg, 0.11 mmol, 51%), after purification by preparative TLC (dichloromethane/ethyl acetate 65/45).

$^1$H NMR (400 MHz, CDCl$_3$) δ 1.04 (s, 9H), 1.99-2.10 (m, 2H), 2.73-2.87 (m, 2H), 3.76 (s, 3H), 4.04 (s, 3H), 4.24 (t, J=5.2 Hz, 2H), 5.06 (s, 1H), 6.83 (d, J=8.2 Hz, 1H), 7.04 (d, J=2.1 Hz, 1H), 7.08 (dd, J=8.2 Hz, J=2.1 Hz, 1H), 7.16 (d, J=3.2 Hz, 1H), 7.75 (d, J=3.2 Hz, 1H).

MS m/z ([M+H]$^+$) 442.

Step 9: preparation of 2-(tert-butoxy)-2-[4-(3,4-dihydro-2H-1-benzopyran-6-yl)-1-methyl-3-(1,3-thiazol-2-yl)-1H-pyrazol-5-yl]acetic acid (example 8)

A mixture of methyl 2-(tert-butoxy)-2-[4-(3,4-dihydro-2H-1-benzopyran-6-yl)-1-methyl-3-(1,3-thiazol-2-yl)-1H-pyrazol-5-yl]acetate (8h) (50 mg, 0.11 mmol) and potassium hydroxide (55 mg, 0.45 mmol) in a mixture of ethanol (1.0 mL) and water (1.0 mL) was refluxed overnight. The mixture was concentrated in vacuo. Water (2 mL) was added to the residue and the aqueous layer was washed with ethyl acetate (2 mL), acidified with 1M hydrochloric acid until pH 3 and extracted with ethyl acetate (2×3 mL). The organic layer was dried over sodium sulfate and concentrated in vacuo to provide 2-(tert-butoxy)-2-[4-(3,4-dihydro-2H-1-benzopyran-6-yl)-1-methyl-3-(1,3-thiazol-2-yl)-1H-pyrazol-5-yl]acetic acid (example 8) (45 mg, 0.10 mmol, 93%).

$^1$H NMR (400 MHz, CDCl$_3$) δ 1.06 (s, 9H), 1.99-2.08 (m, 2H), 2.71-2.86 (m, 2H), 3.99 (s, 3H), 4.24 (t, J=5.2 Hz, 2H), 5.12 (s, 1H), 6.83 (d, J=8.0 Hz, 1H), 7.09-7.16 (m, 2H), 7.19 (d, J=3.2 Hz, 1H), 7.78 (d, J=3.2 Hz, 1H).

MS m/z ([M−H]$^−$) 426.
MS m/z ([M+H]$^+$) 428.

Example 9 synthesis of 2-(tert-butoxy)-2-[4-(3,4-dihydro-2H-1-benzopyran-6-yl)-1-methyl-3-(pyridin-2-yl)-1H-pyrazol-5-yl]acetic acid

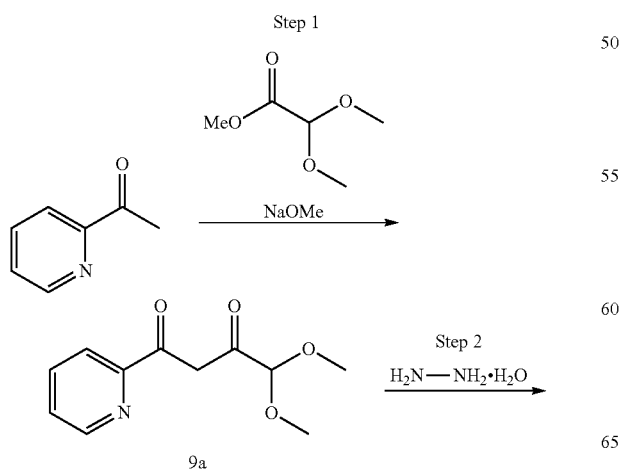

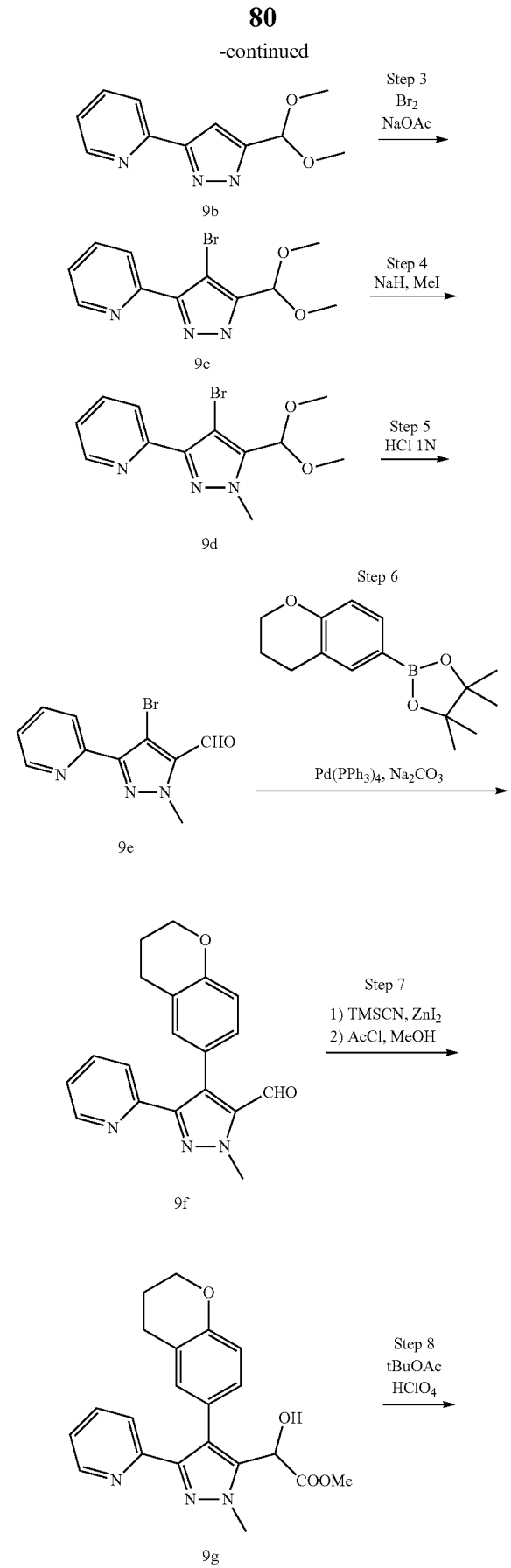

-continued

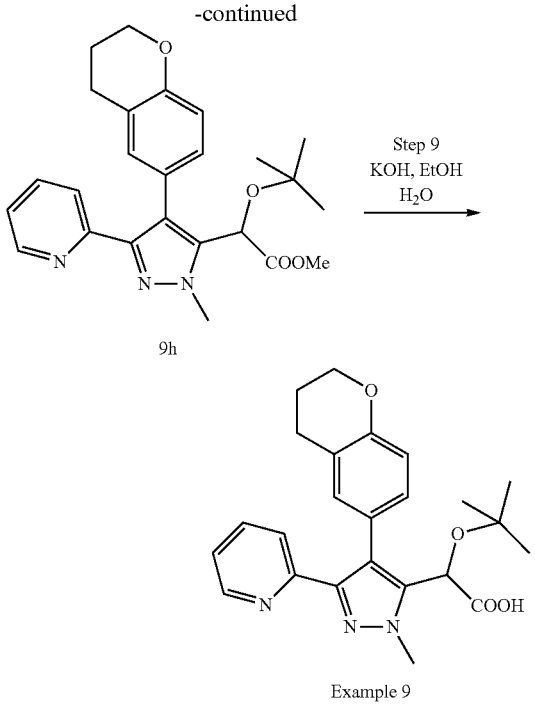

Example 9

Step 1: preparation of intermediate 4,4-dimethoxy-1-(pyridin-2-yl)butane-1,3-dione (9a)

A mixture of 2-acetylpyridine (3.0 g, 24.8 mmol) and methyl dimethoxyacetate (3.32 g, 24.8 mmol) in anhydrous diethyl ether (45 mL) was treated with sodium methoxide 4.37M in methanol (5.67 mL, 24.8 mmol) at 0° C. The resulting mixture was stirred at room temperature for 3 days, and then diluted with ethyl acetate (10 mL). After cooling to 0° C., the reaction mixture was neutralized with 1N hydrochloric acid until pH 6-7 was reached. Water was added (10 mL) and the layers were separated. The organic layer was washed with brine (25 mL), dried over sodium sulfate and concentrated in vacuo to provide 4,4-dimethoxy-1-(pyridin-2-yl)butane-1,3-dione (9a) (5.11 g, 22.9 mmol, 92%) which was used without further purification.

$^1$H NMR (400 MHz, CDCl$_3$) δ 3.44 (s, 6H), 4.87 (s, 1H), 7.17 (s, 1H), 7.43 (ddd, J=7.6 Hz, J=4.7 Hz, J=1.2 Hz, 1H), 7.84 (dt, J=7.6 Hz, J=1.7 Hz, 1H), 8.02-8.17 (m, 1H), 8.61-8.76 (m, 1H).

MS m/z ([M−H]$^−$) 222.

Step 2: preparation of intermediate 2-[5-(dimethoxymethyl)-1H-pyrazol-3-yl]pyridine (9b)

To a stirred slurry of 4,4-dimethoxy-1-(pyridin-2-yl)butane-1,3-dione (9a) (5.11 g, 22.9 mmol) in ethanol (200 mL) was dropwise added hydrazine monohydrate (1.28 mL, 26.3 mmol). The reaction mixture was stirred at room temperature overnight and concentrated in vacuo. A saturated solution of sodium hydrogenocarbonate (30 mL) was added to the residue. The aqueous layer was extracted with ethyl acetate (2×50 mL). The organic layer was dried over sodium sulfate and concentrated in vacuo to provide 2-[5-(dimethoxymethyl)-1H-pyrazol-3-yl]pyridine (9b) (3.51 g, 16.0 mmol, 70%) which was used without further purification.

MS m/z ([M+H]$^+$) 220.

Step 3: preparation of intermediate 2-[4-bromo-5-(dimethoxymethyl)-1H-pyrazol-3-yl]pyridine (9c)

Using the procedure described in example 8, step 3, 2-[5-(dimethoxymethyl)-1H-pyrazol-3-yl]pyridine (9b) (3.50 g, 16.0 mmol) is converted into 2-[4-bromo-5-(dimethoxymethyl)-1H-pyrazol-3-yl]pyridine (9c) (3.50 g, 11.7 mmol, 73%) which was used without further purification.

MS m/z ([M−H]$^−$) 296/298.

Step 4: preparation of intermediate 2-[4-bromo-5-(dimethoxymethyl)-1-methyl-1H-pyrazol-3-yl]pyridine (9d)

Using the procedure described in example 8, step 4, 2-[4-bromo-5-(dimethoxymethyl)-1H-pyrazol-3-yl]pyridine (9c) (3.50 g, 11.7 mmol) is converted into 2-[4-bromo-5-(dimethoxymethyl)-1-methyl-1H-pyrazol-3-yl]pyridine (9d) (1.62 g, 5.19 mmol, 44%) as a single isomer after purification by flash chromatography on silica gel (dichloromethane/ethyl acetate 100/0 to 95/5).

$^1$H NMR (400 MHz, CDCl$_3$) δ 3.45 (s, 6H), 4.05 (s, 3H), 5.44 (s, 1H), 7.25 (ddd, J=7.6 Hz, J=4.9 Hz, J=1.0 Hz, 1H), 7.74 (dt, J=7.8 Hz, J=1.8 Hz, 1H), 7.92-7.97 (m, 1H), 8.69-8.74 (m, 1H).

MS m/z ([M+H]$^+$) 312/314.

Step 5: preparation of intermediate 4-bromo-1-methyl-3-(pyridin-2-yl)-1H-pyrazole-5-carbaldehyde (9e)

Using the procedure described in example 8, step 5, 2-[4-bromo-5-(dimethoxymethyl)-1-methyl-1H-pyrazol-3-yl]pyridine (9d) (1.62 g, 5.19 mmol) is converted into 4-bromo-1-methyl-3-(pyridin-2-yl)-1H-pyrazole-5-carbaldehyde (9e) (1.00 g, 3.76 mmol, 72%) as a light yellow powder, which was used without further purification.

$^1$H NMR (400 MHz, CDCl$_3$) δ 4.25 (s, 3H), 7.31 (ddd, J=7.6 Hz, J=4.9 Hz, J=1.1 Hz, 1H), 7.79 (dt, J=7.8 Hz, J=1.8 Hz, 1H), 7.95-7.99 (m, 1H), 8.73-8.77 (m, 1H), 9.99 (s, 1H).

Ms m/z ([M+H]$^+$) 266/268

Step 6: preparation of intermediate 4-(3,4-dihydro-2H-1-benzopyran-6-yl)-1-methyl-3-(pyridin-2-yl)-1H-pyrazole-5-carbaldehyde (9f)

Using the procedure described in example 8, step 6,4-bromo-1-methyl-3-(pyridin-2-yl)-1H-pyrazole-5-carbaldehyde (9e) (200 mg, 0.75 mmol) is converted into 4-(3,4-dihydro-2H-1-benzopyran-6-yl)-1-methyl-3-(pyridin-2-yl)-1H-pyrazole-5-carbaldehyde (9f) (137 mg, 0.43 mmol, 57%) after purification by preparative TLC (dichloromethane/7M ammonia in methanol 97/3).

$^1$H NMR (300 MHz, CDCl$_3$) δ 1.98-2.09 (m, 2H), 2.77 (t, J=6.4 Hz, 2H), 4.21-4.25 (m, 2H), 4.30 (s, 3H), 6.78-6.83 (m, 1H), 6.99-7.06 (m, 2H), 7.18 (ddd, J=7.5 Hz, J=4.8 Hz, J=1.1 Hz, 1H), 7.24-7.30 (m, 1H), 7.55 (dt, J=7.7 Hz, J=1.8 Hz, 1H), 8.61-8.70 (m, 1H), 9.65 (s, 1H).

MS m/z ([M+H]$^+$) 320.

Step 7: preparation of intermediate methyl 2-[4-(3,4-dihydro-2H-1-benzopyran-6-yl)-1-methyl-3-(pyridin-2-yl)-1H-pyrazol-5-yl]-2-hydroxyacetate (9g)

Under nitrogen atmosphere, to a solution of 4-(3,4-dihydro-2H-1-benzopyran-6-yl)-1-methyl-3-(pyridin-2-yl)-1H-pyrazole-5-carbaldehyde (9f) (137 mg, 0.43 mmol) in anhydrous dichloromethane (2 mL) at 0° C. were successively added zinc iodide (14 mg, 0.04 mmol) and trimethylsilyl cyanide (64 µL, 0.51 mmol). The mixture was stirred at room temperature for 4 hours and then heated at 50° C. for 3 days. After cooling to room temperature, a saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (3 mL) was added to a solution of acetyl chloride (0.36 mL, 5.13 mmol) in anhydrous methanol (2 mL), previously stirred 20 minutes at 0° C. under nitrogen atmosphere. The mixture was stirred at room temperature overnight. The solution was concentrated in vacuo and saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (dichloromethane/7M ammonia in methanol 97/3) to provide methyl 2-[4-(3,4-dihydro-2H-1-benzopyran-6-yl)-1-methyl-3-(pyridin-2-yl)-1H-pyrazol-5-yl]-2-hydroxyacetate (9g) (64 mg, 0.17 mmol, 39%).

$^1$H NMR (300 MHz, CDCl$_3$) δ 1.97-2.05 (m, 2H), 2.75 (t, J=6.4 Hz, 2H), 3.38 (bs, 1H), 3.73 (s, 3H), 3.96 (s, 3H), 4.18-4.24 (m, 2H), 5.24 (s, 1H), 6.74-6.79 (m, 1H), 6.94-7.00 (m, 2H), 7.09-7.17 (m, 2H), 7.48 (dt, J=7.7 Hz, J=1.8 Hz, 1H), 8.60-8.65 (m, 1H).

MS m/z ([M+H]$^+$) 380.

Step 8: preparation of intermediate methyl 2-(tert-butoxy)-2-[4-(3,4-dihydro-2H-1-benzopyran-6-yl)-1-methyl-3-(pyridin-2-yl)-1H-pyrazol-5-yl]acetate (9h)

Using the procedure described in example 8, step 8, methyl 2-[4-(3,4-dihydro-2H-1-benzopyran-6-yl)-1-methyl-3-(pyridin-2-yl)-1H-pyrazol-5-yl]-2-hydroxyacetate (9g) (64 mg, 0.17 mmol) is converted into methyl 2-(tert-butoxy)-2-[4-(3,4-dihydro-2H-1-benzopyran-6-yl)-1-methyl-3-(pyridin-2-yl)-1H-pyrazol-5-yl]acetate (9h) (58 mg, 0.13 mmol, 79%) after purification by preparative TLC (dichloromethane/7M ammonia in methanol 96/4).

$^1$H NMR (300 MHz, CDCl$_3$) δ 1.02 (s, 9H), 1.98-2.08 (m, 2H), 2.75 (t, J=6.4 Hz, 2H), 3.77 (s, 3H), 4.06 (s, 3H), 4.20-4.25 (m, 2H), 5.07 (s, 1H), 6.78 (d, J=8.4 Hz, 1H), 6.94-7.00 (m, 2H), 7.07-7.16 (m, 2H), 7.46 (dt, J=7.7 Hz, J=1.8 Hz, 1H), 8.60-8.65 (m, 1H).

MS m/z ([M+H]$^+$) 436.

Step 9: preparation of 2-(tert-butoxy)-2-[4-(3,4-dihydro-2H-1-benzopyran-6-yl)-1-methyl-3-(pyridin-2-yl)-1H-pyrazol-5-yl]acetic acid (example 9)

A mixture of methyl 2-(tert-butoxy)-2-[4-(3,4-dihydro-2H-1-benzopyran-6-yl)-1-methyl-3-(pyridin-2-yl)-1H-pyrazol-5-yl]acetate (9h) (58 mg, 0.13 mmol) and potassium hydroxide (65 mg, 0.53 mmol) in a mixture of ethanol (1.0 mL) and water (1.0 mL) was refluxed overnight. The mixture was concentrated in vacuo. Water (2 mL) was added to the residue and the aqueous layer was washed with diethyl ether (2 mL), acidified with 1M hydrochloric acid until pH 3 and extracted with ethyl acetate (2×3 mL). The organic layer was dried over sodium sulfate and concentrated in vacuo to provide 2-(tert-butoxy)-2-[4-(3,4-dihydro-2H-1-benzopyran-6-yl)-1-methyl-3-(pyridin-2-yl)-1H-pyrazol-5-yl]acetic acid (example 9) (32 mg, 0.076 mmol, 57%).

$^1$H NMR (300 MHz, CDCl$_3$) δ 0.98 (s, 9H), 1.95-2.04 (m, 2H), 2.59-2.75 (m, 2H), 3.98 (s, 3H), 4.16-4.23 (m, 2H), 5.05 (s, 1H), 6.71 (d, J=8.2 Hz, 1H), 6.86 (d, J=1.8 Hz, 1H), 6.91 (dd, J=1.8 Hz, J=8.2 Hz, 1H), 7.18-7.25 (m, 1H), 7.38 (d, J=7.8 Hz, 1H), 7.64 (dt, J=7.8 Hz, J=1.6 Hz, 1H), 8.64-8.70 (m, 1H).

MS m/z ([M−H]$^−$) 420.
MS m/z ([M+H]$^+$) 422.

Example 10 synthesis of 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetic acid

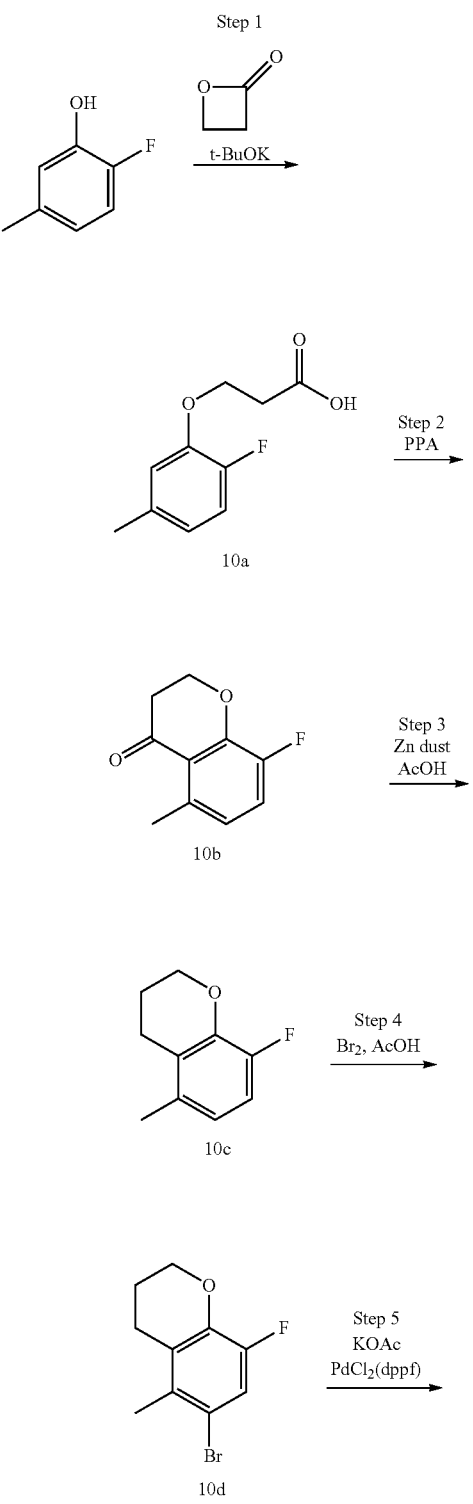

-continued

Step 6

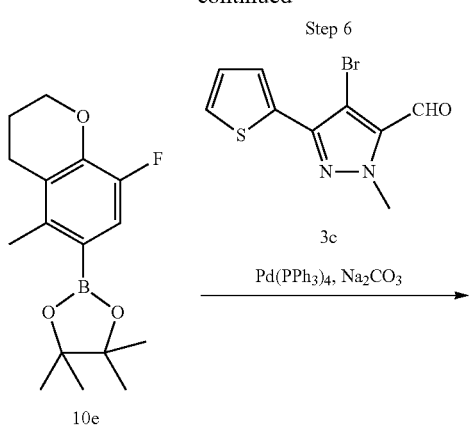
10e

Pd(PPh₃)₄, Na₂CO₃

3c

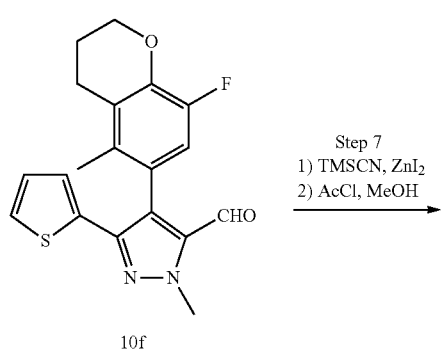
10f

Step 7
1) TMSCN, ZnI₂
2) AcCl, MeOH

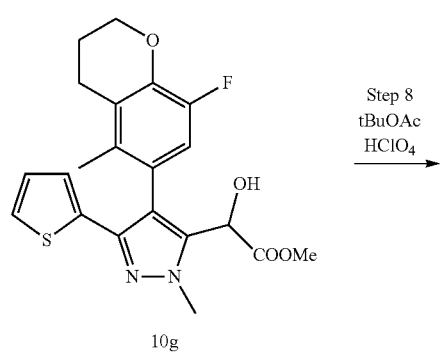
10g

Step 8
tBuOAc
HClO₄

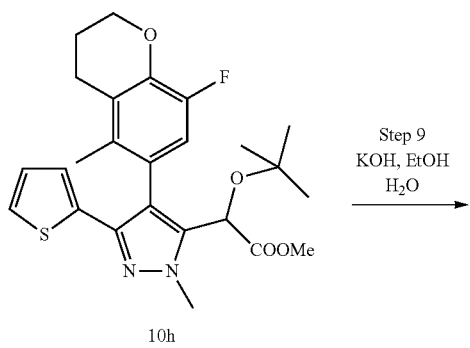
10h

Step 9
KOH, EtOH
H₂O

-continued

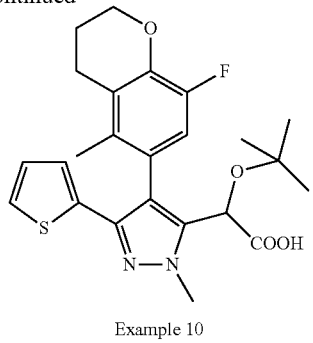

Example 10

Step 1: preparation of intermediate 3-(2-fluoro-5-methylphenoxy)propanoic acid (10a)

To a suspension of 2-fluoro-5-methylphenol (1.0 g, 7.9 mmol) in tetrahydrofuran (10 mL) at 0-5° C. was dropwise added potassium tert-butoxide 1N in tetrahydrofuran (8.3 mL, 8.3 mmol), followed by 3-propiolactone (0.55 mL, 8.7 mmol) in one portion. The mixture was warmed to room temperature for 1 hour, then heated at 50° C. for 2 hours. After cooling to room temperature, the mixture was quenched with a saturated solution of sodium hydrogenocarbonate (1 mL) and diluted with water (9 mL). The aqueous layer was washed with ethyl acetate (10 mL), acidified with 1M hydrochloric acid until pH 2 and extracted with ethyl acetate (2×10 mL). The organic layer was dried over sodium sulfate and concentrated in vacuo to provide 3-(2-fluoro-5-methylphenoxy)propanoic acid (10a) (0.96 g, 4.8 mol, 60%) which was used without further purification.

MS m/z ([M−H]⁻) 197.

Step 2: preparation of intermediate 8-fluoro-5-methyl-3,4-dihydro-2H-1-benzopyran-4-one (10b)

A mixture of 3-(2-fluoro-5-methylphenoxy)propanoic acid (10a) (860 mg, 4.64 mmol) in polyphosphoric acid (12.8 g, 130.3 mmol) was stirred at 100° C. for 2 hours. After cooling to room temperature, the mixture was diluted with water (90 mL), and extracted with ethyl acetate (2×60 mL). The organic layers were combined, washed with brine, dried over sodium sulfate, and concentrated in vacuo to provide 8-fluoro-5-methyl-3,4-dihydro-2H-1-benzopyran-4-one (10b) (573 mg, 3.18 mol, 73%) which was used without further purification. Ms m/z ([M+H]⁺) 181.

Step 3: preparation of intermediate 8-fluoro-5-methyl-3,4-dihydro-2H-1-benzopyran (10c)

A solution of 8-fluoro-5-methyl-3,4-dihydro-2H-1-benzopyran-4-one (10b) (570 mg, 3.16 mmol) in acetic acid (4 mL) was added to a suspension of zinc dust (2.69 g, 41.1 mmol) in acetic acid (4 mL). The reaction mixture was heated at 100° C. for 5 hours. After cooling to room temperature, the mixture was filtered through a pad of Celite® and successively rinsed with ethyl acetate (10 mL) and toluene (10 mL). The filtrate was concentrated in vacuo to provide 8-fluoro-5-methyl-3,4-dihydro-2H-1-benzopyran (10c) (233 mg, 1.40 mol, 44%) which was used without further purification.

¹H NMR (300 MHz, CDCl₃) δ 2.00-2.12 (m, 2H), 2.16 (s, 3H), 2.64 (t, J=6.6 Hz, 2H), 4.17-4.26 (m, 2H), 6.60 (dd, J=5.3 Hz, J=8.2 Hz, 1H), 6.81 (dd, J=10.8 Hz, J=8.2 Hz, 1H).

Step 4: preparation of intermediate 6-bromo-8-fluoro-5-methyl-3,4-dihydro-2H-1-benzopyran (10d)

Using the procedure described in example 7, step 5, 8-fluoro-5-methyl-3,4-dihydro-2H-1-benzopyran (10c) (228 mg, 1.37 mmol) is converted into 6-bromo-8-fluoro-5-methyl-3,4-dihydro-2H-1-benzopyran (10d) (336 mg, 1.37 mmol, 100%) which was used without further purification.

$^1$H NMR (300 MHz, CDCl$_3$) δ 2.00-2.11 (m, 2H), 2.25 (s, 3H), 2.70 (t, J=6.6 Hz, 2H), 4.15-4.22 (m, 2H), 7.15 (d, J=10.3 Hz, 1H).

Step 5: preparation of intermediate 2-(8-fluoro-5-methyl-3,4-dihydro-2H-1-benzopyran-6-yl)-4,4,5,5-tetramethyl-1,3,2-dioxaborolane (10e)

Using the procedure described in example 7, step 6,6-bromo-8-fluoro-5-methyl-3,4-dihydro-2H-1-benzopyran (10d) (336 mg, 1.37 mmol) is converted into 2-(8-fluoro-5-methyl-3,4-dihydro-2H-1-benzopyran-6-yl)-4,4,5,5-tetramethyl-1,3,2-dioxaborolane (10e) (190 mg, 0.65 mmol, 47%) after purification by preparative TLC (cyclohexane/ethyl acetate 92/8.

$^1$H NMR (400 MHz, CDCl$_3$) δ 1.32 (s, 12H), 2.02-2.09 (m, 2H), 2.38 (s, 3H), 2.65 (t, J=6.6 Hz, 2H), 4.18-4.24 (m, 2H), 7.34 (d, J=11.7 Hz, 1H).

MS m/z ([M+H]$^+$) 293.

Step 6: preparation of intermediate 4-(8-fluoro-5-methyl-3,4-dihydro-2H-1-benzopyran-6-yl)-1-methyl-3-(thiophen-2-yl)-1H-pyrazole-5-carbaldehyde (10f)

Using the procedure described in example 7, step 8,4-bromo-1-methyl-3-(thiophen-2-yl)-1H-pyrazole-5-carbaldehyde (3c) (150 mg, 0.55 mmol) is converted by reaction with 2-(8-fluoro-5-methyl-3,4-dihydro-2H-1-benzopyran-6-yl)-4,4,5,5-tetramethyl-1,3,2-dioxaborolane (10e) (189 mg, 0.65 mmol) into 4-(8-fluoro-5-methyl-3,4-dihydro-2H-1-benzopyran-6-yl)-1-methyl-3-(thiophen-2-yl)-1H-pyrazole-5-carbaldehyde (10f) (150 mg, 0.42 mmol, 76%) after purification by preparative TLC (dichloromethane/ethyl acetate 95/5).

$^1$H NMR (300 MHz, CDCl$_3$) δ 1.91 (s, 3H), 2.06-2.19 (m, 2H), 2.70 (t, J=6.6 Hz, 2H), 4.24 (s, 3H), 4.25-4.34 (m, 2H), 6.81 (dd, J=1.1 Hz, J=3.6 Hz, 1H), 6.85-6.93 (m, 2H), 7.18 (dd, J=1.1 Hz, J=5.1 Hz, 1H), 9.44 (s, 1H).

MS m/z ([M+H]$^+$) 357.

Step 7: preparation of intermediate methyl 2-[4-(8-fluoro-5-methyl-3,4-dihydro-2H-1-benzopyran-6-yl)-1-methyl-3-(thiophen-2-yl)-1H-pyrazol-5-yl]-2-hydroxyacetate (10g)

Under nitrogen atmosphere, to a solution of 4-(8-fluoro-5-methyl-3,4-dihydro-2H-1-benzopyran-6-yl)-1-methyl-3-(thiophen-2-yl)-1H-pyrazole-5-carbaldehyde (10f) (150 mg, 0.42 mmol) in anhydrous dichloromethane (2 mL) at 0° C. were successively added zinc iodide (13 mg, 0.04 mmol) and trimethylsilyl cyanide (63 µL, 0.51 mmol). The mixture was stirred at room temperature for 7 hours. A saturated solution of sodium hydrogenocarbonate (5 mL) was added. Layers were separated and the aqueous layer was extracted with dichloromethane (2×6 mL). The organic layers were dried over sodium sulfate and concentrated in vacuo. The residue, dissolved in anhydrous methanol (1 mL) was added to a solution of acetyl chloride (0.36 mL, 5.05 mmol) in anhydrous methanol (2 mL), previously stirred for 20 minutes at 0° C. under nitrogen atmosphere. The mixture was stirred at room temperature overnight. The solution was concentrated in vacuo and saturated solution of sodium hydrogenocarbonate (5 mL) was added to the residue. The aqueous layer was extracted with ethyl acetate (2×6 mL). The organic layer was dried over sodium sulfate and concentrated in vacuo. The residue was purified by preparative TLC (dichloromethane/ethyl acetate 85/15) to provide methyl 2-[4-(8-fluoro-5-methyl-3,4-dihydro-2H-1-benzopyran-6-yl)-1-methyl-3-(thiophen-2-yl)-1H-pyrazol-5-yl]-2-hydroxyacetate (10g) (115 mg, 0.28 mmol, 66%).

$^1$H NMR (300 MHz, CDCl$_3$) δ 1.89 (s, 3H), 2.04-2.18 (m, 2H), 2.69 (t, J=6.6 Hz, 2H), 3.71 and 3.75 (s, 3H), 3.90 and 3.92 (s, 3H), 4.23-4.30 (m, 2H), 5.04 and 5.05 (s, 1H), 6.70 and 6.72 (dd, J=1.1 Hz, J=3.6 Hz, 1H), 6.75-6.89 (m, 2H), 7.12 and 7.13 (dd, J=1.1 Hz, J=5.1 Hz, 1H).

MS m/z ([M+H]$^+$) 417.

Step 8: preparation of intermediate methyl 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetate (10h)

Using the procedure described in example 8, step 8, methyl 2-[4-(8-fluoro-5-methyl-3,4-dihydro-2H-1-benzopyran-6-yl)-1-methyl-3-(thiophen-2-yl)-1H-pyrazol-5-yl]-2-hydroxyacetate (10g) (115 mg, 0.28 mmol) is converted into methyl 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetate (10h) (89 mg, 0.19 mmol, 68%) after purification by preparative TLC (dichloromethane/ethyl acetate 95/5).

$^1$H NMR (400 MHz, CDCl$_3$) δ 1.05 and 1.16 (s, 9H), 1.83 and 1.85 (s, 3H), 2.08-2.18 (m, 2H), 2.62-2.68 (m, 1H), 2.68-2.74 (m, 1H), 3.66 and 3.76 (s, 3H), 4.00 and 4.03 (s, 3H), 4.25-4.32 (m, 2H), 4.85 and 4.87 (s, 1H), 6.68 and 6.70 (dd, J=1.1 Hz, J=3.6 Hz, 1H), 6.78 and 6.91 (d, J=11.4 Hz, 1H), 6.82-6.87 (m, 1H), 7.11 and 7.12 (dd, J=1.1 Hz, J=5.1 Hz, 1H).

Step 9: preparation of 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetic acid (example 10)

Using the procedure described in example 8, step 9, methyl 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetate (10h) (89 mg, 0.19 mmol) is converted into 2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetic acid (example 10) (78 mg, 0.17 mmol, 90%).

$^1$H NMR (400 MHz, CDCl$_3$) δ 1.10 and 1.20 (s, 9H), 1.80 and 1.91 (s, 3H), 2.06-2.17 (m, 2H), 2.60-2.73 (m, 2H), 4.00 and 4.02 (s, 3H), 4.23-4.32 (m, 2H), 4.90 and 4.98 (s, 1H), 6.77-6.81 (m, 1H), 6.78 and 7.05 (d, J=11.5 Hz, 1H), 6.84-6.88 (m, 1H), 7.11-7.16 (m, 1H).

Ms m/z ([M−H]$^−$) 457.

MS m/z ([M+H]$^+$) 459.

Example 11 synthesis of 2-(tert-butoxy)-2-[4-(3,4-dihydro-2H-1-benzopyran-6-yl)-1-methyl-3-(5-propylthiophen-3-yl)-1H-pyrazol-5-yl]acetic acid

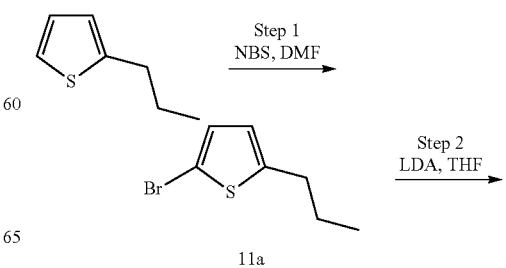

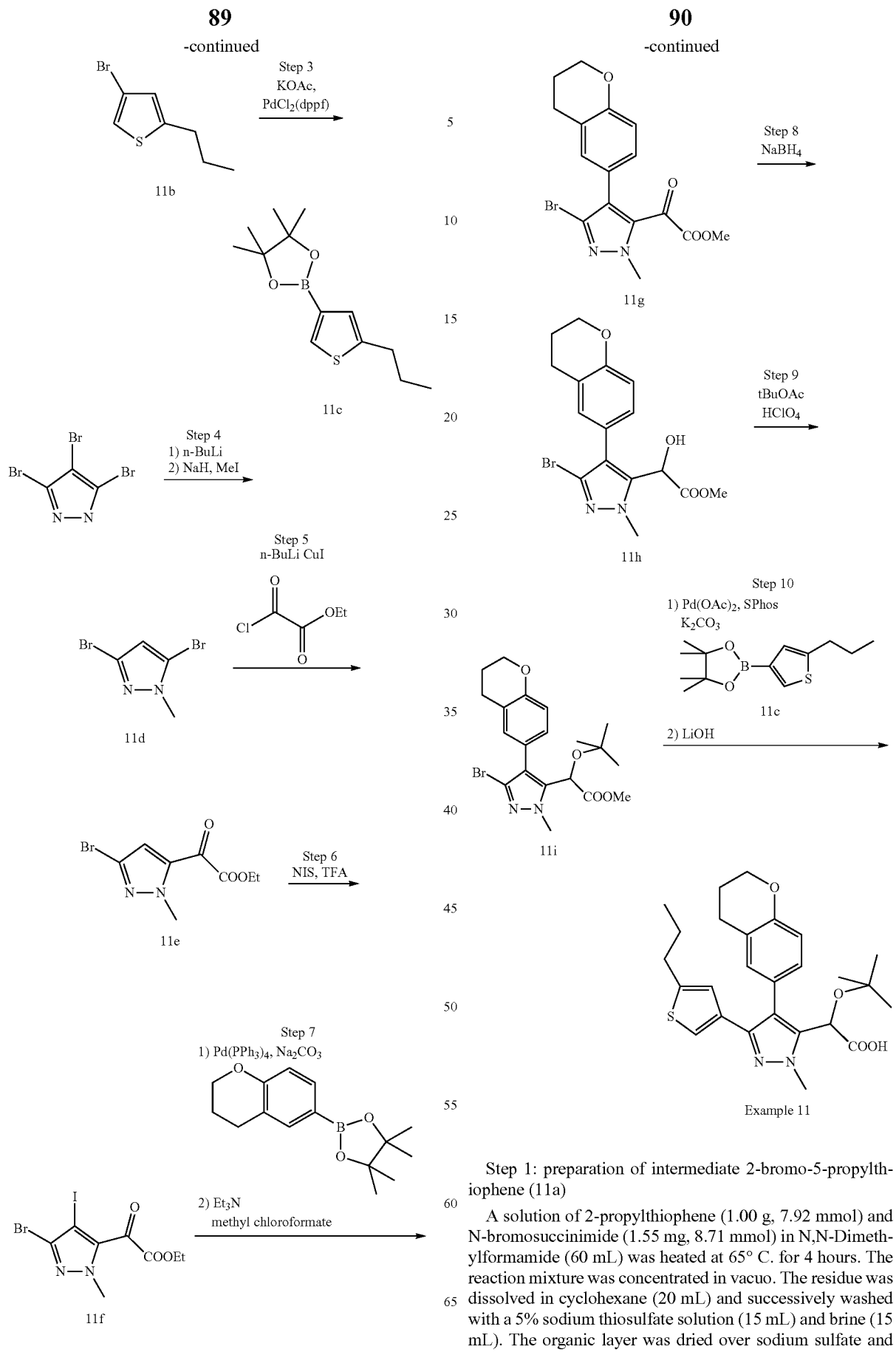

Step 1: preparation of intermediate 2-bromo-5-propylthiophene (11a)

A solution of 2-propylthiophene (1.00 g, 7.92 mmol) and N-bromosuccinimide (1.55 mg, 8.71 mmol) in N,N-Dimethylformamide (60 mL) was heated at 65° C. for 4 hours. The reaction mixture was concentrated in vacuo. The residue was dissolved in cyclohexane (20 mL) and successively washed with a 5% sodium thiosulfate solution (15 mL) and brine (15 mL). The organic layer was dried over sodium sulfate and concentrated in vacuo to provide 2-bromo-5-propylthiophene (11a) (1.45 g, 7.07 mmol, 89%) which was used without further purification.

$^1$H NMR (400 MHz, CDCl$_3$) δ 0.96 (t, J=7.3 Hz, 3H), 1.66 (sex, J=7.3 Hz, 2H), 2.72 (t, J=7.3 Hz, 2H), 6.53 (d, J=3.6 Hz, 1H), 6.84 (d, J=3.6 Hz, 1H).

Step 2: preparation of intermediate 4-bromo-2-propylthiophene (11b)

Under a nitrogen atmosphere, n-butyllithium 1.6M in hexane (1.54 mL, 2.46 mmol) was dropwise added to a solution of diisopropylamine (0.35 mL, 2.47 mmol) in anhydrous tetrahydrofuran (1 mL) at −78° C. The mixture was allowed to warm to 0° C. for 30 minutes. The mixture was cooled to −78° C. and a solution of 2-bromo-5-propylthiophene (11a) (500 mg, 2.44 mmol) in anhydrous tetrahydrofuran (1 mL) was dropwise added. The mixture was stirred at room temperature for 2 hours. A saturated solution of ammonium chloride (4 mL) was added, and the mixture was extracted with ethyl acetate (5 mL). The organic layer was successively washed with water (5 mL) and brine (5 mL), dried over sodium sulfate and concentrated in vacuo. The residue was purified by flash chromatography on silica gel (cyclohexane/ethyl acetate 90/10) to provide 4-bromo-2-propylthiophene (11b) (323 mg, 1.57 mmol, 65%).

$^1$H NMR (400 MHz, CDCl$_3$) δ 0.97 (t, J=7.3 Hz, 3H), 1.68 (sex, J=7.3 Hz, 2H), 2.75 (t, J=7.3 Hz, 2H), 6.70 (d, J=1.4 Hz, 1H), 7.00 (d, J=1.4 Hz, 1H).

Step 3: preparation of intermediate 4,4,5,5-tetramethyl-2-(5-propylthiophen-3-yl)-1,3,2-dioxaborolane (11c)

Using the procedure described in example 7, step 6,4-bromo-2-propylthiophene (11b) (320 mg, 1.56 mmol) is converted, after purification by flash chromatography on silica gel (cyclohexane/dichloromethane 100/0 to 0/100) into 4,4,5,5-tetramethyl-2-(5-propylthiophen-3-yl)-1,3,2-dioxaborolane (11c) (150 mg, 0.59 mmol, 38%).

$^1$H NMR (400 MHz, CDCl$_3$) δ 0.97 (t, J=7.3 Hz, 3H), 1.32 (s, 12H), 1.70 (sex, J=7.3 Hz, 2H), 2.79 (t, J=7.3 Hz, 2H), 7.06 (s, 1H), 7.70 (s, 1H).

Step 4: preparation of intermediate 3,5-dibromo-1-methyl-1H-pyrazole (11d)

Under nitrogen atmosphere, a mixture of 3,4,5-tribromo-1H-pyrazole (10.0 g, 32.8 mmol) in anhydrous tetrahydrofuran (120 mL) was cooled to −78° C. n-Butyllithium 1.6M in hexane (45 mL, 72.2 mmol) was slowly added over 20 minutes and the mixture was stirred at −78° C. for 2 hours. Then a mixture of methanol (20 mL) an tetrahydrofuran (30 mL) was dropwise added. The mixture was allowed to reach room temperature and was concentrated in vacuo. The residue was dissolved in diethyl ether (50 mL), successively washed with 1M hydrochloric acid (30 mL) and brine (20 mL), dried over sodium sulfate and concentrated in vacuo. The crude was dissolved in anhydrous tetrahydrofuran (70 mL) and cooled to 0° C. Sodium hydride 60% in oil (3.28 g, 82.0 mmol) was added portionwise. After 1 hour stirring, iodomethane (4.08 mL, 65.6 mmol) was added and the mixture was stirred at 0° C. for 4 hours before being quenched with a saturated solution of ammonium chloride (20 mL) and extracted with ethyl acetate (2×50 mL). The organic layer was successively washed with water (50 mL), brine (50 mL), dried over sodium sulfate and concentrated in vacuo. The residue was purified by flash chromatography on silica gel (cyclohexane/ethyl acetate 100/0 to 80/20) to provide 3,5-dibromo-1-methyl-1H-pyrazole (11d) (4.20 g, 17.5 mmol, 53% over two steps).

$^1$H NMR (300 MHz, CDCl$_3$) δ 3.85 (s, 3H), 6.30 (s, 1H). MS m/z ([M−H]$^-$) 239/241/243.

Step 5: preparation of intermediate ethyl 2-(3-bromo-1-methyl-1H-pyrazol-5-yl)-2-oxoacetate (11e)

Under nitrogen atmosphere, n-butyllithium 1.6M in hexane (6.5 mL, 10.42 mmol) was added dropwise to a solution of 3,5-dibromo-1-methyl-1H-pyrazole (11d) (2.00 g, 8.34 mmol) in anhydrous tetrahydrofuran (40 mL) at −78° C. After 30 minutes stirring at the same temperature, copper iodide (5.56 g, 29.18 mmol) was added. The temperature was allowed to reach 0° C. for 40 minutes, then cooled to −78° C. Ethyl chlorooxoacetate (2.80 mL, 25.01 mmol) was dropwise added. The mixture was stirred at room temperature for 2 hours. Water (20 mL) was added and the mixture was extracted with ethyl acetate (2×30 mL). The organic layer was washed with a saturated solution of sodium hydrogenocarbonate (20 mL), dried over sodium sulfate and concentrated in vacuo. The residue was purified by flash chromatography on silica gel (cyclohexane/ethyl acetate: 100/0 to 80/20) to provide ethyl 2-(3-bromo-1-methyl-1H-pyrazol-5-yl)-2-oxoacetate (11e) (1.36 g, 5.21 mmol, 62%).

$^1$H NMR (300 MHz, CDCl$_3$) δ 1.42 (t, J=7.2 Hz, 3H), 4.18 (s, 3H), 4.42 (q, J=7.2 Hz, 2H), 7.24 (s, 1H).

MS m/z ([M−H]$^-$) 261/263.

Step 6: preparation of intermediate ethyl 2-(3-bromo-4-iodo-1-methyl-1H-pyrazol-5-yl)-2-oxoacetate (11f)

A solution of ethyl 2-(3-bromo-1-methyl-1H-pyrazol-5-yl)-2-oxoacetate (11e) (1.36 g, 5.21 mmol) and N-iodosuccunimide (1.29 g, 5.73 mmol) in trifluoroacetic acid (20 mL) was stirred at room temperature for 3 hours. Water (5 mL) was added and the mixture was concentrated in vacuo. The residue was dissolved in ethyl acetate (20 mL), successively washed with a saturated solution of sodium hydrogenocarbonate (20 mL), and brine (50 mL), then dried over sodium sulfate and concentrated in vacuo to provide ethyl 2-(3-bromo-4-iodo-1-methyl-1H-pyrazol-5-yl)-2-oxoacetate (11f) (1.96 g, 5.06 mmol, 97%) as an orange oil, which was used without further purification.

$^1$H NMR (300 MHz, CDCl$_3$) δ 1.44 (t, J=7.2 Hz, 3H), 4.16 (s, 3H), 4.48 (q, J=7.2 Hz, 2H). Ms m/z ([M+H]$^+$) 387/389.

Step 7: preparation of intermediate methyl 2-[3-bromo-4-(3,4-dihydro-2H-1-benzopyran-6-yl)-1-methyl-1H-pyrazol-5-yl]-2-oxoacetate (11g)

A solution of ethyl 2-(3-bromo-4-iodo-1-methyl-1H-pyrazol-5-yl)-2-oxoacetate (11f) (750 mg, 1.94 mmol), potassium carbonate (536 mg, 3.88 mmol), and 6-(4,4,5,5-tetramethyl-1,3,2-dioxaborolan-2-yl)chroman (494 mg, 1.90 mmol) in a mixture of dioxane (16 mL) and water (4 mL) was degassed for 5 minutes. Palladium tetrakis(triphenylphosphine) (157 mg, 0.14 mmol) was added and the reaction mixture was heated at 120° C. overnight. After concentrating in vacuo, the residue was dissolved in 1N sodium hydroxide (15 mL). The aqueous layer was washed with diethyl ether (20 mL), acidified with 1M hydrochloric acid until pH 3 and extracted with diethyl ether (2×15 mL). The organic layer was dried over sodium sulfate and concentrated in vacuo. The crude was dissolved in dichloromethane (7 mL), cooled to 0° C., and under a nitrogen atmosphere, triethylamine (0.41 mL, 2.91 mmol) and methyl chloroformate (0.22 mL, 2.91 mmol) were added. The reaction mixture was stirred at 0° C. for 30 minutes, and allowed to reach room temperature. Dichloromethane (10 mL) was added, and the mixture was successively washed with 1N hydrochloric acid (10 mL), a saturated solution of sodium hydrogenocarbonate (10 mL), and brine (10 mL). The organic layer was dried over sodium sulfate and concentrated in vacuo. The residue was purified by flash chromatography on silica gel (cyclohexane/ethyl acetate 90/10) to provide methyl 2-[3-bromo-4-(3,4-dihydro-2H-1-benzopyran-6-yl)-1-methyl-1H-pyrazol-5-yl]-2-oxoacetate (11g) (531 mg, 1.40 mmol, 72%) as a yellow solid.

¹H NMR (300 MHz, CDCl₃) δ 1.97-2.09 (m, 2H), 2.81 (t, J=6.5 Hz, 2H), 3.32 (s, 3H), 4.17 (s, 3H), 4.18-4.25 (m, 2H), 6.84 (d, J=8.4 Hz, 1H), 6.91 (d, J=2.2 Hz, 1H), 7.02 (dd, J=2.2 Hz, J=8.4 Hz, 1H).

MS m/z ([M+H]⁺) 379/381.

Step 8: preparation of intermediate methyl 2-[3-bromo-4-(3,4-dihydro-2H-1-benzopyran-6-yl)-1-methyl-1H-pyrazol-5-yl]-2-hydroxyacetate (11h)

Under a nitrogen atmosphere, sodium borohydride (36 mg, 0.95 mmol) was added portionwise to a solution of methyl 2-[3-bromo-4-(3,4-dihydro-2H-1-benzopyran-6-yl)-1-methyl-1H-pyrazol-5-yl]-2-oxoacetate (11g) (300 mg, 0.79 mmol) in anhydrous tetrahydrofuran (8 mL) at 0° C. After 30 minutes stirring at 0° C., water was added (5 mL) and the mixture was concentrated in vacuo. The crude was dissolved in ethyl acetate (10 mL) then successively washed with water (10 mL), and brine (10 mL). The organic layer was dried over sodium sulfate and concentrated in vacuo. The residue was purified by preparative TLC (dichloromethane/ethyl acetate 80/20) to provide methyl 2-[3-bromo-4-(3,4-dihydro-2H-1-benzopyran-6-yl)-1-methyl-1H-pyrazol-5-yl]-2-hydroxyacetate (11h) (204 mg, 0.54 mmol, 68%).

¹H NMR (400 MHz, CDCl₃) δ 1.98-2.08 (m, 2H), 2.78-2.86 (m, 2H), 3.33 (d, J=3.0 Hz, 1H), 3.74 (s, 3H), 3.84 (s, 3H), 4.19-4.24 (m, 2H), 5.26 (d, J=3.0 Hz, 1H), 6.83 (d, J=8.3 Hz, 1H), 7.02 (d, J=2.2 Hz, 1H), 7.06 (dd, J=2.2 Hz, J=8.3 Hz, 1H).

MS m/z ([M+H]⁺) 381/383.

Step 9: preparation of intermediate methyl 2-[3-bromo-4-(3,4-dihydro-2H-1-benzopyran-6-yl)-1-methyl-1H-pyrazol-5-yl]-2-(tert-butoxy)acetate (11i)

Using the procedure described in example 1, step 6, methyl 2-[3-bromo-4-(3,4-dihydro-2H-1-benzopyran-6-yl)-1-methyl-1H-pyrazol-5-yl]-2-hydroxyacetate (11h) (204 mg, 0.54 mmol) is converted, after purification by preparative TLC (dichloromethane/ethyl acetate 90/10), into methyl 2-[3-bromo-4-(3,4-dihydro-2H-1-benzopyran-6-yl)-1-methyl-1H-pyrazol-5-yl]-2-(tert-butoxy)acetate (11i) (174 mg, 0.40 mmol, 74%).

¹H NMR (300 MHz, CDCl₃) δ 1.02 (s, 9H), 1.99-2.11 (m, 2H), 2.77-2.90 (m, 2H), 3.78 (s, 3H), 3.94 (s, 3H), 4.20-4.28 (m, 2H), 5.09 (s, 1H), 6.84 (d, J=8.2 Hz, 1H), 7.04 (d, J=2.1 Hz, 1H), 7.08 (dd, J=2.1 Hz, J=8.2 Hz, 1H).

MS m/z ([M+H]⁺) 437/439.

Step 10: preparation of 2-(tert-butoxy)-2-[4-(3,4-dihydro-2H-1-benzopyran-6-yl)-1-methyl-3-(5-propylthiophen-3-yl)-1H-pyrazol-5-yl]acetic acid (example 11)

To a degassed solution of methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) in dioxane (1 mL) was added Palladium (II) acetate (1.3 mg, 0.006 mmol) and 2-dicyclohexylphosphino-2',6'-dimethoxybiphenyl (4.7 mg, 0.011 mmol). After stirring for 30 minutes at room temperature, potassium carbonate (47 mg, 0.343 mmol) in solution in water (0.25 mL) and 4,4,5,5-tetramethyl-2-(5-propylthiophen-3-yl)-1,3,2-dioxaborolane (11c) (40 mg, 0.160 mmol) were added and the reaction mixture was heated at 110° C. until consumption of the starting materials. Then lithium hydroxide (11 mg, 0.46 mmol) was added. The heating was maintained until completion of the reaction. The mixture was concentrated in vacuo. Water (2 mL) was added to the residue and the aqueous layer was washed with diethyl ether (2 mL), acidified with 1M hydrochloric acid until pH 3 and extracted with ethyl acetate (2×3 mL). The organic layer was dried over sodium sulfate and concentrated in vacuo to provide 2-(tert-butoxy)-2-[4-(3,4-dihydro-2H-1-benzopyran-6-yl)-1-methyl-3-(5-propylthiophen-3-yl)-1H-pyrazol-5-yl]acetic acid (example 11) (40 mg, 0.09 mmol, 75%).

¹H NMR (300 MHz, CDCl₃) δ 0.92 (t, J=7.3 Hz, 3H), 1.06 (s, 9H), 1.64 (sex, J=7.3 Hz, 2H), 1.97-2.10 (m, 2H), 2.70 (t, J=7.3 Hz, 2H), 2.73-2.82 (m, 2H), 3.93 (s, 3H), 4.19-4.28 (m, 2H), 5.09 (s, 1H), 6.81 (d, J=8.1 Hz, 1H), 6.86 (d, J=1.4 Hz, 1H), 6.97-7.11 (m, 3H).

Ms m/z ([M−H]⁻) 467.

MS m/z ([M+H]⁺) 469.

Example 12

Synthesis of 2-(tert-butoxy)-2-[3-(cyclopent-1-en-1-yl)-4-(3,4-dihydro-2H-1-benzopyran-6-yl)-1-methyl-1H-pyrazol-5-yl]acetic acid

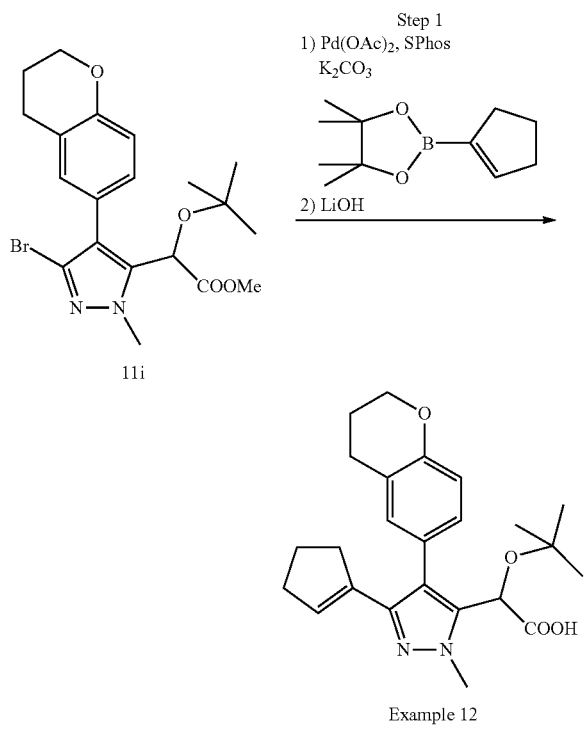

Example 12

Step 1: preparation of 2-(tert-butoxy)-2-[3-(cyclopent-1-en-1-yl)-4-(3,4-dihydro-2H-1-benzopyran-6-yl)-1-methyl-1H-pyrazol-5-yl]acetic acid (example 12)

Using the procedure described in example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with (cyclopent-1-en-1-yl)boronic acid (20 mg, 0.183 mmol), into 2-(tert-butoxy)-2-[3-(cyclopent-1-en-1-yl)-4-(3,4-dihydro-2H-1-benzopyran-6-yl)-1-methyl-1H-pyrazol-5-yl]acetic acid (example 12) (39 mg, 0.095 mmol, 83%).

¹H NMR (300 MHz, CDCl₃) δ 1.05 (s, 9H), 1.85 (quin, J=7.5 Hz, 2H), 1.98-2.09 (m, 2H), 2.27-2.40 (m, 2H), 2.53-2.74 (m, 2H), 2.74-2.86 (m, 2H), 3.89 (s, 3H), 4.19-4.28 (m, 2H), 5.02 (s, 1H), 5.65-5.70 (m, 1H), 6.80 (d, J=8.5 Hz, 1H), 7.02-7.07 (m, 2H).

MS m/z ([M−H]⁻) 409.

MS m/z ([M+H]⁺) 411.

Example 13

Synthesis of 2-(tert-butoxy)-2-[3-(cyclohex-1-en-1-yl)-4-(3,4-dihydro-2H-1-benzopyran-6-yl)-1-methyl-1H-pyrazol-5-yl]acetic acid

Example 14

Synthesis of 2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid

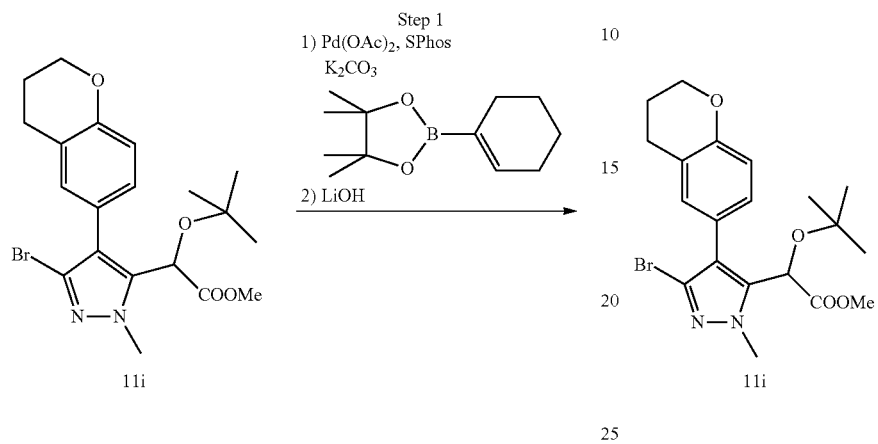

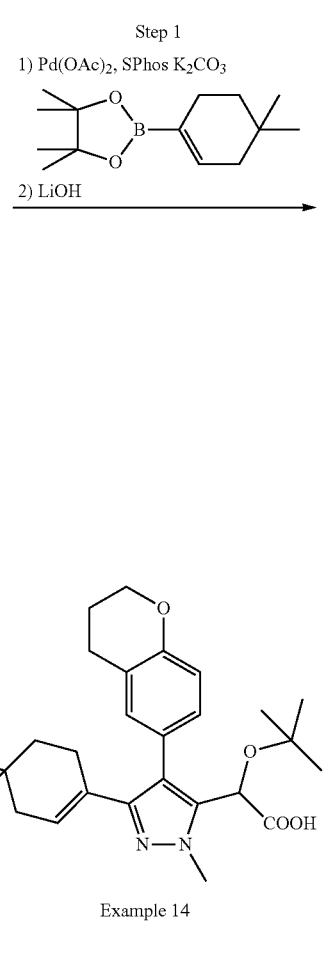

Example 14

Step 1: preparation of 2-(tert-butoxy)-2-[3-(cyclohex-1-en-1-yl)-4-(3,4-dihydro-2H-1-benzopyran-6-yl)-1-methyl-1H-pyrazol-5-yl]acetic acid (example 13)

Using the procedure described in example example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with cyclohex-1-ene boronic acid pinacol ester (38 mg, 0.183 mmol), after purification by preparative TLC (dichloromethane/ethyl acetate 70/30+0.5% formic acid) to 2-(tert-butoxy)-2-[3-(cyclohex-1-en-1-yl)-4-(3,4-dihydro-2H-1-benzopyran-6-yl)-1-methyl-1H-pyrazol-5-yl]acetic acid (example 13) (12 mg, 0.028 mmol, 25%).

$^1$H NMR (400 MHz, CDCl$_3$) δ 1.01 (s, 9H), 1.52-1.68 (m, 4H), 1.99-2.16 (m, 5H), 2.23-2.35 (m, 1H), 2.79 (t, J=6.4 Hz, 2H), 3.87 (s, 3H), 4.20-4.26 (m, 2H), 5.08 (s, 1H), 5.84-5.88 (m, 1H), 6.78 (d, J=8.3 Hz, 1H), 7.02-7.07 (m, 2H).

MS m/z ([M−H]$^-$) 423.
MS m/z ([M+H]$^+$) 425.

Step 1: preparation of 2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid (example 14)

Using the procedure described in example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 4,4-(Dimethylcyclohexene-1-yl)boronic acid, pinacol ester (43 mg, 0.183 mmol), after purification by preparative TLC (dichloromethane/ethyl acetate 50/50+0.5% formic acid) to 2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid (example 14) (30 mg, 0.066 mmol, 58%).

$^1$H NMR (400 MHz, CDCl$_3$) δ 0.88 (s, 3H), 0.90 (s, 3H), 1.02 (s, 9H), 1.31-1.43 (m, 2H), 1.77-1.84 (m, 2H), 1.98-2.17 (m, 3H), 2.26-2.38 (m, 1H), 2.73-2.82 (m, 2H), 3.88 (s, 3H), 4.19-4.26 (m, 2H), 5.10 (s, 1H), 5.73-5.79 (m, 1H), 6.78 (d, J=8.2 Hz, 1H), 6.99-7.08 (m, 2H).

Ms m/z ([M−H]$^-$) 451.
MS m/z ([M+H]$^+$) 453.

Example 15

Synthesis of 2-(3-{bicyclo[2.2.1]hept-2-en-2-yl}-4-(3,4-dihydro-2H-1-benzopyran-6-yl)-1-methyl-1H-pyrazol-5-yl)-2-(tert-butoxy)acetic acid

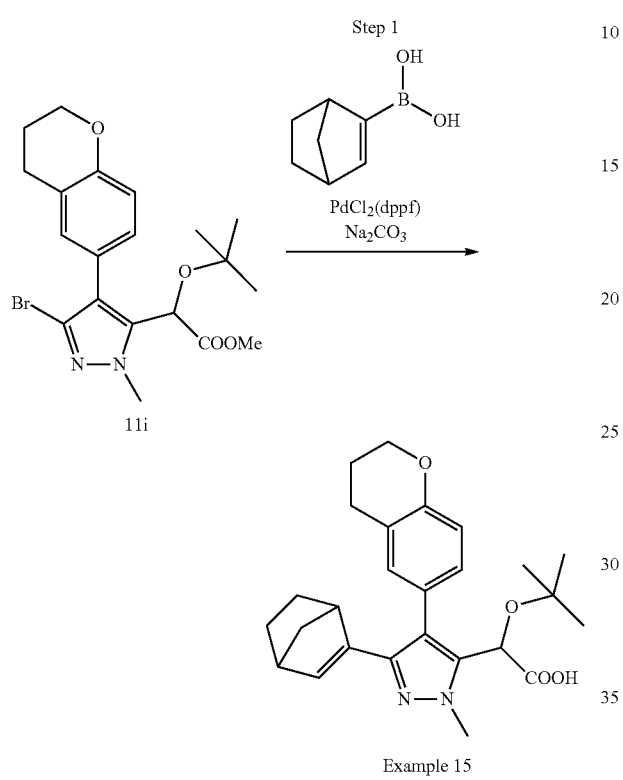

Example 15

Step 1: preparation of 2-(3-{bicyclo[2.2.1]hept-2-en-2-yl}-4-(3,4-dihydro-2H-1-benzopyran-6-yl)-1-methyl-1H-pyrazol-5-yl)-2-(tert-butoxy)acetic acid (example 15)

A solution of methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol), disodium carbonate (36 mg, 0.343 mmol), and bicyclo[2.2.1]hept-2-en-2-ylboronic acid (19 mg, 0.137 mmol) in a mixture of dimethoxyethane (0.45 mL), ethanol (0.19 mL) and water (0.13 mL) was bubbled with nitrogen for 5 minutes. [1,1'-Bis(diphenylphosphino) ferrocene]dichloropalladium(II), complex with dichloromethane (4.7 mg, 0.006 mmol) was added and the reaction mixture was heated at 140° C. for 2 hours. The solution was concentrated in vacuo. Water (2 mL) was added to the residue and the aqueous layer was washed with diethyl ether (2 mL), acidified with 1M hydrochloric acid until pH 3 and extracted with diethyl ether (2×3 mL). The organic layer was dried over sodium sulfate and concentrated in vacuo. The residue was purified by preparative TLC (dichloromethane/ethyl acetate 45/55+0.5% formic acid) to provide 2-(3-{bicyclo[2.2.1]hept-2-en-2-yl}-4-(3,4-dihydro-2H-1-benzopyran-6-yl)-1-methyl-1H-pyrazol-5-yl)-2-(tert-butoxy)acetic acid (example 15) (30 mg, 0.069 mmol, 60%) as a mixture of diastereoisomers.

$^1$H NMR (400 MHz, CDCl$_3$) δ 0.97-1.17 (m, 12H), 1.28-1.45 (m, 1H), 1.60-1.70 (m, 2H), 2.00-2.08 (m, 2H), 2.73-2.87 (m, 3H), 3.21 and 3.34 (bs, 1H), 4.00 (s, 3H), 4.21-4.26 (m, 2H), 5.02 and 5.05 (s, 1H), 5.90 and 5.98 (bs, 1H), 6.80 (d, J=8.2 Hz, 1H), 6.98-7.06 (m, 2H).

Ms m/z ([M−H]$^−$) 435.
MS m/z ([M+H]$^+$) 437.

Example 16

Synthesis of 2-(tert-butoxy)-2-[3-(cyclohept-1-en-1-yl)-4-(3,4-dihydro-2H-1-benzopyran-6-yl)-1-methyl-1H-pyrazol-5-yl]acetic acid

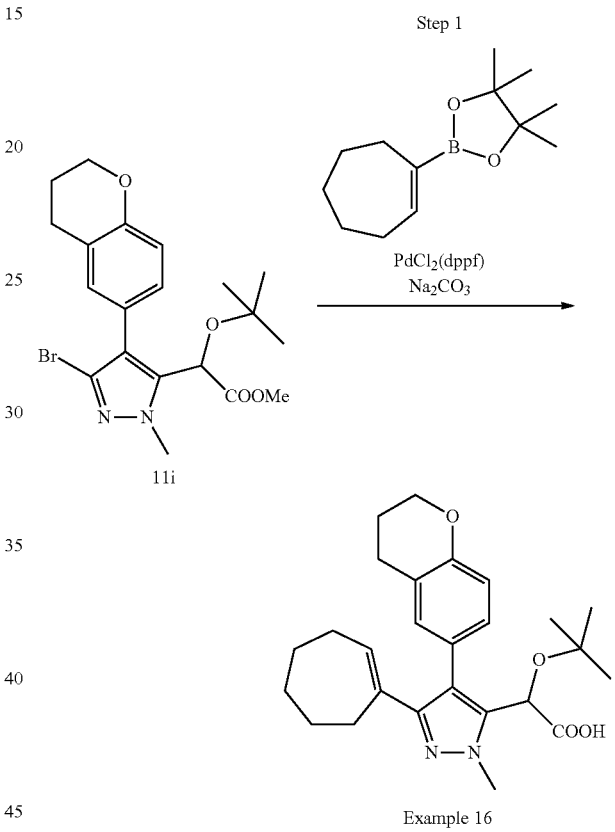

Example 16

Step 1: preparation of 2-(tert-butoxy)-2-[3-(cyclohept-1-en-1-yl)-4-(3,4-dihydro-2H-1-benzopyran-6-yl)-1-methyl-1H-pyrazol-5-yl]acetic acid (example 16)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 1-cycloheptenylboronic acid pinacol ester (30 mg, 0.137 mmol), after purification by preparative TLC (dichloromethane/ethyl acetate 50/50+0.5% formic acid) to 2-(tert-butoxy)-2-[3-(cyclohept-1-en-1-yl)-4-(3,4-dihydro-2H-1-benzopyran-6-yl)-1-methyl-1H-pyrazol-5-yl]acetic acid (example 16) (33 mg, 0.075 mmol, 66%).

$^1$H NMR (300 MHz, CDCl$_3$) δ 1.01 (s, 9H), 1.39-1.51 (m, 4H), 1.65-1.76 (m, 2H), 1.98-2.08 (m, 2H), 2.09-2.19 (m, 2H), 2.22-2.40 (m, 2H), 2.79 (t, J=6.4 Hz, 2H), 3.88 (s, 3H), 4.19-4.25 (m, 2H), 5.11 (s, 1H), 6.06 (t, J=6.6 Hz, 1H), 6.78 (d, J=8.2 Hz, 1H), 7.00-7.08 (m, 2H).

MS m/z ([M−H]$^−$) 437.
MS m/z ([M+H]$^+$) 439.

Example 17

Synthesis of 2-(tert-butoxy)-2-[4-(3,4-dihydro-2H-1-benzopyran-6-yl)-1-methyl-3-(3-methylcyclohex-1-en-1-yl)-1H-pyrazol-5-yl]acetic acid

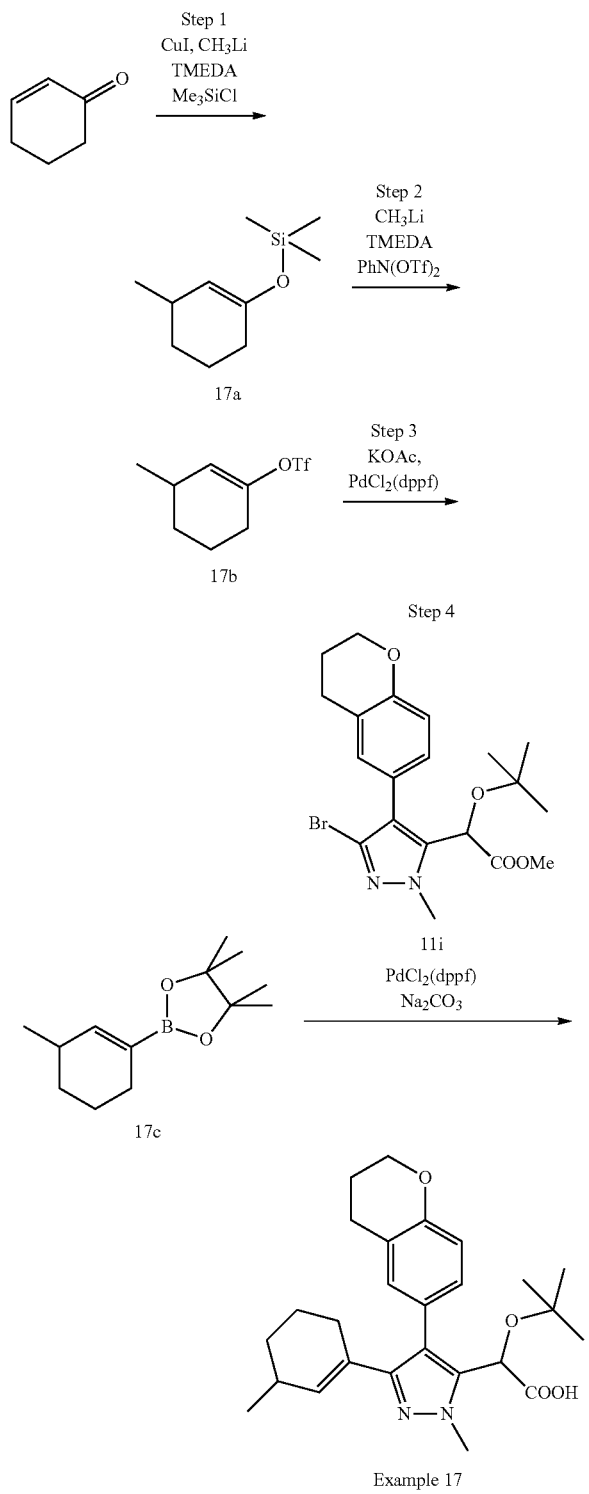

Example 17

Step 1: preparation of intermediate trimethyl[(3-methylcyclohex-1-en-1-yl)oxy]silane (17a)

Under nitrogen atmosphere, a suspension of N,N,N',N'-tetramethylethylenediamine (0.94 mL, 6.24 mmol) and copper iodide (0.42 g, 2.18 mmol) in anhydrous tetrahydrofuran (4 mL) was stirred at room temperature for 5 minutes. The reaction mixture was cooled to −78° C. and a 1.6 M methyl lithium solution in diethyl ether (1.30 mL, 2.08 mmol) was added. After stirring for 20 minutes at the same temperature, trimethylsilyl chloride (0.66 mL, 5.20 mmol) and a solution of cyclohexenone (0.20 g, 2.08 mmol) in anhydrous tetrahydrofuran (2 mL) were added. The reaction mixture was stirred 20 minutes at −78° C. and quenched with a saturated solution of ammonium chloride (10 mL). Diethyl ether (20 mL) was added and the mixture was allowed to reach room temperature. Layers were separated and the organic layer was successively washed with 0.5N hydrochloric acid (15 mL), and a saturated solution of sodium bicarbonate (15 mL), then dried over sodium sulfate and concentrated in vacuo. The residue was purified by flash chromatography on silica gel (dichloromethane) to provide trimethyl[(3-methylcyclohex-1-en-1-yl)oxy]silane (17a) (0.20 g, 1.08 mmol, 52%).

$^1$H NMR (400 MHz, CDCl$_3$) δ 0.18 (s, 9H), 0.94 (d, J=7.0 Hz, 3H), 1.00-1.09 (m, 1H), 1.49-1.60 (m, 1H), 1.64-1.80 (m, 2H), 1.88-2.04 (m, 2H), 2.18-2.29 (m, 1H), 4.73-4.75 (m, 1H).

Step 2: preparation of intermediate 3-methylcyclohex-1-en-1-yl trifluoromethanesulfonate (17b)

Under nitrogen atmosphere, a 1.6M methyl lithium solution in diethyl ether (0.71 mL, 1.13 mmol) was added to a solution of trimethyl[(3-methylcyclohex-1-en-1-yl)oxy]silane (17a) (190 mg, 1.03 mmol) in anhydrous tetrahydrofuran (2 mL), at 0° C. After stirring for 30 minutes at 0° C., N,N,N',N'-tetramethylethylenediamine (0.77 mL, 5.15 mmol) and N-phenyl-bis(trifluoromethanesulfonimide) (442 mg, 1.24 mmol) were added. The reaction mixture was stirred for an additional hour at 0° C. and quenched with a saturated solution of ammonium chloride (10 mL). Diethyl ether (20 mL) was added and the mixture was allowed to reach room temperature. Layers were separated and the organic layer was dried over sodium chloride and concentrated in vacuo. The residue was purified by flash chromatography on silica gel (dichloromethane) to provide 3-methylcyclohex-1-en-1-yl trifluoromethanesulfonate (17b) (119 mg, 0.49 mmol, 47%)

$^1$H NMR (300 MHz, CDCl$_3$) δ 1.05 (d, J=7.0 Hz, 3H), 1.12-1.26 (m, 1H), 1.61-1.95 (m, 3H), 2.20-2.47 (m, 3H), 5.59-5.64 (m, 1H).

Step 3: preparation of intermediate 4,4,5,5-tetramethyl-2-(3-methylcyclohex-1-en-1-yl)-1,3,2-dioxaborolane (17c)

Using the procedure described in example 7, step 6, 3-methylcyclohex-1-en-1-yl trifluoromethanesulfonate (17b) (100 mg, 0.409 mmol) is converted, after purification by flash chromatography on silica gel (cyclohexane/ethyl acetate 98/2), to 4,4,5,5-tetramethyl-2-(3-methylcyclohex-1-en-1-yl)-1,3,2-dioxaborolane (17c) (58 mg, 0.26 mmol, 48%).

$^1$H NMR (300 MHz, CDCl$_3$) δ 0.99 (d, J=7.2 Hz, 3H), 1.09-1.25 (m, 1H), 1.26 (s, 12H), 1.39-1.54 (m, 1H), 1.64-1.81 (m, 2H), 1.95-2.31 (m, 3H), 6.38-6.42 (m, 1H).

Step 4: preparation of 2-(tert-butoxy)-2-[4-(3,4-dihydro-2H-1-benzopyran-6-yl)-1-methyl-3-(3-methylcyclohex-1-en-1-yl)-1H-pyrazol-5-yl]acetic acid (example 17)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 4,4,5,5-tetramethyl-2-(3-methylcyclohex-1-en-1-yl)-1,3,2-dioxaborolane (17c) (31 mg, 0.137 mmol), after purification by preparative TLC (dichloromethane/ethyl acetate 45/55+0.5% formic acid) to 2-(tert-butoxy)-2-[4-(3,4-dihydro-2H-1-benzopyran-6-yl)-1-methyl-3-(3-methylcyclohex-1-en-1-yl)-1H-pyrazol-5-yl]acetic acid (example 17) (36 mg, 0.082 mmol, 60%) as a mixture of diastereoisomers.

$^1$H NMR (400 MHz, CDCl$_3$) δ 0.86 and 0.91 (d, J=7.0 Hz, 3H), 1.02 and 1.03 (s, 9H), 1.08-1.19 (m, 1H), 1.22-1.33 (m, 1H), 1.44-1.58 (m, 1H), 1.65-1.79 (m, 2H), 1.98-2.12 (m, 2H), 2.14-2.40 (m, 2H), 2.74-2.82 (m, 2H), 3.88 (s, 3H), 4.20-4.25 (m, 2H), 5.10 and 5.11 (s, 1H), 5.64 and 5.73 (s, 1H), 6.78 (d, J=8.1 Hz, 1H), 7.00-7.08 (m, 2H).

MS m/z ([M-H]$^-$) 437.

Example 18

Synthesis of 2-(tert-butoxy)-2-[4-(3,4-dihydro-2H-1-benzopyran-6-yl)-1-methyl-3-(6-methylcyclohex-1-en-1-yl)-1H-pyrazol-5-yl]acetic acid

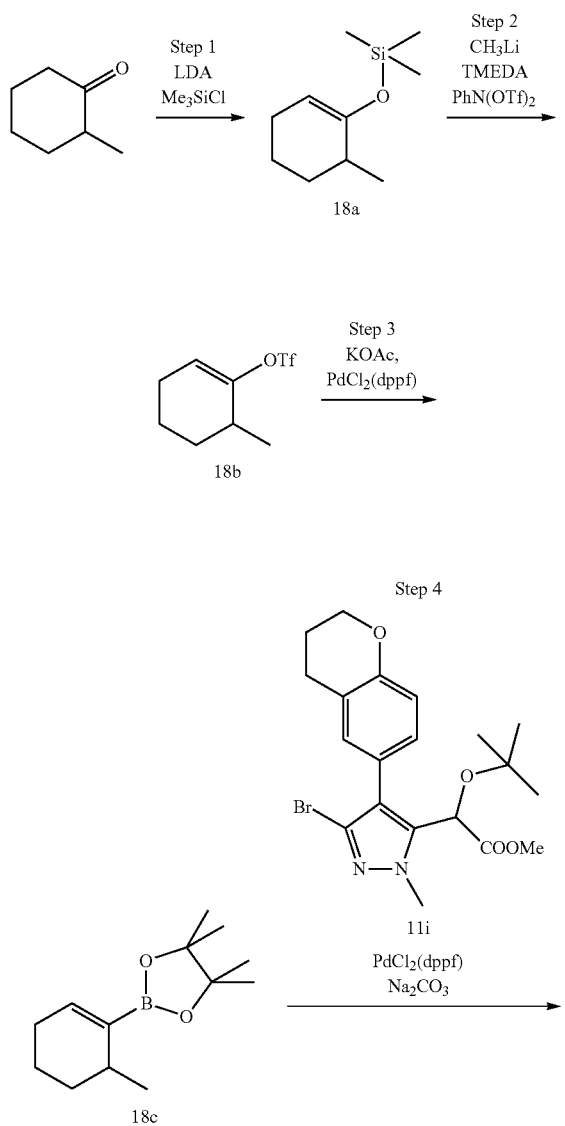

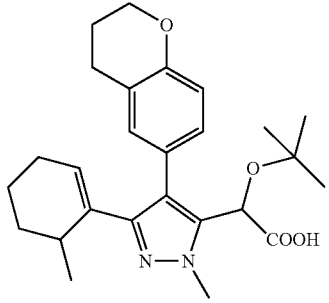

Example 18

Step 1: preparation of intermediate trimethyl[(6-methylcyclohex-1-en-1-yl)oxy]silane (18a)

Under nitrogen atmosphere, a solution of 2-methylcyclohexanone (0.5 g, 4.46 mmol) in anhydrous tetrahydrofuran (1 mL) was added dropwise to a solution of lithium diisopropylamide 2.0M in tetrahydrofuran (2.45 mL, 4.90 mmol) in anhydrous tetrahydrofuran (10 mL), previously cooled at −78° C. After stirring for 30 minutes at the same temperature, trimethylsilyl chloride (0.96 mL, 7.58 mmol) was added and the reaction mixture was stirred at room temperature for 1 hour before being quenched with a saturated solution of ammonium chloride (10 mL) at 0° C. Diethyl ether (20 mL) was added and the mixture was allowed to reach room temperature. Layers were separated and the organic layer was dried over sodium sulfate and concentrated in vacuo. The residue was purified by flash chromatography on silica gel (cyclohexane) to provide trimethyl[(6-methylcyclohex-1-en-1-yl)oxy]silane (18a) (660 mg, 3.58 mmol, 80%)

$^1$H NMR (400 MHz, CDCl$_3$) δ 0.18 (s, 9H), 1.02 (d, J=7.0 Hz, 3H), 1.31-1.50 (m, 2H), 1.52-1.63 (m, 1H), 1.74-1.82 (m, 1H), 1.95-2.01 (m, 2H), 2.07-2.18 (m, 1H), 4.80 (td, J=3.9 Hz, J=1.2 Hz, 1H).

Step 2: preparation of intermediate 6-methylcyclohex-1-en-1-yl trifluoromethanesulfonate (18b)

Using the procedure described in example 17, step 2, trimethyl[(6-methylcyclohex-1-en-1-yl)oxy]silane (18a) (0.66 g, 3.58 mmol) is converted, after purification by flash chromatography on silica gel (cyclohexane), to 6-methylcyclohex-1-en-1-yl trifluoromethanesulfonate (18b) (570 mg, 2.33 mmol, 65%).

$^1$H NMR (400 MHz, CDCl$_3$) δ 1.14 (d, J=7.0 Hz, 3H), 1.40-1.72 (m, 3H), 1.89-1.97 (m, 1H), 2.14-2.20 (m, 2H), 2.48-2.60 (m, 1H), 5.73 (td, J=4.1 Hz, J=1.4 Hz, 1H).

Step 3: preparation of intermediate 4,4,5,5-tetramethyl-2-(6-methylcyclohex-1-en-1-yl)-1,3,2-dioxaborolane (18c)

Using the procedure described in example 7, step 6, 6-methylcyclohex-1-en-1-yl trifluoromethanesulfonate (18b) (300 mg, 1.23 mmol) is converted, after purification by flash chromatography on silica gel (cyclohexane/ethyl acetate 98/2), to 4,4,5,5-tetramethyl-2-(6-methylcyclohex-1-en-1-yl)-1,3,2-dioxaborolane (18c) (140 mg, 0.63 mmol, 51%).

$^1$H NMR (400 MHz, CDCl$_3$) δ 1.04 (d, J=7.0 Hz, 3H), 1.25 (s, 6H), 1.26 (s, 6H), 1.46-1.72 (m, 4H), 1.99-2.10 (m, 2H), 2.32-2.40 (m, 1H), 6.52 (td, J=3.6 Hz, J=1.5 Hz, 1H).

Step 4: preparation of 2-(tert-butoxy)-2-[4-(3,4-dihydro-2H-1-benzopyran-6-yl)-1-methyl-3-(6-methylcyclohex-1-en-1-yl)-1H-pyrazol-5-yl]acetic acid (example 18)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 4,4,5,5-tetramethyl-2-(6-methylcyclohex-1-en-1-yl)-1,3,2-dioxaborolane (18c) (31 mg, 0.137 mmol), after purification by preparative TLC (dichloromethane/ethyl acetate 50/50+0.5% formic acid) to 2-(tert-butoxy)-2-[4-(3,4-dihydro-2H-1-benzopyran-6-yl)-1-methyl-3-(6-methylcyclohex-1-en-1-yl)-1H-pyrazol-5-yl]acetic acid (example 18) (14 mg, 0.032 mmol, 28%) as a mixture of diastereoisomers.

$^1$H NMR (400 MHz, CDCl$_3$) δ 0.85 and 0.90 (d, J=7.0 Hz, 3H), 0.98 and 1.11 (s, 9H), 1.34-1.75 (m, 4H), 1.94-2.06 (m, 4H), 2.39-2.52 (m, 1H), 2.70-2.83 (m, 2H), 3.88 and 3.92 (s, 3H), 4.20-4.24 (m, 2H), 5.03 and 5.14 (s, 1H), 5.70-5.76 (m, 1H), 6.74-6.79 (m, 1H), 6.92-7.07 (m, 2H).

MS m/z ([M−H]$^-$) 437.
MS m/z ([M+H]$^+$) 439.

Example 19

Synthesis of 2-(tert-butoxy)-2-[3-cyclopentyl-4-(3,4-dihydro-2H-1-benzopyran-6-yl)-1-methyl-1H-pyrazol-5-yl]acetic acid

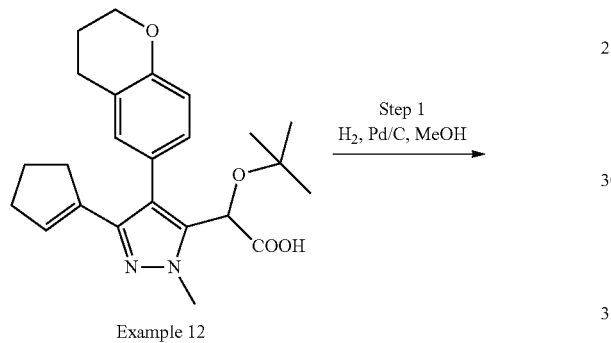

Example 12

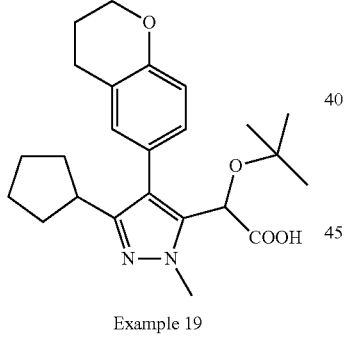

Example 19

MS m/z ([M−H]$^-$) 411.
MS m/z ([M+H]$^+$) 413.

Example 20

Synthesis of 2-(tert-butoxy)-2-[3-cyclohexyl-4-(3,4-dihydro-2H-1-benzopyran-6-yl)-1-methyl-1H-pyrazol-5-yl]acetic acid

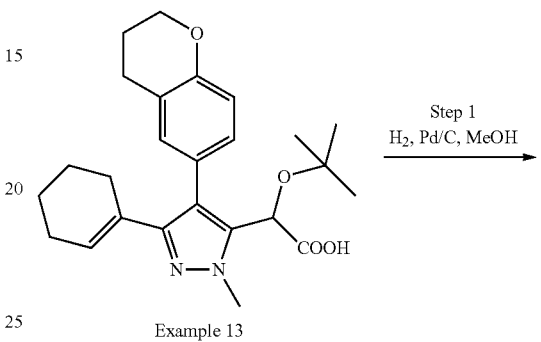

Example 13

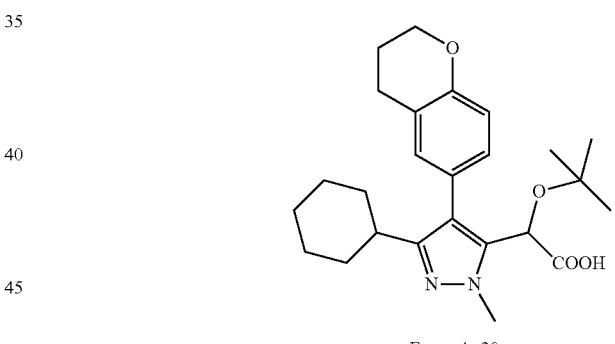

Example 20

Step 1: preparation of 2-(tert-butoxy)-2-[3-cyclopentyl-4-(3,4-dihydro-2H-1-benzopyran-6-yl)-1-methyl-1H-pyrazol-5-yl]acetic acid (example 19)

A mixture of 2-(tert-butoxy)-2-[3-(cyclopent-1-en-1-yl)-4-(3,4-dihydro-2H-1-benzopyran-6-yl)-1-methyl-1H-pyrazol-5-yl]acetic acid (example 12) (19.7 mg, 0.047 mmol) and palladium on carbon (7 mg) in methanol (2.4 mL) was stirred under hydrogen atmosphere overnight. The mixture was filtered over Millipore and the filtrate was concentrated in vacuo to provide 2-(tert-butoxy)-2-[3-cyclopentyl-4-(3,4-dihydro-2H-1-benzopyran-6-yl)-1-methyl-1H-pyrazol-5-yl]acetic acid (example 19) (19.5 mg, 0.047 mmol, 98%) as a white solid.

$^1$H NMR (400 MHz, CDCl$_3$) δ 1.02 (s, 9H), 1.43-1.83 (m, 7H), 1.96-2.05 (m, 3H), 2.80 (m, 2H), 2.95 (m, 1H), 3.88 (s, 3H), 4.22 (t, J=5.1 Hz, 2H), 5.06 (s, 1H), 6.80 (d, J=8.2 Hz, 1H), 7.00-7.05 (m, 2H).

Step 1: preparation of 2-(tert-butoxy)-2-[3-cyclohexyl-4-(3,4-dihydro-2H-1-benzopyran-6-yl)-1-methyl-1H-pyrazol-5-yl]acetic acid (example 20)

Using the procedure described in example 19, step 1, 2-(tert-butoxy)-2-[3-(cyclohex-1-en-1-yl)-4-(3,4-dihydro-2H-1-benzopyran-6-yl)-1-methyl-1H-pyrazol-5-yl]acetic acid (example 13) (23 mg, 0.054 mmol) is converted into 2-(tert-butoxy)-2-[3-cyclohexyl-4-(3,4-dihydro-2H-1-benzopyran-6-yl)-1-methyl-1H-pyrazol-5-yl]acetic acid (example 20) (22.6 mg, 0.053 mmol, 98%) as a white solid.

$^1$H NMR (400 MHz, CDCl$_3$) δ 1.03 (s, 9H), 1.14-1.28 (m, 3H), 1.50-2.08 (m, 9H), 2.56-2.61 (m, 1H), 2.79-2.85 (m, 2H), 3.96 (s, 3H), 4.24 (t, J=5.0 Hz, 2H), 5.06 (s, 1H), 6.82 (d, J=8.2 Hz, 1H), 6.99-7.02 (m, 2H).

MS m/z ([M−H]$^-$) 425.
MS m/z ([M+H]$^+$) 427.

Example 21

Synthesis of 2-(tert-butoxy)-2-[3-(cyclopentylmethyl)-4-(3,4-dihydro-2H-1-benzopyran-6-yl)-1-methyl-1H-pyrazol-5-yl]acetic acid

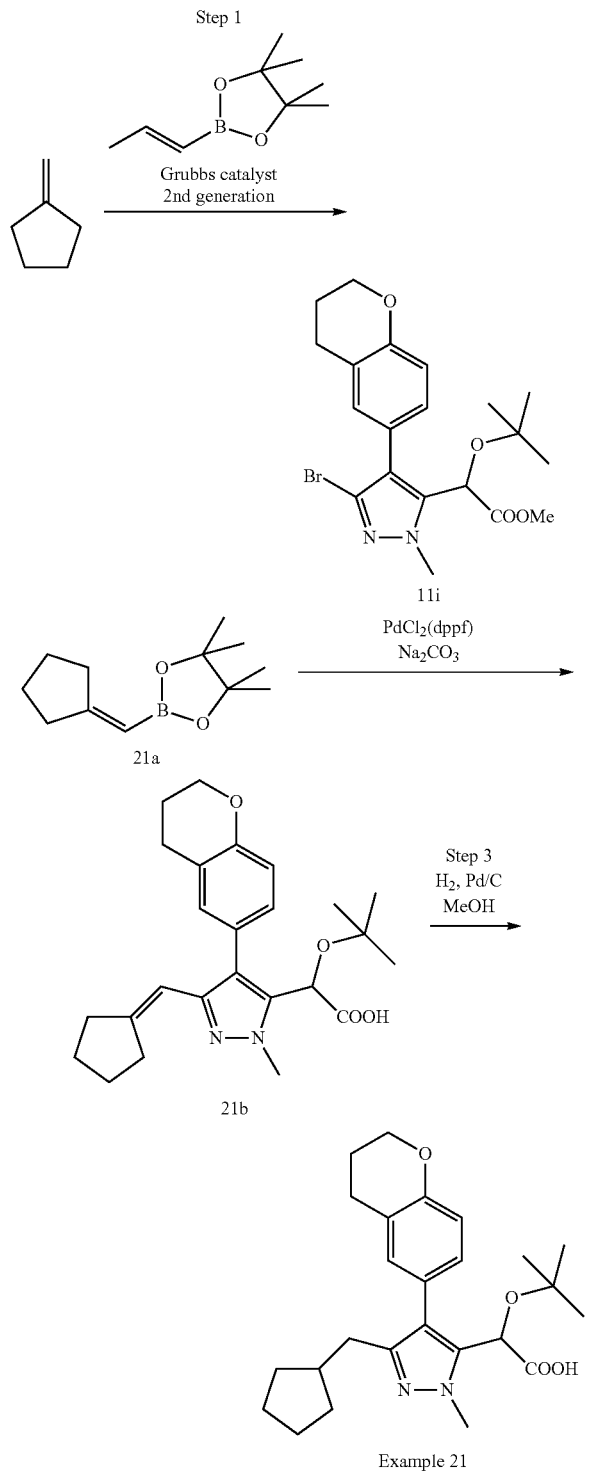

Step 1: preparation of intermediate 2-(cyclopentylidenemethyl)-4,4,5,5-tetramethyl-1,3,2-dioxaborolane (21a)

A solution of methylcyclopentane (100 mg, 1.22 mmol), and trans-1-propenylboronic acid pinacol ester (204 mg, 1.22 mmol) in dry dichloromethane (6 mL) was bubbled with nitrogen for 5 minutes. Grubbs Catalyst, $2^{nd}$ generation (52 mg, 0.06 mmol) was added and the reaction mixture was refluxed overnight. The solution was concentrated in vacuo and the residue was purified by preparative TLC (cyclohexane/ethyl acetate 90/10) to provide 2-(cyclopentylidenemethyl)-4,4,5,5-tetramethyl-1,3,2-dioxaborolane (21a) (88 mg, 0.42 mmol, 35%)

$^1$H NMR (300 MHz, CDCl$_3$) δ 1.25 (s, 12H), 1.57-1.73 (m, 4H), 2.31-2.41 (m, 2H), 2.46-2.56 (m, 2H), 5.26 (quin, J=2.2 Hz, 1H).

Step 2: preparation of intermediate 2-(tert-butoxy)-2-[3-(cyclopentylidenemethyl)-4-(3,4-dihydro-2H-1-benzopyran-6-yl)-1-methyl-1H-pyrazol-5-yl]acetic acid (21b)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (70 mg, 0.160 mmol) is converted by reaction with 2-(cyclopentylidenemethyl)-4,4,5,5-tetramethyl-1,3,2-dioxaborolane (21a) (87 mg, 0.416 mmol), after purification by preparative TLC (dichloromethane/ethyl acetate 50/50+0.5% formic acid) into 2-(tert-butoxy)-2-[3-(cyclopentylidenemethyl)-4-(3,4-dihydro-2H-1-benzopyran-6-yl)-1-methyl-1H-pyrazol-5-yl]acetic acid (21b) (36 mg, 0.085 mmol, 53%).

$^1$H NMR (300 MHz, CDCl$_3$) δ 1.02 (s, 9H), 1.57-1.78 (m, 4H), 1.99-2.08 (m, 2H), 2.32-2.40 (m, 2H), 2.59-2.68 (m, 2H), 2.73-2.90 (m, 2H), 3.89 (s, 3H), 4.20-4.25 (m, 2H), 5.15 (s, 1H), 6.12 (quin, J=2.2 Hz, 1H), 6.83 (d, J=8.2 Hz, 1H), 7.02-7.09 (m, 2H).

MS m/z ([M−H]$^-$) 423.

MS m/z ([M+H]$^+$) 425.

Step 3: preparation of 2-(tert-butoxy)-2-[3-(cyclopentylmethyl)-4-(3,4-dihydro-2H-1-benzopyran-6-yl)-1-methyl-1H-pyrazol-5-yl]acetic acid (example 21)

Using the procedure described in example 19, step 1, 2-(tert-butoxy)-2-[3-(cyclopentylidenemethyl)-4-(3,4-dihydro-2H-1-benzopyran-6-yl)-1-methyl-1H-pyrazol-5-yl]acetic acid (21b) (22 mg, 0.052 mmol) is converted into 2-(tert-butoxy)-2-[3-(cyclopentylmethyl)-4-(3,4-dihydro-2H-1-benzopyran-6-yl)-1-methyl-1H-pyrazol-5-yl]acetic acid (example 21) (21 mg, 0.049 mmol, 95%)

$^1$H NMR (400 MHz, CDCl$_3$) δ 0.97-1.18 (m, 11H), 1.39-1.69 (m, 6H), 1.99-2.10 (m, 3H), 2.50-2.61 (m, 2H), 2.74-2.87 (m, 2H), 3.89 (s, 3H), 4.20-4.25 (m, 2H), 5.09 (s, 1H), 6.81 (d, J=8.2 Hz, 1H), 6.99-7.05 (m, 2H).

MS m/z ([M−H]$^-$) 425.

MS m/z ([M+H]$^+$) 427.

Example 22

Synthesis of 2-(tert-butoxy)-2-[4-(3,4-dihydro-2H-1-benzopyran-6-yl)-1-methyl-3-(prop-1-en-2-yl)-1H-pyrazol-5-yl]acetic acid

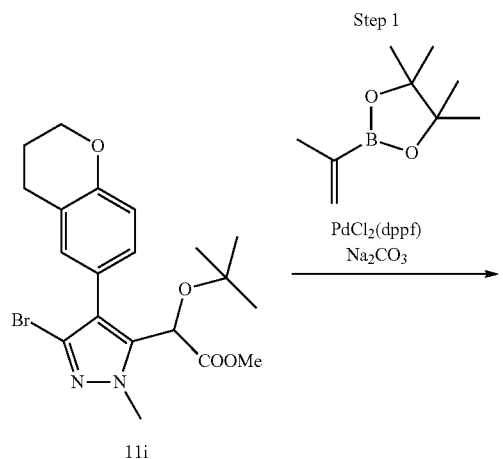

Example 23

Synthesis of 2-(tert-butoxy)-2-[3-(1-cyclopentylethenyl)-4-(3,4-dihydro-2H-1-benzopyran-6-yl)-1-methyl-1H-pyrazol-5-yl]acetic acid

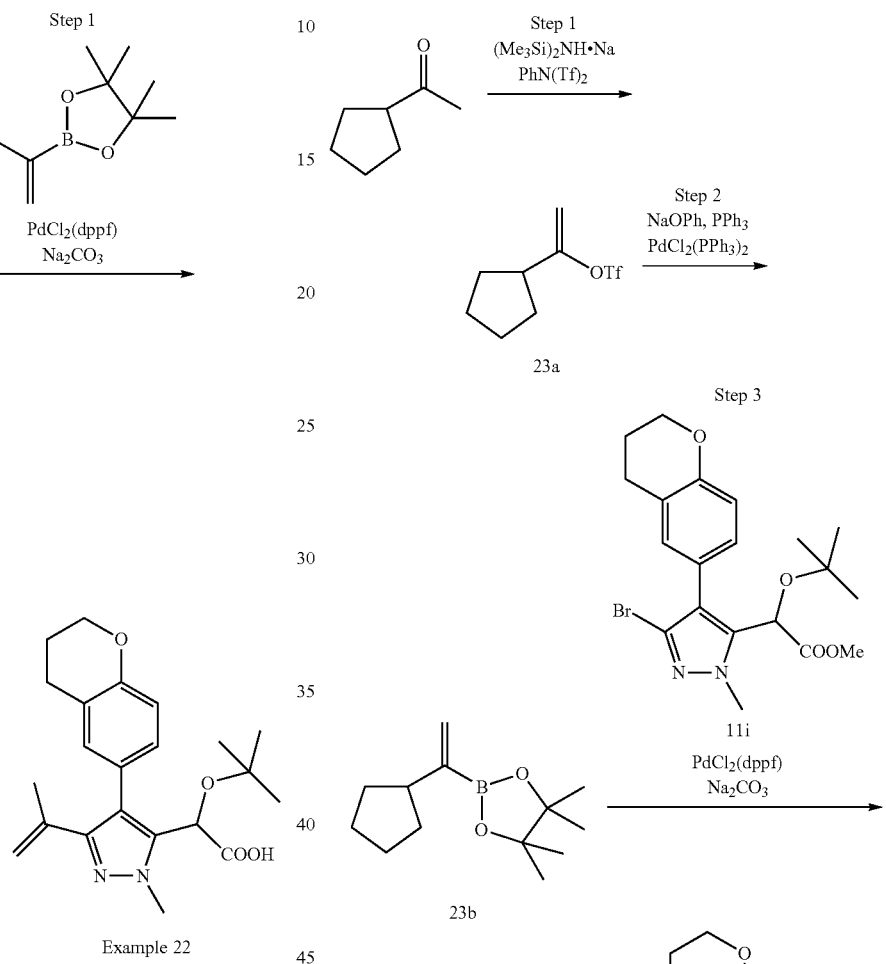

Step 1: preparation of 2-(tert-butoxy)-2-[4-(3,4-dihydro-2H-1-benzopyran-6-yl)-1-methyl-3-(prop-1-en-2-yl)-1H-pyrazol-5-yl]acetic acid (example 22)

Using the procedure described in example 15, step 1, the intermediate methyl 2-[3-bromo-4-(3,4-dihydro-2H-1-benzopyran-6-yl)-1-methyl-1H-pyrazol-5-yl]-2-(tert-butoxy)acetate (11i) (70 mg, 0.160 mmol) was converted by reaction with isopropenylboronic acid pinacol ester (108 mg, 0.640 mmol), after purification by preparative TLC (dichloromethane/ethyl acetate 50/50+0.5% formic acid) into 2-(tert-butoxy)-2-[4-(3,4-dihydro-2H-1-benzopyran-6-yl)-1-methyl-3-(prop-1-en-2-yl)-1H-pyrazol-5-yl]acetic acid (example 22) (41 mg, 0.107 mmol, 66%).

$^1$H NMR (400 MHz, CDCl$_3$) δ 1.04 (s, 9H), 1.99-2.07 (m, 2H), 2.04 (s, 3H), 2.72-2.85 (m, 2H), 3.90 (s, 3H), 4.22 (t, J=5.1 Hz, 2H), 4.93-4.96 (m, 1H), 4.99-5.02 (m, 1H), 5.03 (s, 1H), 6.79 (d, J=8.2 Hz, 1H), 7.02-7.05 (m, 2H).

MS m/z ([M−H]$^−$) 383.

MS m/z ([M+H]$^+$) 385.

Step 1: preparation of intermediate 1-cyclopentylethenyl trifluoromethanesulfonate (23a)

Under nitrogen atmosphere, a solution of sodium bis(trimethylsilyl)amide 1.0M in tetrahydrofuran (2.94 mL, 2.94 mmol) in anhydrous tetrahydrofuran (3 mL) was cooled at −78° C. A solution of cyclopentyl methyl ketone (300 mg, 2.67 mmol) in dry tetrahydrofuran (2 mL) was slowly added and the mixture was stirred at the same temperature for 15 minutes. A solution of N-phenyl-bis(trifluoromethanesulfonide) (955 mg, 2.67 mmol) in anhydrous tetrahydrofuran (2 mL) was added dropwise, and the reaction mixture was stirred at −78° C. for 3 hours. A saturated solution of sodium hydrogenocarbonate (8 mL) was added and the mixture was allowed to reach room temperature. After extraction with diethyl ether (2×10 mL), the organic layer was washed with brine (10 mL), dried over sodium sulfate and concentrated in vacuo. The residue was purified by flash chromatography on silica gel (cyclohexane) to provide 1-cyclopentylethenyl trifluoromethanesulfonate (23a) (357 mg, 1.46 mmol, 55%).

$^1$H NMR (300 MHz, CDCl$_3$) δ 1.48-1.80 (m, 6H), 1.88-2.00 (m, 2H), 2.72 (quin, J=8.1 Hz, 1H), 4.94 (dd, J=1.2 Hz, J=3.8 Hz, 1H), 5.06 (d, J=3.8 Hz, 1H).

Step 2: preparation of intermediate 2-(1-cyclopentylethenyl)-4,4,5,5-tetramethyl1,3,2-dioxaborolane (23b)

Bis(triphenylphosphine)palladium(II) dichloride (17 mg, 0.025 mmol) was added to a previously degassed solution of 1-cyclopentylethenyl trifluoromethanesulfonate (23a) (200 mg, 0.82 mmol), bis(pinacolato)diboron (208 mg, 0.82 mmol), sodium phenoxide (143 mg, 1.23 mmol) and triphenylphosphine (19 mg, 0.074 mmol) in anhydrous toluene (3 mL). The reaction mixture was heated at 50° C. for 4 hours, filtered and the filtrate was concentrated in vacuo. The residue was purified by flash chromatography on silica gel (cyclohexane/ethyl acetate: 90/10) to provide 2-(1-cyclopentylethenyl)-4,4,5,5-tetramethyl1,3,2-dioxaborolane (23b) (135 mg, 0.61 mmol, 74%).

$^1$H NMR (400 MHz, CDCl$_3$) δ 1.26 (s, 12H), 1.33-1.45 (m, 2H), 1.50-1.61 (m, 2H), 1.62-1.72 (m, 2H), 1.74-1.84 (m, 2H), 2.56 (quin, J=8.4 Hz, 1H), 5.58-5.61 (m, 1H), 5.70 (dd, J=0.8 Hz, J=3.2 Hz, 1H).

Step 3: preparation of 2-(tert-butoxy)-2-[3-(1-cyclopentylethenyl)-4-(3,4-dihydro-2H-1-benzopyran-6-yl)-1-methyl-1H-pyrazol-5-yl]acetic acid (example 23)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (70 mg, 0.160 mmol) is converted by reaction with 2-(1-cyclopentylethenyl)-4,4,5,5-tetramethyl1,3,2-dioxaborolane (23b) (124 mg, 0.560 mmol), after purification by preparative TLC (dichloromethane/ethyl acetate 50/50+0.5% formic acid) into 2-(tert-butoxy)-2-[3-(1-cyclopentylethenyl)-4-(3,4-dihydro-2H-1-benzopyran-6-yl)-1-methyl-1H-pyrazol-5-yl]acetic acid (example 23) (29 mg, 0.066 mmol, 41%).

$^1$H NMR (300 MHz, CDCl$_3$) δ 1.02 (s, 9H), 1.23-1.37 (m, 2H), 1.42-1.84 (m, 6H), 1.97-2.07 (m, 2H), 2.74-2.88 (m, 3H), 3.88 (s, 3H), 4.19-4.25 (m, 2H), 4.97 (s, 1H), 5.03 (t, J=1.4 Hz, 1H), 5.10 (s, 1H), 6.77 (d, J=8.6 Hz, 1H), 6.99-7.04 (m, 2H).

MS m/z ([M−H]$^−$) 437.

MS m/z ([M+H]$^+$) 439.

Example 24

Synthesis of 2-(tert-butoxy)-2-[4-(3,4-dihydro-2H-1-benzopyran-6-yl)-1-methyl-3-(propan-2-yl)-1H-pyrazol-5-yl]acetic acid

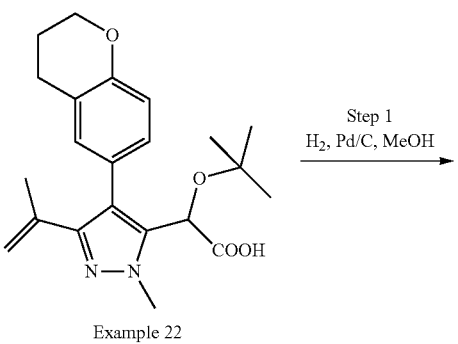

Step 1
H$_2$, Pd/C, MeOH

Example 22

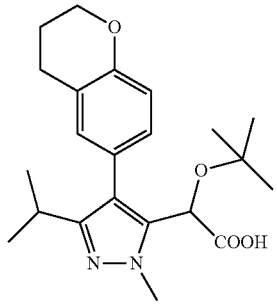

Example 24

Step 1: preparation of 2-(tert-butoxy)-2-[4-(3,4-dihydro-2H-1-benzopyran-6-yl)-1-methyl-3-(propan-2-yl)-1H-pyrazol-5-yl]acetic acid (example 24)

Using the procedure described in example 19, step 1, 2-(tert-butoxy)-2-[4-(3,4-dihydro-2H-1-benzopyran-6-yl)-1-methyl-3-(prop-1-en-2-yl)-1H-pyrazol-5-yl]acetic acid (example 22) (31 mg, 0.080 mmol) is converted into 2-(tert-butoxy)-2-[4-(3,4-dihydro-2H-1-benzopyran-6-yl)-1-methyl-3-(propan-2-yl)-1H-pyrazol-5-yl]acetic acid (example 24) (29.8 mg, 0.077 mmol, 96%) as a white solid.

$^1$H NMR (300 MHz, CDCl$_3$) δ 1.03 (s, 9H), 1.09 (d, J=6.9 Hz, 3H), 1.26 (d, J=6.9 Hz, 3H), 1.96-2.08 (m, 2H), 2.72-2.84 (m, 2H), 2.88-3.01 (m, 1H), 3.87 (s, 3H), 4.22 (t, J=5.1 Hz, 2H), 5.05 (s, 1H), 6.81 (d, J=8.2 Hz, 1H), 7.00-7.04 (m, 2H).

MS m/z ([M−H]$^−$) 385.

MS m/z ([M+H]$^+$) 387.

Example 25

Synthesis of 2-(tert-butoxy)-2-[3-(1-cyclopentyl-ethyl)-4-(3,4-dihydro-2H-1-benzopyran-6-yl)-1-methyl-1H-pyrazol-5-yl]acetic acid

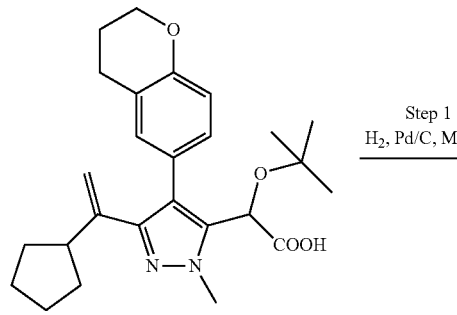

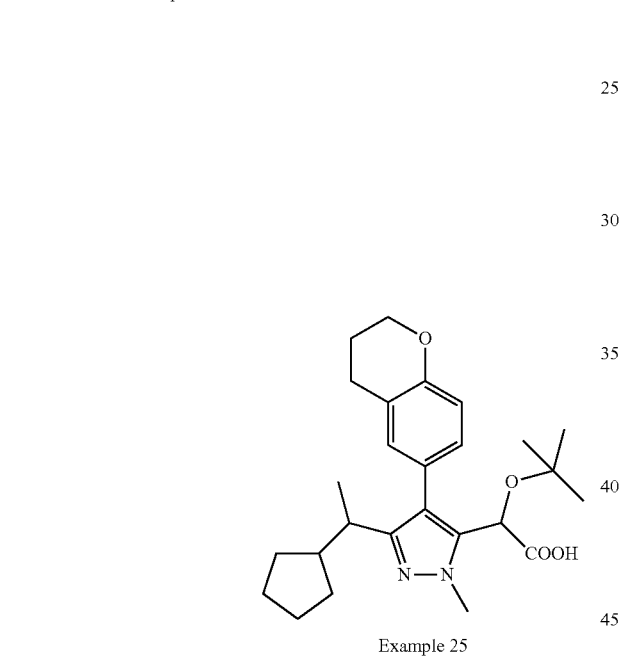

Step 1: preparation of 2-(tert-butoxy)-2-[3-(1-cyclopentyl-ethyl)-4-(3,4-dihydro-2H-1-benzopyran-6-yl)-1-methyl-1H-pyrazol-5-yl]acetic acid (example 25)

Using the procedure described in example 19, step 1, 2-(tert-butoxy)-2-[3-(1-cyclopentylethenyl)-4-(3,4-dihydro-2H-1-benzopyran-6-yl)-1-methyl-1H-pyrazol-5-yl]acetic acid (example 23) (20 mg, 0.046 mmol) is converted into 2-(tert-butoxy)-2-[3-(1-cyclopentylethyl)-4-(3,4-dihydro-2H-1-benzopyran-6-yl)-1-methyl-1H-pyrazol-5-yl]acetic acid (example 25) (19 mg, 0.043 mmol, 95%) as a mixture of diastereoisomers.

$^1$H NMR (400 MHz, CDCl$_3$) δ 1.02 and 1.05 (s, 10H), 1.12 and 1.28 (d, J=6.8 Hz, 3H), 1.32-1.62 (m, 6H), 1.72-1.88 (m, 1H), 1.97-2.17 (m, 3H), 2.48-2.58 (m, 1H), 2.73-2.87 (m, 2H), 3.97 and 3.98 (s, 3H), 4.20-4.25 (m, 2H), 5.00 and 5.04 (s, 1H), 6.80 (d, J=8.3 Hz, 1H), 6.93-7.03 (m, 2H).

MS m/z ([M−H]$^-$) 439.

MS m/z ([M+H]$^+$) 441.

Example 26

Synthesis of 2-(tert-butoxy)-2-[4-(3,4-dihydro-2H-1-benzopyran-6-yl)-1-methyl-3-(5-methylcyclopent-1-en-1-yl)-1H-pyrazol-5-yl]acetic acid

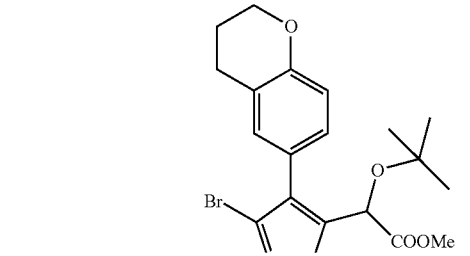

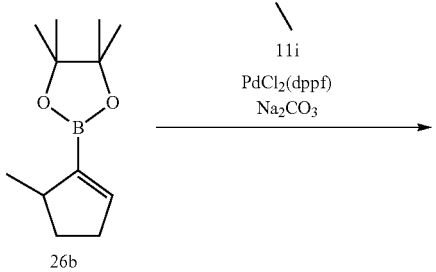

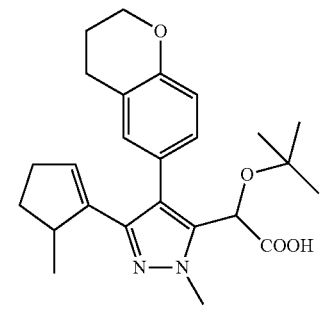

Step 1: preparation of intermediate 5-methylcyclopent-1-en-1-yl trifluoromethanesulfonate (26a)

Under nitrogen atmosphere, a solution of 2-methylcyclopentanone (0.5 g, 5.09 mmol, 2.94 mmol) and N-(5-chloro-2-pyridyl)triflimide (2.2 g, 5.60 mmol) in anhydrous tetrahydrofuran (34 mL) was cooled at −78° C. A solution of potassium bis(trimethylsilyl)amide 1.0M in tetrahydrofuran (5.60 mL, 5.60 mmol) was dropwise added and the reaction was stirred at this temperature for 1 hour before being allowed to reach room temperature for 3 hours. Water (30 mL) was added and the mixture was extracted with diethyl ether (2×30 mL). The organic layer was successively washed with a saturated solution of sodium hydrogenocarbonate (20 mL) and brine (20 mL), then dried over sodium sulfate and concentrated in vacuo. The residue was purified by flash chromatography on silica gel (cyclohexane) to provide 5-methylcyclopent-1-en-1-yl trifluoromethanesulfonate (26a) (350 mg, 1.52 mmol, 30%) as a colourless oil.

$^1$H NMR (300 MHz, CDCl$_3$) δ 1.13 (d, J=6.9 Hz, 3H), 1.51-1.63 (m, 1H), 2.19-2.41 (m, 3H), 2.83-2.96 (m, 1H), 5.60 (dd, J=2.3 Hz, J=4.5 Hz, 1H).

Step 2: preparation of intermediate 4,4,5,5-tetramethyl-2-(5-methylcyclopent-1-en-1-yl)-1,3,2-dioxaborolane (26b)

Using the procedure described in example 23, step 2, 5-methylcyclopent-1-en-1-yl trifluoromethanesulfonate (26a) (200 mg, 0.87 mmol) is converted, after purification by flash chromatography on silica gel (cyclohexane/ethyl acetate 90/10) into 4,4,5,5-tetramethyl-2-(5-methylcyclopent-1-en-1-yl)-1,3,2-dioxaborolane (26b) (80 mg, 0.38 mmol, 44%).

$^1$H NMR (300 MHz, CDCl$_3$) δ 1.05 (d, J=6.9 Hz, 3H), 1.26 (s, 6H), 1.27 (s, 6H), 1.32-1.43 (m, 1H), 1.96-2.11 (m, 1H), 2.23-2.51 (m, 2H), 2.79-2.93 (m, 1H), 6.47 (dd, J=2.2 Hz, J=4.2 Hz, 1H).

Step 3: preparation of 2-(tert-butoxy)-2-[4-(3,4-dihydro-2H-1-benzopyran-6-yl)-1-methyl-3-(5-methylcyclopent-1-en-1-yl)-1H-pyrazol-5-yl]acetic acid (example 26)

Using the procedure described in example 15, step 1, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 4,4,5,5-tetramethyl-2-(5-methylcyclopent-1-en-1-yl)-1,3,2-dioxaborolane (26b) (83 mg, 0.400 mmol), after purification by preparative TLC (dichloromethane/ethyl acetate 50/50+0.5% formic acid) into 2-(tert-butoxy)-2-[4-(3,4-dihydro-2H-1-benzopyran-6-yl)-1-methyl-3-(5-methylcyclopent-1-en-1-yl)-1H-pyrazol-5-yl]acetic acid (example 26) (12 mg, 0.028 mmol, 25%) as one couple of diastereoisomers.

$^1$H NMR (400 MHz, CDCl$_3$) δ 1.06-1.11 (m, 12H), 1.45-1.53 (m, 1H), 1.98-2.08 (m, 3H), 2.16-2.25 (m, 1H), 2.28-2.39 (m, 1H), 2.72-2.85 (m, 2H), 3.04-3.15 (m, 1H), 3.90 (s, 3H), 4.20-4.25 (m, 2H), 4.99 (s, 1H), 5.54-5.58 (m, 1H), 6.79 (d, J=8.1 Hz, 1H), 6.99-7.05 (m, 2H).

Ms m/z ([M−H]$^-$) 423.

MS m/z ([M+H]$^+$) 425.

Example 27

Synthesis of 2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid

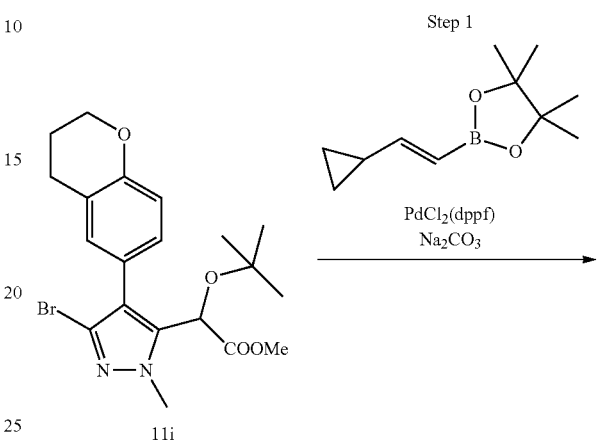

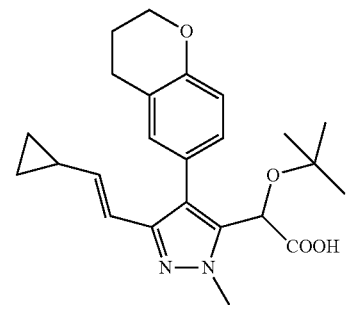

Example 27

Step 1: preparation of 2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid Using the procedure described in example 15, step 1, the intermediate methyl 2-[3-bromo-4-(3,4-dihydro-2H-1-benzopyran-6-yl)-1-methyl-1H-pyrazol-5-yl]-2-(tert-butoxy)acetate (11i) (70 mg, 0.160 mmol) was converted by reaction with cyclopropylvinylboronic acid pinacol ester (124 mg, 0.639 mmol), after purification by preparative TLC (dichloromethane/ethyl acetate 55/45+0.5% formic acid) into 2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid (28.2 mg, 0.069 mmol, 43%).

$^1$H NMR (400 MHz, CDCl$_3$) δ 0.38-0.48 (m, 2H), 0.66-0.77 (m, 2H), 1.02 (s, 9H), 1.38-1.48 (m, 1H), 1.96-2.09 (m, 2H), 2.73-2.88 (m, 2H), 3.88 (s, 3H), 4.23 (t, J=5.1 Hz, 2H), 5.12 (s, 1H), 5.84 (dd, J=9.2/15.8 Hz, 1H), 6.26 (d, J=15.8 Hz, 1H), 6.83 (d, J=8.2 Hz, 1H), 7.04-7.08 (m, 2H).

MS m/z ([M−H]$^-$) 409.

MS m/z ([M+H]$^+$) 411.

Example 28

Synthesis of 2-(tert-butoxy)-2-[3-(2-cyclopropylethyl)-4-(3,4-dihydro-2H-1-benzopyran-6-yl)-1-methyl-1H-pyrazol-5-yl]acetic acid

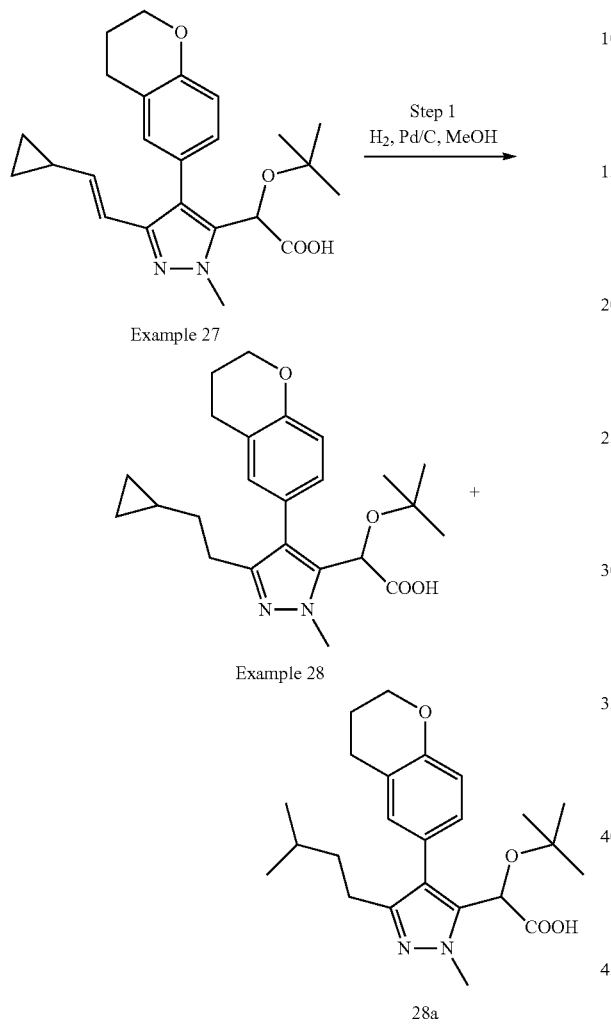

MS m/z ([M−H]⁻) 411; MS m/z ([M+H]⁺) 413 (example 28).

MS m/z ([M−H]⁻) 413; MS m/z ([M+H]⁺) 415 for minor compound (28a).

Example 29

Synthesis of 2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid

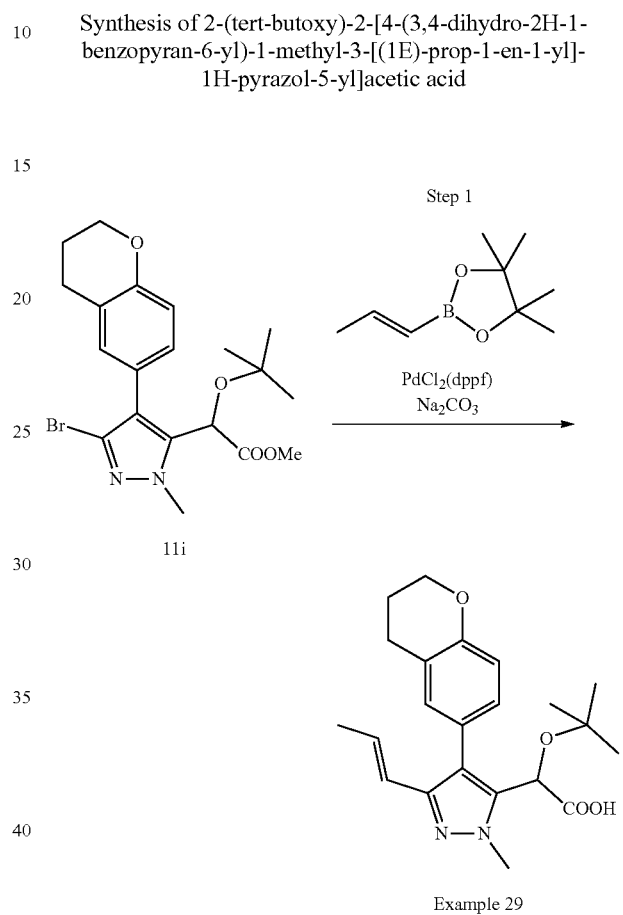

Step 1: preparation of 2-(tert-butoxy)-2-[3-(2-cyclopropylethyl)-4-(3,4-dihydro-2H-1-benzopyran-6-yl)-1-methyl-1H-pyrazol-5-yl]acetic acid (example 28)

Using the procedure described in example 19, step 1, 2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid (example 27) (20.4 mg, 0.050 mmol) is converted into a 73/27 mixture of 2-(tert-butoxy)-2-[3-(2-cyclopropylethyl)-4-(3,4-dihydro-2H-1-benzopyran-6-yl)-1-methyl-1H-pyrazol-5-yl]acetic acid (example 28) and 2-(tert-butoxy)-2-[4-(3,4-dihydro-2H-1-benzopyran-6-yl)-1-methyl-3-(3-methylbutyl)-1H-pyrazol-5-yl]acetic acid respectively (28a) (18.1 mg, 0.044 mmol, 90%).

¹H NMR (300 MHz, CDCl₃) δ −0.1−−0.02 (m, 2H), 0.26-0.37 (m, 2H), 1.02 (s, 9H), 1.18-1.29 (m, 1H), 1.38-1.49 (m, 2H), 1.98-2.09 (m, 2H), 2.60-2.70 (m, 2H), 2.75-2.85 (m, 2H), 3.87 (s, 3H), 4.23 (t, J=5.1 Hz, 2H), 5.10 (s, 1H), 6.82 (d, J=8.2 Hz, 1H), 7.02-7.07 (m, 2H).

Step 1: preparation of 2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid (example 29)

Using the procedure described in example 15, step 1, the intermediate methyl 2-[3-bromo-4-(3,4-dihydro-2H-1-benzopyran-6-yl)-1-methyl-1H-pyrazol-5-yl]-2-(tert-butoxy) acetate (11i) (70 mg, 0.160 mmol) was converted by reaction with trans-1-propenylboronic acid pinacol ester (108 mg, 0.643 mmol), after purification by preparative TLC (dichloromethane/ethyl acetate 50/50+0.5% formic acid) into 2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid (example 29) (32 mg, 0.083 mmol, 52%).

¹H NMR (400 MHz, CDCl₃) δ 1.02 (s, 9H), 1.76 (dd, J=1.0/6.3 Hz, 3H), 1.98-2.08 (m, 2H), 2.75-2.88 (m, 2H), 3.90 (s, 3H), 4.23 (t, J=5.1 Hz, 2H), 5.11 (s, 1H), 6.20 (d, J=15.9 Hz 1H), 6.25-6.35 (m, 1H), 6.83 (d, J=8.2 Hz, 1H), 7.04-7.07 (m, 2H).

MS m/z ([M−H]⁻) 383.

MS m/z ([M+H]⁺) 385.

Example 30

Synthesis of 2-(tert-butoxy)-2-[4-(3,4-dihydro-2H-1-benzopyran-6-yl)-1-methyl-3-propyl-1H-pyrazol-5-yl]acetic acid

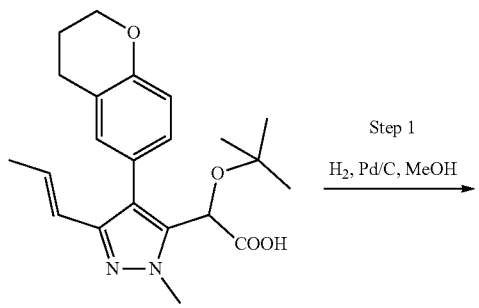

Example 29

Step 1
H₂, Pd/C, MeOH

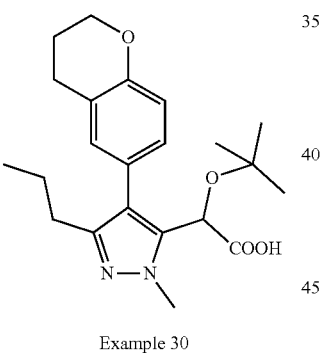

Example 30

Step 1: preparation of 2-(tert-butoxy)-2-[4-(3,4-dihydro-2H-1-benzopyran-6-yl)-1-methyl-3-propyl-1H-pyrazol-5-yl]acetic acid (example 30)

Using the procedure described in example 19, step 1, 2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid (example 29) (23.2 mg, 0.060 mmol) is converted into 2-(tert-butoxy)-2-[4-(3,4-dihydro-2H-1-benzopyran-6-yl)-1-methyl-3-propyl-1H-pyrazol-5-yl]acetic acid (example 30) (22.6 mg, 0.058 mmol, 97%) as a white solid.

¹H NMR (400 MHz, CDCl₃) δ 0.84 (t, J=7.3 Hz, 3H), 1.02 (s, 9H), 1.51-1.64 (m, 2H), 2.02-2.12 (m, 2H), 2.48-2.64 (m, 2H), 2.77-2.91 (m, 2H), 3.90 (s, 3H), 4.22 (t, J=5.1 Hz, 2H), 5.09 (s, 1H), 6.81 (d, J=8.2 Hz, 1H), 7.01-7.05 (m, 2H).

MS m/z ([M−H]⁻) 385.
MS m/z ([M+H]⁺) 387.

Example 31

Synthesis of 2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid

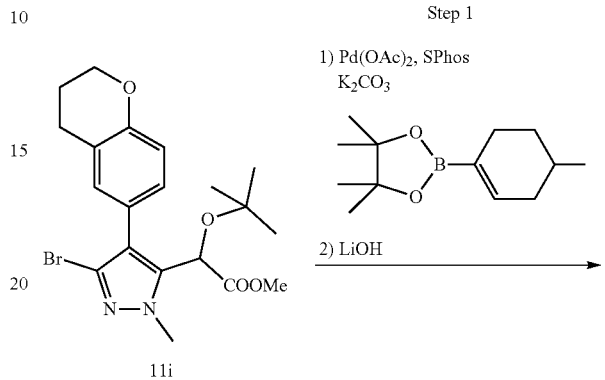

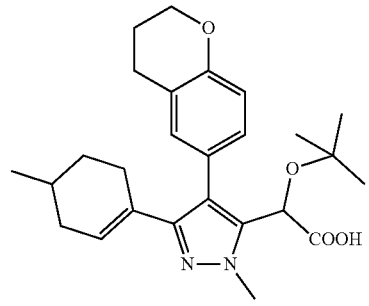

Example 31

Step 1: preparation of 2-(tert-butoxy)-2-[4-(3,4-dihydro-2H-1-benzopyran-6-yl)-1-methyl-3-(4-methylcyclohex-1-en-1-yl)-1H-pyrazol-5-yl]acetic acid (example 31)

Using the procedure described in example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 4-methyl-1-cyclohexene-1-boronic acid pinacol ester (51 mg, 0.229 mmol), after purification by preparative TLC (dichloromethane/ethyl acetate 50/50+0.5% formic acid) into 2-(tert-butoxy)-2-[4-(3,4-dihydro-2H-1-benzopyran-6-yl)-1-methyl-3-(4-methylcyclohex-1-en-1-yl)-1H-pyrazol-5-yl]acetic acid (example 31) (38 mg, 0.086 mmol, 76%) as a mixture of diastereoisomers.

¹H NMR (300 MHz, CDCl₃) δ 0.93 (d, J=6.0 Hz, 3H), 1.02 and 1.03 (s, 9H), 1.16-1.34 (m, 2H), 1.42-1.73 (m, 4H), 1.94-2.34 (m, 3H), 2.75-2.85 (m, 2H), 3.86 (s, 3H), 4.20-4.25 (m, 2H), 5.07 and 5.10 (s, 1H), 5.79-5.86 (m, 1H), 6.78 (d, J=8.9 Hz, 1H), 7.01-7.07 (m, 2H).

Ms m/z ([M−H]⁻) 437.
MS m/z ([M+H]⁺) 439.

Example 32

Synthesis of 2-(tert-butoxy)-2-[4-(3,4-dihydro-2H-1-benzopyran-6-yl)-3-(5,5-dimethylcyclopent-1-en-1-yl)-1-methyl-1H-pyrazol-5-yl]acetic acid

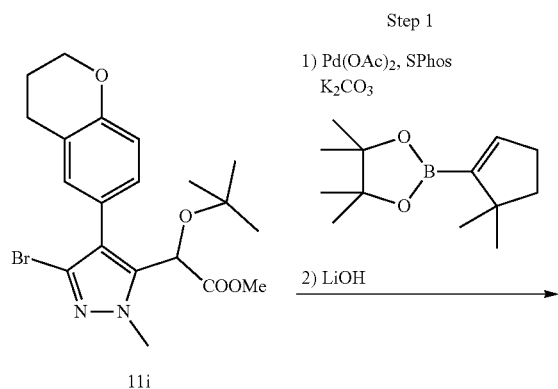

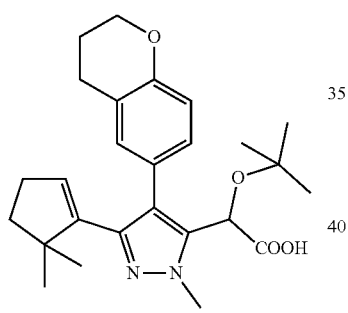

Example 32

Example 33

Synthesis of 2-(tert-butoxy)-2-[3-cyclopropyl-4-(3,4-dihydro-2H-1-benzopyran-6-yl)-1-methyl-1H-pyrazol-5-yl]acetic acid

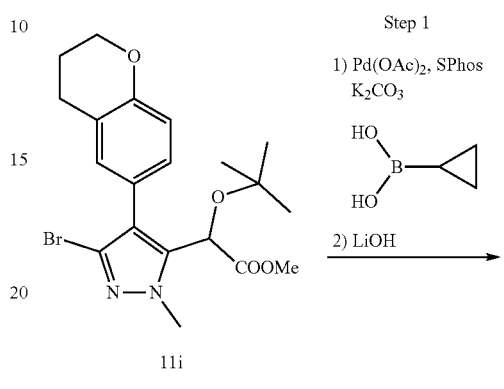

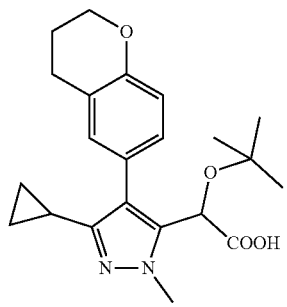

Example 33

Step 1: preparation of 2-(tert-butoxy)-2-[4-(3,4-dihydro-2H-1-benzopyran-6-yl)-3-(5,5-dimethylcyclopent-1-en-1-yl)-1-methyl-1H-pyrazol-5-yl]acetic acid (example 32)

Using the procedure described in example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with 2-(5,5-dimethylcyclopent-1-enyl)-4,4,5,5-tetramethyl-1,3,2-dioxaborolane (41 mg, 0.183 mmol), into 2-(tert-butoxy)-2-[4-(3,4-dihydro-2H-1-benzopyran-6-yl)-3-(5,5-dimethylcyclopent-1-en-1-yl)-1-methyl-1H-pyrazol-5-yl]acetic acid (example 32) (4 mg, 0.009 mmol, 8%).

$^1$H NMR (300 MHz, CDCl$_3$) δ 1.03 (s, 9H), 1.17 (s, 3H), 1.20 (s, 3H), 1.65-1.75 (m, 2H), 1.98-2.08 (m, 2H), 2.17-2.27 (m, 2H), 2.78 (t, J=6.4 Hz, 2H), 3.88 (s, 3H), 4.18-4.26 (m, 2H), 5.07 (s, 1H), 5.41 (t, J=2.5 Hz, 1H), 6.76 (d, J=8.9 Hz, 1H), 6.97-7.02 (m, 2H).

Ms m/z ([M−H]$^-$) 437.

MS m/z ([M+H]$^+$) 439.

Step 1: preparation of 2-(tert-butoxy)-2-[3-cyclopropyl-4-(3,4-dihydro-2H-1-benzopyran-6-yl)-1-methyl-1H-pyrazol-5-yl]acetic acid (example 33)

Using the procedure described in example 11, step 10, methyl 2-[3-bromo-4-(3,4-dihydro-2H-1-benzopyran-6-yl)-1-methyl-1H-pyrazol-5-yl]-2-(tert-butoxy)acetate (11i) (50 mg, 0.114 mmol) is converted by reaction with cyclopropylboronic acid (49 mg, 0.572 mmol), after purification by preparative TLC (dichloromethane/ethyl acetate 20/80+0.5% formic acid) into 2-(tert-butoxy)-2-[3-cyclopropyl-4-(3,4-dihydro-2H-1-benzopyran-6-yl)-1-methyl-1H-pyrazol-5-yl]acetic acid (example 33) (22 mg, 0.057 mmol, 50%).

$^1$H NMR (400 MHz, CDCl$_3$) δ 0.70-0.90 (m, 4H), 1.02 (s, 9H), 1.71-1.81 (m, 1H), 1.98-2.10 (m, 2H), 2.78-2.88 (m, 2H), 3.82 (s, 3H), 4.19-4.26 (m, 2H), 5.15 (s, 1H), 6.84 (d, J=8.2 Hz, 1H), 7.12 (s, 1H), 7.15 (d, J=8.2 Hz, 1H).

MS m/z ([M−H]$^-$) 383.

MS m/z ([M+H]$^+$) 385.

Example 34

Synthesis of 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetic acid

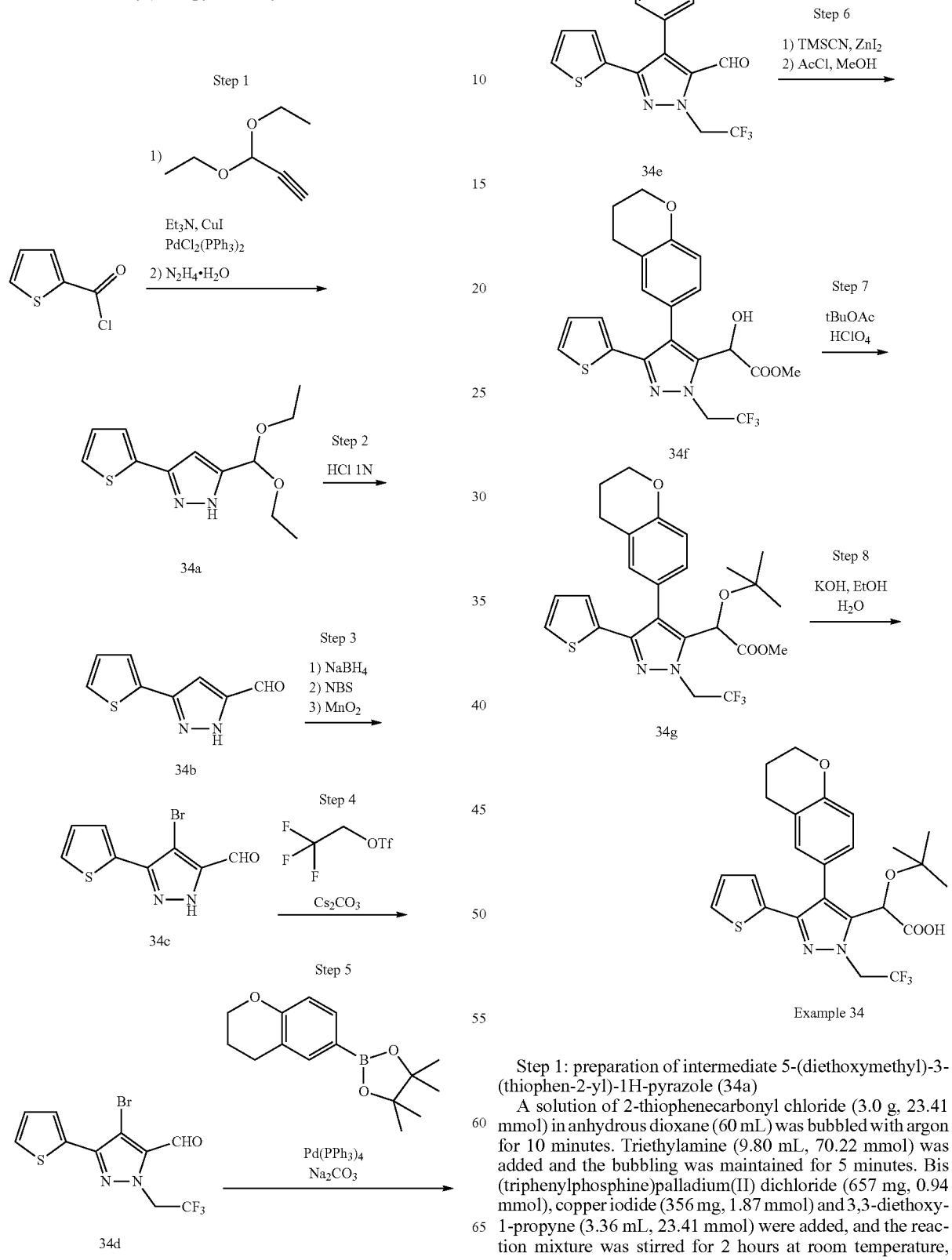

Example 34

Step 1: preparation of intermediate 5-(diethoxymethyl)-3-(thiophen-2-yl)-1H-pyrazole (34a)

A solution of 2-thiophenecarbonyl chloride (3.0 g, 23.41 mmol) in anhydrous dioxane (60 mL) was bubbled with argon for 10 minutes. Triethylamine (9.80 mL, 70.22 mmol) was added and the bubbling was maintained for 5 minutes. Bis(triphenylphosphine)palladium(II) dichloride (657 mg, 0.94 mmol), copper iodide (356 mg, 1.87 mmol) and 3,3-diethoxy-1-propyne (3.36 mL, 23.41 mmol) were added, and the reaction mixture was stirred for 2 hours at room temperature, under argon atmosphere. The solution was filtered and water (50 mL) was added to the filtrate. Layers were separated and the aqueous layer was extracted with dichloromethane (2×50 mL). The combined organic layers were washed with a saturated solution of sodium hydrogenocarbonate (50 mL), dried over sodium sulfate and concentrated in vacuo. The residue was dissolved in ethanol (200 mL) and hydrazine hydrate (2.51 g, 35.10 mmol) was added. The reaction mixture was stirred overnight and concentrated in vacuo. The residue was dissolved in ethyl acetate (40 mL) and successively washed with water (40 mL) and brine (40 mL). The organic layer was dried over sodium sulfate and concentrated in vacuo to provide 5-(diethoxymethyl)-3-(thiophen-2-yl)-1H-pyrazole (34a) (4.39 g, 17.40 mmol, 74%) which was used without further purification.

$^1$H NMR (300 MHz, CDCl$_3$) δ 1.26 (t, J=7.1 Hz, 6H), 3.55-3.72 (m, 4H), 5.70 (s, 1H), 6.51 (s, 1H), 7.05 (dd, J=3.6 Hz, J=5.0 Hz, 1H), 7.26 (dd, J=1.0 Hz, J=5.0 Hz, 1H), 7.34 (dd, J=1.0 Hz, J=3.6 Hz, 1H), 8.38 (bs, 1H).

Step 2: preparation of intermediate 3-(thiophen-2-yl)-1H-pyrazole-5-carbaldehyde (34b)

Using the procedure described in example 8, step 5, 5-(diethoxymethyl)-3-(thiophen-2-yl)-1H-pyrazole (34a) (3.0 g, 11.89 mmol) is converted, after trituration in diethyl ether to 3-(thiophen-2-yl)-1H-pyrazole-5-carbaldehyde (34b) (2.0 g, 11.22 mmol, 95%).

MS m/z ([M+H]$^+$) 179.

Step 3: preparation of intermediate 4-bromo-3-(thiophen-2-yl)-1H-pyrazole-5-carbaldehyde (34c)

Under a nitrogen atmosphere, sodium borohydride (0.51 g, 13.60 mmol) was added portionwise to a solution of 3-(thiophen-2-yl)-1H-pyrazole-5-carbaldehyde (34b) (2.02 g, 11.33 mmol) in anhydrous methanol (80 mL). The reaction mixture was stirred at room temperature for 4 hours. Water was added (50 mL) and the mixture was concentrated in vacuo. The residue was dissolved in ethyl acetate (40 mL) and successively washed with water (40 mL) and brine (40 mL). The organic layer was dried over sodium sulfate and concentrated in vacuo. The residue was dissolved in acetonitrile (100 mL) and N-bromosuccinimide (1.35 g, 7.59 mmol) was added. The mixture was stirred for 60 minutes at room temperature, then concentrated in vacuo. The residue was dissolved in ethyl acetate (40 mL) and washed with brine (40 mL). The organic layer was dried over sodium sulfate and concentrated in vacuo. The residue was dissolved in a mixture of chloroform (14 mL) and N,N-dimethylformamide (28 mL). Manganese dioxide (3.74 g, 43.02 mmol) was added and the mixture was stirred at 50° C. for 1 hour. The mixture was filtered through a pad of Celite®, rinced with N,N-dimethylformamide, the filtrate was concentrated in vacuo, and co-evaporated with toluene. The residue was triturated with diethyl ether and filtered to provide 4-bromo-3-(thiophen-2-yl)-1H-pyrazole-5-carbaldehyde (34c) (1.07 g, 4.16 mmol, 37%).

Ms m/z ([M+H]$^+$) 257/259.

Step 4: preparation of intermediate 4-bromo-3-(thiophen-2-yl)-1-(2,2,2-trifluoroethyl)-1H-pyrazole-5-carbaldehyde (34d)

Cesium carbonate (1.56 g, 4.78 mmol) and 2,2,2-triflouroethyl trifluoromethanesulfonate (0.92 mL, 6.38 mmol) were added to a solution of 4-bromo-3-(thiophen-2-yl)-1H-pyrazole-5-carbaldehyde (34c) (0.82 g, 3.19 mmol) in N,N-dimethylformamide (15 mL). The reaction mixture was stirred at 100° C. for 50 minutes. Water (20 mL) was added, and the mixture was extracted with ethyl acetate (2×40 mL). The organic layer was washed with brine (50 mL), dried over sodium sulfate and concentrated in vacuo. The residue was purified by flash chromatography on silica gel (cyclohexane/ethyl acetate: 100/0 to 94/6), to provide 4-bromo-3-(thiophen-2-yl)-1-(2,2,2-trifluoroethyl)-1H-pyrazole-5-carbaldehyde (34d) (350 mg, 1.03 mmol, 32%).

MS m/z ([M+H]$^+$) 339/341.

Step 5: preparation of intermediate 4-(3,4-dihydro-2H-1-benzopyran-6-yl)-3-(thiophen-2-yl)-1-(2,2,2-trifluoroethyl)-1H-pyrazole-5-carbaldehyde (34e)

Using the procedure described in example 1, step 4, 4-bromo-3-(thiophen-2-yl)-1-(2,2,2-trifluoroethyl)-1H-pyrazole-5-carbaldehyde (34d) (0.57 g, 3.16 mmol) is converted by reaction with 6-(4,4,5,5-tetramethyl-1,3,2-dioxaborolan-2-yl)chroman (2.69 g, 41.12 mmol), after purification by flash chromatography (cyclohexane/ethyl acetate 100/0 to 95/5) to 4-(3,4-dihydro-2H-1-benzopyran-6-yl)-3-(thiophen-2-yl)-1-(2,2,2-trifluoroethyl)-1H-pyrazole-5-carbaldehyde (34e) (128 mg, 0.33 mmol, 32%).

$^1$H NMR (400 MHz, CDCl$_3$) δ 2.02-2.11 (m, 2H), 2.81 (t, J=6.4 Hz, 2H), 4.23-4.29 (m, 2H), 5.28 (q, J=8.1 Hz, 2H), 6.87 (d, J=8.3 Hz, 1H), 6.93 (dd, J=3.7 Hz, J=5.1 Hz, 1H), 7.04 (dd, J=1.1 Hz, J=3.7 Hz, 1H), 7.07 (d, J=2.1 Hz, 1H), 7.11 (dd, J=8.3 Hz, J=2.1 Hz, 1H), 7.24 (dd, J=1.1 Hz, J=5.1 Hz, 1H), 9.58 (s, 1H).

MS m/z ([M+H]$^+$) 393.

Step 6: preparation of intermediate methyl 2-[4-(3,4-dihydro-2H-1-benzopyran-6-yl)-3-(thiophen-2-yl)-1-(2,2,2-trifluoroethyl)-1H-pyrazol-5-yl]-2-hydroxyacetate (34f)

Using the procedure described in example 1, step 5, 4-(3,4-dihydro-2H-1-benzopyran-6-yl)-3-(thiophen-2-yl)-1-(2,2,2-trifluoroethyl)-1H-pyrazole-5-carbaldehyde (34e) (122 mg, 0.31 mmol) is converted, after purification by preparative TLC (dichloromethane/ethyl acetate 70/30) into methyl 2-[4-(3,4-dihydro-2H-1-benzopyran-6-yl)-3-(thiophen-2-yl)-1-(2,2,2-trifluoroethyl)-1H-pyrazol-5-yl]-2-hydroxyacetate (34f) (91 mg, 0.20 mmol, 65%).

$^1$H NMR (300 MHz, CDCl$_3$) δ 2.00-2.08 (m, 2H), 2.78 (t, J=6.4 Hz, 2H), 3.72 (s, 3H), 4.20-4.26 (m, 2H), 4.74-4.86 (m, 1H), 4.93-5.05 (m, 1H), 5.22 (s, 1H), 6.82 (d, J=8.2 Hz, 1H), 6.85-6.91 (m, 2H), 7.00 (d, J=2.1 Hz, 1H), 7.04 (dd, J=8.2 Hz, J=2.1 Hz, 1H), 7.17 (dd, J=1.6 Hz, J=4.5 Hz, 1H).

MS m/z ([M+H]$^+$) 453.

Step 7: preparation of intermediate methyl 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetate (34g)

Using the procedure described in example 1, step 6, methyl 2-[4-(3,4-dihydro-2H-1-benzopyran-6-yl)-3-(thiophen-2-yl)-1-(2,2,2-trifluoroethyl)-1H-pyrazol-5-yl]-2-hydroxyacetate (34f) (90 mg, 0.199 mmol) is converted, after purification by preparative TLC (cyclohexane/ethyl acetate 80/20) into methyl 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetate (34g) (70 mg, 0.138 mmol, 69%).

$^1$H NMR (300 MHz, CDCl$_3$) δ 1.06 (s, 9H), 2.01-2.11 (m, 2H), 2.80 (t, J=6.4 Hz, 2H), 3.74 (s, 3H), 4.22-4.29 (m, 2H), 4.87-5.12 (m, 3H), 6.82-6.92 (m, 3H), 7.01-7.08 (m, 2H), 7.10 (dd, J=1.3 Hz, J=4.9 Hz, 1H).

Step 8: preparation of 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetic acid (example 34)

Using the procedure described in example 1, step 7, methyl 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetate (34g) (70 mg, 0.138 mmol) is converted, after purification by preparative TLC (dichloromethane/ethyl acetate 92/8) into 2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetic acid (example 34) (35 mg, 0.071 mmol, 51%).

¹H NMR (400 MHz, DMSO) δ 0.99 (s, 9H), 1.89-2.01 (m, 2H), 2.69-2.79 (m, 2H), 4.15-4.23 (m, 2H), 4.83 (s, 1H), 4.99-5.20 (m, 1H), 5.26-5.51 (m, 1H), 6.77-6.85 (m, 2H), 6.94 (dd, J=3.7 Hz, J=4.8 Hz, 1H), 7.02-7.12 (m, 2H), 7.41 (d, J=5.0 Hz, 1H). MS m/z ([M−H]⁻) 493.

Ms m/z ([M+H]⁺) 495.

Example 35

Synthesis of 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetic acid

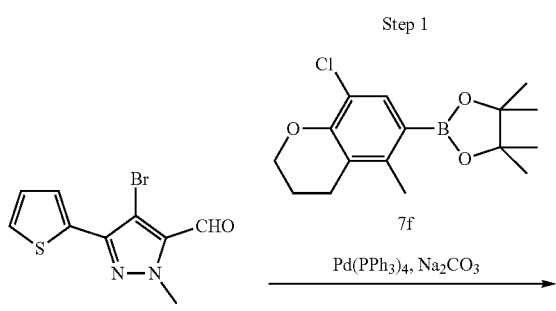

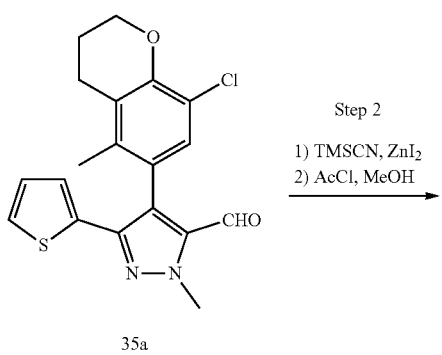

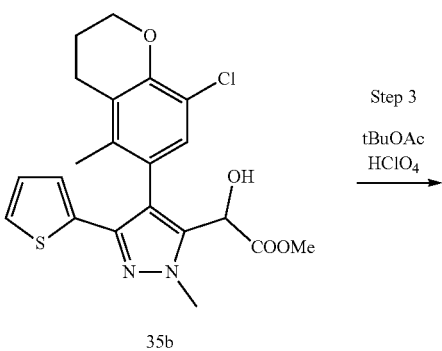

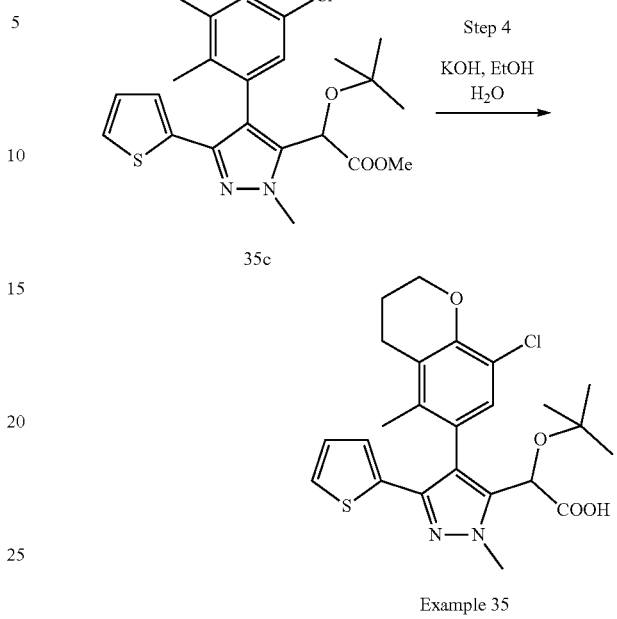

Step 1: preparation of intermediate 4-(8-chloro-5-methyl-3,4-dihydro-2H-1-benzopyran-6-yl)-1-methyl-3-(thiophen-2-yl)-1H-pyrazole-5-carbaldehyde (35a)

Using the procedure described in example 1, step 4, 4-bromo-1-methyl-3-(thiophen-2-yl)-1H-pyrazole-5-carbaldehyde (3c) (200 mg, 0.74 mmol) is converted by reaction with 2-(8-chloro-5-methyl-3,4-dihydro-2H-1-benzopyran-6-yl)-4,4,5,5-tetramethyl-1,3,2-dioxaborolane (7f) (273 mg, 0.88 mmol), after purification by preparative TLC (cyclohexane/ethyl acetate: 70/30), into 4-(8-chloro-5-methyl-3,4-dihydro-2H-1-benzopyran-6-yl)-1-methyl-3-(thiophen-2-yl)-1H-pyrazole-5-carbaldehyde (35a) (180 mg, 0.48 mmol, 65%).

¹H NMR (300 MHz, CDCl₃) δ 1.93 (s, 3H), 2.06-2.20 (m, 2H), 2.71 (t, J=6.6 Hz, 2H), 4.24 (s, 3H), 4.30-4.36 (m, 2H), 6.82 (dd, J=1.1 Hz, J=3.6 Hz, 1H), 6.90 (dd, J=3.6 Hz, J=5.1 Hz, 1H), 7.16 (s, 1H), 7.19 (dd, J=1.1 Hz, J=5.1 Hz, 1H), 9.44 (s, 1H).

MS m/z ([M+H]⁺) 373.

Step 2: preparation of intermediate methyl 2-[4-(8-chloro-5-methyl-3,4-dihydro-2H-1-benzopyran-6-yl)-1-methyl-3-(thiophen-2-yl)-1H-pyrazol-5-yl]-2-hydroxyacetate (35b)

Using the procedure described in example 1, step 5, 4-(8-chloro-5-methyl-3,4-dihydro-2H-1-benzopyran-6-yl)-1-methyl-3-(thiophen-2-yl)-1H-pyrazole-5-carbaldehyde (35a) (180 mg, 0.48 mmol) is converted, after purification by preparative TLC (dichloromethane/ethyl acetate 70/30) into 2-[4-(8-chloro-5-methyl-3,4-dihydro-2H-1-benzopyran-6-yl)-1-methyl-3-(thiophen-2-yl)-1H-pyrazol-5-yl]-2-hydroxyacetate (35b) (69 mg, 0.16 mmol, 33%).

¹H NMR (300 MHz, CDCl₃) δ 1.90 (s, 3H), 2.04-2.18 (m, 2H), 2.69 (t, J=6.5 Hz, 2H), 3.70 and 3.75 (s, 3H), 3.90 and 3.93 (s, 3H), 4.26-4.35 (m, 2H), 5.03 and 5.06 (s, 1H), 6.69 and 6.72 (dd, J=1.1 Hz, J=3.6 Hz, 1H), 6.83-6.88 (m, 1H), 7.04-7.15 (m, 2H).

Ms m/z ([M+H]⁺) 433.

Step 3: preparation of intermediate methyl 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetate (35c)

Using the procedure described in example 1, step 6, methyl 2-[4-(8-chloro-5-methyl-3,4-dihydro-2H-1-benzopyran-6-yl)-1-methyl-3-(thiophen-2-yl)-1H-pyrazol-5-yl]-2-hydroxyacetate (35b) (69 mg, 0.16 mmol) is converted, after purification by preparative TLC (cyclohexane/ethyl acetate: 70/30) into methyl 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetate (35c) (40 mg, 0.08 mmol, 51%).

$^1$H NMR (300 MHz, CDCl$_3$) δ 1.05 and 1.17 (s, 9H), 1.86 and 1.87 (s, 3H), 2.05-2.18 (m, 2H), 2.66 and 2.72 (t, J=6.5 Hz, 2H), 3.65 and 3.76 (s, 3H), 4.01 and 4.03 (s, 3H), 4.30-4.36 (m, 2H), 4.84 and 4.85 (s, 1H), 6.66-6.72 (m, 1H), 6.82-6.87 (m, 1H), 7.06 and 7.18 (s, 1H), 7.08-7.14 (m, 1H).

Step 4: preparation of 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetic acid (example 35)

Using the procedure described in example 1, step 7, methyl 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetate (35c) (40 mg, 0.08 mmol) is converted into 2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetic acid (example 35) (38 mg, 0.08 mmol, 98%).

$^1$H NMR (300 MHz, CDCl$_3$) δ 1.10 and 1.21 (s, 9H), 1.82 and 1.94 (s, 3H), 2.05-2.17 (m, 2H), 2.65 and 2.71 (t, J=6.5 Hz, 2H), 3.98 and 3.99 (s, 3H), 4.29-4.35 (m, 2H), 4.88 and 4.97 (s, 1H), 6.68-6.72 (m, 1H), 6.82-6.87 (m, 1H), 7.07 and 7.31 (s, 1H), 7.10-7.15 (m, 1H).

MS m/z ([M−H]$^−$) 473.
MS m/z ([M+H]$^+$) 475.

Example 36

Synthesis of 2-(tert-butoxy)-2-[3-(5-chlorothiophen-2-yl)-4-(3,4-dihydro-2H-1-benzopyran-6-yl)-1-methyl-1H-pyrazol-5-yl]acetic acid

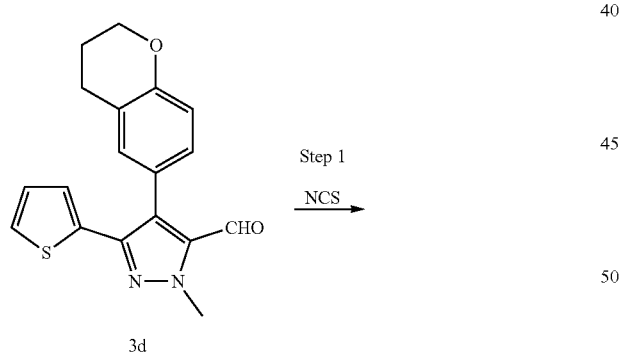

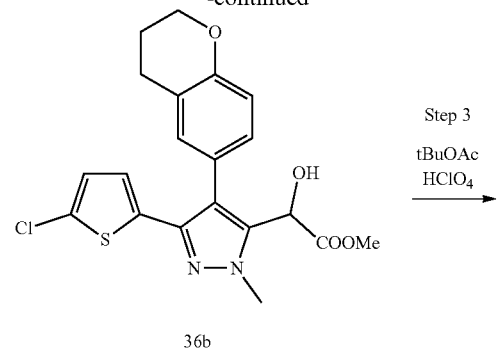

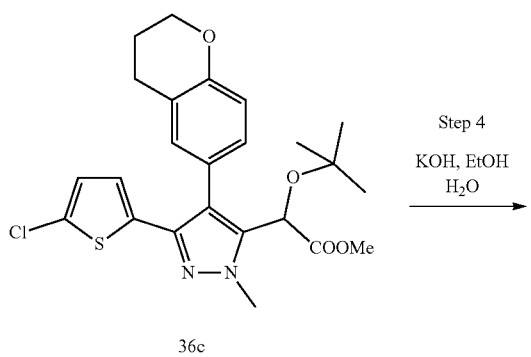

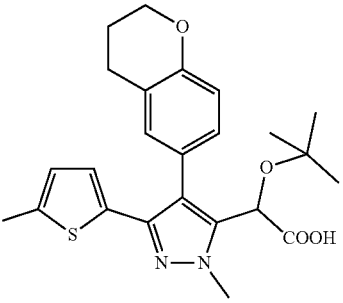

Example 36

Step 1: preparation of intermediate 3-(5-chlorothiophen-2-yl)-4-(3,4-dihydro-2H-1-benzopyran-6-yl)-1-methyl-1H-pyrazole-5-carbaldehyde (36a)

A solution of 4-(3,4-dihydro-2H-1-benzopyran-6-yl)-1-methyl-3-(thiophen-2-yl)-1H-pyrazole-5-carbaldehyde (3d) (166 mg, 0.51 mmol) and N-chlorosuccinimide (67 mg, 0.50 mmol) in acetonitrile (18 mL) was heated overnight at 60° C. The reaction mixture was concentrated in vacuo. Water (10 mL) was added and the aqueous layer was extracted with ethyl acetate (2×12 mL). The organic layer was dried over sodium sulfate and concentrated in vacuo. The residue was purified by preparative TLC (cyclohexane/ethyl acetate 80/20), to provide 3-(5-chlorothiophen-2-yl)-4-(3,4-dihydro-2H-1-benzopyran-6-yl)-1-methyl-1H-pyrazole-5-carbaldehyde (36a) (183 mg, 0.51 mmol, 99%).

¹H NMR (300 MHz, CDCl₃) δ 2.01-2.11 (m, 2H), 2.81 (t, J=6.5 Hz, 2H), 4.21 (s, 3H), 4.23-4.28 (m, 2H), 6.71 (d, J=3.9 Hz, 1H), 6.74 (d, J=3.9 Hz, 1H), 6.86 (d, J=8.3 Hz, 1H), 7.03 (d, J=2.1 Hz, 1H), 7.07 (dd, J=2.1 Hz, J=8.3 Hz, 1H), 9.56 (s, 1H).

MS m/z ([M+H]⁺) 359/361.

Step 2: preparation of intermediate methyl 2-[3-(5-chlorothiophen-2-yl)-4-(3,4-dihydro-2H-1-benzopyran-6-yl)-1-methyl-1H-pyrazol-5-yl]-2-hydroxyacetate (36b)

Using the procedure described in example 1, step 5, 3-(5-chlorothiophen-2-yl)-4-(3,4-dihydro-2H-1-benzopyran-6-yl)-1-methyl-1H-pyrazole-5-carbaldehyde (36a) (236 mg, 0.66 mmol) is converted, after purification by preparative TLC (dichloromethane/ethyl acetate 80/20), to methyl 2-[3-(5-chlorothiophen-2-yl)-4-(3,4-dihydro-2H-1-benzopyran-6-yl)-1-methyl-1H-pyrazol-5-yl]-2-hydroxy acetate (36b) (203 mg, 0.48 mmol, 74%).

¹H NMR (300 MHz, CDCl₃) δ 1.98-2.09 (m, 2H), 2.78 (t, J=6.4 Hz, 2H), 3.26 (d, J=2.3 Hz, 1H), 3.74 (s, 3H), 3.87 (s, 3H), 4.19-4.27 (m, 2H), 5.16 (d, J=2.3 Hz, 1H), 6.61 (d, J=3.5 Hz, 1H), 6.67 (d, J=3.5 Hz, 1H), 6.81 (d, J=8.1 Hz, 1H), 6.93-7.04 (m, 2H).

Ms m/z ([M+H]⁺) 419.

Step 3: preparation of intermediate methyl 2-(tert-butoxy)-2-[3-(5-chlorothiophen-2-yl)-4-(3,4-dihydro-2H-1-benzopyran-6-yl)-1-methyl-1H-pyrazol-5-yl]acetate (36c)

Using the procedure described in example 1, step 6, methyl 2-[3-(5-chlorothiophen-2-yl)-4-(3,4-dihydro-2H-1-benzopyran-6-yl)-1-methyl-1H-pyrazol-5-yl]-2-hydroxyacetate (36b) (203 mg, 0.48 mmol) is converted, after purification by preparative TLC (dichloromethane/ethyl acetate: 98/2), to methyl 2-(tert-butoxy)-2-[3-(5-chlorothiophen-2-yl)-4-(3,4-dihydro-2H-1-benzopyran-6-yl)-1-methyl-1H-pyrazol-5-yl] acetate (36c) (146 mg, 0.31 mmol, 63%).

¹H NMR (300 MHz, CDCl₃) δ 1.05 (s, 9H), 2.01-2.11 (m, 2H), 2.79 (t, J=6.4 Hz, 2H), 3.75 (s, 3H), 3.97 (s, 3H), 4.22-4.28 (m, 2H), 4.97 (s, 1H), 6.60 (d, J=3.9 Hz, 1H), 6.66 (d, J=3.9 Hz, 1H), 6.83 (d, J=8.2 Hz, 1H), 6.97 (d, J=2.0 Hz, 1H), 7.01 (dd, J=2.0 Hz, J=8.2 Hz, 1H).

Step 4: preparation of 2-(tert-butoxy)-2-[3-(5-chlorothiophen-2-yl)-4-(3,4-dihydro-2H-1-benzopyran-6-yl)-1-methyl-1H-pyrazol-5-yl]acetic acid (example 36)

Using the procedure described in example 1, step 7, methyl 2-(tert-butoxy)-2-[3-(5-chlorothiophen-2-yl)-4-(3,4-dihydro-2H-1-benzopyran-6-yl)-1-methyl-1H-pyrazol-5-yl]acetate (36c) (140 mg, 0.29 mmol) is converted to 2-(tert-butoxy)-2-[3-(5-chlorothiophen-2-yl)-4-(3,4-dihydro-2H-1-benzopyran-6-yl)-1-methyl-1H-pyrazol-5-yl]acetic acid (example 36) (134 mg, 0.29 mmol, 99%).

¹H NMR (400 MHz, CDCl₃) δ 1.07 (s, 9H), 1.99-2.10 (m, 2H), 2.73-2.85 (m, 2H), 3.93 (s, 3H), 4.22-4.28 (m, 2H), 5.04 (s, 1H), 6.63 (d, J=3.9 Hz, 1H), 6.67 (d, J=3.9 Hz, 1H), 6.83 (d, J=8.4 Hz, 1H), 7.03-7.09 (m, 2H).

MS m/z ([M–H]⁻) 459.
MS m/z ([M+H]⁺) 461.

Example 37

Synthesis of 2-(tert-butoxy)-2-(3-{4H,5H,6H-cyclopenta[b]thiophen-2-yl}-4-(3,4-dihydro-2H-1-benzoovran-6-yl)-1-methyl-1H-pyrazol-5-yl)acetic acid

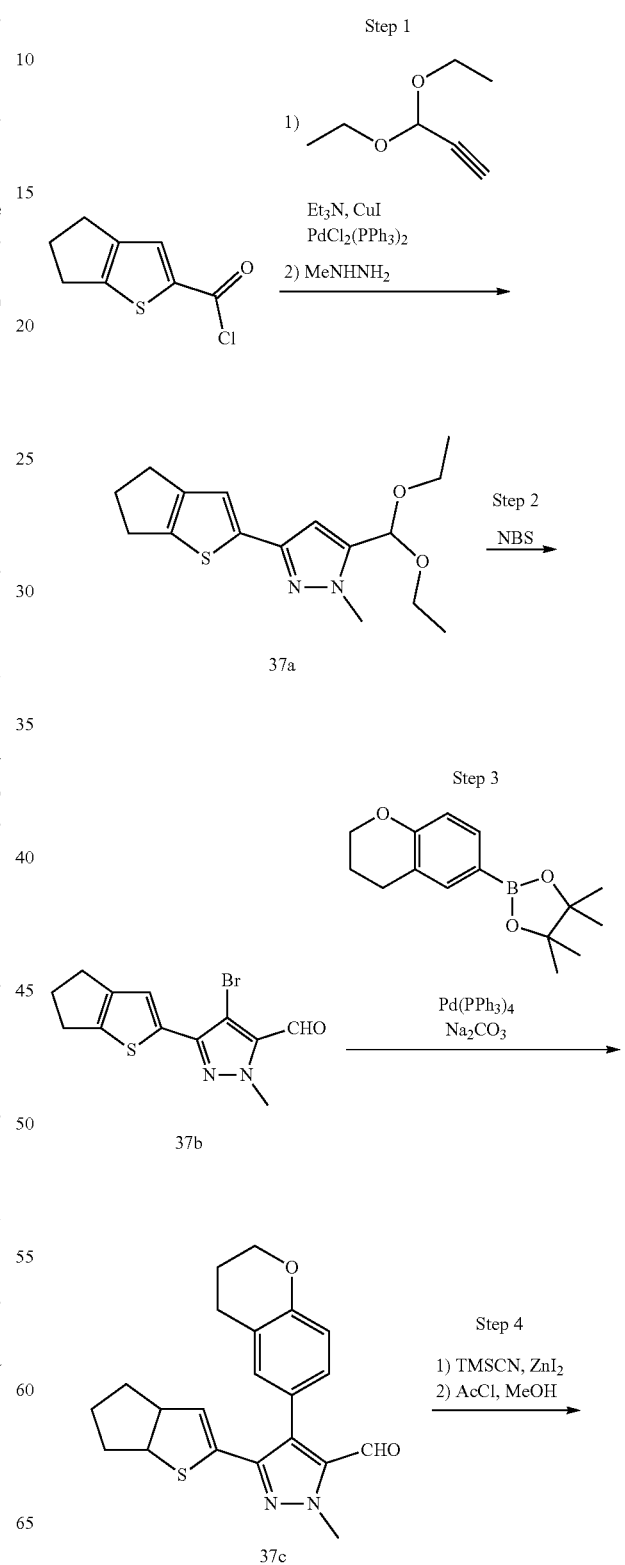

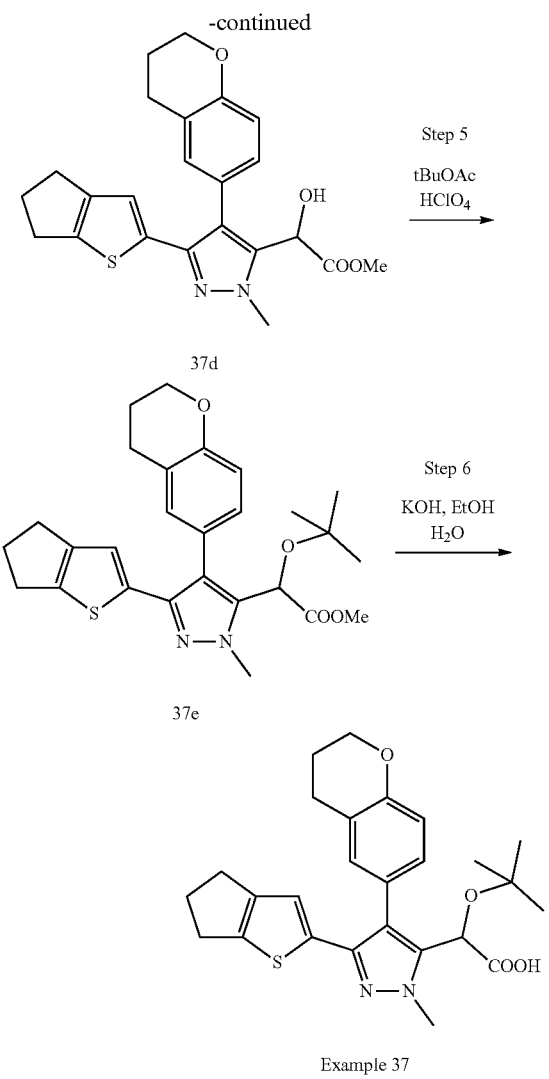

Example 37

Step 1: preparation of intermediate 3-{4H,5H,6H-cyclopenta[b]thiophen-2-yl}-5-(diethoxymethyl)-1-methyl-1H-pyrazole (37a)

A solution of 5,6-dihydro-4H-cyclopenta[b]thiophene-2-carbonyl chloride (1.75 g, 9.36 mmol) in anhydrous dioxane (20 mL) was bubbled with argon for 10 minutes. Triethylamine (3.27 mL, 23.41 mmol) was added and the bubbling was maintained for 5 minutes. Bis(triphenylphosphine)palladium(II) dichloride (219 mg, 0.31 mmol), copper iodide (119 mg, 0.62 mmol) and propargylaldehyde diethyl acetal (1.12 mL, 7.80 mmol) were added, and the reaction mixture was stirred for 2 hours at room temperature, under argon atmosphere. The solution was filtered and water (20 mL) was added to the filtrate. Layers were separated, and the aqueous layer was extracted with dichloromethane (2×20 mL). The combined organic layers were washed with a saturated solution of sodium hydrogenocarbonate (20 mL), dried over sodium sulfate and concentrated in vacuo. The residue was added to a solution of methylhydrazine (0.82 mL, 15.6 mmol) in ethanol (80 mL). The reaction mixture was stirred overnight at room temperature, concentrated in vacuo and dissolved in ethyl acetate (20 mL). The organic layer was successively washed with water (20 mL) and brine (20 mL) before being dried over sodium sulfate and concentrated in vacuo. The residue was purified by flash chromatography on silica gel (cyclohexane/ethyl acetate 100/0 to 90/10) to provide 3-{4H,5H,6H-cyclopenta[b]thiophen-2-yl}-5-(diethoxymethyl)-1-methyl-1H-pyrazole (37a) (1.80 g, 5.87 mmol, 75%).

$^1$H NMR (300 MHz, CDCl$_3$) δ 1.23 (t, J=7.1 Hz, 6H), 2.38-2.50 (m, 2H), 2.72 (t, J=7.2 Hz, 2H), 2.89 (t, J=7.2 Hz, 2H), 3.50-3.67 (m, 4H), 3.89 (s, 3H), 5.55 (s, 1H), 6.45 (s, 1H), 7.02 (s, 1H).

Step 2: preparation of intermediate 4-bromo-3-{4H,5H,6H-cyclopenta[b]thiophen-2-yl}-1-methyl-1H-pyrazole-5-carbaldehyde (37b)

A solution of 3-{4H,5H,6H-cyclopenta[b]thiophen-2-yl}-5-(diethoxymethyl)-1-methyl-1H-pyrazole (37a) (1.69 g, 5.51 mmol) and N-bromosuccinimide (0.88 g, 4.96 mmol) in acetonitrile (10 mL) was stirred at room temperature for 4 hours. The reaction mixture was concentrated in vacuo. Water (10 mL) was added and the aqueous layer was extracted with ethyl acetate (2×10 mL). The organic layer was dried over sodium sulfate and concentrated in vacuo. The residue was purified by flash chromatography on silica gel (cyclohexane/ethyl acetate 100/0 to 95/5) to provide 4-bromo-3-{4H,5H,6H-cyclopenta[b]thiophen-2-yl}-1-methyl-1H-pyrazole-5-carbaldehyde (37b) (586 mg, 1.88 mmol, 34%).

$^1$H NMR (300 MHz, CDCl$_3$) δ 2.42-2.53 (m, 2H), 2.73-2.82 (m, 2H), 2.90-2.97 (m, 2H), 4.16 (s, 3H), 7.45 (s, 1H), 9.91 (s, 1H).

Step 3: Preparation of intermediate 3-{4H,5H,6H-cyclopenta[b]thiophen-2-yl}-4-(3,4-dihydro-2H-1-benzopyran-6-yl)-1-methyl-1H-pyrazole-5-carbaldehyde (37c)

Using the procedure described in example 1, step 4, 4-bromo-3-{4H,5H,6H-cyclopenta[b]thiophen-2-yl}-1-methyl-1H-pyrazole-5-carbaldehyde (37b) (200 mg, 0.64 mmol) is converted by reaction with 6-(4,4,5,5-tetramethyl-1,3,2-dioxaborolan-2-yl)chroman (250 mg, 0.96 mmol), after purification by preparative TLC (cyclohexane/ethyl acetate 80/20) into 3-{4H,5H,6H-cyclopenta[b]thiophen-2-yl}-4-(3,4-dihydro-2H-1-benzopyran-6-yl)-1-methyl-1H-pyrazole-5-carbaldehyde (37c) (234 mg, 0.64 mmol, 100%).

$^1$H NMR (300 MHz, CDCl$_3$) δ 2.00-2.10 (m, 2H), 2.33-2.45 (m, 2H), 2.59-2.68 (m, 2H), 2.77-2.89 (m, 4H), 4.21 (s, 3H), 4.22-4.28 (m, 2H), 6.70 (s, 1H), 6.85 (d, J=8.2 Hz, 1H), 7.05 (d, J=2.0 Hz, 1H), 7.10 (dd, J=2.0 Hz, J=8.2 Hz, 1H), 9.55 (s, 1H).

Step 4: preparation of intermediate methyl 2-(3-{4H,5H,6H-cyclopenta[b]thiophen-2-yl}-4-(3,4-dihydro-2H-1-benzopyran-6-yl)-1-methyl-1H-pyrazol-5-yl)-2-hydroxyacetate (37d)

Using the procedure described in example 1, step 5, 3-{4H,5H,6H-cyclopenta[b]thiophen-2-yl}-4-(3,4-dihydro-2H-1-benzopyran-6-yl)-1-methyl-1H-pyrazole-5-carbaldehyde (37c) (234 mg, 0.64 mmol) is converted, after purification by preparative TLC (dichloromethane/ethyl acetate 80/20) into methyl 2-(3-{4H,5H,6H-cyclopenta[b]thiophen-2-yl}-4-(3,4-dihydro-2H-1-benzopyran-6-yl)-1-methyl-1H-pyrazol-5-yl)-2-hydroxyacetate (37d) (252 mg, 0.59 mmol, 92%).

$^1$H NMR (300 MHz, CDCl$_3$) δ 1.99-2.08 (m, 2H), 2.32-2.41 (m, 2H), 2.57-2.65 (m, 2H), 2.75-2.88 (m, 4H), 3.73 (s, 3H), 3.88 (s, 3H), 4.20-4.26 (m, 2H), 5.16 (s, 1H), 6.62 (s, 1H), 6.81 (d, J=8.2 Hz, 1H), 6.98 (d, J=2.1 Hz, 1H), 7.02 (dd, J=2.1 Hz, J=8.2 Hz, 1H).

Step 5: preparation of intermediate methyl 2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetate (37e)

Using the procedure described in example 1, step 6, methyl 2-(3-{4H,5H,6H-cyclopenta[b]thiophen-2-yl}-4-(3,4-dihydro-2H-1-benzopyran-6-yl)-1-methyl-1H-pyrazol-5-yl)-2- hydroxyacetate (37d) (252 mg, 0.59 mmol) is converted, after purification by preparative TLC (dichloromethane/ethyl acetate 95/5) into methyl 2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetate (37e) (171 mg, 0.36 mmol, 60%).

$^1$H NMR (300 MHz, CDCl$_3$) δ 1.05 (s, 9H), 2.00-2.10 (m, 2H), 2.31-2.42 (m, 2H), 2.56-2.64 (m, 2H), 2.75-2.87 (m, 4H), 3.74 (s, 3H), 3.98 (s, 3H), 4.22-4.28 (m, 2H), 4.97 (s, 1H), 6.60 (s, 1H), 6.83 (d, J=8.2 Hz, 1H), 7.00 (d, J=2.1 Hz, 1H), 7.04 (dd, J=2.1 Hz, J=8.2 Hz, 1H).

Step 6: preparation of 2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetic acid (example 37)

Using the procedure described in example 1, step 7, methyl 2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetate (37e) (171 mg, 0.36 mmol) is converted into 2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetic acid (example 37) (131 mg, 0.28 mmol, 79%).

$^1$H NMR (300 MHz, CDCl$_3$) δ 1.07 (s, 9H), 1.99-2.09 (m, 2H), 2.30-2.42 (m, 2H), 2.56-2.64 (m, 2H), 2.75-2.87 (m, 4H), 3.94 (s, 3H), 4.21-4.29 (m, 2H), 5.04 (s, 1H), 6.63 (s, 1H), 6.79-6.85 (m, 1H), 7.05-7.11 (m, 2H).

MS m/z ([M−H]$^−$) 465.
MS m/z ([M+H]$^+$) 467.

Example 38

Synthesis of 2-[3-benzo[b]thiophen-3-yl-4-(3,4-dihydro-2H-1-benzopyran-6-yl)-1-methyl-1H-pyrazol-5-yl]-2-(tert-butoxy)acetic acid

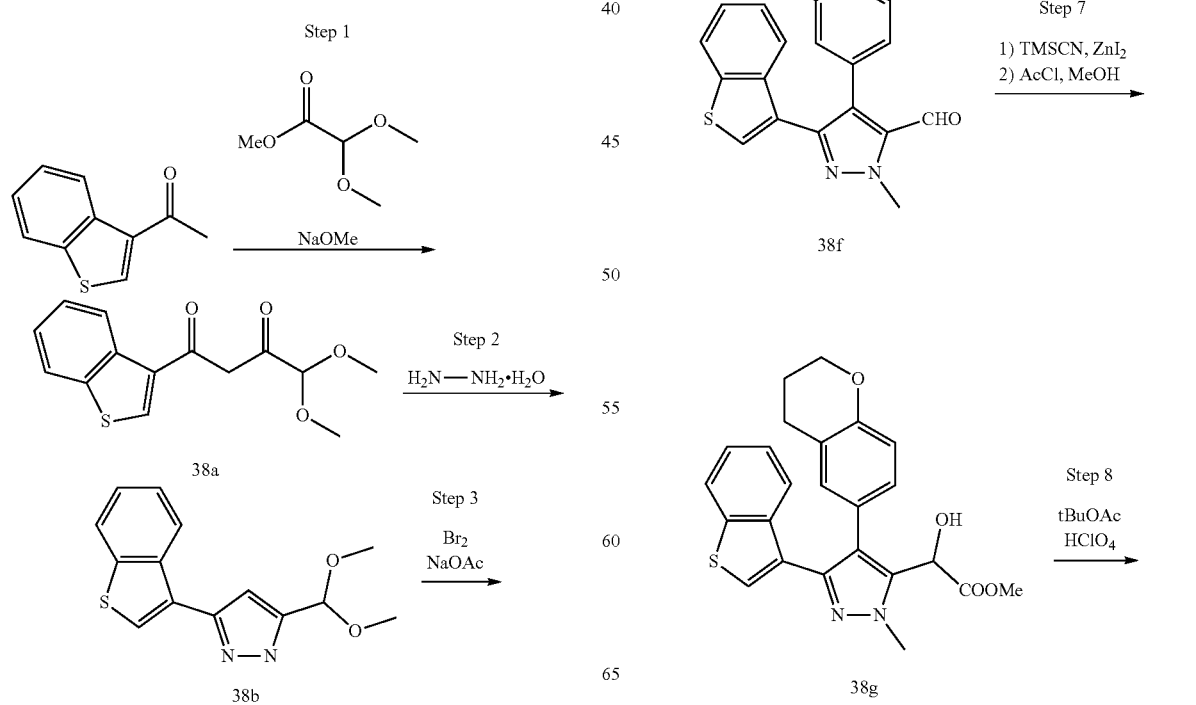

-continued

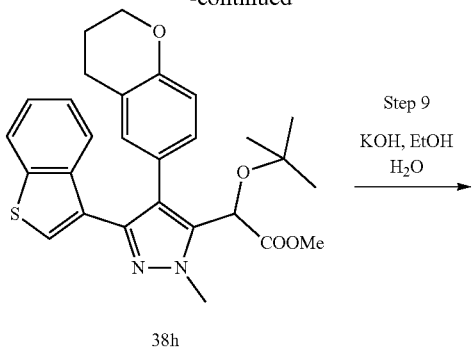

38h

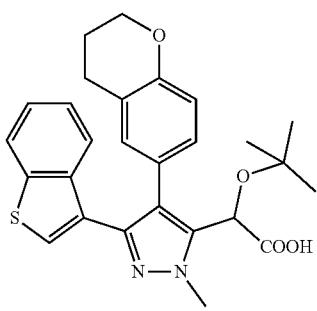

Example 38

Step 1: preparation of intermediate 1-benzo[b]thiophen-3-yl-4,4-dimethoxybutane-1,3-dione (38a)

Using the procedure described in example 8, step 1, 3-acetylbenzo[b]thiophene (2.0 g, 11.35 mmol) is converted into 1-benzo[b]thiophen-3-yl-4,4-dimethoxybutane-1,3-dione (38a) (2.78 g, 9.99 mmol, 88%) which was used without further purification.

MS m/z ([M−H]⁻) 277.

Step 2: preparation of intermediate 3-benzo[b]thiophen-3-yl-5-dimethoxymethyl-1H-pyrazole (38b)

Using the procedure described in example 8, step 2, 1-benzo[b]thiophen-3-yl-4,4-dimethoxybutane-1,3-dione (38a) (2.78 g, 9.99 mmol) is converted, after purification by flash chromatography (dichloromethane/methanol 100/0 to 99/1) into 3-benzo[b]thiophen-3-yl-5-dimethoxymethyl-1H-pyrazole (38b) (1.79 g, 6.52 mmol, 65%).

$^1$H NMR (300 MHz, CDCl$_3$) δ 3.42 (s, 6H), 5.65 (s, 1H), 6.66 (s, 1H), 7.35-7.47 (m, 2H), 7.66 (s, 1H), 7.87-7.91 (m, 1H), 8.34-8.39 (m, 1H).

MS m/z ([M−H]⁻) 273.

Step 3: preparation of intermediate 3-benzo[b]thiophen-3-yl-4-bromo-5-dimethoxymethyl-1H-pyrazole (38c)

Using the procedure described in example 8, step 3, 3-benzo[b]thiophen-3-yl-5-dimethoxymethyl-1H-pyrazole (38b) (1.47 g, 5.36 mmol) is converted into 3-benzo[b]thiophen-3-yl-4-bromo-5-dimethoxymethyl-1H-pyrazole (38c) (1.80 g, 5.10 mmol, 95%) which was used without further purification.

MS m/z ([M−H]⁻) 351/353.

Step 4: preparation of intermediate 3-benzo[b]thiophen-3-yl-4-bromo-5-dimethoxymethyl-1-methyl-1H-pyrazole (38d)

Using the procedure described in example 8, step 4, 3-benzo[b]thiophen-3-yl-4-bromo-5-dimethoxymethyl-1H-pyrazole (38c) (2.04 g, 5.77 mmol) is converted, after purification by flash chromatography (dichloromethane/ethyl acetate 100/0 to 98/2) into 3-benzo[b]thiophen-3-yl-4-bromo-5-dimethoxymethyl-1-methyl-1H-pyrazole (38d) (785 mg, 2.14 mmol, 37%).

$^1$H NMR (400 MHz, CDCl$_3$) δ 3.50 (s, 6H), 4.08 (s, 3H), 5.47 (s, 1H), 7.35-7.45 (m, 2H), 7.89 (d, J=7.5 Hz, 1H), 7.95 (s, 1H), 8.38 (d, J=7.5 Hz, 1H).

MS m/z ([M+H]⁺) 367/369.

Step 5: preparation of intermediate 3-benzo[b]thiophen-3-yl-4-bromo-1-methyl-1H-pyrazole-5-carbaldehyde (38e)

Using the procedure described in example 8, step 5, 3-benzo[b]thiophen-3-yl-4-bromo-5-dimethoxymethyl-1-methyl-1H-pyrazole (38d) (785 mg, 2.14 mmol) is converted into 3-benzo[b]thiophen-3-yl-4-bromo-1-methyl-1H-pyrazole-5-carbaldehyde (38e) (645 mg, 2.01 mmol, 94%) as a white solid, which was used without further purification.

$^1$H NMR (400 MHz, CDCl$_3$) δ 4.28 (s, 3H), 7.38-7.47 (m, 2H), 7.91 (dd, J=1.2 Hz, J=7.1 Hz, 1H), 8.02 (s, 1H), 8.32-8.36 (m, 1H), 10.00 (s, 1H).

Step 6: preparation of intermediate 3-benzo[b]thiophen-3-yl-4-(3,4-dihydro-2H-1-benzopyran-6-yl)-1-methyl-1H-pyrazole-5-carbaldehyde (38f)

Using the procedure described in example 1, step 4, 3-benzo[b]thiophen-3-yl)-4-bromo-1-methyl-1H-pyrazole-5-carbaldehyde (38e) (200 mg, 0.62 mmol) is converted, after purification by preparative TLC (cyclohexane/ethyl acetate 80/20) into 3-benzo[b]thiophen-3-yl-4-(3,4-dihydro-2H-1-benzopyran-6-yl)-1-methyl-1H-pyrazole-5-carbaldehyde (38f) (233 mg, 0.62 mmol, 100%).

$^1$H NMR (400 MHz, CDCl$_3$) δ 1.97-2.05 (m, 2H), 2.73 (t, J=6.5 Hz, 2H), 4.20-4.24 (m, 2H), 4.32 (s, 3H), 6.79 (d, J=8.3 Hz, 1H), 6.98 (d, J=2.2 Hz, 1H), 7.01 (dd, J=8.3 Hz, J=2.2 Hz, 1H), 7.18 (s, 1H), 7.34-7.42 (m, 2H), 7.85 (dd, J=7.2 Hz, J=1.9 Hz, 1H), 8.32 (dd, J=7.2 Hz, J=1.9 Hz, 1H), 9.72 (s, 1H).

MS m/z ([M+H]⁺) 375.

Step 7: preparation of intermediate methyl 2-[3-benzo[b]thiophen-3-yl-4-(3,4-dihydro-2H-1-benzopyran-6-yl)-1-methyl-1H-pyrazol-5-yl]-2-hydroxyacetate (38g)

Using the procedure described in example 1, step 5, 3-benzo[b]thiophen-3-yl-4-(3,4-dihydro-2H-1-benzopyran-6-yl)-1-methyl-1H-pyrazole-5-carbaldehyde (38f) (233 mg, 0.62 mmol) is converted, after purification by preparative TLC (dichloromethane/ethyl acetate 80/20) into methyl 2-[3-benzo[b]thiophen-3-yl-4-(3,4-dihydro-2H-1-benzopyran-6-yl)-1-methyl-1H-pyrazol-5-yl]-2-hydroxyacetate (38g) (220 mg, 0.51 mmol, 81%).

$^1$H NMR (400 MHz, CDCl$_3$) 1.95-2.03 (m, 2H), 2.70 (t, J=6.5 Hz, 2H), 3.43 (d, J=2.8 Hz, 1H), 3.76 (s, 3H), 3.97 (s, 3H), 4.17-4.22 (m, 2H), 5.31 (d, J=2.8 Hz, 1H), 6.76 (d, J=8.3 Hz, 1H), 6.92 (d, J=2.1 Hz, 1H), 6.97 (dd, J=8.3 Hz, J=2.1 Hz, 1H), 7.08 (s, 1H), 7.33 (td, J=7.1 Hz, J=1.1 Hz, 1H), 7.37 (td, J=7.1 Hz, J=1.1 Hz, 1H), 7.82 (dd, J=7.1 Hz, J=1.1 Hz, 1H), 8.41 (dd, J=7.1 Hz, J=1.1 Hz, 1H).

Step 8: preparation of intermediate methyl 2-[3-benzo[b]thiophen-3-yl-4-(3,4-dihydro-2H-1-benzopyran-6-yl)-1-methyl-1H-pyrazol-5-yl]-2-(tert-butoxy)acetate (38h)

Using the procedure described in example 1, step 6, methyl 2-[3-benzo[b]thiophen-3-yl-4-(3,4-dihydro-2H-1-benzopyran-6-yl)-1-methyl-1H-pyrazol-5-yl]-2-hydroxyacetate (38g) (196 mg, 0.45 mmol) is converted, after purification by preparative TLC (cyclohexane/ethyl acetate 70/30) into methyl 2-[3-benzo[b]thiophen-3-yl-4-(3,4-dihydro-2H-1-benzopyran-6-yl)-1-methyl-1H-pyrazol-5-yl]-2-(tert-butoxy)acetate (38h) (152 mg, 0.31 mmol, 69%).

$^1$H NMR (300 MHz, CDCl$_3$) δ 1.07 (s, 9H), 1.97-2.06 (m, 2H), 2.72 (t, J=6.4 Hz, 2H), 3.80 (s, 3H), 4.08 (s, 3H), 4.19-4.25 (m, 2H), 5.14 (s, 1H), 6.78 (d, J=8.3 Hz, 1H), 6.94 (d, J=2.2 Hz, 1H), 7.00 (dd, J=8.3 Hz, J=2.2 Hz, 1H), 7.08 (s,

1H), 7.32 (td, J=7.1 Hz, J=1.3 Hz, 1H), 7.29-7.41 (m, 2H), 7.79-7.84 (m, 1H), 8.46-8.51 (m, 1H).

MS m/z ([M+H]⁺) 491.

Step 9: preparation of 2-[3-benzo[b]thiophen-3-yl-4-(3,4-dihydro-2H-1-benzopyran-6-yl)-1-methyl-1H-pyrazol-5-yl]-2-(tert-butoxy)acetic acid (example 38)

Using the procedure described in example 1, step 7, methyl 2-[3-benzo[b]thiophen-3-yl-4-(3,4-dihydro-2H-1-benzopyran-6-yl)-1-methyl-1H-pyrazol-5-yl]-2-(tert-butoxy)acetate (38h) (152 mg, 0.31 mmol) is converted into 2-[3-benzo[b]thiophen-3-yl]-4-(3,4-dihydro-2H-1-benzopyran-6-yl)-1-methyl-1H-pyrazol-5-yl]-2-(tert-butoxy)acetic acid (example 38) (145 mg, 0.30 mmol, 98%).

¹H NMR (400 MHz, CDCl₃) δ 1.08 (s, 9H), 1.96-2.04 (m, 2H), 2.64-2.77 (m, 2H), 4.02 (s, 3H), 4.18-4.23 (m, 2H), 5.21 (s, 1H), 6.75 (d, J=8.2 Hz, 1H), 6.97-7.04 (m, 2H), 7.12 (s, 1H), 7.29-7.39 (m, 2H), 7.80-7.83 (m, 1H), 8.38-8.42 (m, 1H).

MS m/z ([M−H]⁻) 475.

MS m/z ([M+H]⁺) 477.

Example 39

Synthesis of 2-(tert-butoxy)-2-[4-(4,4-dimethylcyclohex-1-en-1-yl)-1-methyl-3-(pyridin-4-yl)-1H-pyrazol-5-yl]acetic acid

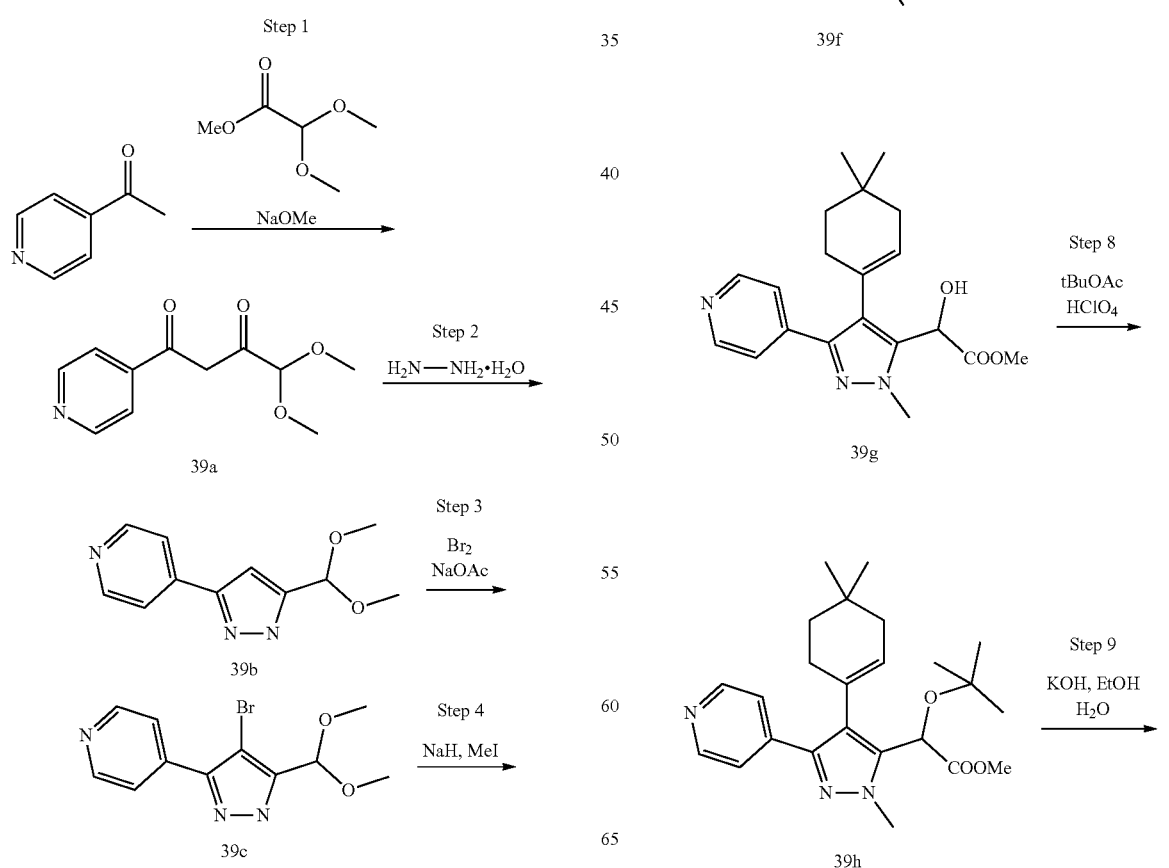

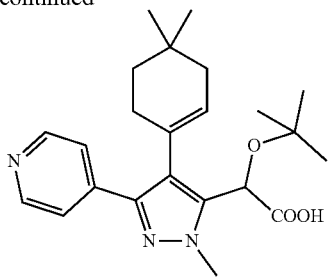

Example 39

Step 1: preparation of intermediate 4,4-dimethoxy-1-(pyridin-4-yl)butane-1,3-dione (39a)

Using the procedure described in example 8, step 1, 4-acetylpyridine (3.0 g, 24.8 mmol) is converted into 4,4-dimethoxy-1-(pyridin-4-yl)butane-1,3-dione (39a) (4.37 g, 19.6 mmol, 81%) as an orange oil, which was used without further purification.

$^1$H NMR (400 MHz, CDCl$_3$) δ 3.45 (s, 6H), 4.79 (s, 1H), 6.60 (s, 1H), 7.73 (d, J=4.5 Hz, 2H), 8.77 (d, J=4.5 Hz, 2H).

MS m/z ([M+H]$^+$) 224.

Step 2: preparation of intermediate 4-[5-(dimethoxymethyl)-1H-pyrazol-3-yl]pyridine (39b)

Using the procedure described in example 8, step 2, 4,4-dimethoxy-1-(pyridin-4-yl)butane-1,3-dione (39a) (4.37 g, 19.6 mmol) is converted, after purification by trituration in 2-propanol into 4-[5-(dimethoxymethyl)-1H-pyrazol-3-yl]pyridine (39b) (2.53 g, 11.5 mmol, 59%) MS m/z ([M+H]$^+$) 220.

Step 3: preparation of intermediate 4-[4-bromo-5-(dimethoxymethyl)-1H-pyrazol-3-yl]pyridine (39c)

Using the procedure described in example 8, step 3, 4-[5-(dimethoxymethyl)-1H-pyrazol-3-yl]pyridine (39b) (2.53 g, 11.5 mmol) is converted into 4-[4-bromo-5-(dimethoxymethyl)-1H-pyrazol-3-yl]pyridine (39c) (3.3 g, 11.1 mmol, 96%) which was used without further purification.

MS m/z ([M+H]$^+$) 298/300.

Step 4: preparation of intermediate 4-[4-bromo-5-(dimethoxymethyl)-1-methyl-1H-pyrazol-3-yl]pyridine (39d)

Using the procedure described in example 8, step 4, 4-[4-bromo-5-(dimethoxymethyl)-1H-pyrazol-3-yl]pyridine (39c) (1.5 g, 5.03 mmol) is converted, after purification by flash chromatography (dichloromethane/ethyl acetate 100/0 to 70/30) into 4-[4-bromo-5-(dimethoxymethyl)-1-methyl-1H-pyrazol-3-yl]pyridine (39d) (846 mg, 2.7 mmol, 54%).

$^1$H NMR (400 MHz, CDCl$_3$) δ 3.45 (s, 6H), 4.01 (s, 3H), 5.40 (s, 1H), 7.83 (dd, J=4.5 Hz, J=1.6 Hz, 2H), 8.64 (dd, J=4.5 Hz, J=1.6 Hz, 2H) MS m/z ([M+H]$^+$) 312/314.

Step 5: preparation of intermediate 4-bromo-1-methyl-3-(pyridin-4-yl)-1H-pyrazole-5-carbaldehyde (39e)

Using the procedure described in example 8, step 5, 4-[4-bromo-5-(dimethoxymethyl)-1-methyl-1H-pyrazol-3-yl]pyridine (39d) (846 mg, 2.71 mmol) is converted, after purification by trituration in diethyl ether, into 4-bromo-1-methyl-3-(pyridin-4-yl)-1H-pyrazole-5-carbaldehyde (39e) (585 mg, 2.20 mmol, 81%).

$^1$H NMR (300 MHz, CDCl$_3$) δ 4.23 (s, 3H), 7.86 (d, J=5.6 Hz, 2H), 8.71, (bs, 2H), 9.97 (s, 1H).

MS m/z ([M+H]$^+$) 266/268

Step 6: preparation of intermediate 4-(4,4-dimethylcyclohex-1-en-1-yl)-1-methyl-3-(pyridin-4-yl)-1H-pyrazole-5-carbaldehyde (39f)

Using the procedure described in example 1, step 4,4-bromo-1-methyl-3-(pyridin-4-yl)-1H-pyrazole-5-carbaldehyde (39e) (200 mg, 0.75 mmol) is converted by reaction with 4,4-(dimethylcyclohexen-1-yl)boronic acid pinacol ester (231 mg, 0.98 mmol), after purification by preparative TLC (dichloromethane/7M ammonia in methanol 98/2) into 4-(4,4-dimethylcyclohex-1-en-1-yl)-1-methyl-3-(pyridin-4-yl)-1H-pyrazole-5-carbaldehyde (39f) (222 mg, 0.75 mmol, 100%).

$^1$H NMR (300 MHz, CDCl$_3$) δ 1.01 (s, 6H), 1.48 (t, J=6.2 Hz, 2H), 2.01-2.16 (m, 4H), 4.21 (s, 3H), 5.82-5.89 (m, 1H), 7.63 (dd, J=4.5 Hz, J=1.6 Hz, 2H), 8.62 (dd, J=4.5 Hz, J=1.6 Hz, 2H), 9.73 (s, 1H).

MS m/z ([M+H]$^+$) 296.

Step 7: preparation of intermediate methyl 2-[4-(4,4-dimethylcyclohex-1-en-1-yl)-1-methyl-3-(pyridin-4-yl)-1H-pyrazol-5-yl]-2-hydroxyacetate (39g)

Using the procedure described in example 1, step 5, 4-(4,4-dimethylcyclohex-1-en-1-yl)-1-methyl-3-(pyridin-4-yl)-1H-pyrazole-5-carbaldehyde (39f) (222 mg, 0.75 mmol) is converted, after purification by preparative TLC (dichloromethane/7M ammonia in methanol 95/5) into methyl 2-[4-(4,4-dimethylcyclohex-1-en-1-yl)-1-methyl-3-(pyridin-4-yl)-1H-pyrazol-5-yl]-2-hydroxyacetate (39g) (63 mg, 0.18 mmol, 23%).

$^1$H NMR (400 MHz, CDCl$_3$) δ 0.99 (s, 6H), 1.42 (t, J=6.2 Hz, 2H), 1.93-2.09 (m, 4H), 3.82 (s, 3H), 3.89 (s, 3H), 5.32 (s, 1H), 5.73-5.77 (m, 1H), 7.63 (dd, J=4.5 Hz, J=1.6 Hz, 2H), 8.55 (dd, J=4.5 Hz, J=1.6 Hz, 2H).

MS m/z ([M+H]$^+$) 356.

Step 8: preparation of intermediate methyl 2-(tert-butoxy)-2-[4-(4,4-dimethylcyclohex-1-en-1-yl)-1-methyl-3-(pyridin-4-yl)-1H-pyrazol-5-yl]acetate (39h)

Using the procedure described in example 1, step 6, methyl 2-[4-(4,4-dimethylcyclohex-1-en-1-yl)-1-methyl-3-(pyridin-4-yl)-1H-pyrazol-5-yl]-2-hydroxy acetate (39g) (63 mg, 0.18 mmol) is converted, after purification by preparative TLC (dichloromethane/7M ammonia in methanol 97/3) into methyl 2-(tert-butoxy)-2-[4-(4,4-dimethylcyclohex-1-en-1-yl)-1-methyl-3-(pyridin-4-yl)-1H-pyrazol-5-yl]acetate (39h) (56 mg, 0.14 mmol, 77%).

$^1$H NMR (300 MHz, CDCl$_3$) δ 1.02 (s, 3H), 1.04 (s, 3H), 1.19 (s, 9H), 1.38-1.50 (m, 2H), 1.84-2.17 (m, 4H), 3.73 (s, 3H), 4.01 (s, 3H), 5.24 (s, 1H), 5.77-5.82 (m, 1H), 7.65 (dd, J=4.6 Hz, J=1.5 Hz, 2H), 8.57 (dd, J=4.6 Hz, J=1.5 Hz, 2H).

MS m/z ([M+H]$^+$) 412.

Step 9: preparation of 2-(tert-butoxy)-2-[4-(4,4-dimethylcyclohex-1-en-1-yl)-1-methyl-3-(pyridin-4-yl)-1H-pyrazol-5-yl]acetic acid (example 39)

Using the procedure described in example 1, step 7, methyl 2-(tert-butoxy)-2-[4-(4,4-dimethylcyclohex-1-en-1-yl)-1-methyl-3-(pyridin-4-yl)-1H-pyrazol-5-yl]acetate (39h) (56 mg, 0.14 mmol) is converted into 2-(tert-butoxy)-2-[4-(4,4-dimethylcyclohex-1-en-1-yl)-1-methyl-3-(pyridin-4-yl)-1H-pyrazol-5-yl]acetic acid (example 39) (35 mg, 0.09 mmol, 65%).

$^1$H NMR (300 MHz, CDCl$_3$) δ 1.01 (s, 3H), 1.03 (s, 3H), 1.22 (s, 9H), 1.33-1.51 (m, 2H), 1.87-2.24 (m, 4H), 4.03 (s, 3H), 5.24 (s, 1H), 5.92-5.98 (m, 1H), 7.76 (d, J=6.3 Hz, 2H), 8.58 (d, J=6.3 Hz, 2H).

MS m/z ([M−H]$^−$) 396.

MS m/z ([M+H]$^+$) 398.

Example 40

Synthesis of 2-(tert-butoxy)-2-[4-(3,4-dihydro-2H-1-benzopyran-6-yl)-1-methyl-3-(pyridin-4-yl)-1H-Dvrazol-5-yl]acetic acid

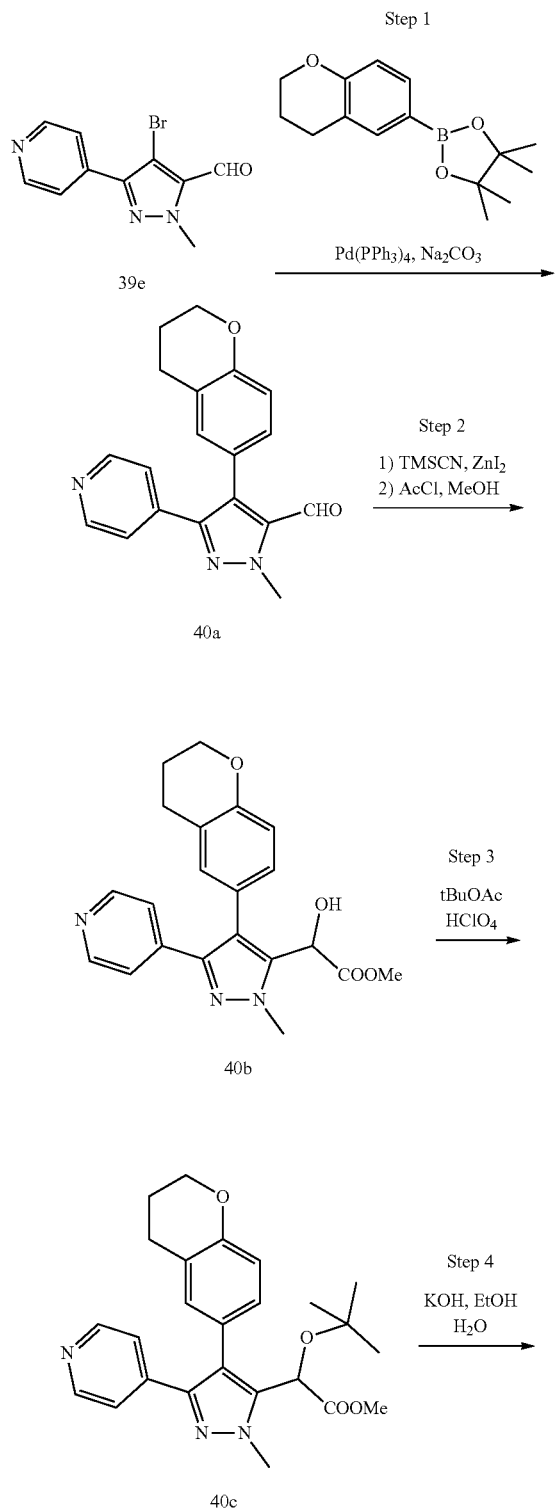

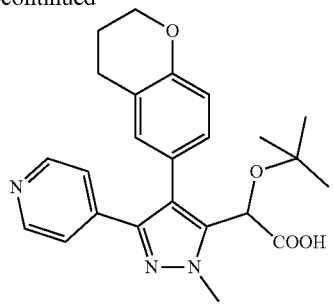

Example 40

Step 1: preparation of intermediate 4-(3,4-dihydro-2H-1-benzopyran-6-yl)-1-methyl-3-(pyridin-4-yl)-1H-pyrazole-5-carbaldehyde (40a)

Using the procedure described in example 1, step 4,4-bromo-1-methyl-3-(pyridin-4-yl)-1H-pyrazole-5-carbaldehyde (39e) (200 mg, 0.75 mmol) is converted by reaction with 6-(4,4,5,5-tetramethyl-1,3,2-dioxaborolan-2-yl)chroman (239 mg, 1.13 mmol), after purification by preparative TLC (dichloromethane/7M ammonia in methanol 98/2) into 4-(3,4-dihydro-2H-1-benzopyran-6-yl)-1-methyl-3-(pyridin-4-yl)-1H-pyrazole-5-carbaldehyde (40a) (240 mg, 0.75 mmol, 100%).

$^1$H NMR (300 MHz, CDCl$_3$) δ 2.00-2.10 (m, 2H), 2.78 (t, J=6.4 Hz, 2H), 4.25 (t, J=5.2 Hz, 2H), 4.27 (s, 3H), 6.84 (d, J=8.2 Hz, 1H), 6.97 (d, J=2.1 Hz, 1H), 7.00 (dd, J=8.2 Hz, J=2.1 Hz, 1H), 7.39 (dd, J=4.5 Hz, J=1.6 Hz, 2H), 8.51 (dd, J=4.5 Hz, J=1.6 Hz, 2H), 9.63 (s, 1H).

MS m/z ([M+H]$^+$) 320.

Step 2: preparation of intermediate methyl 2-[4-(3,4-dihydro-2H-1-benzopyran-6-yl)-1-methyl-3-(pyridin-4-yl)-1H-pyrazol-5-yl]-2-hydroxyacetate (40b)

Using the procedure described in example 1, step 5, 4-(3,4-dihydro-2H-1-benzopyran-6-yl)-1-methyl-3-(pyridin-4-yl)-1H-pyrazole-5-carbaldehyde (40a) (240 mg, 0.75 mmol) is converted, after purification by preparative TLC (dichloromethane/7M ammonia in methanol 95/5) into methyl 2-[4-(3,4-dihydro-2H-1-benzopyran-6-yl)-1-methyl-3-(pyridin-4-yl)-1H-pyrazol-5-yl]-2-hydroxyacetate (40b) (83 mg, 0.22 mmol, 29%).

$^1$H NMR (400 MHz, CDCl$_3$) δ 1.98-2.08 (m, 2H), 2.75 (t, J=6.4 Hz, 2H), 3.76 (s, 3H), 3.94 (s, 3H), 4.23 (t, J=5.2 Hz, 2H), 5.23 (s, 1H), 6.80 (d, J=8.2 Hz, 1H), 6.90 (d, J=2.1 Hz, 1H), 6.95 (dd, J=8.2 Hz, J=2.1 Hz, 1H), 7.36 (dd, J=4.5 Hz, J=1.6 Hz, 2H), 8.44 (dd, J=4.5 Hz, J=1.6 Hz, 2H).

MS m/z ([M+H]$^+$) 380.

Step 3: preparation of intermediate methyl 2-(tert-butoxy)-2-[4-(3,4-dihydro-2H-1-benzopyran-6-yl)-1-methyl-3-(pyridin-4-yl)-1H-pyrazol-5-yl]acetate (40c)

Using the procedure described in example 1, step 6, methyl 2-[4-(3,4-dihydro-2H-1-benzopyran-6-yl)-1-methyl-3-(pyridin-4-yl)-1H-pyrazol-5-yl]-2-hydroxyacetate (40b) (83 mg, 0.22 mmol) is converted, after purification by preparative TLC (dichloromethane/7M ammonia in methanol 97/3) into methyl 2-(tert-butoxy)-2-[4-(3,4-dihydro-2H-1-benzopyran-6-yl)-1-methyl-3-(pyridin-4-yl)-1H-pyrazol-5-yl]acetate (40c) (70 mg, 0.16 mmol, 73%).

$^1$H NMR (300 MHz, CDCl$_3$) δ 1.04 (s, 9H), 1.97-2.11 (m, 2H), 2.77 (t, J=6.4 Hz, 2H), 3.78 (s, 3H), 4.04 (s, 3H), 4.25 (t, J=5.1 Hz, 2H), 5.04 (s, 1H), 6.83 (d, J=8.2 Hz, 1H), 6.91 (d,

J=2.1 Hz, 1H), 6.97 (dd, J=8.2 Hz, J=2.1 Hz, 1H), 7.38 (dd, J=4.5 Hz, J=1.6 Hz, 2H), 8.44 (dd, J=4.5 Hz, J=1.6 Hz, 2H).

MS m/z ([M+H]$^+$) 436.

Step 4: preparation of 2-(tert-butoxy)-2-[4-(3,4-dihydro-2H-1-benzopyran-6-yl)-1-methyl-3-(pyridin-4-yl)-1H-pyrazol-5-yl]acetic acid (example 40)

Using the procedure described in example 1, step 7, methyl 2-(tert-butoxy)-2-[4-(3,4-dihydro-2H-1-benzopyran-6-yl)-1-methyl-3-(pyridin-4-yl)-1H-pyrazol-5-yl]acetate (40c) (70 mg, 0.16 mmol) is converted into 2-(tert-butoxy)-2-[4-(3,4-dihydro-2H-1-benzopyran-6-yl)-1-methyl-3-(pyridin-4-yl)-1H-pyrazol-5-yl]acetic acid (example 40) (55 mg, 0.13 mmol, 81%).

$^1$H NMR (300 MHz, CDCl$_3$) δ 1.04 (s, 9H), 1.97-2.10 (m, 2H), 2.76 (t, J=6.3 Hz, 2H), 4.05 (s, 3H), 4.25 (t, J=5.0 Hz, 2H), 5.06 (s, 1H), 6.82 (d, J=8.2 Hz, 1H), 6.99-7.10 (m, 2H), 7.59 (d, J=5.9 Hz, 2H), 8.48 (d, J=5.9 Hz, 2H).

MS m/z ([M−H]$^−$) 420.

MS m/z ([M+H]$^+$) 422

Example 41

Synthesis of 2-(tert-butoxy)-2-{1-methyl-3-phenyl-4-[4-(propan-2-yl)cyclohex-1-en-1-yl]-1H-pyrazol-5-yl}acetic acid

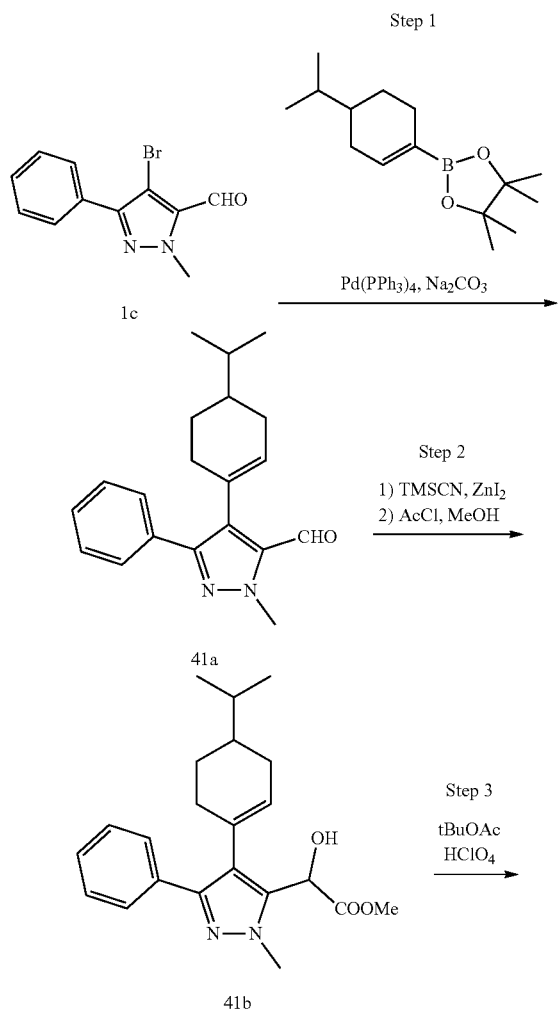

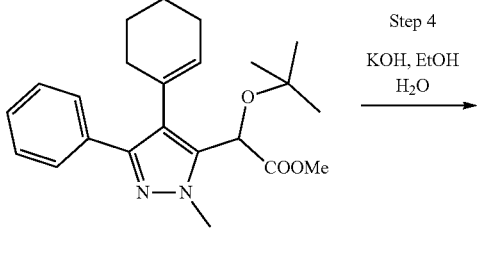

Step 1: preparation of intermediate 1-methyl-3-phenyl-4-[4-(propan-2-yl)cyclohex-1-en-1-yl]-1H-pyrazole-5-carbaldehyde (41a)

Using the procedure described in example 1, step 4,4-bromo-1-methyl-3-phenyl-1H-pyrazole-5-carbaldehyde (1c) (150 mg, 0.57 mmol) is converted by reaction with 2-(4-isopropyl-cyclohexen-1-yl)boronic acid pinacol ester (184 mg, 0.74 mmol), after purification by preparative TLC (cyclohexane/ethyl acetate 80/20) into 1-methyl-3-phenyl-4-[4-(propan-2-yl)cyclohex-1-en-1-yl]-1H-pyrazole-5-carbaldehyde (41a) (151 mg, 0.49 mmol, 86%).

$^1$H NMR (300 MHz, CDCl$_3$) δ 0.94 (d, J=6.8 Hz, 6H), 1.21-1.48 (m, 2H), 1.54 (sex, J=6.6 Hz, 1H), 1.75-1.85 (m, 1H), 1.91-2.06 (m, 1H), 2.07-2.17 (m, 2H), 2.22-2.37 (m, 1H), 4.20 (s, 3H), 5.85-5.93 (m, 1H), 7.29-7.44 (m, 3H), 7.66-7.74 (m, 2H), 9.73 (s, 1H).

MS m/z ([M+H]$^+$) 309.

Step 2: preparation of intermediate methyl 2-hydroxy-2-{1-methyl-3-phenyl-4-[4-(propan-2-yl)cyclohex-1-en-1-yl]-1H-pyrazol-5-yl}acetate (41b)

Using the procedure described in example 1, step 5, 1-methyl-3-phenyl-4-[4-(propan-2-yl)cyclohex-1-en-1-yl]-1H-pyrazole-5-carbaldehyde (41a) (150 mg, 0.49 mmol) is converted, after purification by preparative TLC (cyclohexane/ethyl acetate 50/50) into methyl 2-hydroxy-2-{1-methyl-3-phenyl-4-[4-(propan-2-yl)cyclohex-1-en-1-yl]-1H-pyrazol-5-yl}acetate (41 b) (72 mg, 0.20 mmol, 40%).

$^1$H NMR (400 MHz, CDCl$_3$) δ 0.92 (d, J=6.7 Hz, 3H), 0.93 (d, J=6.7 Hz, 3H), 1.28-1.42 (m, 1H), 1.52 (sex, J=6.6 Hz, 1H), 1.57-1.70 (m, 1H), 1.70-1.80 (m, 1H), 1.86-2.16 (m, 3H), 2.19-2.29 (m, 1H), 3.72 (bs, 1H), 3.82 and 3.83 (s, 3H), 3.86 and 3.87 (s, 3H), 5.33 and 5.35 (s, 1H), 5.77-5.82 (m, 1H), 7.27-7.31 (m, 1H), 7.32-7.39 (m, 2H), 7.67-7.73 (m, 2H).

Ms m/z ([M+H]$^+$) 369.

Step 3: preparation of intermediate methyl 2-(tert-butoxy)-2-{1-methyl-3-phenyl-4-[4-(propan-2-yl)cyclohex-1-en-1-yl]-1H-pyrazol-5-yl}acetate (41c)

Using the procedure described in example 1, step 6, methyl 2-hydroxy-2-{1-methyl-3-phenyl-4-[4-(propan-2-yl)cyclohex-1-en-1-yl]-1H-pyrazol-5-yl}acetate (41 b) (70 mg, 0.19 mmol) is converted, after purification by preparative TLC (dichloromethane/ethyl acetate 90/10) into methyl 2-(tert-butoxy)-2-{1-methyl-3-phenyl-4-[4-(propan-2-yl)cyclohex-1-en-1-yl]-1H-pyrazol-5-yl}acetate (41c) (63 mg, 0.15 mmol, 78%).

$^1$H NMR (400 MHz, CDCl$_3$) δ 0.91-0.97 (m, 6H), 1.19 and 1.20 (s, 9H), 1.21-1.40 (m, 2H), 1.51 (sex, J=6.6 Hz, 1H), 1.71-1.83 (m, 1H), 1.85-2.05 (m, 2H), 2.06-2.23 (m, 1H), 2.25-2.38 (m, 1H), 3.73 and 3.74 (s, 3H), 3.97 and 3.98 (s, 3H), 5.28 and 5.29 (s, 1H), 5.80-5.90 (m, 1H), 7.24-7.30 (m, 1H), 7.32-7.38 (m, 2H), 7.68-7.74 (m, 2H).

Step 4: preparation of 2-(tert-butoxy)-2-{1-methyl-3-phenyl-4-[4-(propan-2-yl)cyclohex-1-en-1-yl]-1H-pyrazol-5-yl}acetic acid (example 41)

Using the procedure described in example 1, step 7, methyl 2-(tert-butoxy)-2-{1-methyl-3-phenyl-4-[4-(propan-2-yl)cyclohex-1-en-1-yl]-1H-pyrazol-5-yl}acetate (41c) (63 mg, 0.15 mmol) is converted, after purification by preparative TLC (dichloromethane/methanol 95/5) into 2-(tert-butoxy)-2-{1-methyl-3-phenyl-4-[4-(propan-2-yl)cyclohex-1-en-1-yl]-1H-pyrazol-5-yl}acetic acid (example 41) (40 mg, 0.10 mmol, 66%).

$^1$H NMR (400 MHz, CDCl$_3$) δ 0.88-0.96 (m, 6H), 1.14 (s, 9H), 1.22-1.42 (m 2H), 1.45-1.58 (m, 1H), 1.67-1.79 (m, 1H), 1.79-2.03 (m, 2H), 2.08-2.34 (m, 2H), 3.89 (s, 3H), 5.28 (bs, 1H), 5.96 (bs, 1H), 7.23-7.30 (m, 1H), 7.32-7.38 (m, 2H), 7.63-7.70 (m, 2H).

MS m/z ([M−H]$^-$) 409.

MS m/z ([M+H]$^+$) 411.

Example 42

Synthesis of 2-(tert-butoxy)-2-[4-(8-fluoro-3,4-dihydro-2H-1-benzopyran-6-yl)-1-methyl-3-(thiophen-2-yl)-1H-pyrazol-5-yl]acetic acid Step 1

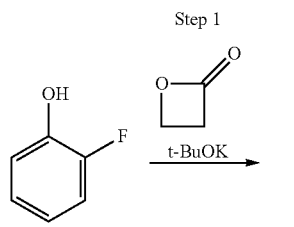

t-BuOK

Step 2

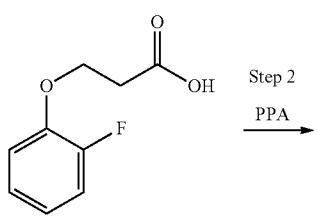

42a

PPA

-continued

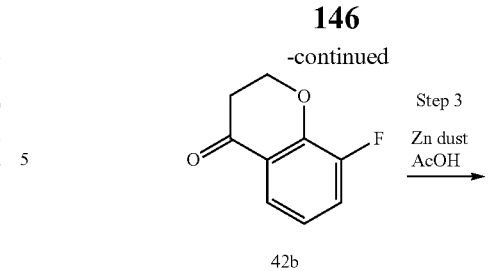

42b

Step 3

Zn dust
AcOH

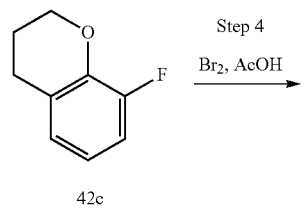

42c

Step 4

Br$_2$, AcOH

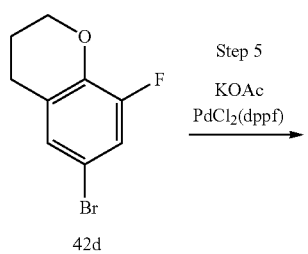

42d

Step 5

KOAc
PdCl$_2$(dppf)

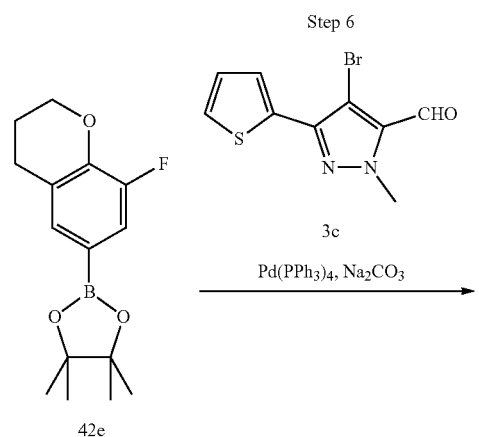

42e

Step 6

Pd(PPh$_3$)$_4$, Na$_2$CO$_3$

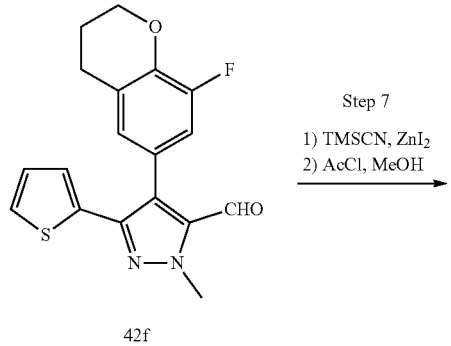

42f

Step 7

1) TMSCN, ZnI$_2$
2) AcCl, MeOH

-continued

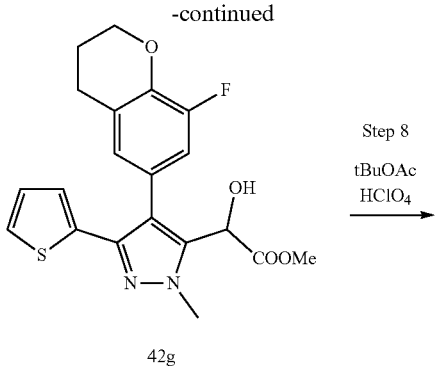

42g

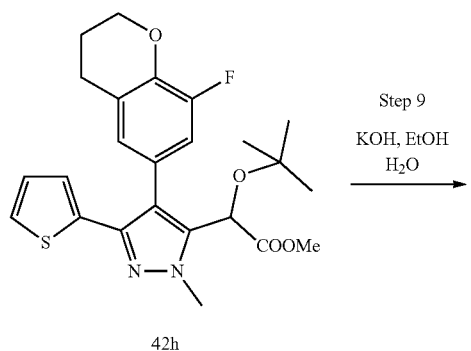

42h

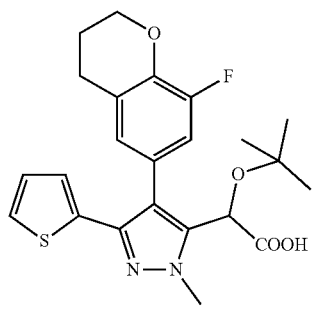

Example 42

Step 1: preparation of intermediate 3-(2-fluorophenoxy) propanoic acid (42a)

Using the procedure described in example 10, step 1, 2-fluorophenol (3.0 g, 26.8 mmol) is converted into 3-(2-fluorophenoxy)propanoic acid (42a) (3.73 g, 20.3 mmol, 76%) which was used without further purification.

MS m/z ([M−H]$^-$) 183.

Step 2: preparation of intermediate 8-fluoro-3,4-dihydro-2H-1-benzopyran-4-one (42b)

Using the procedure described in example 10, step 2, 3-(2-fluorophenoxy)propanoic acid (42a) (3.7 g, 20.3 mmol) is converted into 8-fluoro-3,4-dihydro-2H-1-benzopyran-4-one (42b) (1.80 g, 10.8 mmol, 53%) which was used without further purification.

$^1$H NMR (300 MHz, CDCl$_3$) δ 2.83-2.90 (m, 2H), 4.60-4.68 (m, 2H), 6.95 (td, J=8.0 Hz, J=4.4 Hz, 1H), 7.30 (ddd, J=1.4 Hz, J=8.0 Hz, J=10.6 Hz, 1H), 7.67 (td, J=1.4 Hz, J=8.0 Hz, 1H).

MS m/z ([M+H]$^+$) 167.

Step 3: preparation of intermediate 8-fluoro-3,4-dihydro-2H-1-benzopyran (42c)

Using the procedure described in example 10, step 3, 8-fluoro-3,4-dihydro-2H-1-benzopyran-4-one (42b) (1.80 g, 10.83 mmol) is converted, after purification by flash chromatography on silica gel (cyclohexane/ethyl acetate 100/0 to 95/5) into 8-fluoro-3,4-dihydro-2H-1-benzopyran (42c) (827 mg, 5.43 mmol, 50%).

$^1$H NMR (300 MHz, CDCl$_3$) δ 1.99-2.08 (m, 2H), 2.81 (t, J=6.5 Hz, 2H), 4.23-4.29 (m, 2H), 6.69-6.93 (m, 3H).

Step 4: preparation of intermediate 6-bromo-8-fluoro-3,4-dihydro-2H-1-benzopyran (42d)

Using the procedure described in example 7, step 5, 8-fluoro-3,4-dihydro-2H-1-benzopyran (42c) (820 mg, 5.39 mmol) is converted to 6-bromo-8-fluoro-3,4-dihydro-2H-1-benzopyran (42d) (1.21 g, 5.24 mmol, 92%) which was used without further purification.

$^1$H NMR (300 MHz, CDCl$_3$) δ 1.97-2.07 (m, 2H), 2.78 (t, J=6.5 Hz, 2H), 4.21-4.27 (m, 2H), 6.95-6.98 (m, 1H), 7.05 (dd, J=2.3 Hz, J=10.2 Hz, 1H).

Step 5: preparation of intermediate 2-(8-fluoro-3,4-dihydro-2H-1-benzopyran-6-yl)-4,4,5,5-tetramethyl-1,3,2-dioxaborolane (42e)

Using the procedure described in example 7, step 6,6-bromo-8-fluoro-3,4-dihydro-2H-1-benzopyran (42d) (900 mg, 3.89 mmol) is converted, after purification by flash chromatography on silica gel (cyclohexane/ethyl acetate 100/0 to 95/5) into 2-(8-fluoro-3,4-dihydro-2H-1-benzopyran-6-yl)-4,4,5,5-tetramethyl-1,3,2-dioxaborolane (42e) (515 mg, 1.85 mmol, 47%).

$^1$H NMR (400 MHz, CDCl$_3$) δ 1.32 (s, 12H), 1.99-2.06 (m, 2H), 2.80 (t, J=6.4 Hz, 2H), 4.25-4.31 (m, 2H), 7.26-7.35 (m, 2H).

MS m/z ([M+H]$^+$) 279.

Step 6: preparation of intermediate 4-(8-fluoro-3,4-dihydro-2H-1-benzopyran-6-yl)-1-methyl-3-(thiophen-2-yl)-1H-pyrazole-5-carbaldehyde (42f)

Using the procedure described in example 7, step 8,4-bromo-1-methyl-3-(thiophen-2-yl)-1H-pyrazole-5-carbaldehyde (3c) (120 mg, 0.44 mmol) is converted by reaction with 2-(8-fluoro-3,4-dihydro-2H-1-benzopyran-6-yl)-4,4,5,5-tetramethyl-1,3,2-dioxa borolane (42e) (147 mg, 0.53 mmol), after purification by preparative TLC (dichloromethane/ethyl acetate 98/2) into 4-(8-fluoro-3,4-dihydro-2H-1-benzopyran-6-yl)-1-methyl-3-(thiophen-2-yl)-1H-pyrazole-5-carbaldehyde (42f) (151 mg, 0.44 mmol, 100%).

$^1$H NMR (300 MHz, CDCl$_3$) δ 2.04-2.14 (m, 2H), 2.83 (t, J=6.4 Hz, 2H), 4.23 (s, 3H), 4.30-4.37 (m, 2H), 6.82-6.86 (m, 1H), 6.91-7.00 (m, 3H), 7.22 (dd, J=1.2 Hz, J=5.0 Hz, 1H), 9.58 (s, 1H).

MS m/z ([M+H]$^+$) 343.

Step 7: preparation of intermediate methyl 2-[4-(8-fluoro-3,4-dihydro-2H-1-benzopyran-6-yl)-1-methyl-3-(thiophen-2-yl)-1H-pyrazol-5-yl]-2-hydroxyacetate (42g)

Using the procedure described in example 1, step 5, 4-(8-fluoro-3,4-dihydro-2H-1-benzopyran-6-yl)-1-methyl-3-(thiophen-2-yl)-1H-pyrazole-5-carbaldehyde (42f) (151 mg, 0.44 mmol) is converted, after purification by preparative TLC (dichloromethane/ethyl acetate 80/20) into methyl 2-[4-(8-fluoro-3,4-dihydro-2H-1-benzopyran-6-yl)-1-methyl-3-(thiophen-2-yl)-1H-pyrazol-5-yl]-2-hydroxyacetate (42g) (107 mg, 0.27 mmol, 60%).

¹H NMR (400 MHz, CDCl₃) δ 2.03-2.11 (m, 2H), 2.80 (t, J=6.4 Hz, 2H), 3.77 (s, 3H), 3.92 (s, 3H), 4.28-4.34 (m, 2H), 5.18 (s, 1H), 6.78-6.81 (m, 1H), 6.85-6.92 (m, 2H), 6.94 (dd, J=1.2 Hz, J=3.6 Hz, 1H), 7.18 (dd, J=1.2 Hz, J=5.0 Hz, 1H).

MS m/z ([M+H]⁺) 403.

Step 8: preparation of intermediate methyl 2-(tert-butoxy)-2-[4-(8-fluoro-3,4-dihydro-2H-1-benzopyran-6-yl)-1-methyl-3-(thiophen-2-yl)-1H-pyrazol-5-yl]acetate (42h)

Using the procedure described in example 1, step 6, methyl 2-[4-(8-fluoro-3,4-dihydro-2H-1-benzopyran-6-yl)-1-methyl-3-(thiophen-2-yl)-1H-pyrazol-5-yl]-2-hydroxyacetate (42f) (107 mg, 0.27 mmol) is converted, after purification by preparative TLC (cyclohexane/ethyl acetate 70/30) into methyl 2-(tert-butoxy)-2-[4-(8-fluoro-3,4-dihydro-2H-1-benzopyran-6-yl)-1-methyl-3-(thiophen-2-yl)-1H-pyrazol-5-yl]acetate (42h) (79 mg, 0.17 mmol, 65%).

¹H NMR (300 MHz, CDCl₃) δ 1.07 (s, 9H), 2.03-2.14 (m, 2H), 2.81 (t, J=6.4 Hz, 2H), 3.76 (s, 3H), 3.99 (s, 3H), 4.30-4.36 (m, 2H), 4.99 (s, 1H), 6.79-6.82 (m, 1H), 6.85-6.94 (m, 3H), 7.15 (dd, J=1.6 Hz, J=4.6 Hz, 1H).

Step 9: preparation of 2-(tert-butoxy)-2-[4-(8-fluoro-3,4-dihydro-2H-1-benzopyran-6-yl)-1-methyl-3-(thiophen-2-yl)-1H-pyrazol-5-yl]acetic acid (example 42)

Using the procedure described in example 1, step 7, methyl 2-(tert-butoxy)-2-[4-(8-fluoro-3,4-dihydro-2H-1-benzopyran-6-yl)-1-methyl-3-(thiophen-2-yl)-1H-pyrazol-5-yl]acetate (42h) (79 mg, 0.17 mmol) is converted into 2-(tert-butoxy)-2-[4-(8-fluoro-3,4-dihydro-2H-1-benzopyran-6-yl)-1-methyl-3-(thiophen-2-yl)-1H-pyrazol-5-yl]acetic acid (example 42) (76 mg, 0.17 mmol, 99%).

¹H NMR (300 MHz, CDCl₃) δ 1.09 (s, 9H), 2.03-2.13 (m, 2H), 2.81 (t, J=6.4 Hz, 2H), 3.96 (s, 3H), 4.29-4.36 (m, 2H), 5.06 (s, 1H), 6.86-6.91 (m, 3H), 6.95 (dd, J=1.9 Hz, J=11.4 Hz, 1H), 7.14-7.18 (m, 1H).

MS m/z ([M−H]⁻) 443.
MS m/z ([M+H]⁺) 445.

Example 43

Synthesis of 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetic acid

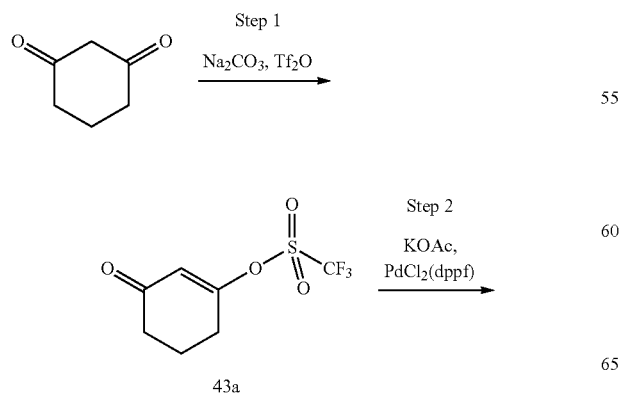

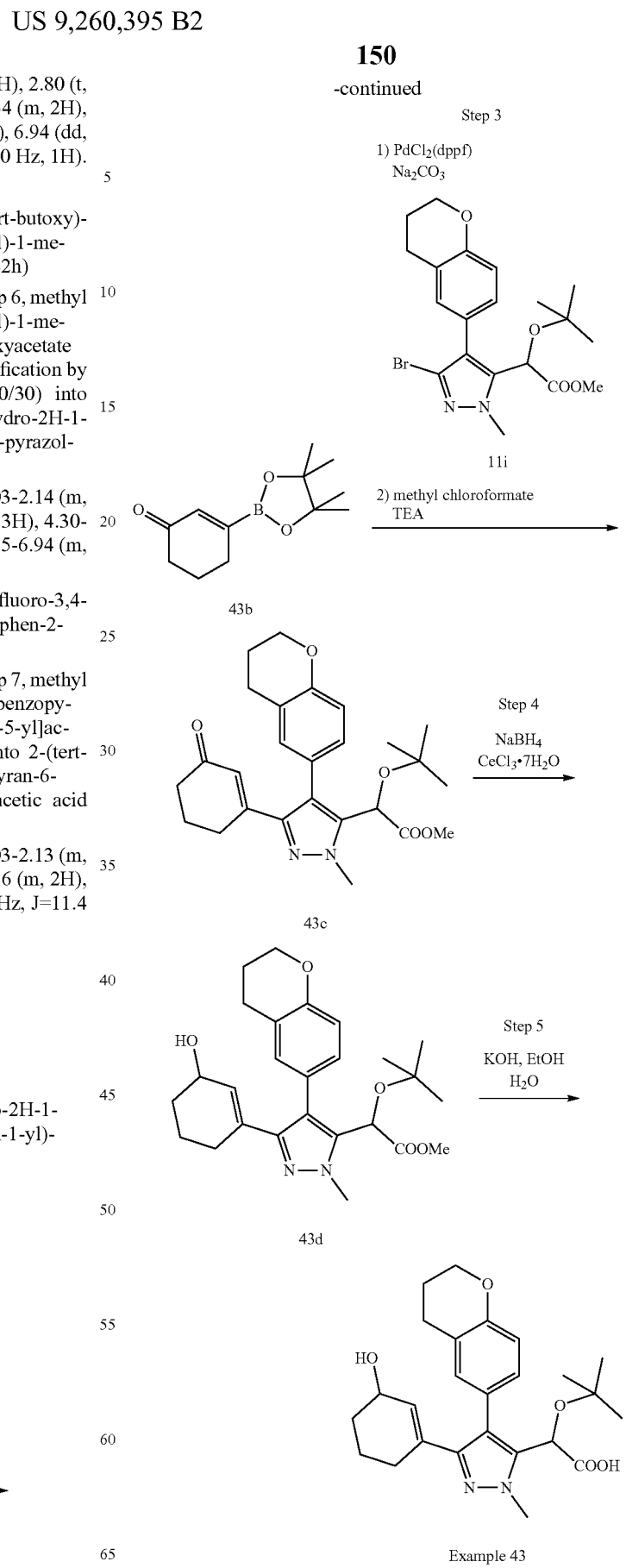

Step 1: Preparation of intermediate 3-oxocyclohex-1-en-1-yl trifluoromethanesulfonate (43a)

To a solution of 1,3-cyclohexanedione (800 mg, 7.13 mmol) in anhydrous dichloromethane (18 mL) under nitrogen atmosphere at 0° C. were successively added sodium carbonate (756 mg, 7.13 mmol) and trifluoromethanesulfonic anhydride (1.68 mL, 7.13 mol). The mixture was stirred at this temperature for 1 hour and filtered. A saturated solution of sodium hydrogenaocarbonate (20 mL) was slowly added to the filtrate. Layers were separated, and the aqueous layer was extracted with dichloromethane (20 mL). The combined organic layers were washed with brine (30 mL), dried over sodium sulfate and concentrated in vacuo to provide 3-oxocyclohex-1-en-1-yl trifluoromethanesulfonate (43a) (1.15 g, 4.71 mmol, 66%) which was used without further purification.

$^1$H NMR (300 MHz, CDCl$_3$) δ 2.07-2.19 (m, 2H), 2.42-2.48 (m, 2H), 2.69 (td, J=6.2 Hz, J=1.3 Hz, 2H), 6.01 (t, J=1.3 Hz, 1H).

MS m/z ([M+H]$^+$) 245.

Step 2: Preparation of intermediate 3-(tetramethyl-1,3,2-dioxaborolan-2-yl)cyclohex-2-en-1-one (43b)

[1,1-Bis(diphenylphosphino)ferrocene]dichloropalladium(II) (0.19 g, 0.23 mmol) was added to a previously degassed solution of 3-oxocyclohex-1-en-1-yl trifluoromethanesulfonate (43a) (1.14 g, 4.67 mmol), bis(pinacolato)diboron (2.37 g, 9.34 mmol) and potassium acetate (1.37 g, 14.00 mmol) in anhydrous dioxane (14 mL). The reaction mixture was heated at 85° C. for 16 hours. Water (10 mL) was added and the reaction mixture was concentrated in vacuo. The residue was taken in water (20 mL) and extracted with ethyl acetate (2×30 mL). The organic layer was washed with brine then dried over sodium sulfate, concentrated in vacuo, and co-elutated with toluene. The crude was purified by flash chromatography on silica gel (dichloromethane/ethyl acetate: 100/0 to 90/10) then by trituration in diethyl ether to provide 3-(tetramethyl-1,3,2-dioxaborolan-2-yl)cyclohex-2-en-1-one (43b) (850 mg, 3.83 mmol, 63%).

$^1$H NMR (400 MHz, CDCl$_3$) □ 1.29 (s, 12H), 1.95-2.04 (m, 2H), 2.37-2.44 (m, 4H), 6.49-6.53 (m, 1H).

Step 3: Preparation of intermediate methyl 2-(tert-butoxy)-2-[4-(3,4-dihydro-2H-1-benzopyran-6-yl)-1-methyl-3-(3-oxocyclohex-1-en-1-yl)-1H-pyrazol-5-yl]acetate A solution of methyl 2-[3-bromo-4-(3,4-dihydro-2H-1-benzopyran-6-yl)-1-methyl-1H-pyrazol-5-yl]-2-(tert-butoxy)acetate (11i) (100 mg, 0.229 mmol), disodium carbonate (73 mg, 0.686 mmol), and 3-(tetramethyl-1,3,2-dioxaborolan-2-yl)cyclohex-2-en-1-one (43b) (51 mg, 0.229 mmol) in a mixture of dimethoxyethane (0.87 mL), ethanol (0.37 mL) and water (0.25 mL) was bubbled with nitrogen for 5 minutes. [1,1'-Bis(diphenylphosphino)ferrocene]dichloropalladium(II), complex with dichloromethane (9.3 mg, 0.011 mmol) was added and the reaction mixture was heated at 140° C. for 2 hours. The solution was concentrated in vacuo. Water (2 mL) was added to the residue and the aqueous layer was washed with diethyl ether (2 mL), acidified with 1M hydrochloric acid until pH 3 and extracted with diethyl ether (2×3 mL). The organic layer was dried over sodium sulfate and concentrated in vacuo. The crude was dissolved in dichloromethane (1 mL), cooled to 0° C., and under a nitrogen atmosphere, triethylamine (48 μL, 0.343 mmol) and methyl chloroformate (27 μL, 0.343 mmol) were added. The reaction mixture was stirred at 0° C. for 40 minutes and allowed to reach room temperature. Dichloromethane (2 mL) was added, and the mixture was successively washed with 1N hydrochloric acid (2 mL), a saturated solution of sodium hydrogenocarbonate (2 mL), and brine (2 mL). The organic layer was dried over sodium sulfate and concentrated in vacuo. The residue was purified by flash chromatography on silica gel (dichloromethane/ethyl acetate 70/30) to provide methyl 2-(tert-butoxy)-2-[4-(3,4-dihydro-2H-1-benzopyran-6-yl)-1-methyl-3-(3-oxocyclohex-1-en-1-yl)-1H-pyrazol-5-yl]acetate (43c) (63 mg, 0.139 mmol, 61%).

$^1$H NMR (400 MHz, CDCl$_3$) δ 1.02 (s, 9H), 1.97-2.09 (m, 4H), 2.34-2.40 (m, 2H), 2.63-2.90 (m, 4H), 3.75 (s, 3H), 3.99 (s, 3H), 4.21-4.26 (m, 2H), 4.94 (s, 1H), 6.06 (s, 1H), 6.80 (d, J=8.2 Hz, 1H), 6.90 (s, 1H), 6.93 (d, J=8.2 Hz, 1H).

MS m/z ([M+H]$^+$) 453.

Step 4: Preparation of intermediate methyl 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetate (43d)

Cerium(III) chloride heptahydrate (62 mg, 0.167 mmol) was added to a solution of methyl 2-(tert-butoxy)-2-[4-(3,4-dihydro-2H-1-benzopyran-6-yl)-1-methyl-3-(3-oxocyclohex-1-en-1-yl)-1H-pyrazol-5-yl]acetate (43c) (63 mg, 0.139 mmol) in ethanol (0.46 mL). The reaction mixture was cooled to 0° C. and sodium borohydride (6 mg, 0.167 mmol) was slowly added. After stirring for 1 hour at the same temperature, the reaction was quenched with water (2 mL) and concentrated in vacuo to remove ethanol. The resulting aqueous layer was extracted with ethyl acetate (2×2 mL). The organic layer was washed with brine (3 mL), dried over sodium sulfate and concentrated in vacuo. The residue was purified by preparative TLC (dichloromethane/ethyl acetate 50/50) to provide methyl 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetate (43d) (55 mg, 0.121 mmol, 87%) as a mixture of diastereoisomers.

$^1$H NMR (400 MHz, CDCl$_3$) δ 0.99 and 1.02 (s, 9H), 1.51-1.88 (m, 4H), 1.98-2.48 (m, 4H), 2.78 (t, J=6.4 Hz, 2H), 3.73 and 3.75 (s, 3H), 3.93 and 3.94 (s, 3H), 4.14-4.26 (m, 3H), 4.98 and 4.99 (s, 1H), 5.81-5.89 (m, 1H), 6.78 and 6.79 (d, J=8.2 Hz, 1H), 6.92-7.00 (m, 2H).

MS m/z ([M+H]$^+$) 455.

Step 10: preparation of 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetic acid (example 43)

Using the procedure described in example 1, step 7, the intermediate methyl 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetate (15 mg, 0.033 mmol) is converted to 2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetic acid (7 mg, 0.016 mmol, 48%)%) as a mixture of diastereoisomers.

$^1$H NMR (400 MHz, CDCl$_3$) δ 1.01 and 1.03 (s, 9H), 1.49-1.63 (m, 2H), 1.66-1.88 (m, 2H), 1.97-2.42 (m, 4H), 2.78 (t, J=6.4 Hz, 2H), 3.90 (s, 3H), 4.15-4.25 (m, 3H), 5.05 and 5.06 (s, 1H), 5.86-5.90 (m, 1H), 6.75-6.81 (m, 1H), 6.98-7.05 (m, 2H).

MS m/z ([M−H]$^−$) 439.

MS m/z ([M+H]$^+$) 441.

Antiviral Activity

The antiviral activity, particularly against HIV, of compounds according to the invention is evaluated by the protocol described below.

Preparation of Virus stock of the NL4-3 strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting 2×10$^6$ 293 T cells (CRL-1573, ATCC) with following modifications: 6 μg of NL4-3 proviral DNA molecular clone were mixed with Fugene 6 transfection reagent from Roche, and used according to manufacturer's instructions.

Forty eight hours later, transfected cell supernatants were harvested, filtered through 0.45-µm-pore-size filters, quantified for HIV-1 p24 antigen by using a Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and I in 96 well Falcon 353072 Microtest☐distributed in a volume of 20™ tissue culture plate, in order to get 0.5% DMSO final concentration in each well, after the addition of infected cells. Control wells contained also 0.5% DMSO final concentration but no compound.

Infection of Cells:

MT4 cells (from the NIH AIDS Research and Reference Reagent Program) in RPMI complete medium were counted ($10 \times 10^6$ cells per well in Falcon 353047 Multiwell™ 24 well) and infected for 2 hours at 37°, at a multiplicity of infection (moi) of 0.0001-0.00001. Cells were then centrifuged 3 min at 3000 rpm, and washed two times in 1 ml PBS to remove viruses that have not entered in cells. Infected cells were resuspended in complete RPMI at $1.25 \times 10^6$ cells/ml and 80 µl of infected cells were distributed in each well containing compound to be tested or control wells. The plates were then incubated at 37° for 5 days.

Assay used to measure the inhibition of HIV replication by the compounds (according to Gregg S. Jones et al., Antimicrobial Agents and Chemotherapy, 2009, 53 (3): 1194-1203).

After 5 days of incubation, microplates were equilibrated to room temperature for 30 mn and then 50 µl of CellTiter-Glo reagent (Promega Biosciences, Inc., Madison Wis., USA) were added to each well. Cell lysis was carried out at room temperature during 10 min, 150µl of lysates were transferred in Packard Optiplate 96 well, and luminescence was read on a Fluoroskan (Thermo Scientific).

The EC50, or effective concentration 50, is the concentration of compound leading to 50% of cyto-protection in a Cell-Titer-Glo® viability assay based on MT4 cells infected with NL4-3 virus (table 1).

TABLE 1

| Example number | EC50 (µM) |
| --- | --- |
| 1 | 0.48 |
| 2 | 0.68 |
| 3 | 0.29 |
| 4 | 0.28 |
| 5 | 0.27 |
| 6 | 0.47 |
| 7 | 0.41 |
| 8 | 3.70 |
| 9 | 3.70 |
| 10 | 1.10 |
| 11 | 0.83 |
| 12 | 0.24 |
| 13 | 0.17 |
| 14 | 1.70 |
| 15 | 0.55 |
| 16 | 0.87 |
| 17 | 0.74 |
| 18 | 0.50 |
| 19 | 3.90 |
| 20 | 1.40 |
| 21 | 9.30 |
| 22 | 8.00 |
| 23 | 2.00 |
| 26 | 0.63 |
| 27 | 5.3 |
| 29 | 1.40 |
| 30 | 32 |
| 31 | 3.8 |

TABLE 1-continued

| Example number | EC50 (µM) |
| --- | --- |
| 32 | 3.20 |
| 34 | 3.5 |
| 36 | 2.70 |
| 37 | 3.30 |
| 38 | 2.20 |
| 39 | 5.70 |
| 40 | 6.00 |
| 41 | 6.00 |
| 42 | 1.80 |
| 43 | 9.20 |
| — | — |
| — | — |
| — | — |
| — | — |

The results show that the compounds according to the invention can inhibit the HIV replication and thus can be used as anti-HIV compounds.

The invention claimed is:

1. A compound of formula (I):

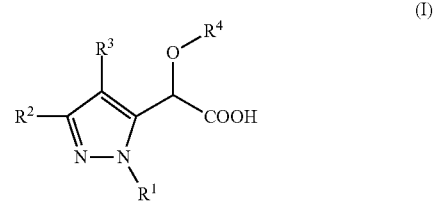

wherein $R^1$ represents —$CF_3$; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl, —$CH_2OH$ or —$CH_2$—O—$CH_3$;

$R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a linear or branched $C_1$-$C_8$ heteroalkyl; a linear or branched $C_2$-$C_8$ heteroalkenyl; a linear or branched $C_2$-$C_8$ heteroalkynyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated or aromatic 4-, 5-, 6- or 7-membered heterocycle; a $C_1$-$C_8$ alkyl-(saturated, partially or totally unsaturated or aromatic $C_3$-$C_7$ carbocycle); a $C_1$-$C_8$ alkenyl-(saturated, partially or totally unsaturated or aromatic $C_3$-$C_7$ carbocycle); a $C_1$-$C_8$ heteroalkyl-(saturated, partially or totally unsaturated or aromatic $C_3$-$C_7$ carbocycle); a $C_1$-$C_8$ alkyl-(saturated, partially or totally unsaturated or aromatic $C_4$-$C_7$ heterocycle); a $C_1$-$C_8$ heteroalkyl-(saturated, partially or totally unsaturated or aromatic $C_4$-$C_7$ heterocycle); a bicyclo[2.2.1]heptane; a bicyclo[2.2.1]heptene; a bicyclo[2.2.2]octane; or a bicyclo[2.2.2]octene;

$R^3$, non-substituted or substituted by at least one $T^2$, represents an aryl; an aryl fused with a saturated, partially or totally unsaturated or aromatic 3-, 4-, 5-, 6- or 7-membered carbocycle; an aryl fused with a saturated, partially or totally unsaturated or aromatic 4-, 5-, 6- or 7-membered heterocycle; a heteroaryl; a heteroaryl fused with a saturated, partially or totally unsaturated or aromatic 3-, 4-, 5-, 6- or 7-membered carbocycle; a heteroaryl fused with a saturated, partially or totally unsaturated or aromatic 4-, 5-, 6- or 7-membered heterocycle; or an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 4-, 5-, 6- or 7-membered heterocycle;

$R^4$, substituted or non-substituted by at least one $T^5$, represents a linear or branched $C_2$-$C_6$ alkyl; a linear or branched $C_1$-$C_6$ fluoroalkyl; or a $C_3$-$C_6$ cycloalkyl;

$T^1$ independently represents a hydrogen atom, a halogen atom; an alkyl; —OH; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulpher atom; NT$^3$; S=O or S(O)$_2$;

$T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; a linear or branched $C_1$-$C_3$ alkyl; or a $C_3$-$C_6$ cycloalkyl; optionally $T^5$, $T^6$ and the carbon atom to which they are bonded form a cyclopropyl;

x independently represents 0 or 1;
y independently represents 0, 1, 2 or 3;
and a racemate, enantiomer, tautomer, atropisomer, diastereoisomer or a pharmaceutically acceptable salt thereof.

2. The compound according to claim 1, wherein $R^4$ represents tBu.

3. The compound according to claim 1, wherein:

$R^2$, non-substituted or substituted by at least one $T^1$, represents a linear or branched $C_2$-$C_8$ alkyl; a linear or branched $C_2$-$C_8$ alkenyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated 4-, 5-, 6- or 7-membered heterocycle; a bicyclo[2.2.1]heptane; a $C_1$-$C_8$ alkyl-(saturated, partially or totally unsaturated or aromatic $C_3$-$C_7$ carbocycle); or a $C_1$-$C_8$ alkenyl-(saturated, partially or totally unsaturated or aromatic $C_3$-$C_7$ carbocycle);

$T^1$ independently represents a hydrogen atom; a halogen atom; —CH$_3$; —CH$_2$F; —CHF$_2$; —CF$_3$; —OCH$_3$; —OCH$_2$F; —OCHF$_2$; —OCF$_3$; —OH; —$(X)_x$—$C_3$-$C_6$ cycloalkyl; —$(X)_x$—$(CT^5T^6)_y$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$S(O)$_2$NT$^3$T$^4$ or $(X)_x$—$(CT^5T^6)_y$NT$^3$S(O)$_2$T$^4$;

X independently represents an oxygen atom; a sulphur atom; NT$^3$; S=O or S(O)$_2$;

$T^3$ and $T^4$, identical or different, independently represent H; a branched or linear C1-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; or methyl;

x independently represents 0 or 1;

y independently represents 0, 1, 2 or 3.

4. The compound according to claim 1 of formula (A), (B), (C) or (D):

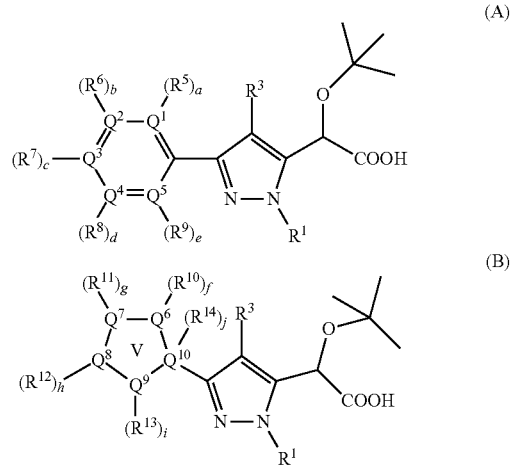

-continued

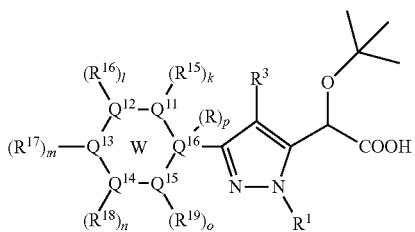

(C)

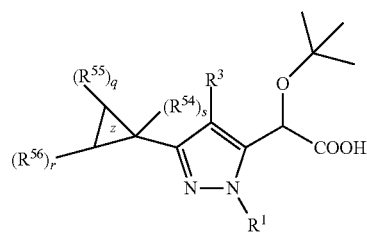

(D)

wherein f, g, h, i, k, l, m, n, o, q or r independently represent 0, 1 or 2;

a, b, c, d, e, j, p or s independently represent 0 or 1;

V represents a substituted or non substituted, saturated, partially or totally unsaturated carbocycle or aromatic carbocyle; or a substituted or non substituted, saturated, partially or totally unsaturated or aromatic heterocycle;

W represents a substituted or non-substituted, saturated or partially unsaturated carbocycle; or a substituted or non substituted, saturated, partially unsaturated heterocycle;

Z represents a substituted or non-substituted, cyclopropyl;

$Q^1$ represents $CR^5$ or N;

$Q^2$ represents $CR^6$ or N;

$Q^3$ represents $CR^7$ or N;

$Q^4$ represents $CR^8$ or N;

$Q^5$ represents $CR^9$ or N;

$Q^6$ represents $CR^{10}$, C=O, N, $NR^{10}$, O, S, S=O or $S(O)_2$;

$Q^7$ represents $CR^{11}$, C=O, N, $NR^{11}$, O, S, S=O or $S(O)_2$;

$Q^8$ represents $CR^{12}$, C=O, N, $NR^{12}$, O, S, S=O or $S(O)_2$;

$Q^9$ represents $CR^{13}$, C=O, N, $NR^{13}$, O, S, S=O or $S(O)_2$;

$Q^{10}$ represents C, $CR^{14}$, or N;

$Q^{11}$ represents C, $CR^{15}$, C=O, N, $NR^{15}$, O, S, S=O or $S(O)_2$;

$Q^{12}$ represents C, $CR^{16}$, C=O, N, $NR^{16}$, O, S, S=O or $S(O)_2$;

$Q^{13}$ represents C, $CR^{17}$, C=O, N, $NR^{17}$, O, S, S=O or $S(O)_2$;

$Q^{14}$ represents C, $CR^{18}$, C=O, N, $NR^{18}$, O, S, S=O or $S(O)_2$;

$Q^{15}$ represents C, $CR^{19}$, C=O, N, $NR^{19}$, O, S, S=O or $S(O)_2$;

$Q^{16}$ represents C, CR, N;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, R, $R^{54}$, $R^{55}$ or $R^{56}$ identical or different, independently represent a hydrogen atom; a halogen atom; —OH; —$CH_3$; —$CH_2CH_3$; —CH—$(CH_3)_2$; —$(CH_2)_2$ $CH_3$—$CH_2F$; —$CHF_2$; —$CF_3$; —$OCH_3$; —$OCH_2F$; —$OCHF_2$; —$OCF_3$; —$(X)_x$—$C_1$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$$OT^3$; —$(X)_x$—$(CT^5T^6)_y$$ST^3$; —$(X)_x$—$(CT^5T^6)_y$$S(O)T^3$; —$(X)_x$—$(CT^5T^6)_y$$S(O)_2T^3$; —$(X)_x$—$(CT^5T^6)_y$$NT^3T^4$; —$(X)_x$—$(CT^5T^6)_y$$C(O)T^3$; —$(X)_x$—$(CT^5T^6)_y$$C(O)OT^3$; —$(X)_x$—$(CT^5T^6)_y$$C(O)NT^3T^4$; —$(X)_x$—$(CT^5T^6)_y$$NT^3C(O)NT^3T^4$; —$(X)_x$—$(CT^5T^6)_y$ $NT^3C(O)T^4$; —$(X)_x$—$(CT^5T^6)_y$$NT^3C(O)OT^4$; —$(X)_x$—$(CT^5T^6)_y$$OC(O)NT^3T^4$; —$(X)_x$—$(CT^5T^6)_y$ $S(O)_2$ $NT^3T^4$ or $(X)_x$—$(CT^5T^6)_y$$NT^3S(O)_2T^4$;

$T^2$ independently represents a hydrogen atom; a halogen atom; methyl; —$CH_2F$; —$CHF_2$; —$CF_3$; —OMe; —$OCH_2F$; —$OCHF_2$; —$OCF_3$; or CN; optionally two geminal $T^2$ form with the carbon atom to which they are bonded, a $C_3$-$C_7$ cycloalkyl;

$R^1$, $R^3$, X, x, y and $T^3$ to $T^6$ are independently defined as in any of claims 1 to 3.

5. The compound according to claim 1, wherein $R^1$ represents:
   a linear or branched $C_1$-$C_3$ alkyl;
   a linear or branched $C_1$-$C_3$ fluoroalkyl;
   a $C_3$-$C_6$ cycloalkyl; or
   —$CH_2OH$.

6. The compound according to claim 1, wherein $R^2$, non-substituted or substituted by at least one $T^1$, represents a linear or branched $C_2$-$C_8$ alkyl; a linear or branched $C_2$-$C_8$ alkenyl; a saturated, partially or totally unsaturated or aromatic 3-, 4-, 5-, 6- or 7-membered carbocycle; a saturated, partially or totally unsaturated or aromatic 5- or 6-membered heterocycle; a saturated, partially or totally unsaturated or aromatic 5- or 6-membered heterocycle fused with a saturated, partially or totally unsaturated or aromatic 5-, 6-membered carbocycle; a $C_1$-$C_8$ alkyl-(saturated, partially or totally unsaturated or aromatic $C_3$-$C_7$ carbocycle); a $C_2$-$C_8$ alkenyl-(saturated, partially or totally unsaturated or aromatic $C_3$-$C_7$ carbocycle); or a bicyclo[2.2.1]heptene.

7. The compound according to claim 1, wherein $R^3$, non-substituted or substituted by at least one $T^2$, represents an aryl; an aryl fused with a saturated, partially or totally unsaturated or aromatic 4-, 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; or a $C_5$-$C_7$ cycloalkenyl.

8. The compound according to claim 1, wherein:
   $T^1$ independently represents a hydrogen atom; a halogen atom; an alkyl; a linear or branched fluoroalkyl; —OH; —$(X)_x$—$C_1$-$C_6$ alkyl; —$(X)_x$—$C_1$-$C_6$ cycloalkyl; —$(X)_x$—$(CT^5T^6)_y$—$(C_1$-$C_6$cycloalkyl); or $(X)_x$—$(CT^5T^6)_y$-aryl;
   $T^2$ independently represents a hydrogen atom; a halogen atom; a linear or branched —O—$C_1$-$C_3$ alkyl; a linear or branched $C_1$-$C_3$ fluoroalkyl; or a linear or branched $C_1$-$C_3$ alkyl; optionally two geminal $T^2$ form with the carbon atom to which they are bonded, a cyclopropyl;
   X represents an oxygen atom;
   $T^3$ and $T^4$, identical or different, independently represent a hydrogen atom; or a branched or linear $C_1$-$C_6$ alkyl;
   $T^5$ and $T^6$, identical or different, independently represent a hydrogen atom; a fluorine atom; or a linear or branched $C_1$-$C_3$ alkyl;
   x independently represents 0 or 1;
   y independently represents 0, 1, 2 or 3.

9. The compound according to claim 1 selected from the group consisting of:
   2-(tert-butoxy)-2-[4-(4,4-dimethylcyclohex-1-en-1-yl)-1-methyl-3-phenyl-1H-pyrazol-5-yl]acetic acid;
   2-(tert-butoxy)-2-{1-methyl-3-phenyl-4-[4-(propan-2-yl) cyclohex-1-en-1-yl]-1H-pyrazol-5-yl}acetic acid;
   2-(tert-butoxy)-2-[4-(3,4-dihydro-2H-1-benzopyran-6-yl)-1-methyl-3-phenyl -1H-pyrazol-5-yl]acetic acid;

2-(tert-butoxy)-2-[4-(3,4-dihydro-2H-1-benzopyran-6-yl)-1-methyl-3-(pyridine-2-yl)-1H-pyrazol-5-yl]acetic acid;

2-(tert-butoxy)-2-[4-(4,4-dimethylcyclohex-1-en-1-yl)-1-methyl-3-(pyridine-4-yl)-1H-pyrazol-5-yl]acetic acid;

2-(tert-butoxy)-2-[4-(3,4-dihydro-2H-1-benzopyran-6-yl)-1-methyl-3-(pyridine-4-yl)-1H-pyrazol-5-yl]acetic acid;

2-(tert-butoxy)-2-[4-(4,4-dimethylcyclohex-1-en-1-yl)-1-methyl-3-(thiophen-2-yl)-1H-pyrazol-5-yl]acetic acid;

2-(tert-butoxy)-2-[4-(3,4-dihydro-2H-1-benzopyran-6-yl)-1-methyl-3-(thiophen-2-yl)-1H-pyrazol-5-yl]acetic acid;

2-(tert-butoxy)-2-[1-methyl-4-(5-methyl-3,4-dihydro-2H-1-benzopyran-6-yl)-3-(thiophen-2-yl)-1H-pyrazol-5-yl]acetic acid;

2-(tert-butoxy)-2-[3-(5-chlorothiophen-2-yl)-4-(3,4-dihydro-2H-1-benzopyran-6-yl)-1-methyl-1H-pyrazol-5-yl]acetic acid;

2-(tert-butoxy)-2-[4-(8-fluoro-5-methyl-3,4-dihydro-2H-1-benzopyran-6-yl)-1-methyl-3-(thiophen-2-yl)-1H-pyrazol-5-yl]acetic acid;

2-(tert-butoxy)-2-[4-(8-chloro-5-methyl-3,4-dihydro-2H-1-benzopyran-6-yl)-1-methyl-3-(thiophen-2-yl)-1H-pyrazol-5-yl]acetic acid;

2-(tert-butoxy)-2-[4-(3,4-dihydro-2H-1-benzopyran-6-yl)-3-(thiophen-2-yl)-1-(2,2,2-trifluoroethyl)-1H-pyrazol-5-yl]acetic acid;

2-(tert-butoxy)-2-[4-(8-fluoro-3,4-dihydro-2H-1-benzopyran-6-yl)-1-methyl-3-(thiophen-2-yl)-1H-pyrazol-5-yl]acetic acid;

2-(tert-butoxy)-2-(3-{4H,5H,6H-cyclopenta[b]thiophen-2-yl}-4-(3,4-dihydro-2H-1-benzopyran-6-yl)-1-methyl-1H-pyrazol-5-yl)acetic acid;

2-(tert-butoxy)-2-[4-(4,4-dimethylcyclohex-1-en-1-yl)-1-methyl-3-(thiophen-3-yl)-1H-pyrazol-5-yl]acetic acid;

2-(tert-butoxy)-2-[4-(3,4-dihydro-2H-1-benzopyran-6-yl)-1-methyl-3-(thiophen-3-yl)-1H-pyrazol-5-yl]acetic acid;

2-(tert-butoxy)-2-[4-(3,4-dihydro-2H-1-benzopyran-6-yl)-1-methyl-3-(5-propylthiophen-3-yl)-1H-pyrazol-5-yl]acetic acid;

2-[3-benzo[b]thiophen-3-yl-4-(3,4-dihydro-2H-1-benzopyran-6-yl)-1-methyl-1H-pyrazol-5-yl]-2-(tert-butoxy)acetic acid;

2-(tert-butoxy)-2-[4-(3,4-dihydro-2H-1-benzopyran-6-yl)-1-methyl-3-(1,3-thiazol-2-yl)-1H-pyrazol-5-yl]acetic acid;

2-(tert-butoxy)-2-[3-(cyclopent-1-en-1-yl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-3-(5,5-dimethylcyclopent-1-en-1-yl)-1-methyl-1H-pyrazol-5-yl]acetic acid;

2-(tert-butoxy)-2-[4-(3,4-dihydro-2H-1-benzopyran-6-yl)-1-methyl-3-(5-methylcyclopent-1-en-1-yl)-1H-pyrazol-5-yl]acetic acid;

2-(tert-butoxy)-2-[3-cyclopentyl-4-(3,4-dihydro-2H-1-benzopyran-6-yl)-1-methyl-1H-pyrazol-5-yl]acetic acid;

2-(tert-butoxy)-2-[3-cyclohexyl-4-(3,4-dihydro-2H-1-benzopyran-6-yl)-1-methyl-1H-pyrazol-5-yl]acetic acid;

2-(tert-butoxy)-2-[3-(cyclohex-1-en-1-yl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-3-(4,4-dimethylcyclohex-1-en-1-yl)-1-methyl-1H-pyrazol-5-yl]acetic acid;

2-(tert-butoxy)-2-[4-(3,4-dihydro-2H-1-benzopyran-6-yl)-1-methyl-3-(3-methylcyclohex-1-en-1-yl)-1H-pyrazol-5-yl]acetic acid;

2-(tert-butoxy)-2-[4-(3,4-dihydro-2H-1-benzopyran-6-yl)-1-methyl-3-(6-methylcyclohex-1-en-1-yl)-1H-pyrazol-5-yl]acetic acid;

2-(tert-butoxy)-2-[4-(3,4-dihydro-2H-1-benzopyran-6-yl)-1-methyl-3-(4-methylcyclohex-1-en-1-yl)-1H-pyrazol-5-yl]acetic acid;

2-(tert-butoxy)-2-[4-(3,4-dihydro-2H-1-benzopyran-6-yl)-3-(3-hydroxycyclohex-1-en-1-yl)-1-methyl-1H-pyrazol-5-yl]acetic acid;

2-(tert-butoxy)-2-[3-cyclopropyl-4-(3,4-dihydro-2H-1-benzopyran-6-yl)-1-methyl-1H-pyrazol-5-yl]acetic acid;

2-(3-{bicyclo[2.2.1]hept-2-en-2-yl}-4-(3,4-dihydro-2H-1-benzopyran-6-yl)-1-methyl-1H-pyrazol-5-yl)-2-(tert-butoxy)acetic acid;

2-(tert-butoxy)-2-[3-(cyclohept-1-en-1-yl)-4-(3,4-dihydro-2H-1-benzopyran-6-yl)-1-methyl-1H-pyrazol-5-yl]acetic acid;

2-(tert-butoxy)-2-[3-(cyclopentylmethyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-(prop-1-en-2-yl)-1H-pyrazol-5-yl]acetic acid;

2-(tert-butoxy)-2-[3-(1-cyclopentylethenyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-(propan-2-yl)-1H-pyrazol-5-yl]acetic acid;

2-(tert-butoxy)-2-[3-(1-cyclopentylethyl)-4-(3,4-dihydro-2H-1-benzopyran-6-yl)-1-methyl-1H-pyrazol-5-yl]acetic acid;

2-(tert-butoxy)-2-{3-[(E)-2-cyclopropylethenyl]-4-(3,4-dihydro-2H-1-benzopyran-6-yl)-1-methyl-1H-pyrazol-5-yl}acetic acid;

2-(tert-butoxy)-2-[3-(2-cyclopropylethyl)-4-(3,4-dihydro-2H-1-benzopyran-6-yl)-1-methyl-1H-pyrazol-5-yl]acetic acid;

2-(tert-butoxy)-2-[4-(3,4-dihydro-2H-1-benzopyran-6-yl)-1-methyl-3-[(1E)-prop-1-en-1-yl]-1H-pyrazol-5-yl]acetic acid; or 2-(tert-butoxy)-2-[4-(3,4-dihydro-2H-1-benzopyran-6-yl)-1-methyl-3-propyl-1H-pyrazol-5-yl]acetic acid.

10. A method for the treatment of HIV comprising administering to a patient in need thereof a compound according to claim 1.

11. A pharmaceutical composition comprising a compound according to claim 1 as an active ingredient and at least a pharmaceutically acceptable carrier.

12. The pharmaceutical composition according to claim 11 comprising a further antiviral agent.

13. The method according to claim 10 for the treatment of an HIV infection in a mammal being infected.

* * * * *